United States Patent
Um et al.

(10) Patent No.: US 12,336,425 B2
(45) Date of Patent: Jun. 17, 2025

(54) COMPOUND AND LIGHT-EMITTING DEVICE INCLUDING THE SAME

(71) Applicant: Samsung Display Co., Ltd., Yongin-si (KR)

(72) Inventors: Hyunah Um, Yongin-si (KR); Hyeongmin Kim, Yongin-si (KR); Heechoon Ahn, Yongin-si (KR); Yeseul Lee, Yongin-si (KR); Yirang Im, Yongin-si (KR); Seowon Cho, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 641 days.

(21) Appl. No.: 17/075,619

(22) Filed: Oct. 20, 2020

(65) Prior Publication Data

US 2021/0359215 A1 Nov. 18, 2021

(30) Foreign Application Priority Data

May 11, 2020 (KR) ........................ 10-2020-0056151

(51) Int. Cl.
*H10K 85/60* (2023.01)
*C07D 403/04* (2006.01)
(Continued)

(52) U.S. Cl.
CPC ......... *H10K 85/654* (2023.02); *C07D 403/04* (2013.01); *C07D 403/14* (2013.01);
(Continued)

(58) Field of Classification Search
CPC ............. H10K 85/654; H10K 85/6572; H10K 85/6574; H10K 50/11; H10K 2101/10;
(Continued)

(56) References Cited

U.S. PATENT DOCUMENTS 9,379,361 B2 6/2016 Tsurutani et al.
9,595,679 B2 3/2017 Huh et al.
(Continued)

FOREIGN PATENT DOCUMENTS

CN 105593336 A 5/2016
CN 107531650 A * 1/2018 ........... C07D 251/12
(Continued)

OTHER PUBLICATIONS

Chang, Chih-Hao et al. "A dicarbazole-triazine hybrid bipolar host material for highly efficient green phosphorescent OLEDs" *J. Mater. Chem.*, 2012, 22, pp. 3832-3838.
(Continued)

*Primary Examiner* — Ruiyun Zhang
(74) *Attorney, Agent, or Firm* — Womble Bond Dickinson (US) LLP

(57) ABSTRACT

A compound represented by Formula 1, when used in a light-emitting device according to an embodiment of the disclosure, may have higher efficiency characteristics than compounds in the related art, and in particular, may have excellent effects in terms of lifespan improvement, resulting in a significant improvement in the lifespan of the light-emitting device:

(Continued)

US 12,336,425 B2
Page 2

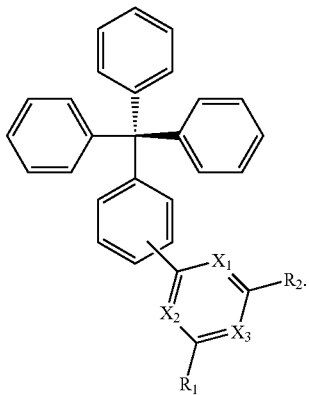

Formula 1

(58) Field of Classification Search
CPC ............ C09K 11/06; C09K 2211/1007; C09K 2211/1018
USPC .......................................................... 428/690
See application file for complete search history.

(56) References Cited

U.S. PATENT DOCUMENTS

| | | |
|---|---|---|
| 10,669,473 B2 | 6/2020 | Ambrosek et al. |
| 2005/0067951 A1 | 3/2005 | Richter et al. |
| 2016/0225993 A1* | 8/2016 | Huh ...................... H10K 85/633 |
| 2017/0342057 A1 | 11/2017 | Shim et al. |
| 2019/0296254 A1* | 9/2019 | Ko ........................... H10K 85/40 |
| 2020/0199090 A1* | 6/2020 | Jang ..................... H10K 85/633 |
| 2020/0328359 A1 | 10/2020 | Ko et al. |
| 2020/0358009 A1* | 11/2020 | Ahn ..................... H10K 85/342 |

FOREIGN PATENT DOCUMENTS

| | | | |
|---|---|---|---|
| CN | 110299457 A | 10/2019 | |
| CN | 111825720 A | 10/2020 | |
| EP | 2182039 A2 * | 5/2010 | .......... C09B 57/008 |
| KR | 10-0938524 B1 | 1/2010 | |
| KR | 10-2017-0096769 A | 8/2017 | |
| WO | WO 2010/126270 A1 | 11/2010 | |
| WO | WO 2016/116487 A1 | 7/2016 | |

OTHER PUBLICATIONS

Chinese Office Action dated Dec. 9, 2024, issued in corresponding Chinese Patent Application No. 202110126423.8 (10 pages).

\* cited by examiner

20 Claims, 3 Drawing Sheets

(51) Int. Cl.
| | |
|---|---|
| C07D 403/14 | (2006.01) |
| C07D 405/14 | (2006.01) |
| C09K 11/06 | (2006.01) |
| H10K 50/11 | (2023.01) |
| H10K 101/10 | (2023.01) |

(52) U.S. Cl.
CPC ............ *C07D 405/14* (2013.01); *C09K 11/06* (2013.01); *H10K 85/6572* (2023.02); *H10K 85/6574* (2023.02); *C09K 2211/1007* (2013.01); *C09K 2211/1018* (2013.01); *H10K 50/11* (2023.02); *H10K 2101/10* (2023.02)

| 150 |
|---|
| 130 |
| 110 |

COMPOUND AND LIGHT-EMITTING DEVICE INCLUDING THE SAME

CROSS-REFERENCE TO RELATED APPLICATION

This application claims priority to and the benefit of Korean Patent Application No. 10-2020-0056151, filed on May 11, 2020, in the Korean Intellectual Property Office, the entire content of which is incorporated herein by reference.

BACKGROUND

1. Field

One or more aspects of embodiments of the present disclosure relate to a compound and a light-emitting device including the same.

2. Description of Related Art

Organic light-emitting devices are self-emission devices, which may have wide viewing angles, high contrast ratios, short response times, and/or excellent characteristics in terms of brightness, driving voltage, and/or response speed, compared to devices in the related art.

An example organic light-emitting device includes a first electrode disposed on a substrate, and a hole transport region, an emission layer, an electron transport region, and a second electrode sequentially disposed on the first electrode. Holes provided from the first electrode may move toward the emission layer through the hole transport region, and electrons provided from the second electrode may move toward the emission layer through the electron transport region. Carriers (such as the holes and electrons) may recombine in the emission layer to produce excitons. These excitons may transition from an excited state to the ground state to thereby generate light.

SUMMARY

One or more aspects of embodiments of the present disclosure are directed toward a host compound higher in T1 value (i.e., higher T1 triplet energy value) than compounds in the related art and a device including the same.

Additional aspects will be set forth in part in the description that follows and, in part, will be apparent from the description, or may be learned by practice of the presented embodiments of the disclosure.

One or more example embodiments of the present disclosure provide a compound represented by Formula 1:

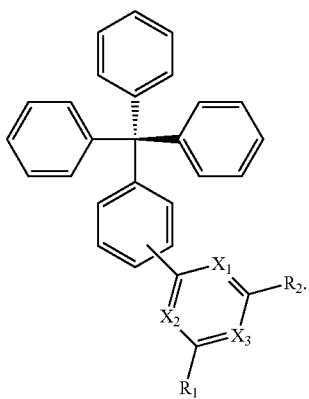

Formula 1

In Formula 1, $X_1$ may be N or $CR_3$, $X_2$ may be N or $CR_4$, and $X_3$ may be N or $CR_5$, $R_1$ to $R_5$ may each independently be selected from hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —B($Q_1$)($Q_2$), —C(=O)($Q_1$), —Si($Q_1$)($Q_2$)($Q_3$), and —P(=O)($Q_1$)($Q_2$), $R_{10a}$ may be:

deuterium (-D), —F, —Cl, —Br, —I, a hydroxyl group, a cyano group, or a nitro group, a $C_1$-$C_{60}$ alkyl group, a $C_2$-$C_{60}$ alkenyl group, a $C_2$-$C_{60}$ alkynyl group, or a $C_1$-$C_{60}$ alkoxy group, each being unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), —P(=O)($Q_{11}$)($Q_{12}$), or any combination thereof, a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each being unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof, or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or $C_1$-$C_{60}$ heterocyclic group, each being unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

One or more example embodiments of the present disclosure provide a light-emitting device including:
a first electrode,
a second electrode facing the first electrode, and
an interlayer located between the first electrode and the second electrode and including an emission layer,
wherein, the interlayer includes the compound.

One or more example embodiments of the present disclosure provide an electronic apparatus including the light-emitting device.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 1 is a schematic view of a light-emitting device, according to an embodiment;

DETAILED DESCRIPTION

Figure 2:
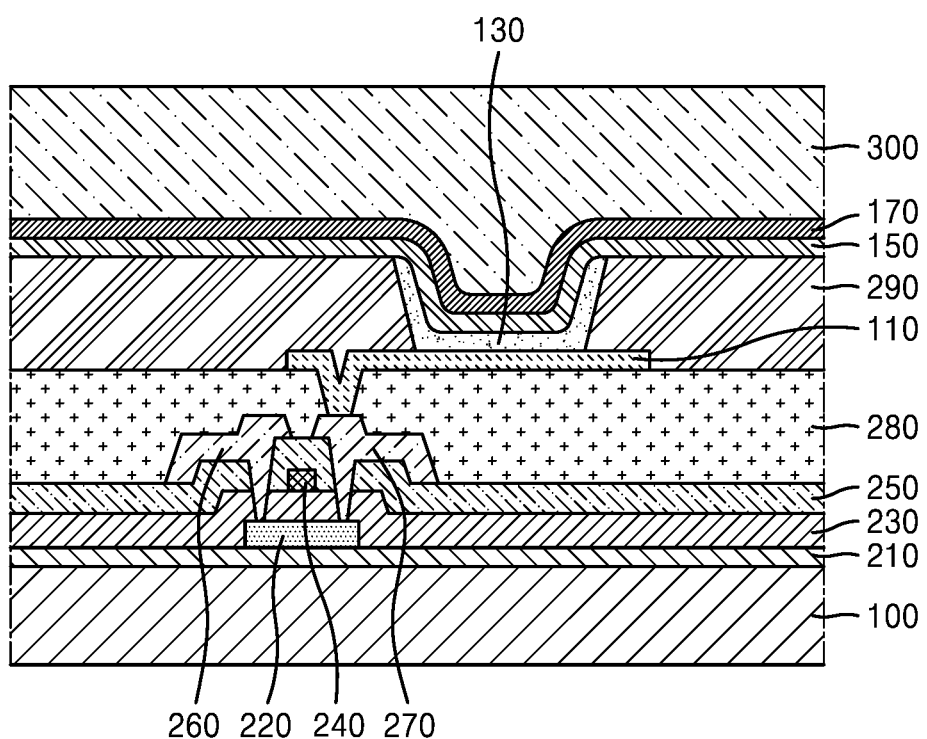
FIG. 2 is a cross-sectional view of a light-emitting apparatus, according to an embodiment of the disclosure.

Reference will now be made in more detail to embodiments, examples of which are illustrated in the accompanying drawings, wherein like reference numerals refer to like elements throughout, and duplicative descriptions thereof may not be provided. In this regard, the present embodiments may have different forms and should not be construed as being limited to the descriptions set forth herein. Accordingly, the embodiments are merely described below, by referring to the drawings, to explain aspects of the present description. As used herein, the term "and/or" includes any and all combinations of one or more of the associated listed items. Throughout the disclosure, the expression "at least one of a, b, or c" may indicate only a, only b, only c, both a and b, both a and c, both b and c, all of a, b, and c, or variations thereof.

As used herein, expressions such as "at least one of," "one of," and "selected from," when preceding a list of elements, modify the entire list of elements and do not modify the individual elements of the list. It will be further understood that the terms "includes," "including," "comprises," and/or "comprising," when used in this specification, specify the presence of stated features, steps, operations, elements, and/or components, but do not preclude the presence or addition of one or more other features, steps, operations, elements, components, and/or groups thereof.

Further, the use of "may" when describing embodiments of the present disclosure refers to "one or more embodiments of the present disclosure".

A compound represented by Formula 1 according to an aspect is as follows:

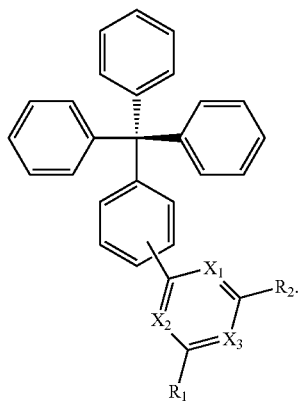

Formula 1

In Formula 1, $X_1$ may be N or $CR_3$, $X_2$ may be N or $CR_4$, and $X_3$ may be N or $CR_5$, $R_1$ to $R_5$ may each independently be selected from hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —$B(Q_1)(Q_2)$, —$C(=O)(Q_1)$, —$Si(Q_1)(Q_2)(Q_3)$, and —$P(=O)(Q_1)(Q_2)$, $R_{10a}$ may be:

deuterium (-D), —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each being unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, —$P(=O)(Q_{11})(Q_{12})$, or any combination thereof;

a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each being unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, —$P(=O)(Q_{21})(Q_{22})$, or any combination thereof; or —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$, wherein $Q_1$ to $Q_3$, $Q_{11}$ to $Q_{13}$, $Q_{21}$ to $Q_{23}$, and $Q_{31}$ to $Q_{33}$ may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or $C_1$-$C_{60}$ heterocyclic group, each being unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

The compound represented by Formula 1 according to an embodiment introduces a steric hindrance effect (e.g., may be subject to steric interactions between the substituted aryl group and the phenyl substituents of the tetraphenylmethane moiety), and may thereby exhibit a higher T1 value (e.g., higher T1 triplet energy) and higher efficiency than compounds in the related art due to the improved exciton binding energy. In addition, the compound may have an improved hole transport capability compared to compounds in the related art.

In the compound represented by Formula 1 according to an embodiment, the phenyl groups of the tetraphenylmethane moiety are not substituted (e.g., three of the phenyl groups do not serve as linkers to any other moieties of the compound, and do not have any substituents other than hydrogen).

In an embodiment, the compound represented by Formula 1 may be represented by Formula 2:

Formula 2

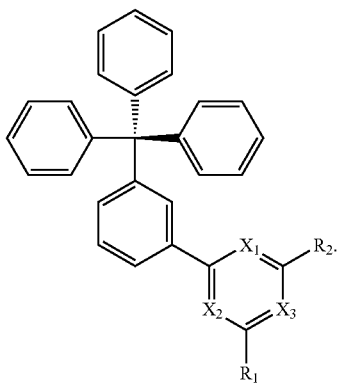

In Formula 2, $X_1$, $X_2$, $X_3$, $R_1$, and $R_2$ may each independently be the same as described in connection with Formula 1.

In an embodiment, the compound represented by Formula 1 may be represented by Formula 3:

Formula 3

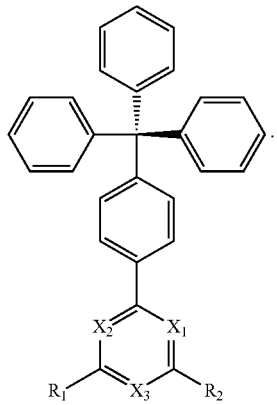

In Formula 3, $X_1$, $X_2$, $X_3$, $R_1$, and $R_2$ may each independently be the same as described in connection with Formula 1.

In an embodiment, the compound represented by Formula 1 may be represented by Formula 4:

Formula 4

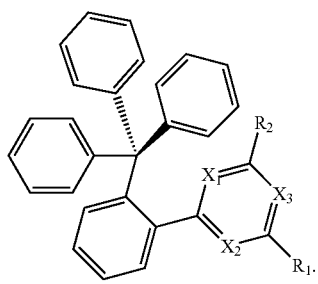

In Formula 4, $X_1$, $X_2$, $X_3$, $R_1$, and $R_2$ may each independently be the same as described in connection with Formula 1.

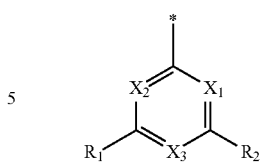

In an embodiment, the moiety of Formula 1 may be selected from Formulae 2a to 2d:

2a
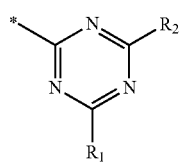

2b
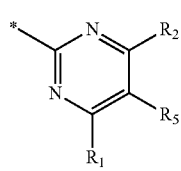

2c
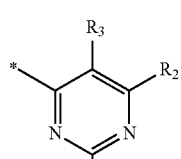

2d
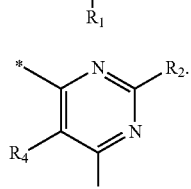

In Formulae 2a to 2d, * is a binding site to a neighboring atom, and $R_1$ to $R_5$ may each independently be the same as described in connection with Formula 1.

In some embodiments, in Formulae 2a to 2d, $R_3$, $R_4$, and $R_5$ may each be hydrogen.

In an embodiment, $R_1$ of Formula 1 may be selected from: a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspirobifluorenyl group, an azacarbazolyl group, an azadibenzofuranyl group, an azadibenzothiophenyl group, and an azadibenzosilolyl group; and a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspirobifluorenyl group, an azacarbazolyl group, an azadibenzofuranyl group, an azadibenzothiophenyl group, and an azadibenzosilolyl group, each being substituted with deuterium, —F, —Cl, —Br, —I, a hydroxyl group, a cyano group, a nitro group, a $C_1$-$C_{20}$ alkyl group, a $C_2$-$C_{20}$ alkenyl group, a $C_2$-$C_{20}$ alkynyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{20}$ aryl group, a $C_1$-$C_{20}$ heteroaryl group, or any combination thereof.

In an embodiment, $R_1$ of Formula 1 may be selected from Formulae 3a and 3b:

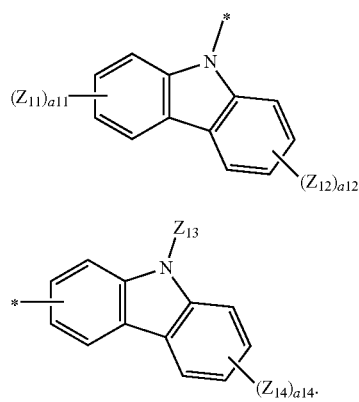

In Formulae 3a and 3b, $Z_{11}$ to $Z_{14}$ may each independently be hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a dibenzofuranyl group, a dibenzothiophenyl group, a triazinyl group, a benzimidazolyl group, a phenanthrolinyl group, or any combination thereof, a11 to a14 may each independently be an integer from 1 to 4, and * indicates a binding site to a neighboring atom.

For example, in Formula 3a, $Z_{11}$ and $Z_{12}$ may each independently be hydrogen or deuterium.

In an embodiment, $R_2$ of Formula 1 may be a $C_6$-$C_{60}$ aryl group unsubstituted or substituted with at least one $R_{10a}$, or a $C_1$-$C_{60}$ heteroaryl group unsubstituted or substituted with at least one $R_{10a}$.

In an embodiment, $R_2$ of Formula 1 may be selected from Formulae 4a to 4c.

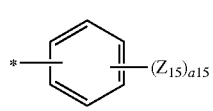

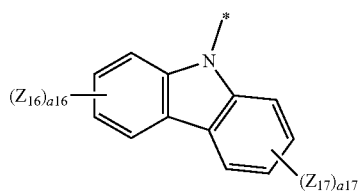

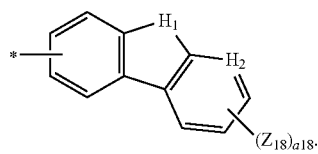

In Formulae 4a to 4c, $H_1$ may be O, S, $CR_{11}R_{12}$, or $NR_{13}$, and $H_2$ may be $CR_{14}$ or N, $R_{11}$ to $R_{14}$ and $Z_{15}$ to $Z_{18}$ may each independently be: hydrogen, deuterium, —F, —Cl, —Br, —I, a hydroxyl group, a cyano group, a nitro group, a $C_1$-$C_{20}$ alkyl group, a $C_1$-$C_{20}$ heteroaryl group, or —Si($Q_{41}$)($Q_{42}$)($Q_{43}$); or a $C_1$-$C_{60}$ heteroaryl group substituted with deuterium, —F, —Cl, —Br, —I, a hydroxyl group, a cyano group, a nitro group, an amidino group, a hydrazino group, a hydrazono group, a $C_1$-$C_{20}$ alkyl group, a $C_2$-$C_{20}$ alkenyl group, a $C_2$-$C_{20}$ alkynyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{20}$ aryl group, a $C_6$-$C_{20}$ aryloxy group, a $C_6$-$C_{20}$ arylthio group, a $C_1$-$C_{20}$ heteroaryl group, a monovalent non-aromatic condensed polycyclic group, a monovalent non-aromatic condensed heteropolycyclic group, —B($Q_{51}$)($Q_{52}$), —C(=O)($Q_{51}$), —Si($Q_{51}$)($Q_{52}$)($Q_{53}$), —P(=O)($Q_{51}$)($Q_{52}$), or any combination thereof, $Q_{41}$ to $Q_{43}$ and $Q_{51}$ to $Q_{53}$ may each independently be a $C_1$-$C_{20}$ alkyl group or a $C_6$-$C_{20}$ aryl group, a15 may be an integer from 1 to 5, a16 and a17 may each independently be an integer from 1 to 4, a18 may be an integer from 1 to 3, and * indicates a binding site to a neighboring atom.

In an embodiment, the compound represented by Formula 1 may be represented by Formula 5.

Formula 5

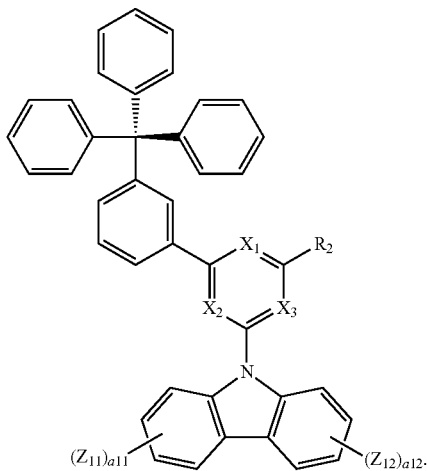

In Formula 5, $X_1$, $X_2$, $X_3$, and $R_2$ are the same as described in connection with those in Formula 1, $Z_{11}$ and $Z_{12}$ may each independently be hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a dibenzofuranyl group, a dibenzothiophenyl group, a triazinyl group, a benzimidazolyl group, a phenanthrolinyl group, or any combination thereof, a11 and a12 may each independently be an integer from 1 to 4, and * indicates a binding site to a neighboring atom.

In an embodiment, the compound represented by Formula 1 may be represented by Formula 6:

Formula 6

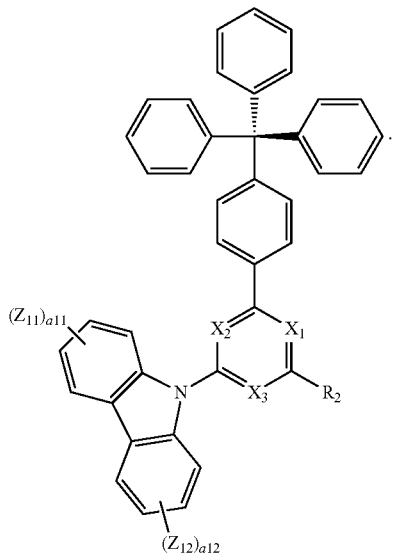

In Formula 6, $X_1$, $X_2$, $X_3$, and $R_2$ may each independently be the same as described in connection with Formula 1, $Z_{11}$ and $Z_{12}$ may each independently be hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a dibenzofuranyl group, a dibenzothiophenyl group, a triazinyl group, a benzimidazolyl group, a phenanthrolinyl group, or any combination thereof, a11 and a12 may each independently be an integer from 1 to 4, and * indicates a binding site to a neighboring atom.

In an embodiment, the compound represented by Formula 1 may be represented by Formula 7.

Formula 7

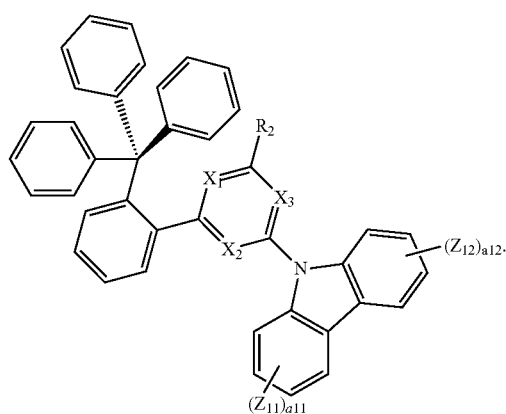

In Formula 7, $X_1$, $X_2$, $X_3$, and $R_2$ may each independently be the same as described in connection with Formula 1, $Z_{11}$ and $Z_{12}$ may each independently be hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a dibenzofuranyl group, a dibenzothiophenyl group, a triazinyl group, a benzimidazolyl group, a phenanthrolinyl group, or any combination thereof, a11 and a12 may each independently be an integer from 1 to 4, and * indicates a binding site to a neighboring atom.

In an embodiment, the compound represented by Formula 1 may be selected from the following compounds:

1
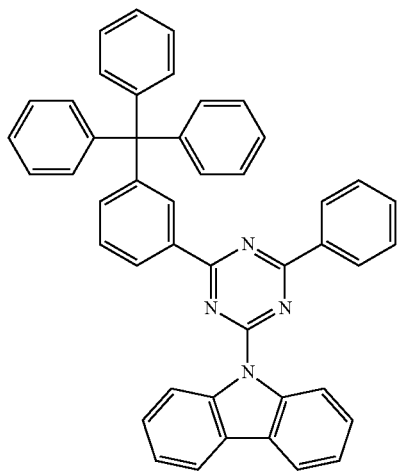
2
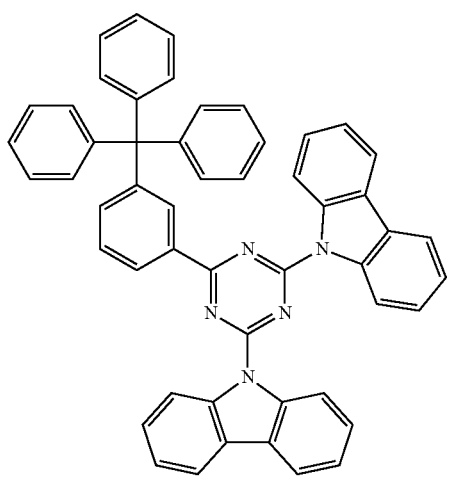
3
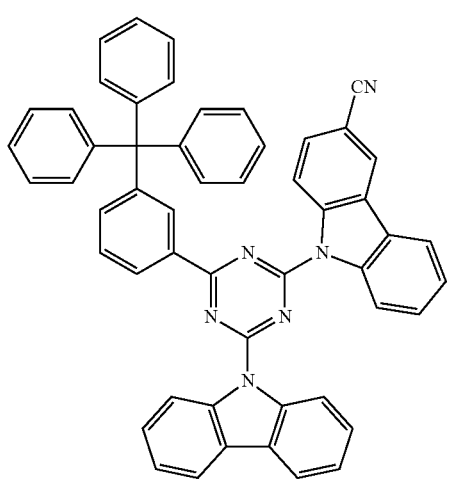
4
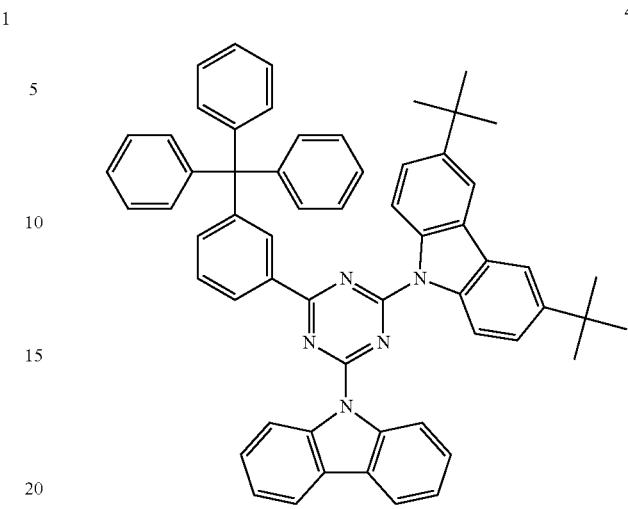
5
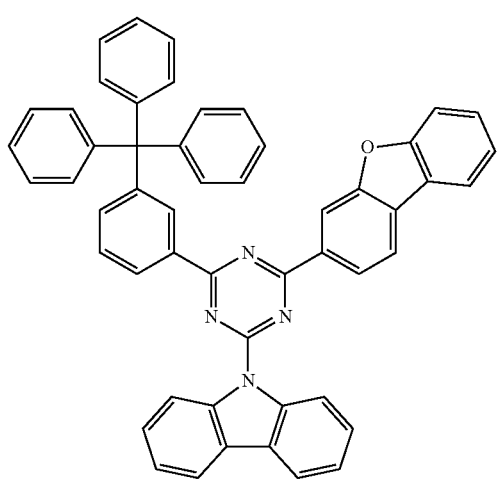
6
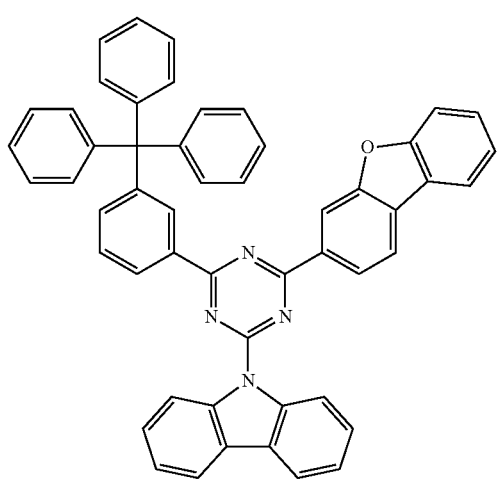

7
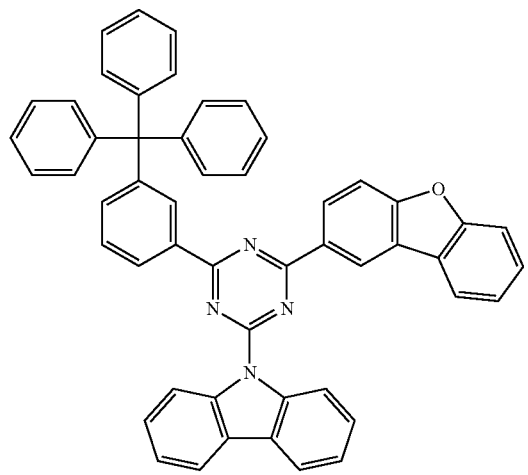
8
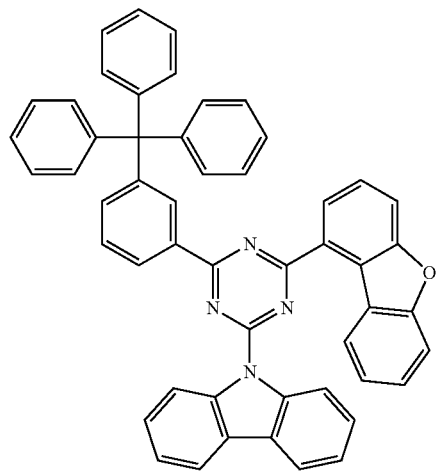
9
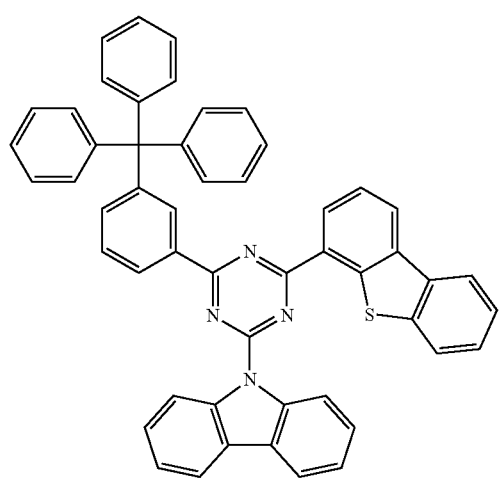
10
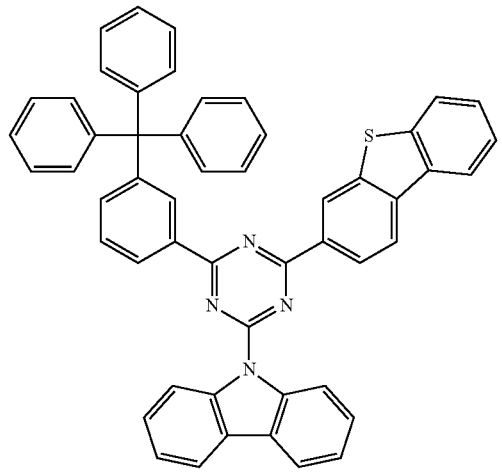
11
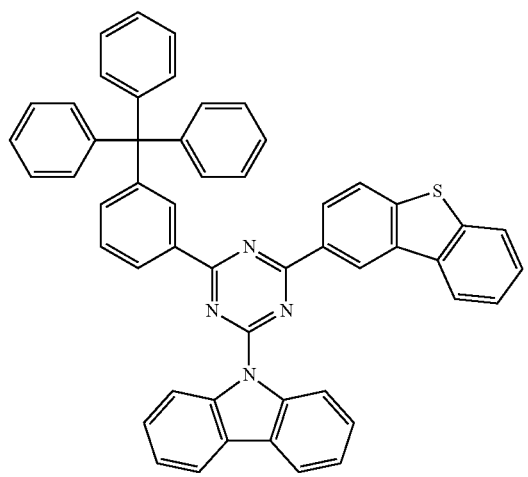
12
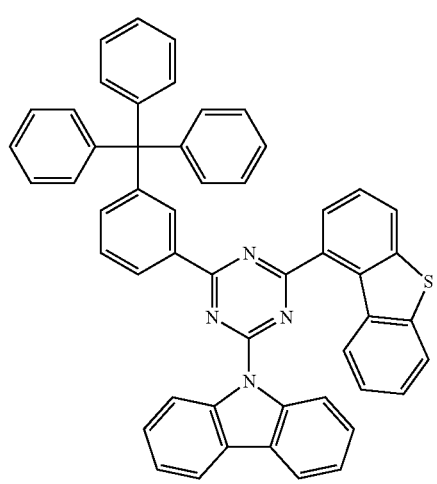

13
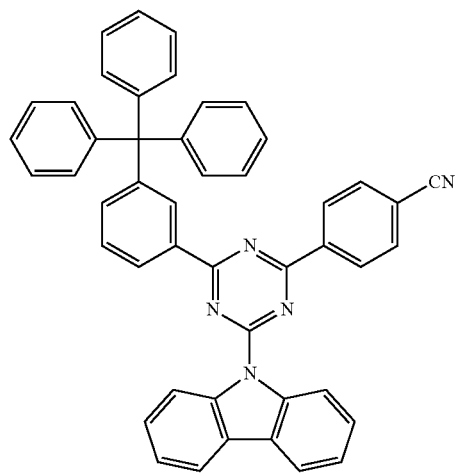
14
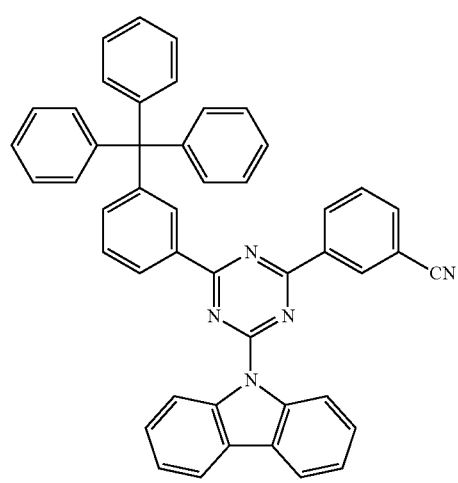
15
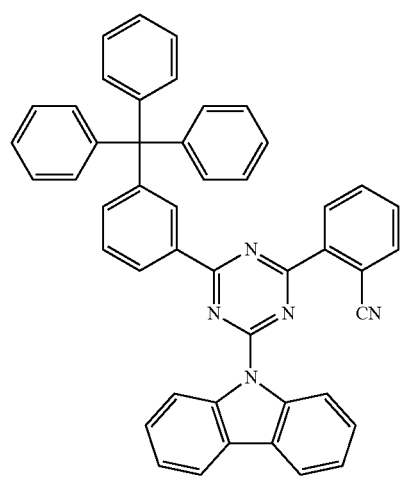
16
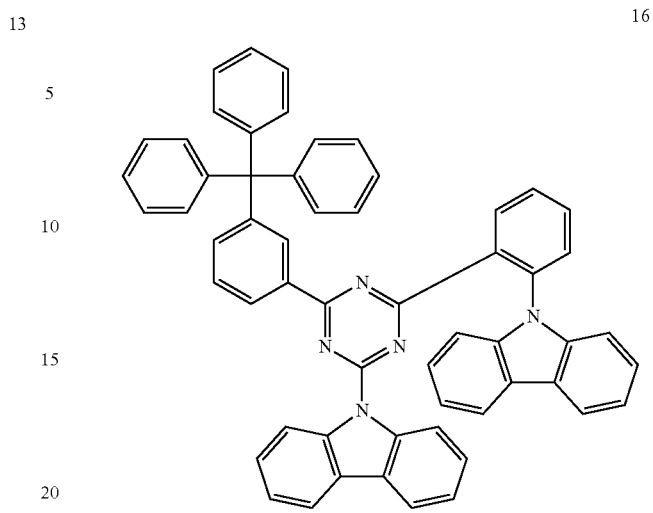
17
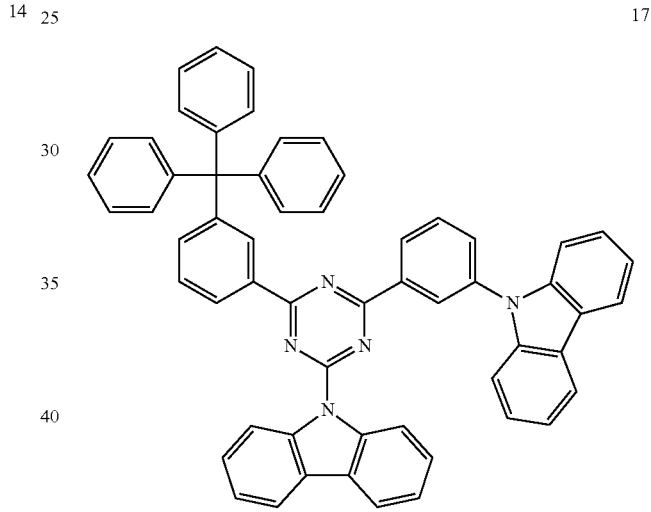
18
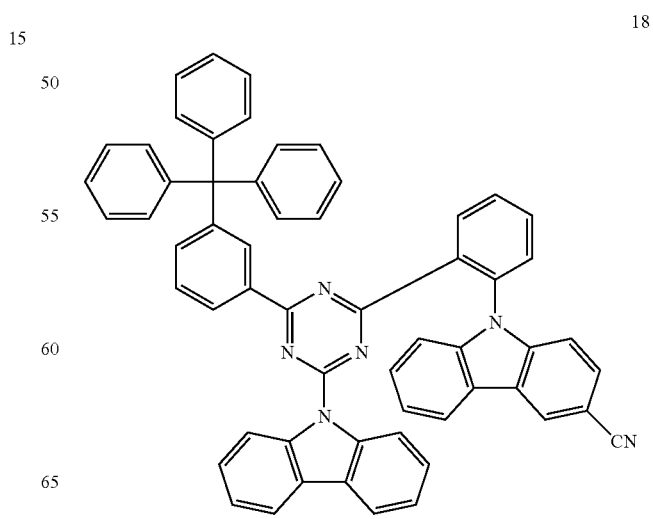

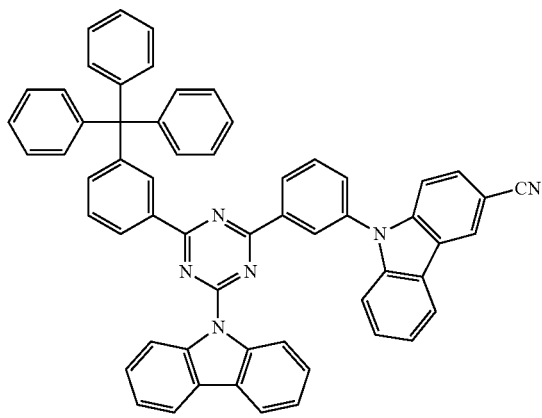
19
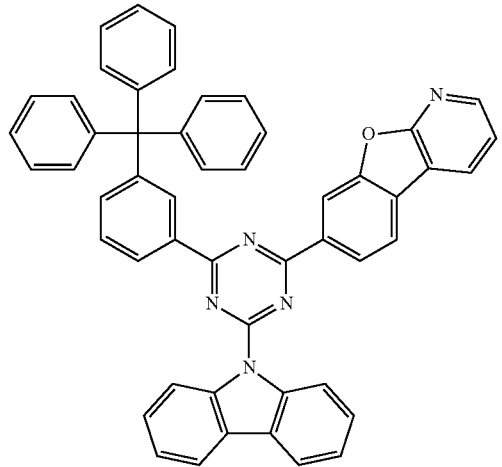
22
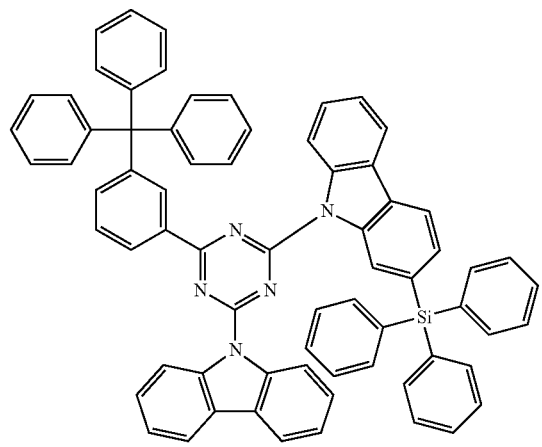
20
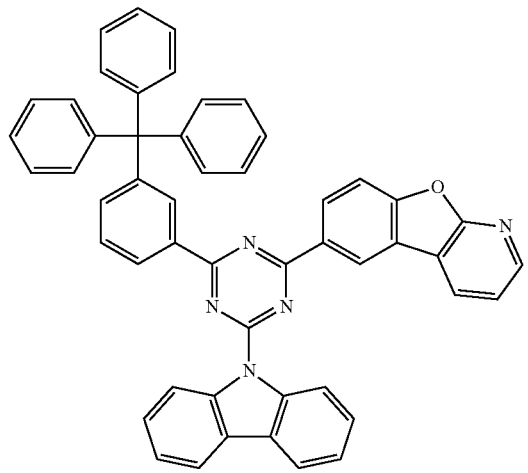
23
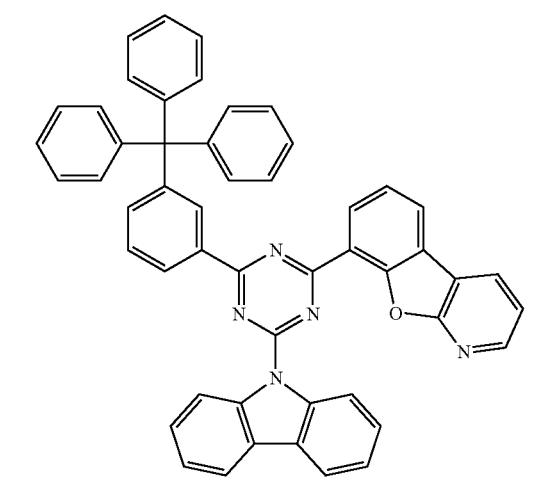
21
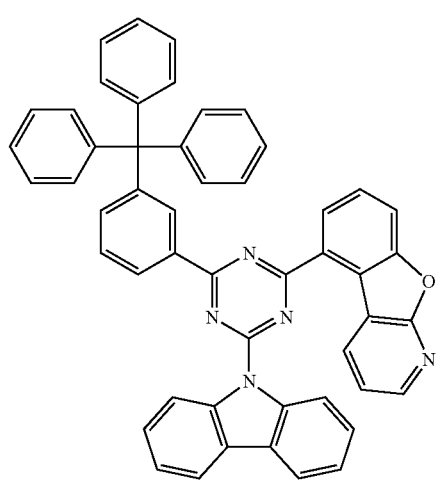
24

25
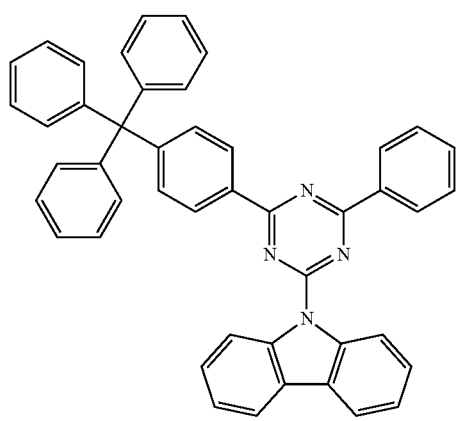
26
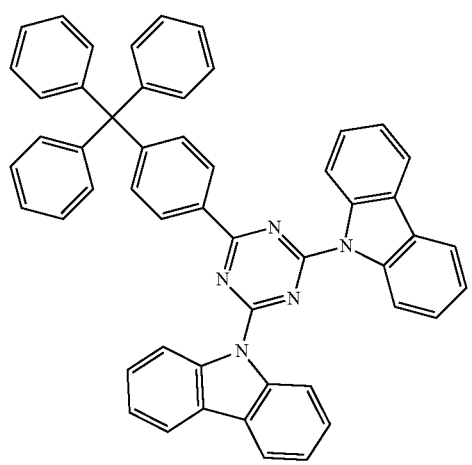
27
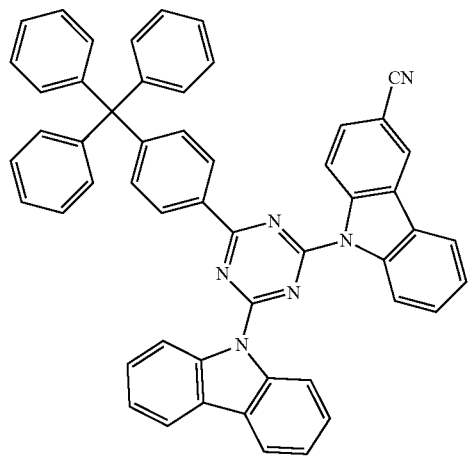
28
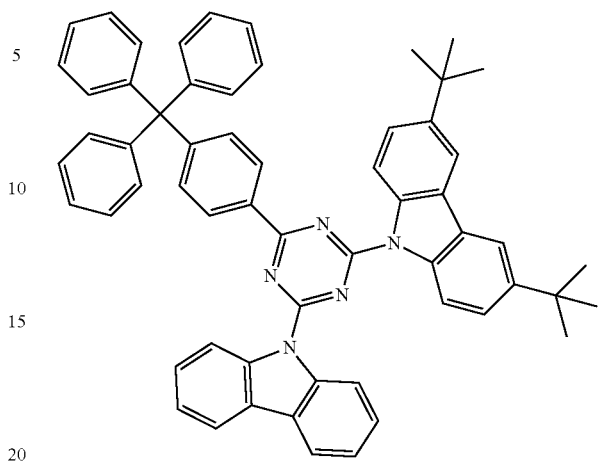
29
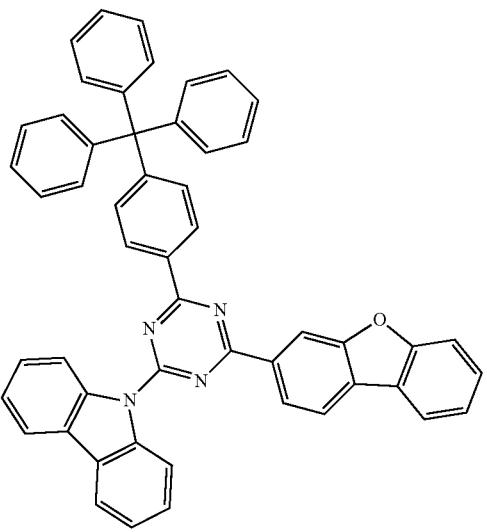
30

31
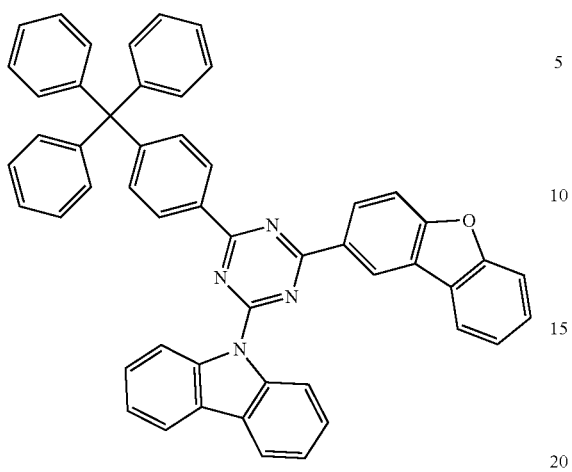
32
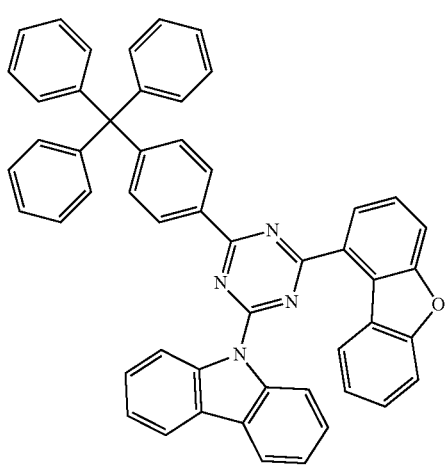
33
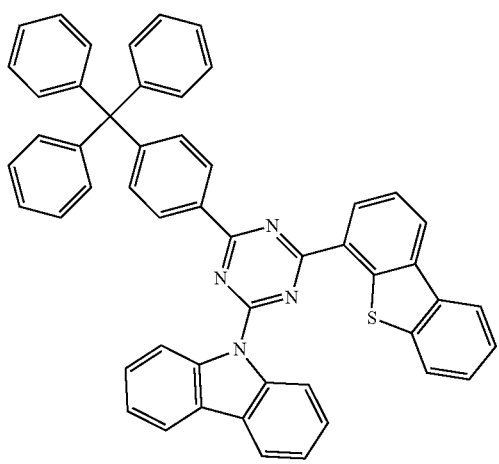
34
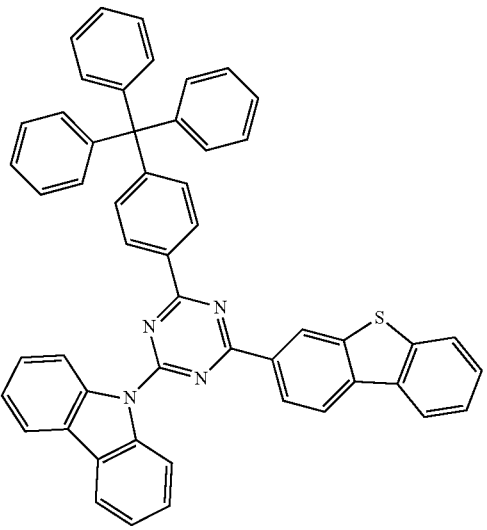
35
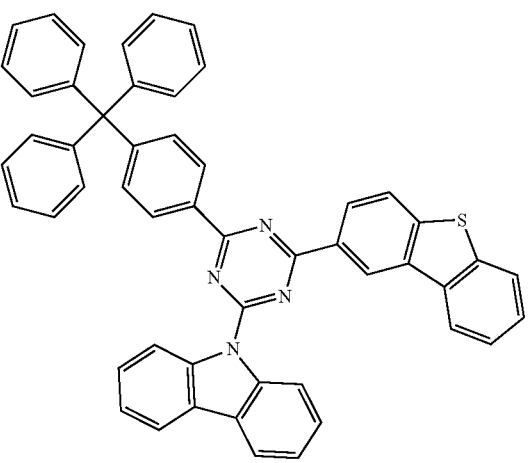
36
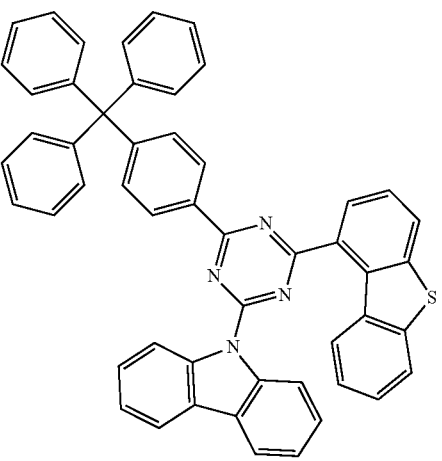

37
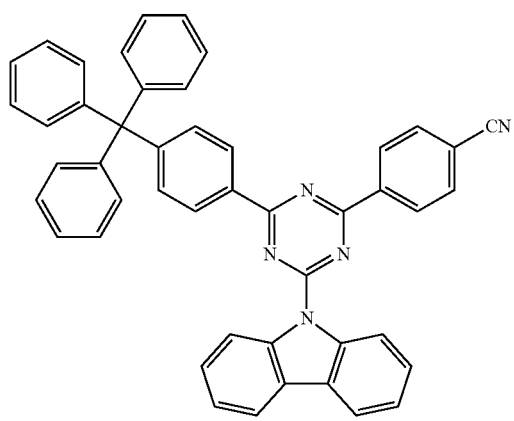
38
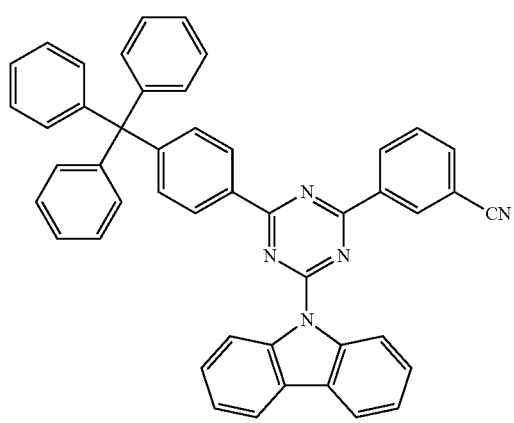
39
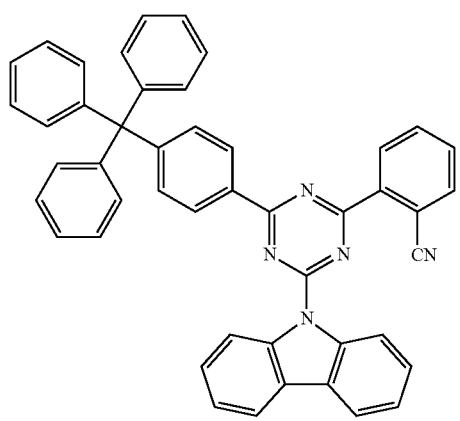
40
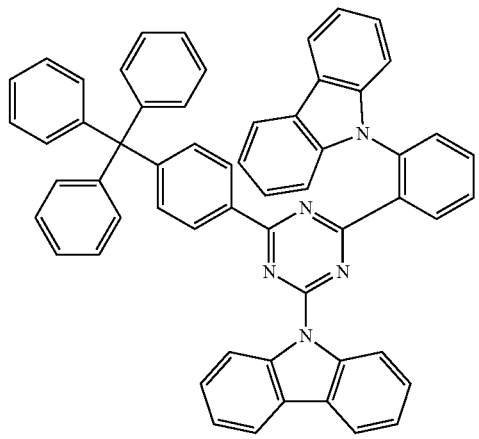
41
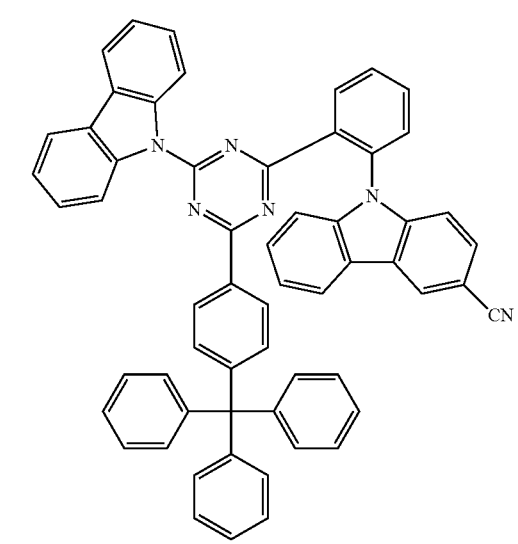
42

43
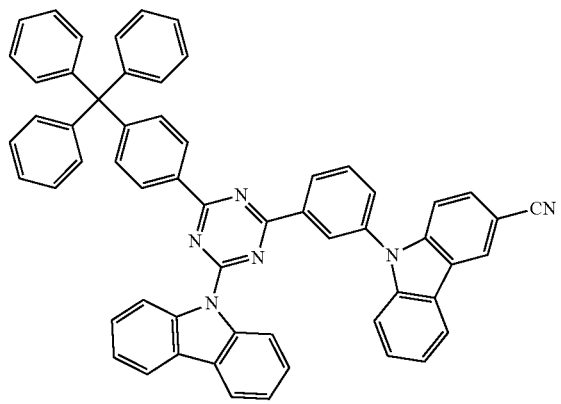
44
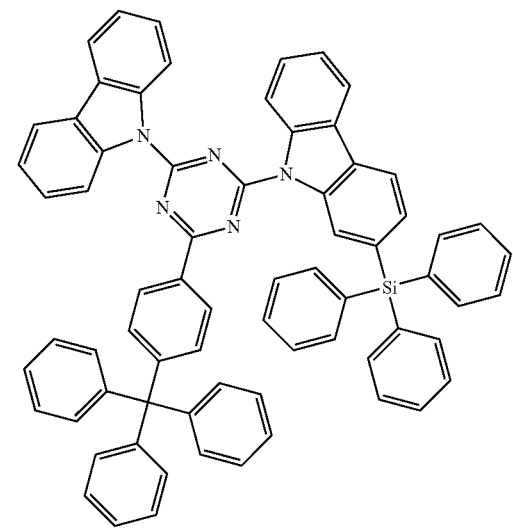
45
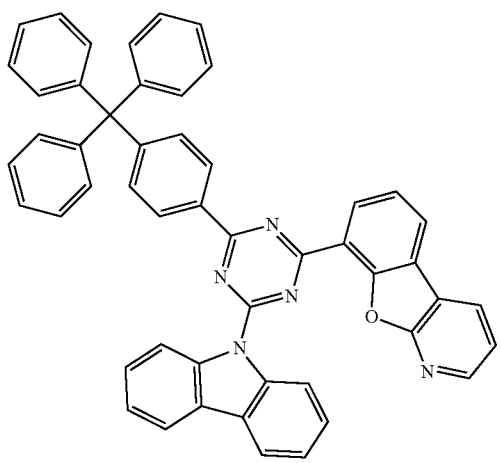
46
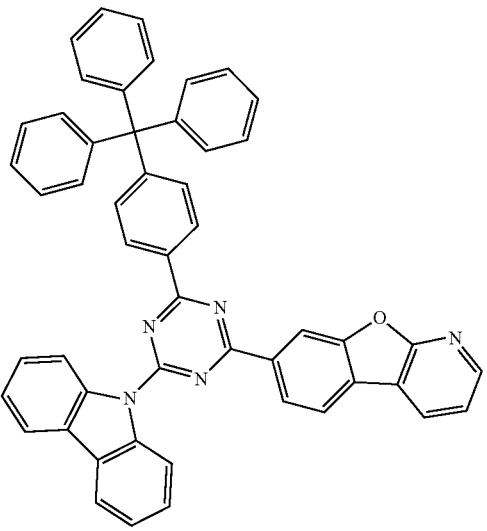
47
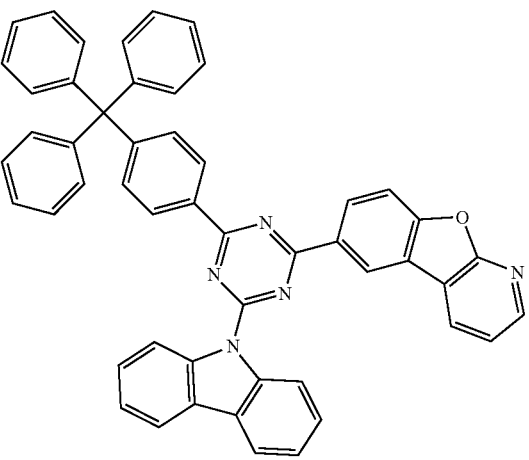
48
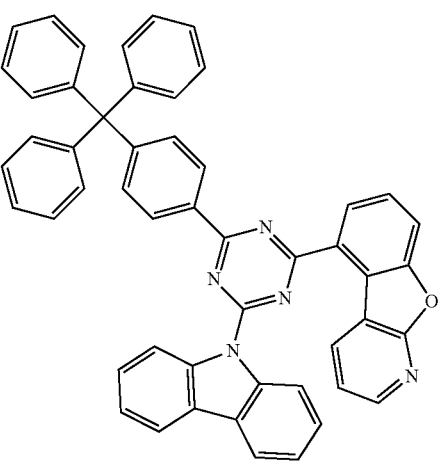

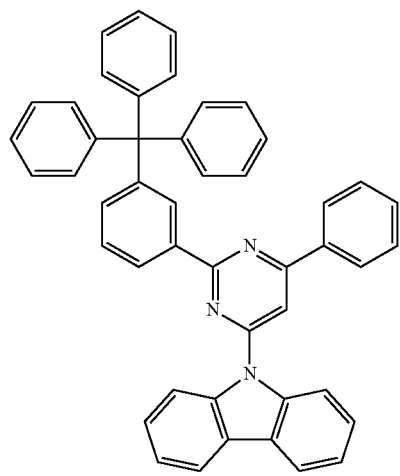
49
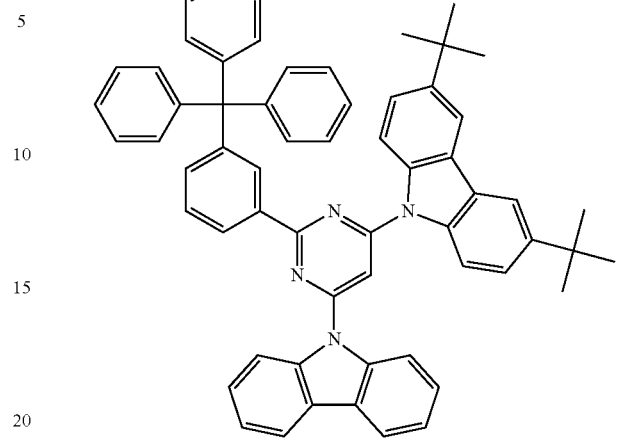
52
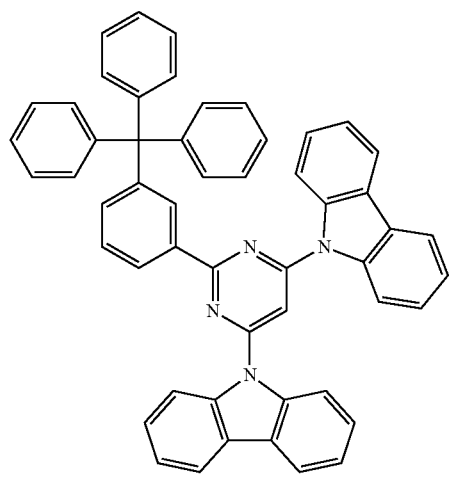
50
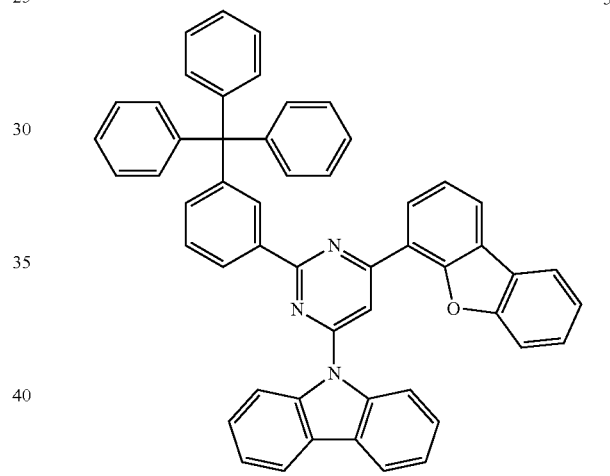
53
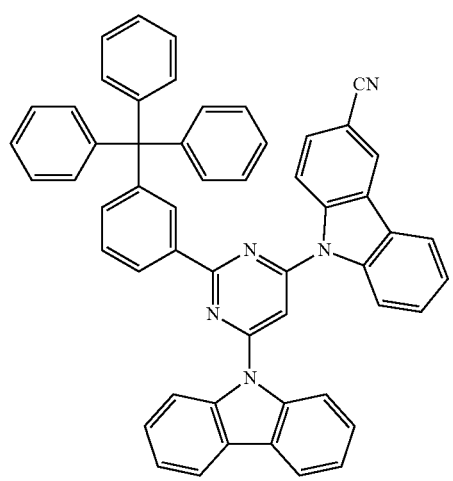
51
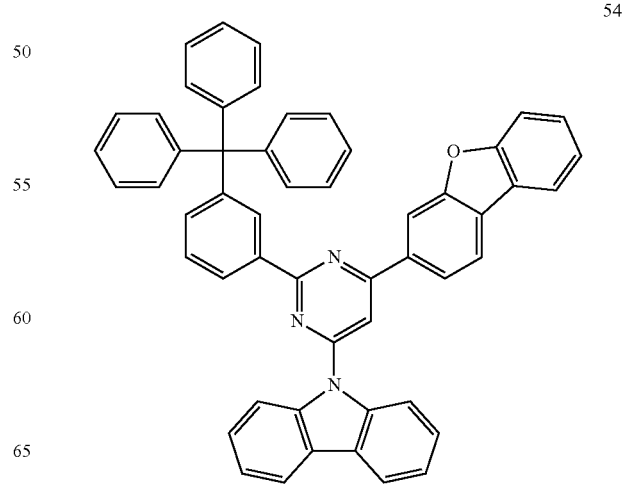
54

55
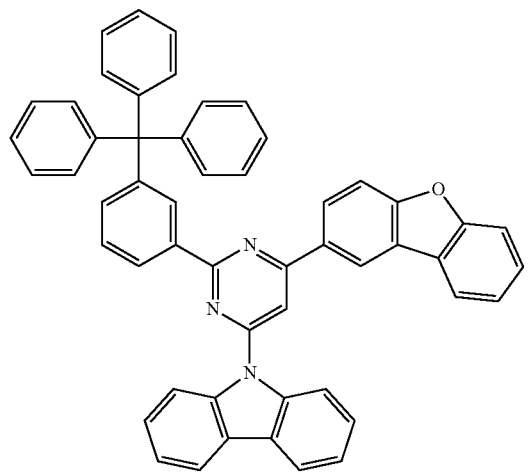
56
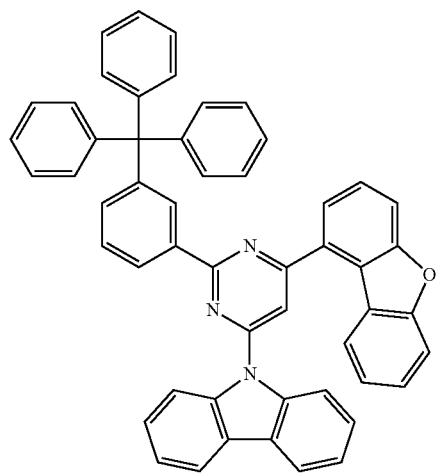
57
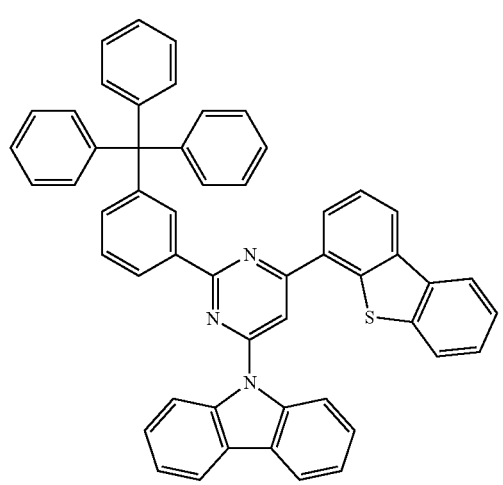
58
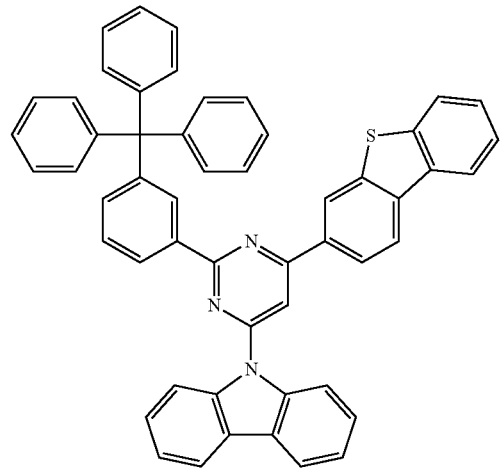
59
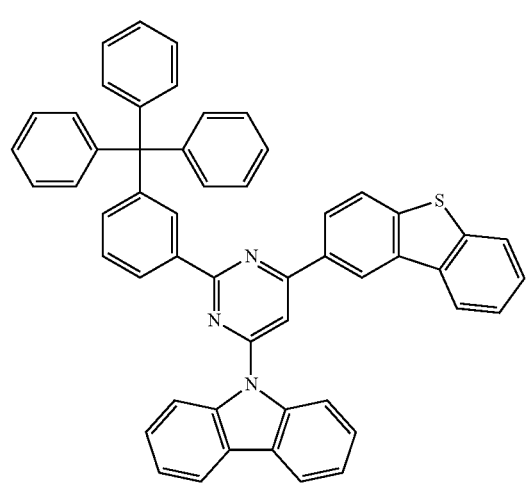
60
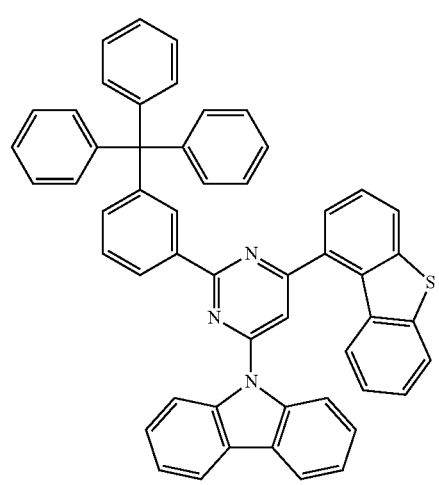

61
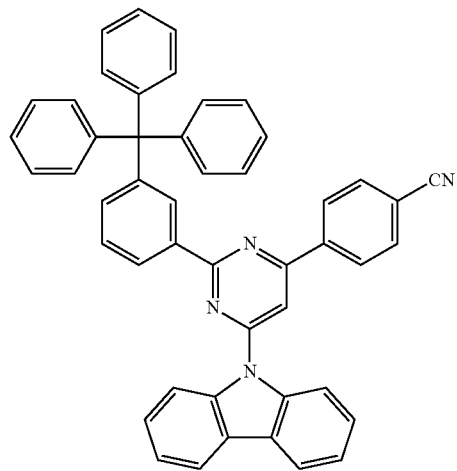
62
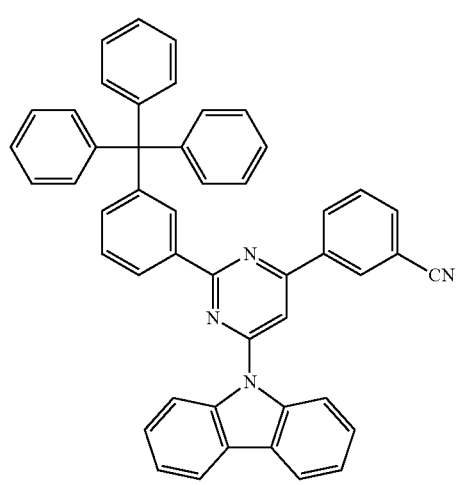
63
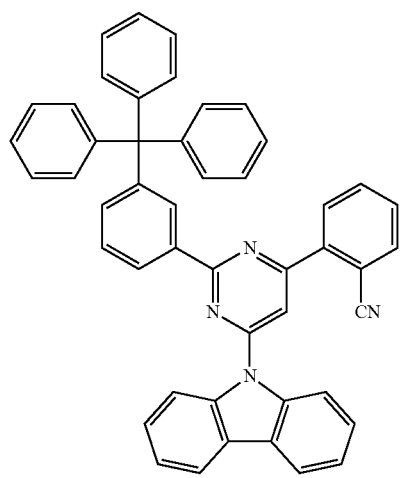
64
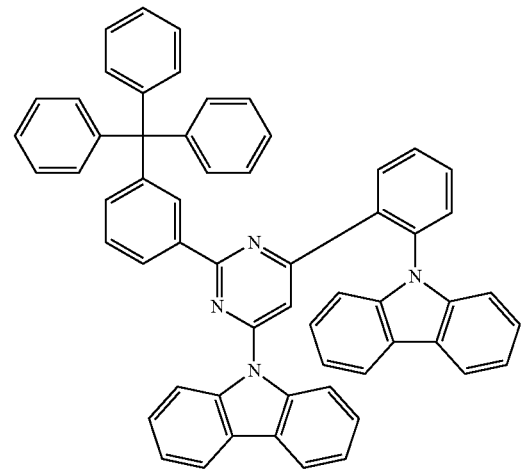
65
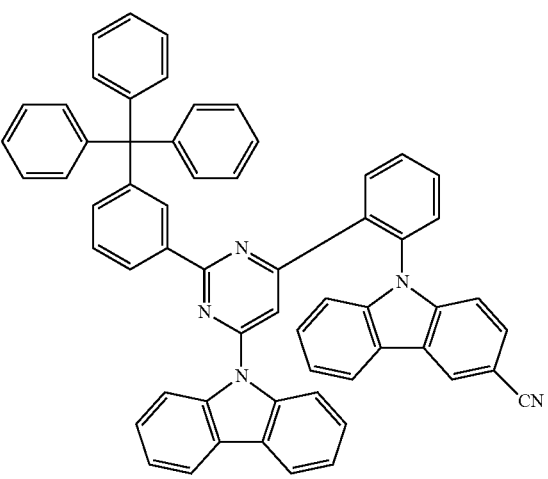
66

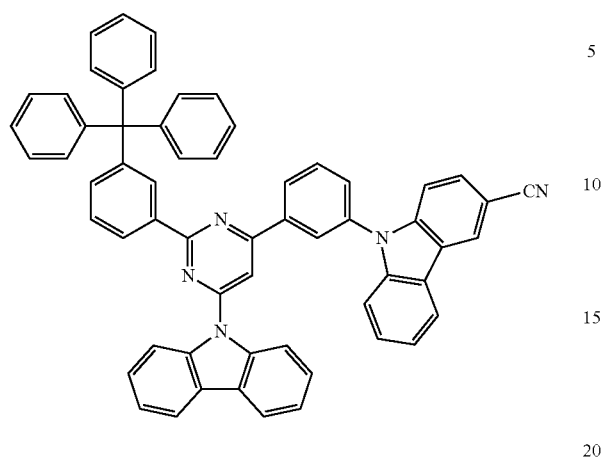
67
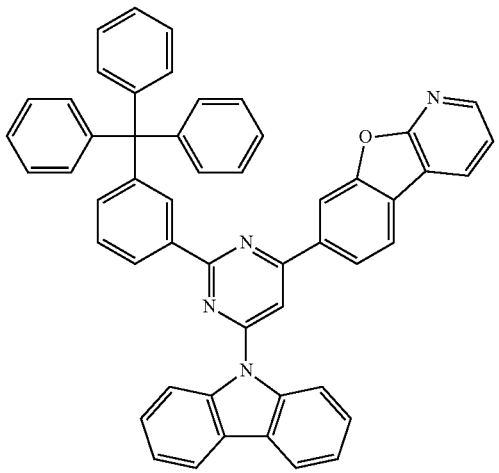
70
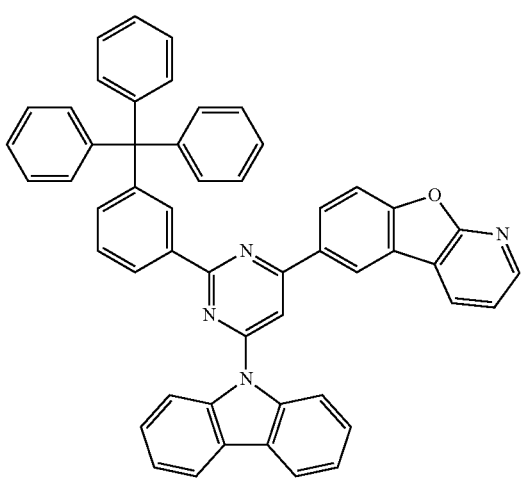
71
68
69
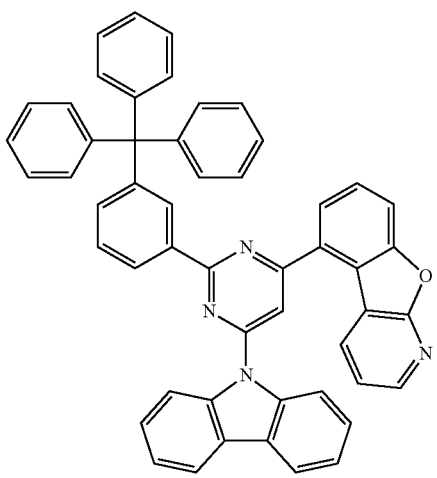
72

73
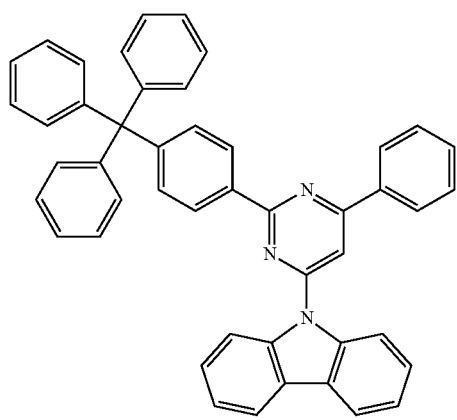
74
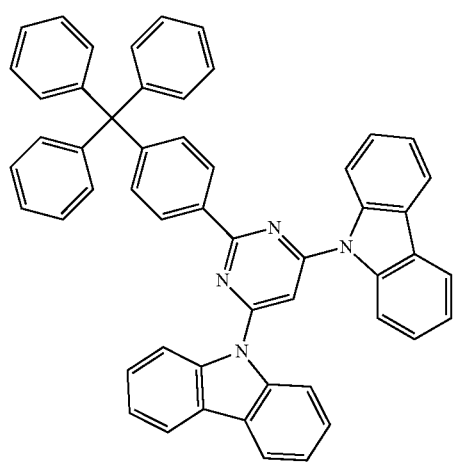
75
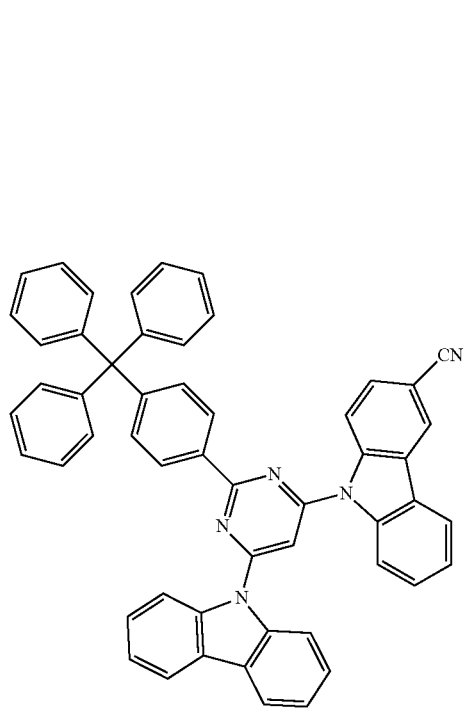
76
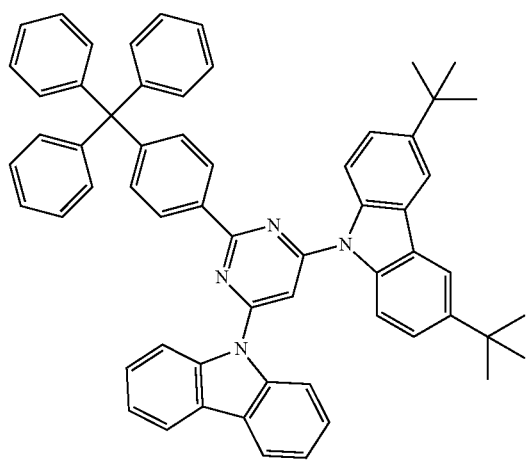
77
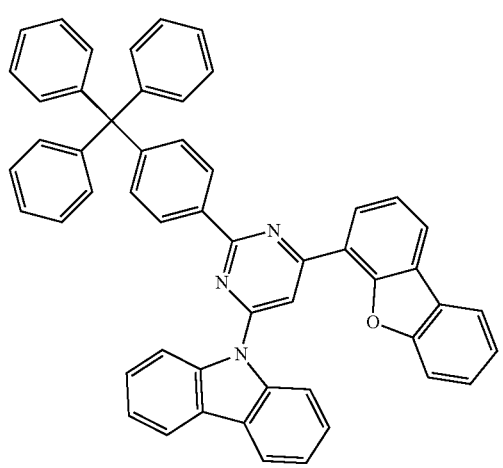
78
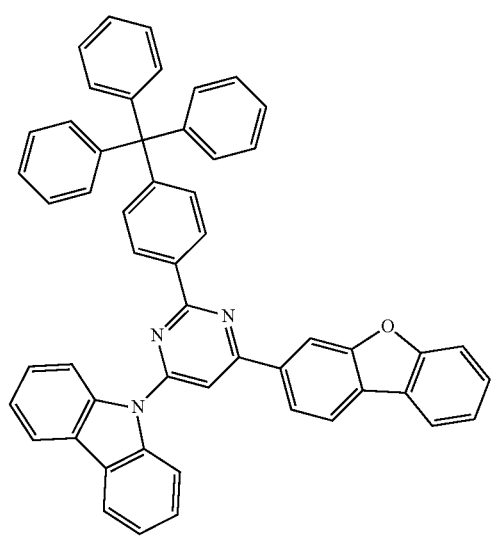

79
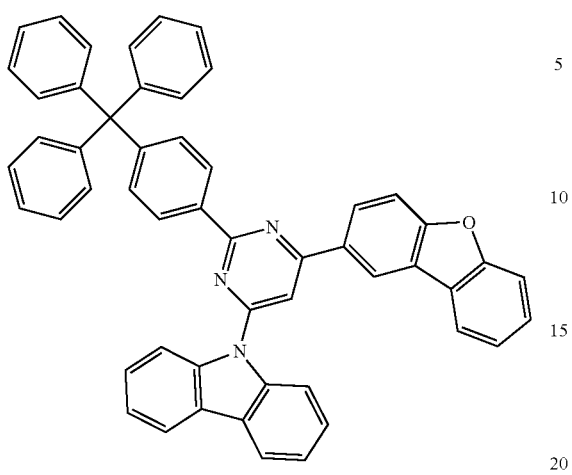
80
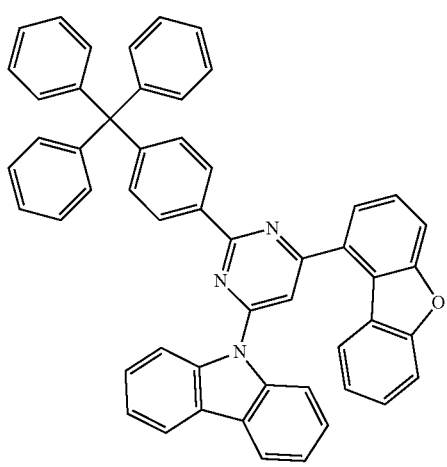
81
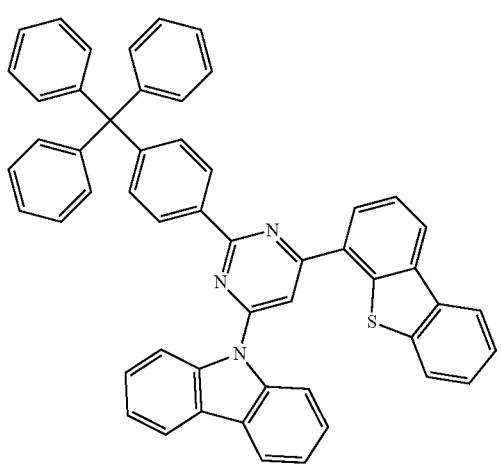
82
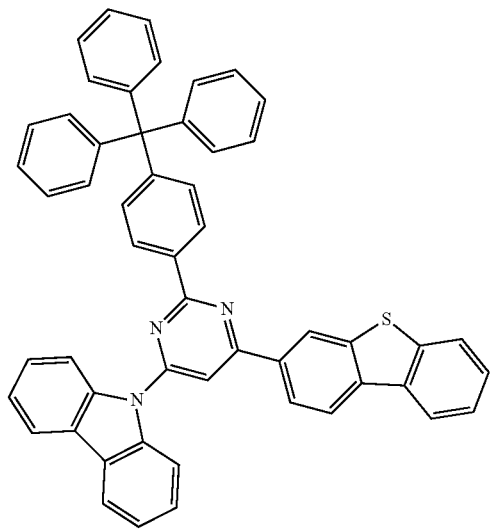
83
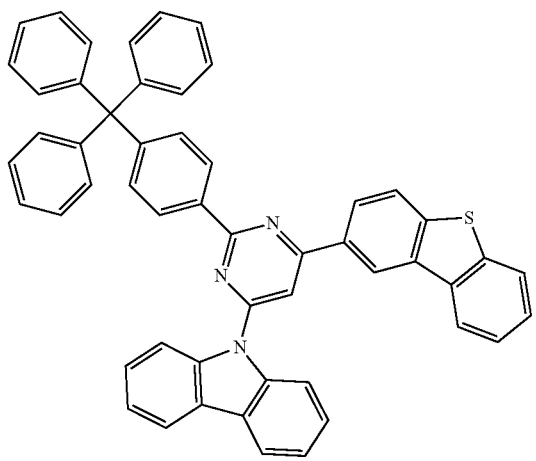
84
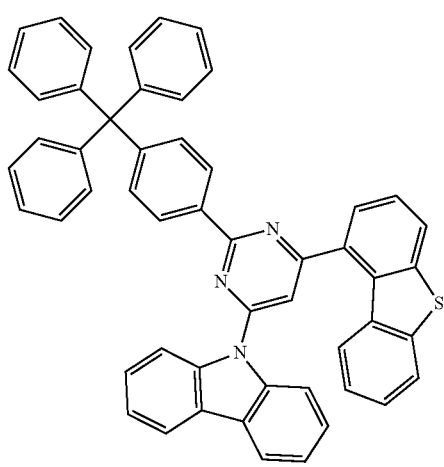

-continued
85
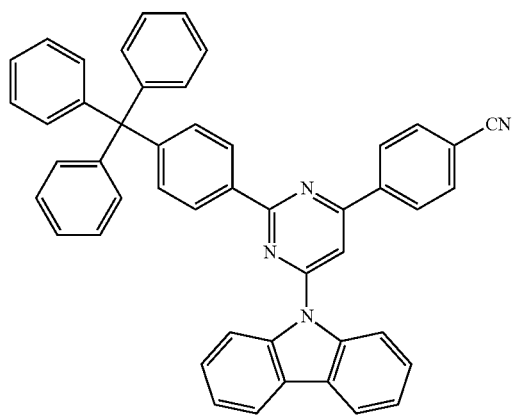
86
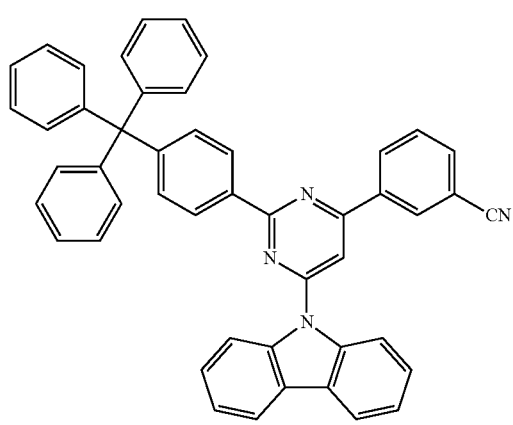
87
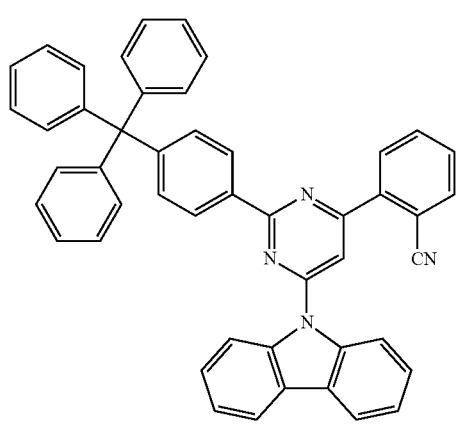
-continued
88
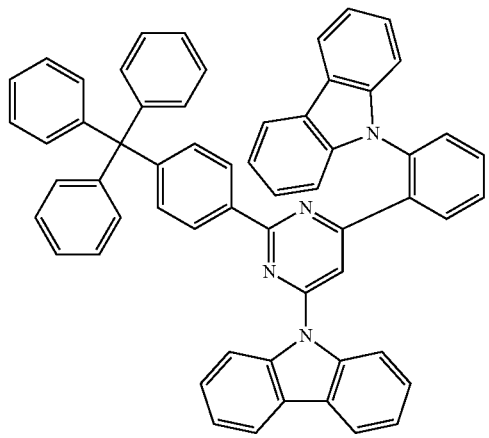
89
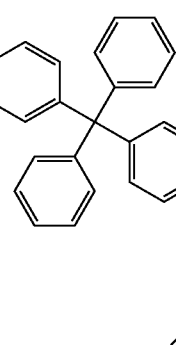
90
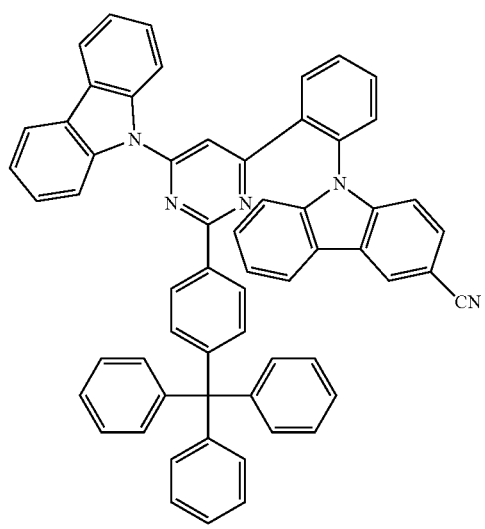

91
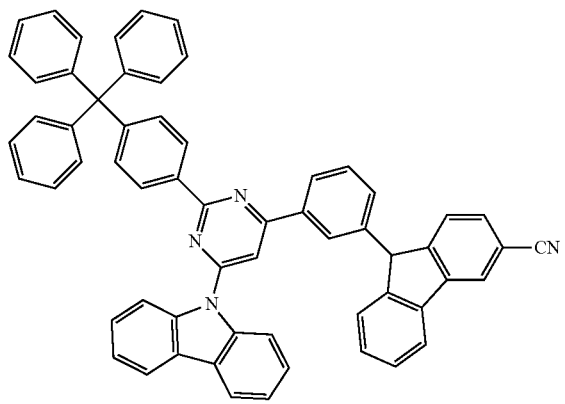
92
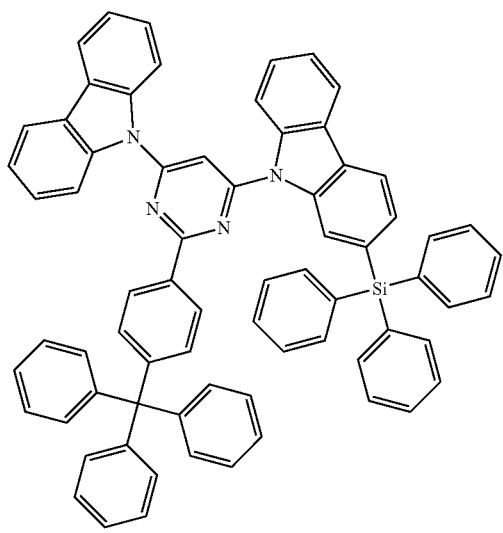
93
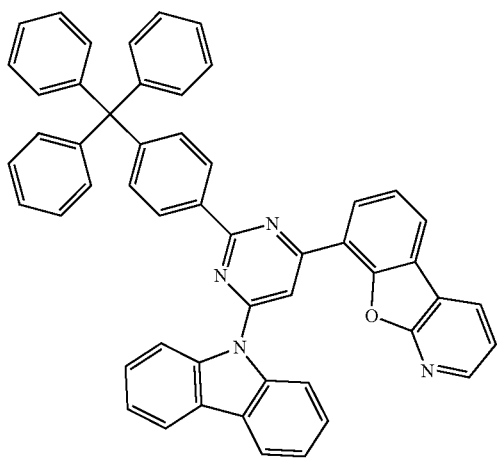
94
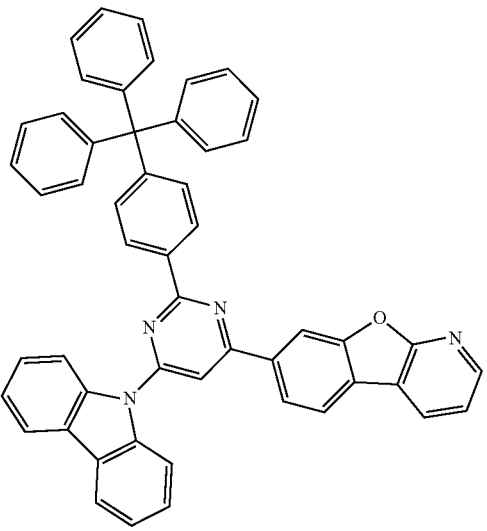
95
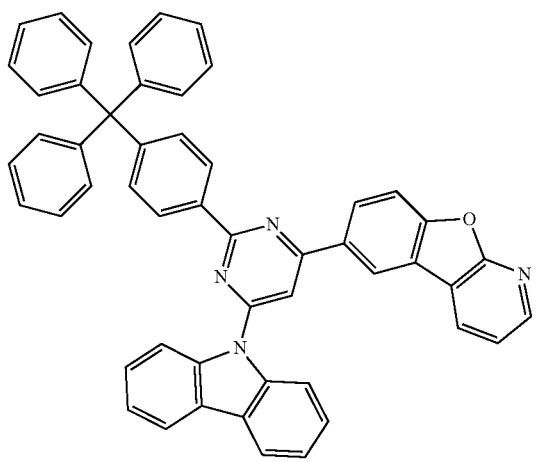
96
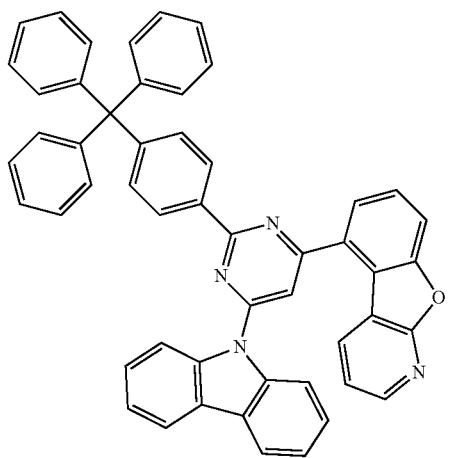

97
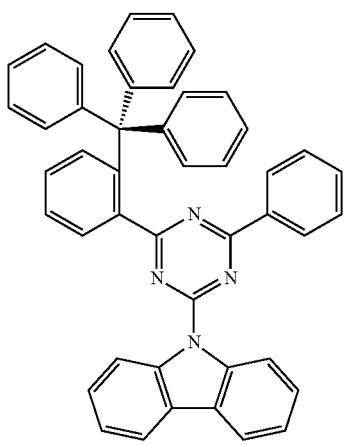
98
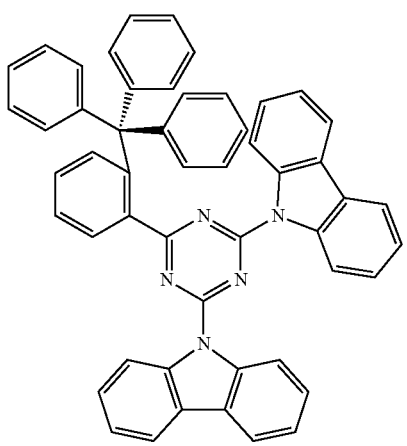
99
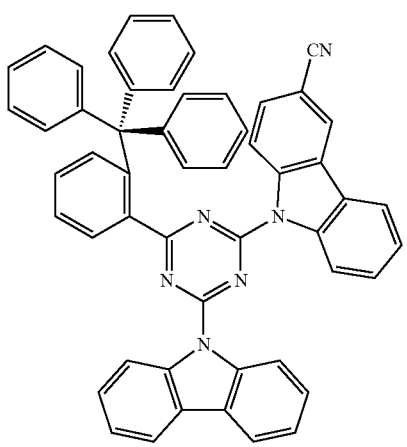
100
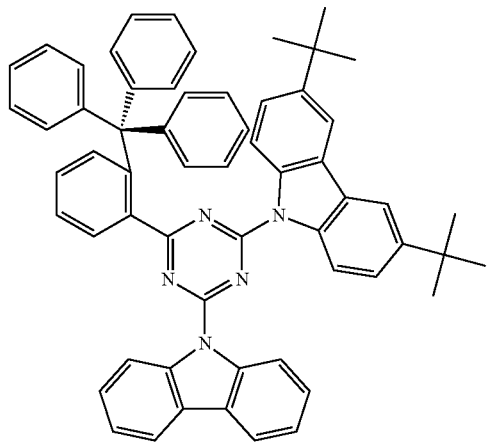
101
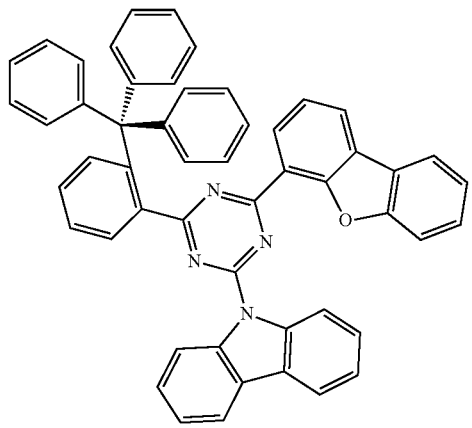
102
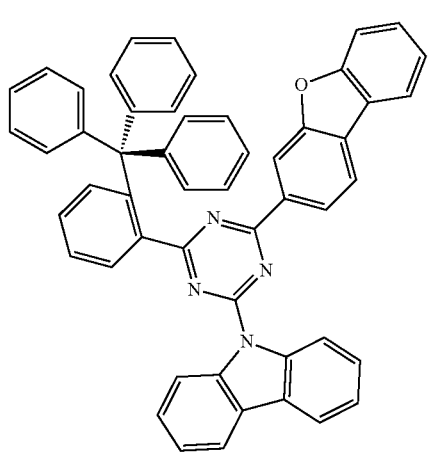

103
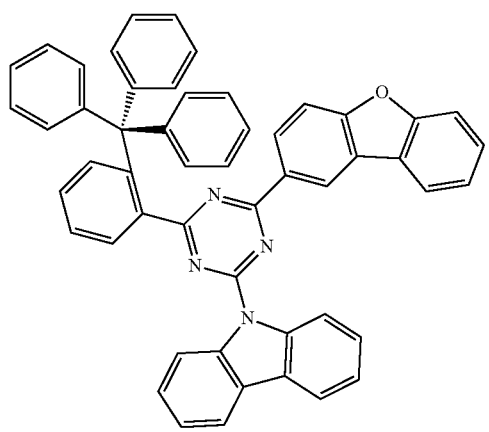
104
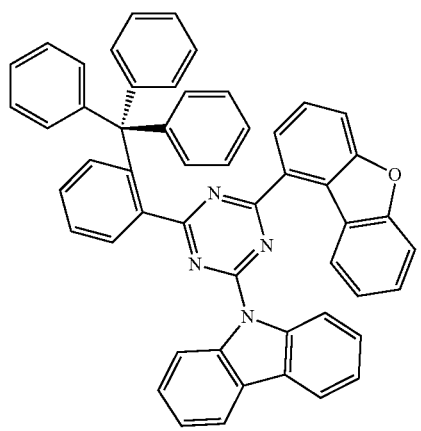
105
106
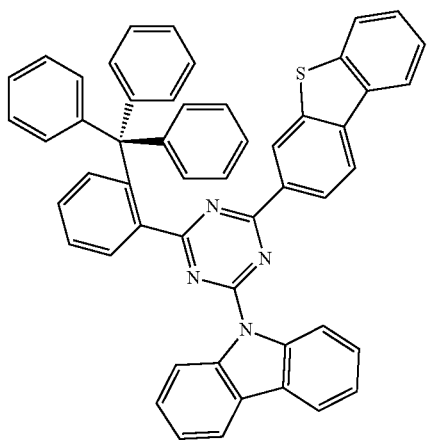
107
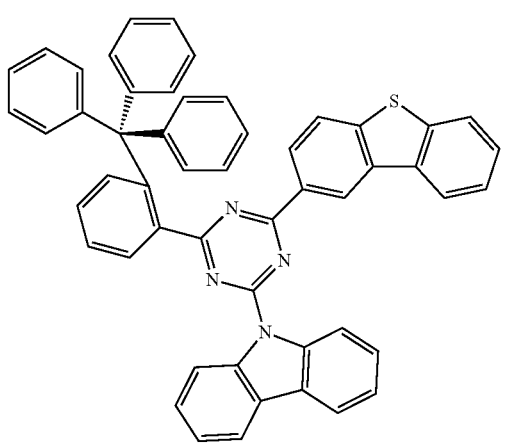
108
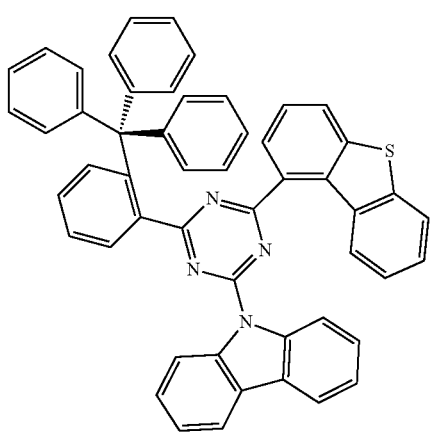

109
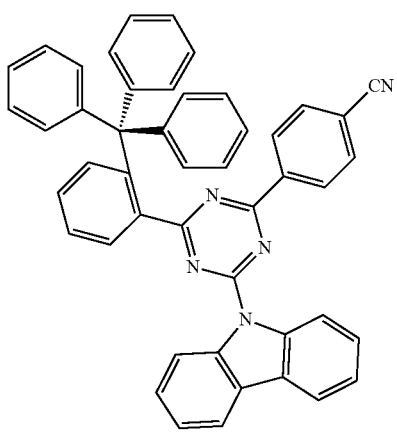
110
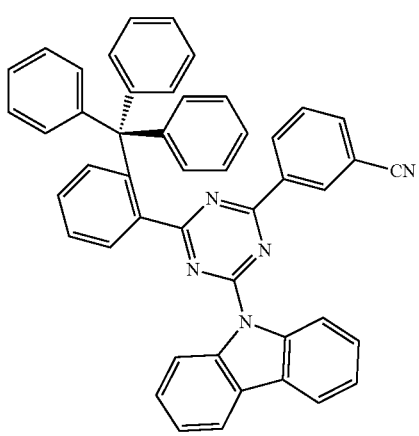
111
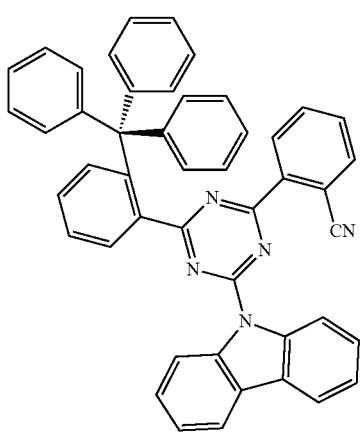
112
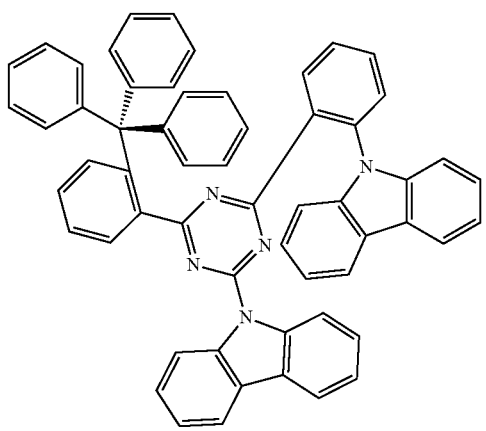
113
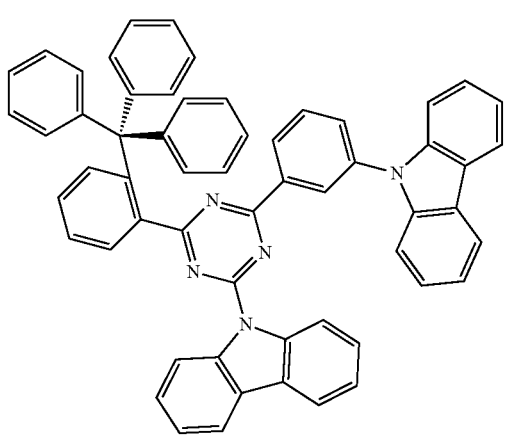
114
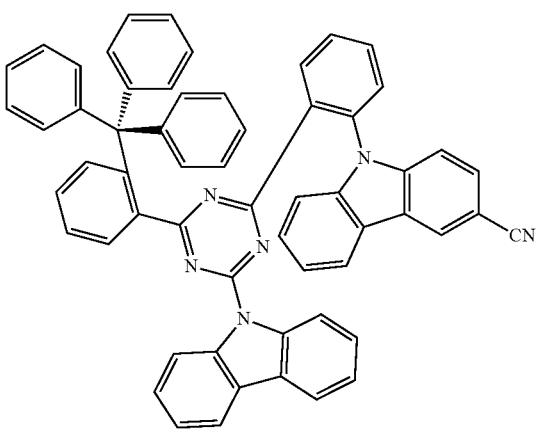

115

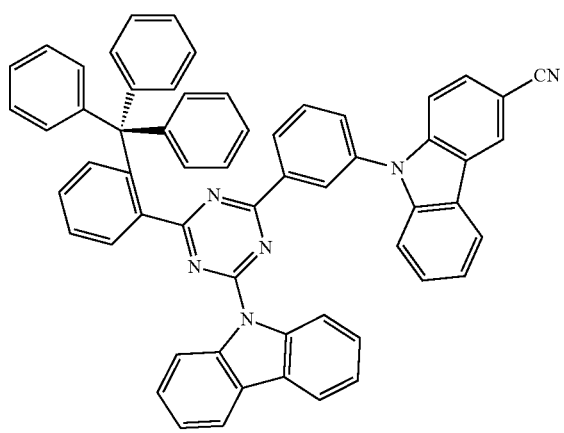

116

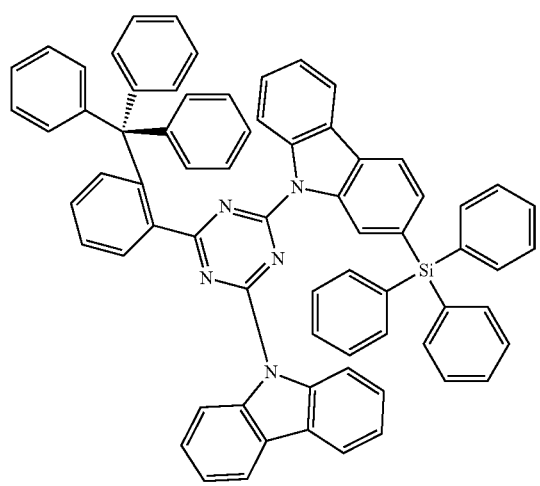

117

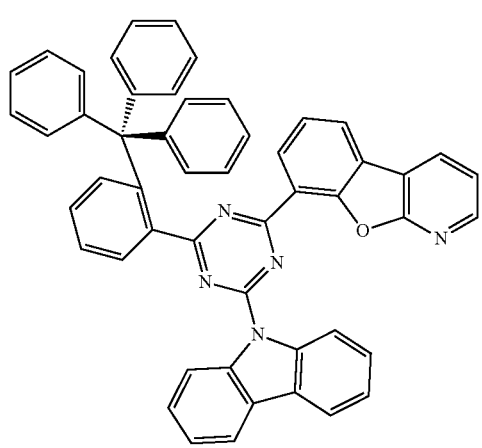

118

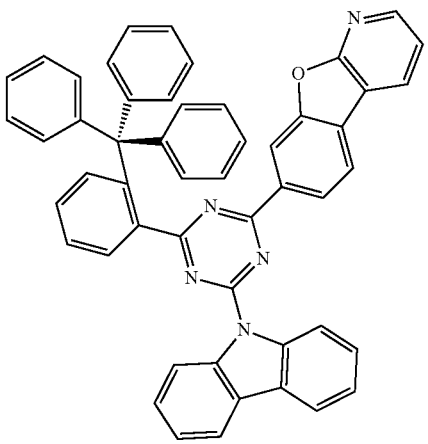

119

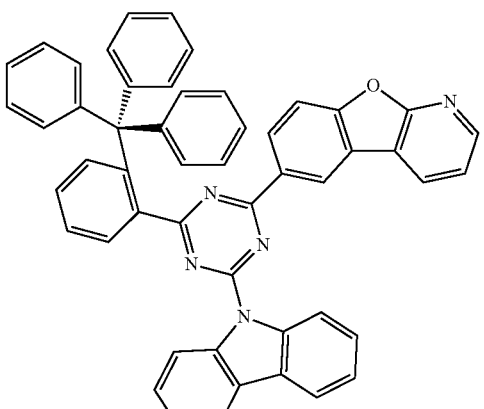

120

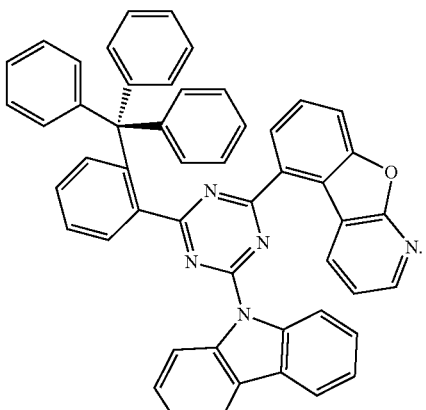

The expression "(an interlayer) includes at least one compound" as used herein may include a case in which "(an interlayer) includes identical compounds (e.g., a single compound) represented by Formula 1" as well as a case in which "(an interlayer) includes two or more different compounds represented by Formula 1".

For example, the interlayer may include, only Compound 1 (e.g., a first compound) as the compound. In this regard, Compound 1 may be included in an emission layer of a light-emitting device. In an embodiment, the interlayer may include Compound 1 and Compound 2 (e.g., a first compound and a second compound) as the compound. In this regard, Compound 1 and Compound 2 may be included in the same layer (for example, Compound 1 and Compound 2 may be simultaneously included in an emission layer), or in different layers (for example, Compound 1 may be included in an emission layer and Compound 2 may be included in an electron transport region).

One or more example embodiments of the present disclosure provide a light-emitting device including:
a first electrode;
a second electrode facing the first electrode; and
an interlayer located between the first electrode and the second electrode and including an emission layer,
wherein the interlayer includes the compound represented by Formula 1. For example, the light-emitting device may be an organic light-emitting device.

In an embodiment,
the first electrode of the light-emitting device may be an anode,
the second electrode of the light-emitting device may be a cathode,
the interlayer may further include a hole transport region between the first electrode and the emission layer, and an electron transport region between the emission layer and the second electrode,
the hole transport region may include a hole injection layer, a hole transport layer, an emission auxiliary layer, an electron blocking layer, or any combination thereof, and
the electron transport region may include a hole blocking layer, an electron transport layer, an electron injection layer, or any combination thereof.

In an embodiment, the emission layer may be a phosphorescent emission layer. For example, the emission layer may be a blue phosphorescent emission layer.

In an embodiment, the compound represented by Formula 1 may be included as a host compound in the phosphorescent emission layer (e.g., as a phosphorescent host).

In an embodiment, the emission layer may be a fluorescent emission layer. For example, the emission layer may be a blue fluorescent emission layer.

In an embodiment, the compound represented by Formula 1 may be included as thermally activated delayed fluorescence (TADF) material in the fluorescent emission layer (e.g., as a TADF host).

One or more example embodiments of the present disclosure provide an electronic apparatus including the light-emitting device.

In an embodiment, the electronic apparatus may further include a thin-film transistor,
the thin-film transistor may include a source electrode, a drain electrode, an activation layer, and a gate electrode, and the first electrode of the light-emitting device may be electrically connected to one of the source electrode and the drain electrode of the thin-film transistor.

The term "interlayer" as used herein may refers to a single layer and/or multiple (all) layers between the first electrode and the second electrode of the light-emitting device. The materials included in the "interlayer(s)" may be an organic material, an inorganic material, or any combination thereof.

Description of FIG. 1

Figure 1:
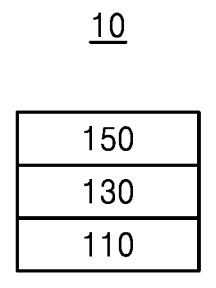

FIG. 1 is a schematic cross-sectional view of a light-emitting device 10 according to an embodiment. The light-emitting device 10 includes a first electrode 110, an interlayer 130, and a second electrode 150.

Hereinafter, the structure of the light-emitting device 10 according to an embodiment and a method of manufacturing the light-emitting device 10 will be described in connection with FIG. 1.

First Electrode 110

In FIG. 1, a substrate may be located under the first electrode 110 and/or above the second electrode 150. The substrate may be a glass substrate and/or a plastic substrate. In an embodiment, the substrate may be a flexible substrate and may include a plastic having excellent or suitable heat resistance and/or excellent or suitable durability (such as polyimide, polyethylene terephthalate (PET), polycarbonate, polyethylene naphthalate, polyarylate (PAR), polyetherimide, or any combination thereof).

The first electrode 110 may be formed by depositing and/or sputtering a material for forming the first electrode 110 on the substrate. When the first electrode 110 is an anode, a material having a high work function that can easily inject holes may be used for forming the first electrode 110.

The first electrode 110 may be a reflective electrode, a semi-transparent electrode, or a transparent electrode. When the first electrode 110 is a transparent electrode, a material for forming the first electrode 110 may include indium tin oxide (ITO), indium zinc oxide (IZO), tin oxide ($SnO_2$), zinc oxide (ZnO), or any combination thereof. In an embodiment, when the first electrode 110 is a semi-transparent electrode or a reflective electrode, the material for forming the first electrode 110 may include magnesium (Mg), silver (Ag), aluminum (Al), aluminum-lithium (Al—Li), calcium (Ca), magnesium-indium (Mg—In), magnesium-silver (Mg—Ag), or any combination thereof.

The first electrode 110 may have a single-layered structure (consisting of a single layer), or a multi-layered structure including a plurality of layers. For example, the first electrode 110 may have a three-layered structure of ITO/Ag/ITO, but the structure of the first electrode 110 is not limited thereto.

Interlayer 130

The interlayer 130 is located on the first electrode 110. The interlayer 130 includes an emission layer.

The interlayer 130 may further include a hole transport region between the first electrode 110 and the emission layer, and an electron transport region between the emission layer and the second electrode 150.

The interlayer 130 may further include metal-containing compounds (such as organometallic compounds, inorganic materials such as quantum dots, and/or the like), in addition to various organic materials.

In some embodiments, the interlayer 130 may include: i) two or more emitting units that are sequentially stacked between the first electrode 110 and the second electrode 150, and ii) a charge generating layer between the two or more emitting units. When the interlayer 130 includes the two or more emitting units and the charge generating layer, the light-emitting device 10 may be a tandem light-emitting device.

Hole Transport Region in Interlayer 130

The hole transport region may have: i) a single-layered structure consisting of a single material, ii) a single-layered structure including a plurality of different materials, or iii) a multi-layered structure including a plurality of layers including different materials.

The hole transport region may include a hole injection layer, a hole transport layer, an emission auxiliary layer, an electron blocking layer, or any combination thereof.

For example, the hole transport region may have a multi-layered structure including a hole injection layer/hole transport layer, a hole injection layer/hole transport layer/emission auxiliary layer, a hole injection layer/emission auxiliary layer, a hole transport layer/emission auxiliary layer, or a hole injection layer/hole transport layer/electron blocking layer, wherein the constituting layers of each structure are sequentially stacked on the first electrode 110.

The hole transport region may include a compound represented by Formula 201, a compound represented by Formula 202, or any combination thereof:

Formula 201

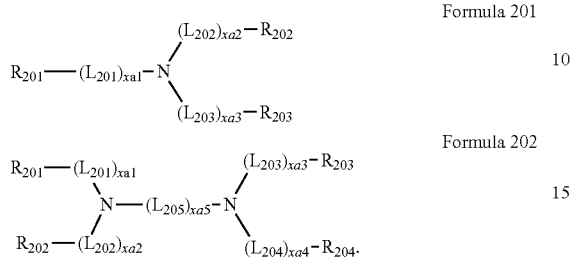

Formula 202

In Formulae 201 and 202,

- $L_{201}$ to $L_{204}$ may each independently be a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$,
- $L_{205}$ may be *—O—*', *—S—*', *—N($Q_{201}$)-*', a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$,
- xa1 to xa4 may each independently be an integer from 0 to 5,
- xa5 may be an integer from 1 to 10,
- $R_{201}$ to $R_{204}$ and $Q_{201}$ may each independently be a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$,
- $R_{201}$ and $R_{202}$ may be optionally linked to each other via a single bond, a $C_1$-$C_5$ alkylene group unsubstituted or substituted with at least one $R_{10a}$, or a $C_2$-$C_5$ alkenylene group unsubstituted or substituted with at least one $R_{10a}$ to thereby form a $C_8$-$C_{60}$ polycyclic group unsubstituted or substituted with at least one $R_{10a}$ (for example, a carbazole group, such as in Compound HT16),
- $R_{203}$ and $R_{204}$ may be optionally linked to each other via a single bond, a $C_1$-$C_5$ alkylene group unsubstituted or substituted with at least one $R_{10a}$, or a $C_2$-$C_5$ alkenylene group unsubstituted or substituted with at least one $R_{10a}$ to thereby form a $C_8$-$C_{60}$ polycyclic group unsubstituted or substituted with at least one $R_{10a}$, and
- na1 may be an integer from 1 to 4.

For example, each of Formula 201 and Formula 202 may include at least one of the groups represented by Formulae CY201 to CY217:

CY201

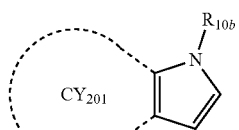

CY202

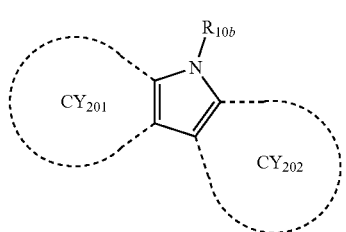

CY203

CY204

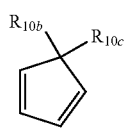

CY205

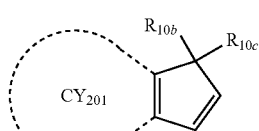

CY206

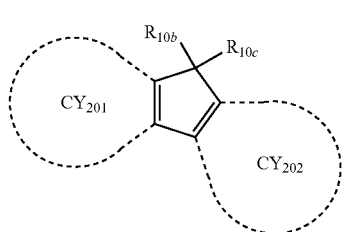

CY207

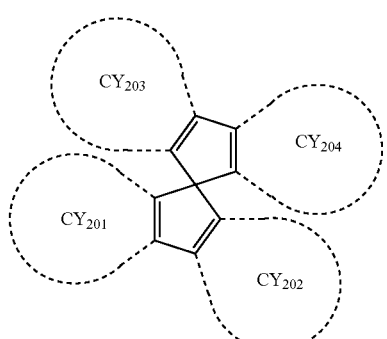

CY208

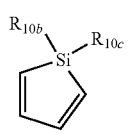

CY209

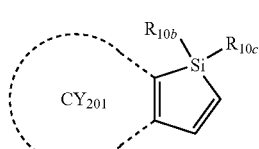

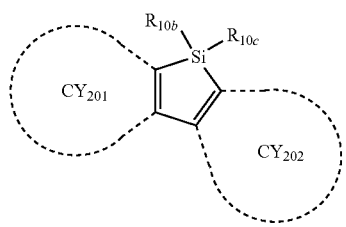

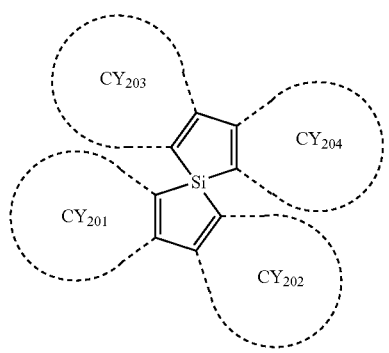

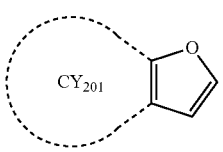

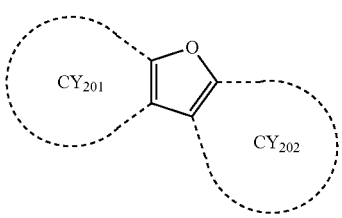

CY210

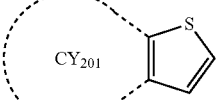

CY211

CY212

CY213

CY214

CY215

CY216

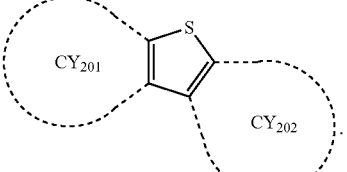

CY217

In Formulae CY201 to CY217, $R_{10b}$ and $R_{10c}$ may each independently be the same as described in connection with $R_{10a}$, ring CY201 to ring CY204 may each independently be a $C_3$-$C_{20}$ carbocyclic group or a $C_1$-$C_{20}$ heterocyclic group, and Formulae CY201 to CY217 may be unsubstituted or at least one hydrogen may be substituted with at least one $R_{10a}$ as described in the present specification.

In an embodiment, ring CY201 to ring CY204 in Formulae CY201 to CY217 may each independently be a benzene group, a naphthalene group, a phenanthrene group, or an anthracene group.

In an embodiment, each of Formula 201 and Formula 202 may include at least one of the groups represented by Formulae CY201 to CY203.

In an embodiment, Formula 201 may include at least one of the groups represented by Formulae CY201 to CY203 and at least one of the groups represented by Formulae CY204 to CY217.

In an embodiment, in Formula 201, xa1 may be 1, $R_{201}$ may be a group represented by one of Formulae CY201 to CY203, xa2 may be 0, and $R_{202}$ may be a group represented by one of Formulae CY204 to CY207.

In an embodiment, each of Formula 201 and Formula 202 may not include any of the groups represented by Formulae CY201 to CY203.

In an embodiment, each of Formula 201 and Formula 202 may not include any of the groups represented by Formulae CY201 to CY203, and may include at least one of the groups represented by Formulae CY204 to CY217.

In one embodiment, each of Formula 201 and Formula 202 may not include any of the groups represented by Formulae CY201 to CY217.

In an embodiment, the hole transport region may include one of Compounds HT1 to HT44, m-MTDATA, TDATA, 2-TNATA, NPB(NPD), β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzene sulfonic acid (PANI/DBSA), poly(3,4-ethylene dioxythiophene)/poly(4-styrene sulfonate) (PEDOT/PSS), polyaniline/camphor sulfonic acid (PANI/CSA), polyaniline/poly(4-styrene sulfonate) (PANI/PSS), or any combination thereof:

HT1
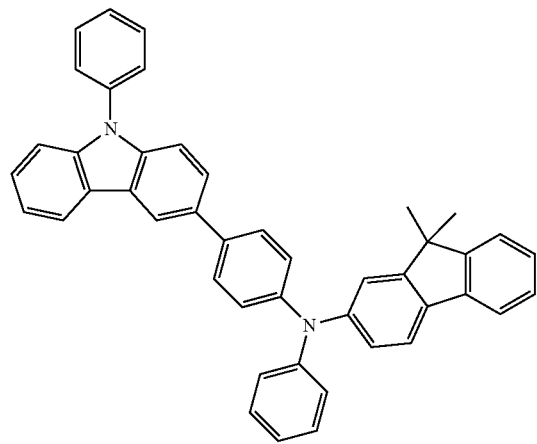
HT2
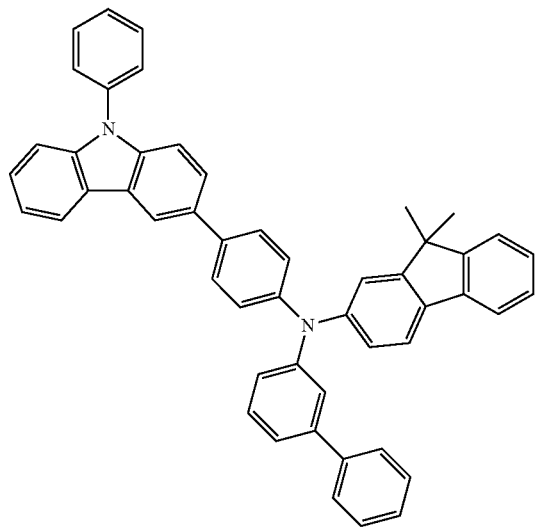
HT3
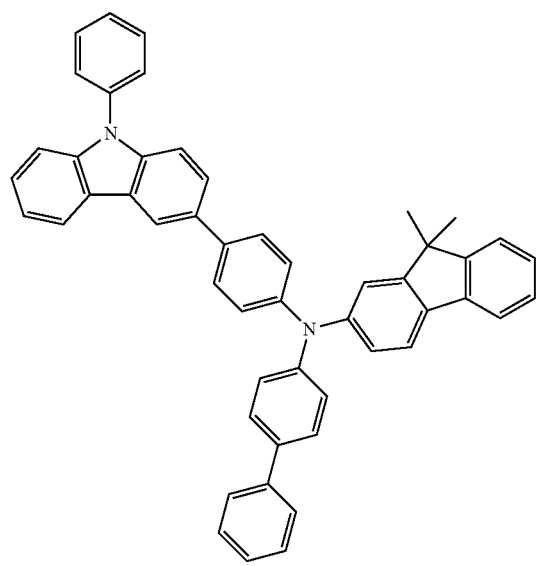
HT4
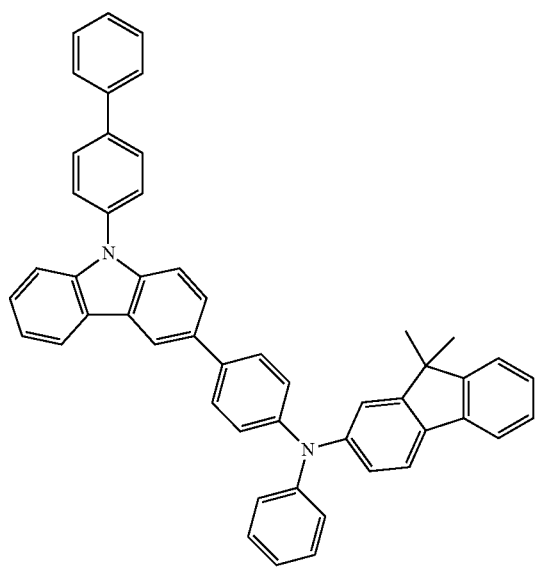

-continued
HT5
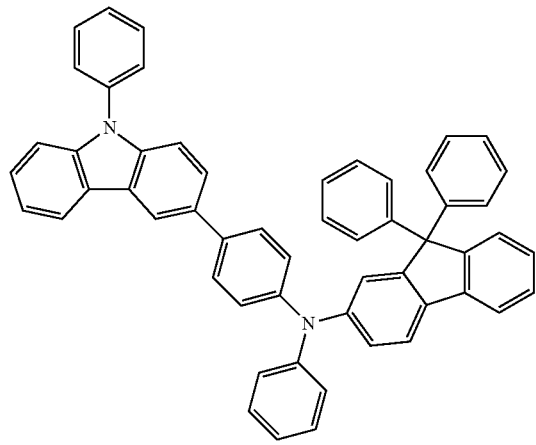
HT6
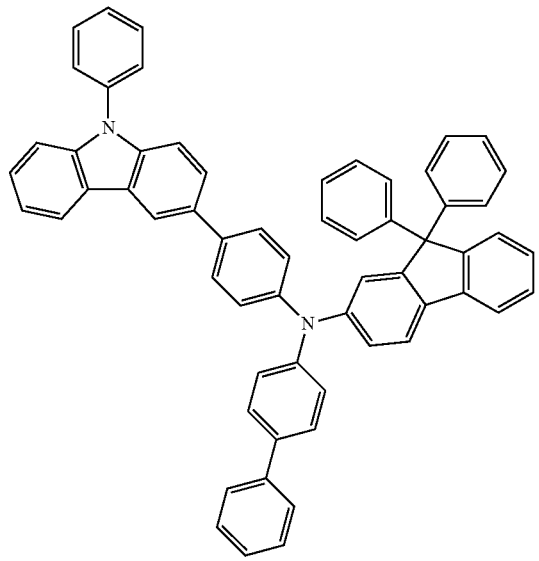
HT7
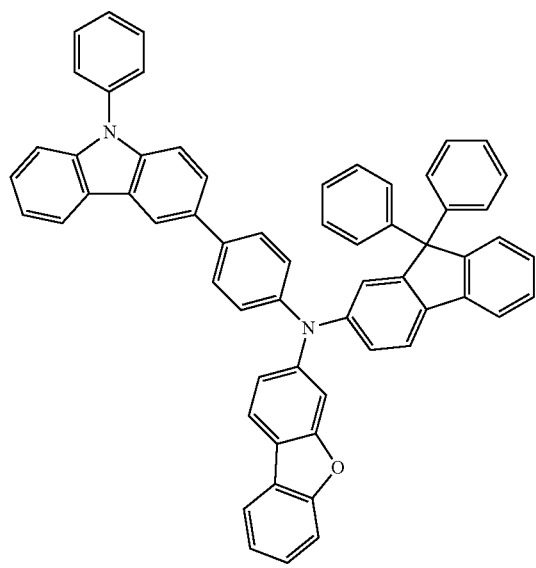
HT8
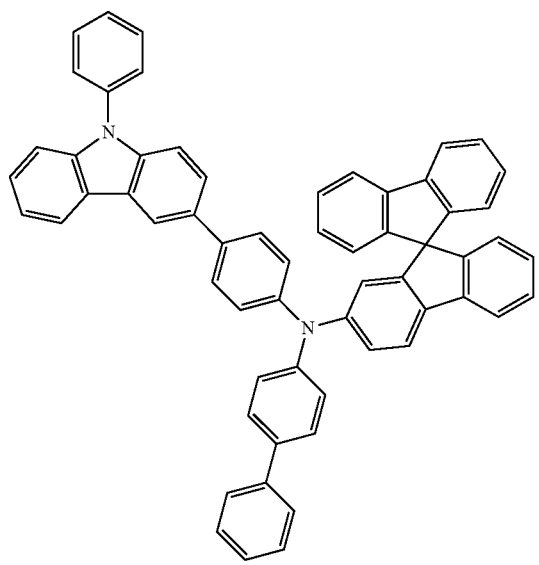

-continued
HT9
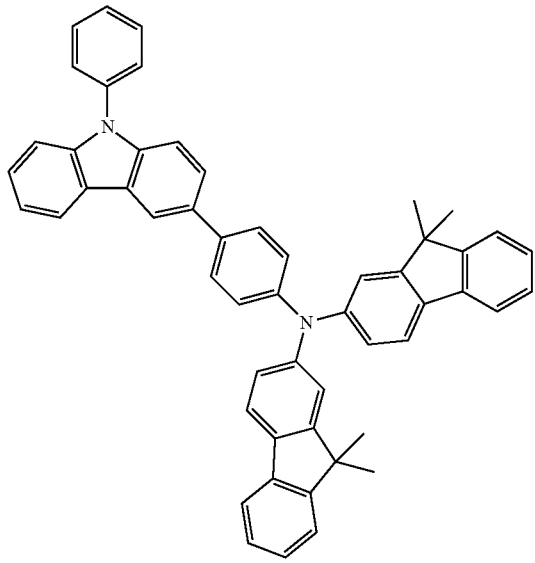
HT10
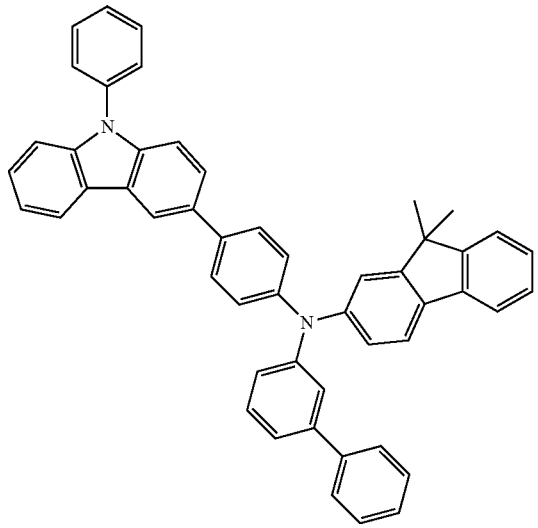
HT11
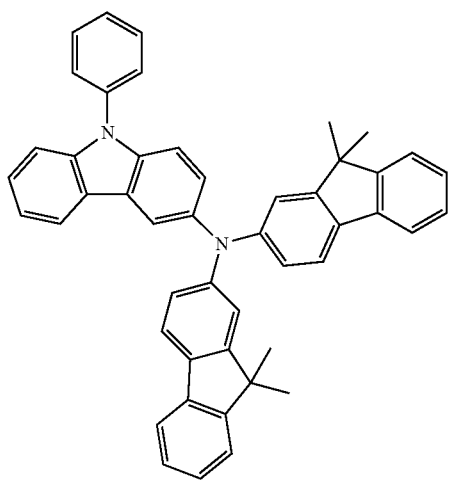
HT12
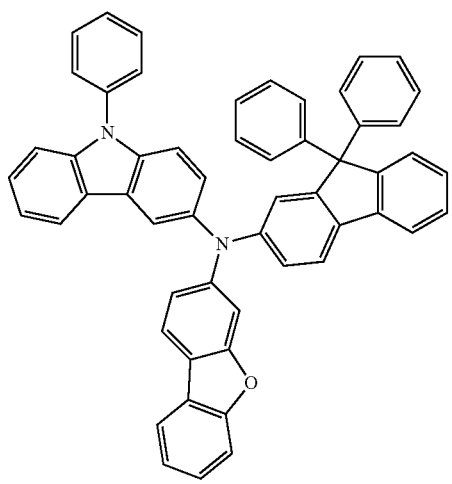
HT13
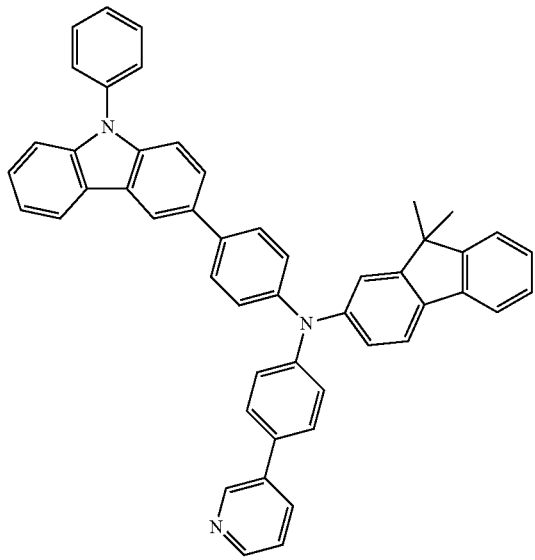
HT14
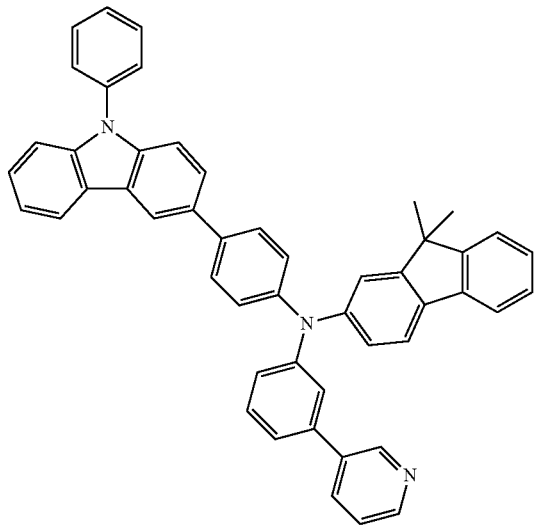

-continued
HT15
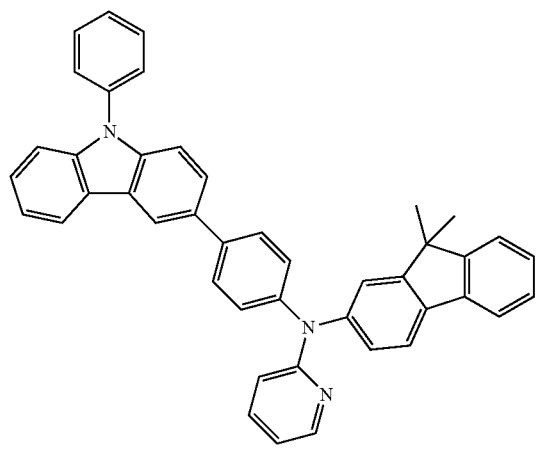
HT16
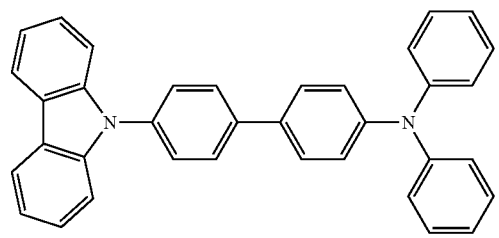
HT17
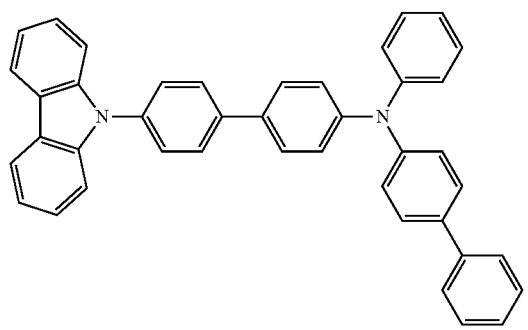
HT18
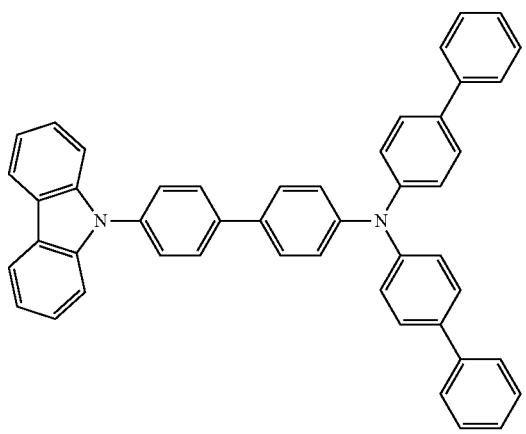
HT19
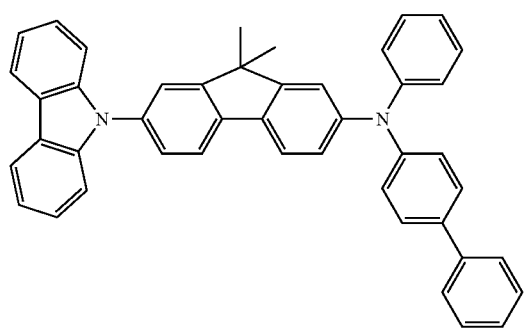
HT20
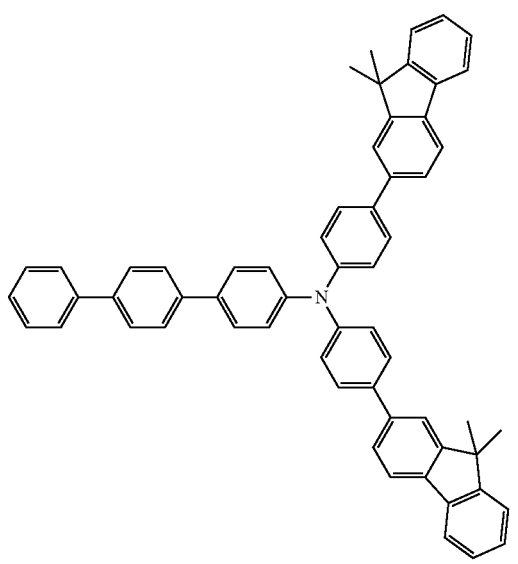

-continued
HT21
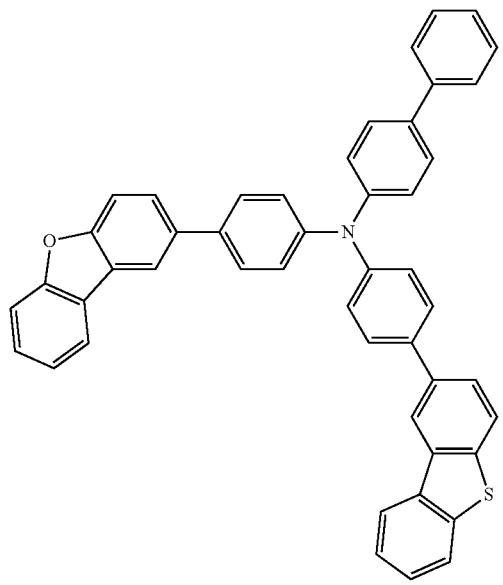
HT22
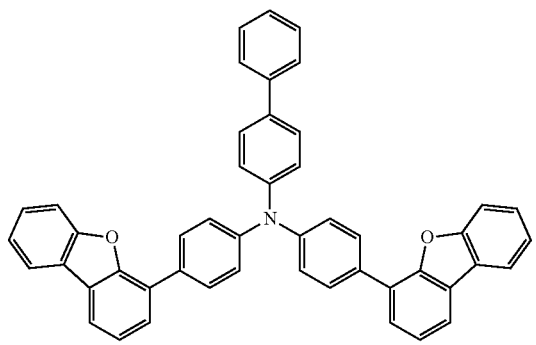
HT23
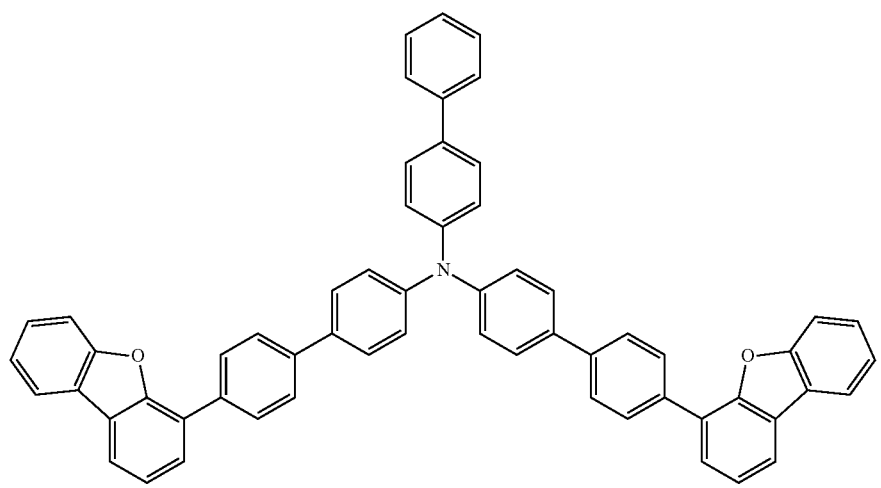
HT24
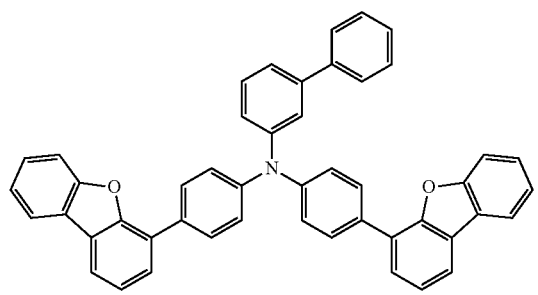
HT25
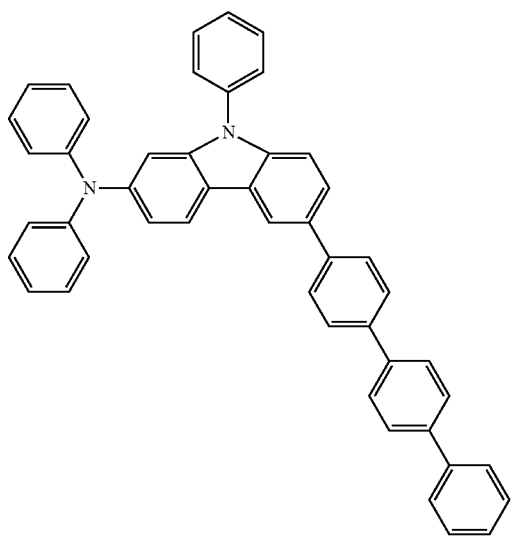

-continued
HT26
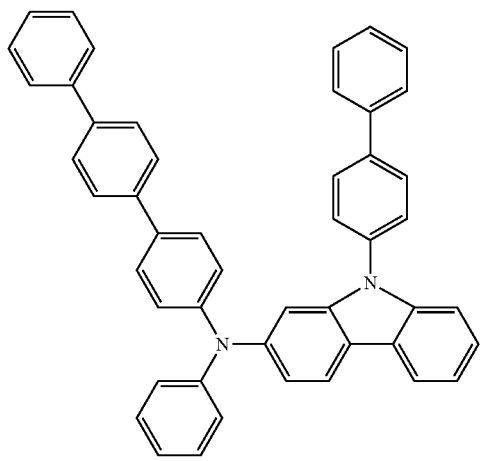
HT27
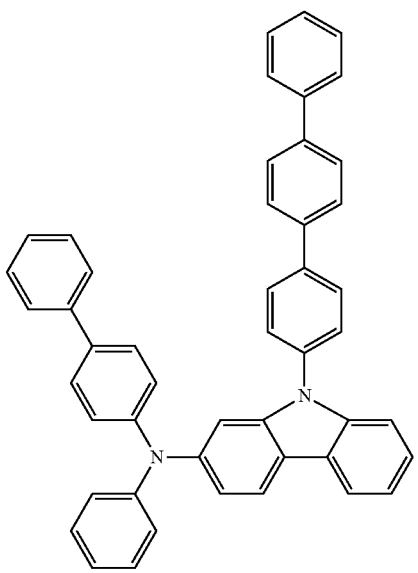
HT28
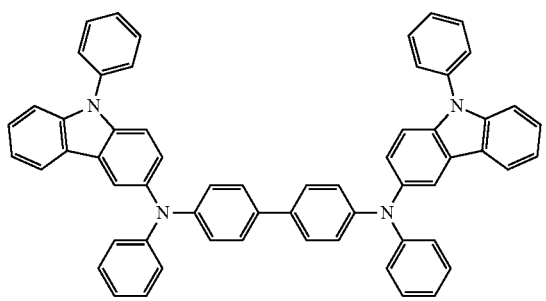
HT29
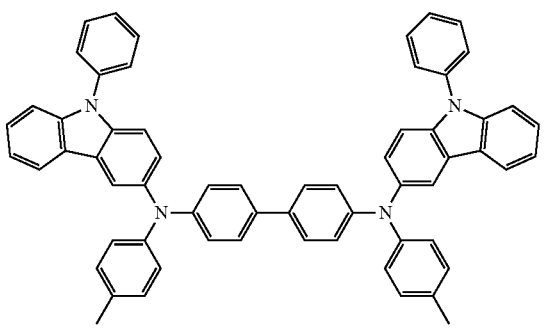
HT30
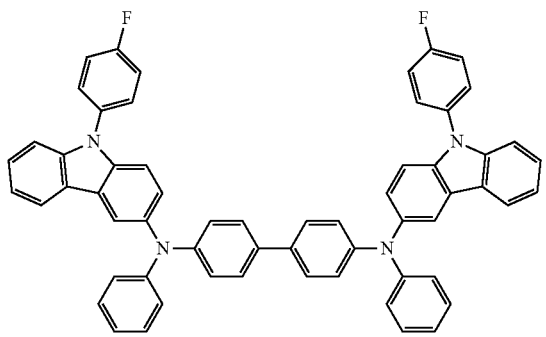
HT31
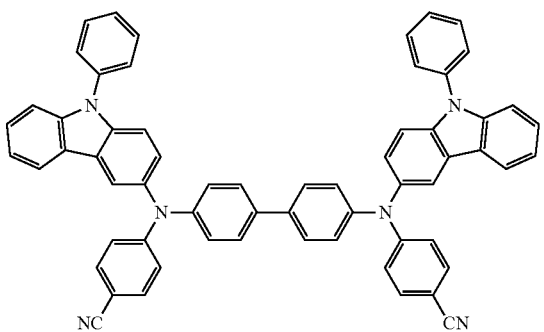

-continued
HT32
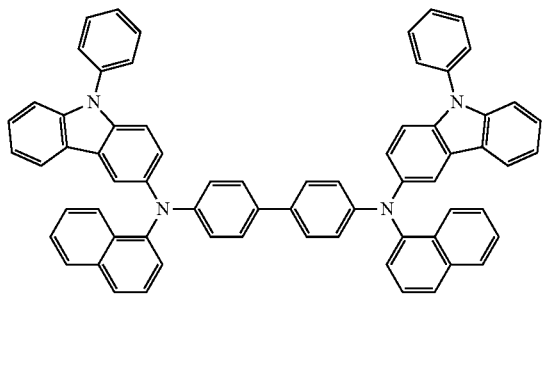
HT33
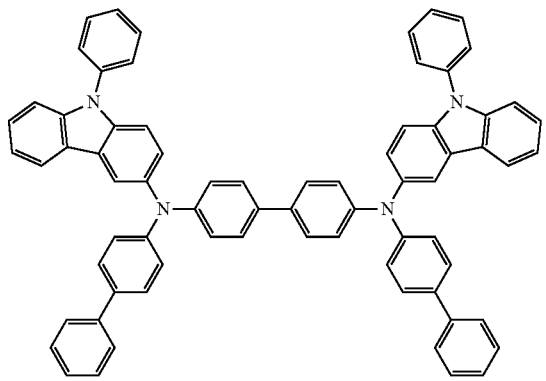
HT34
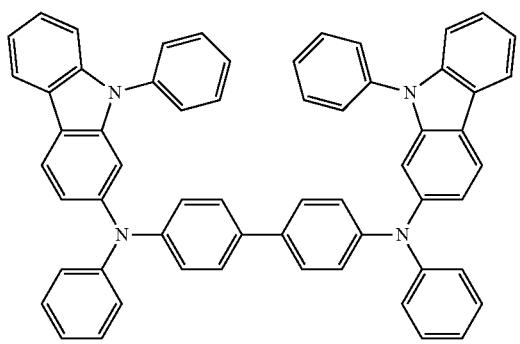
HT35
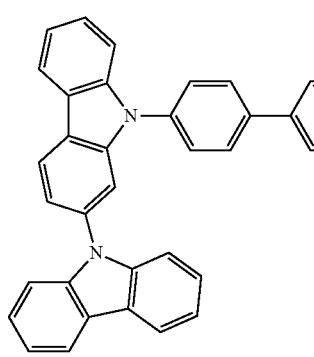
HT36
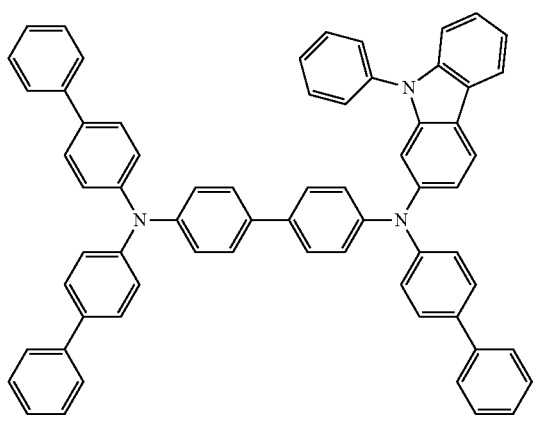
HT37
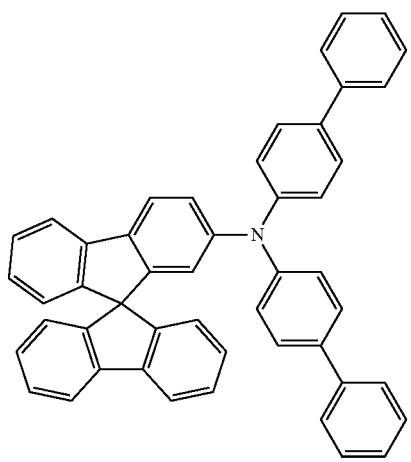

-continued
HT38
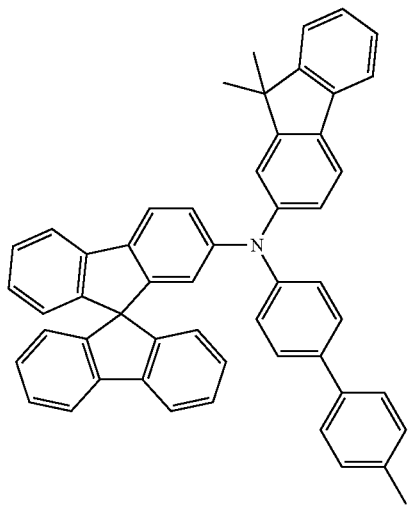
HT39
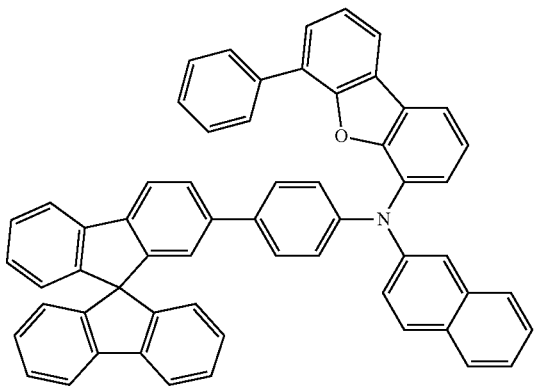
HT40
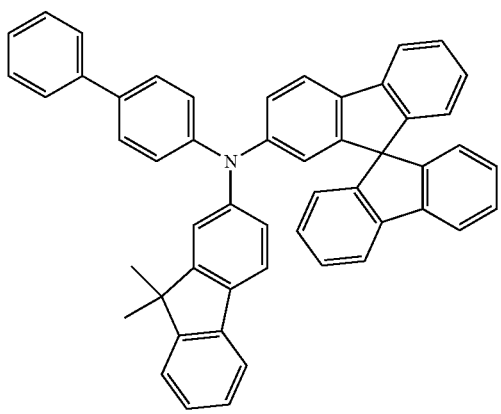
HT41
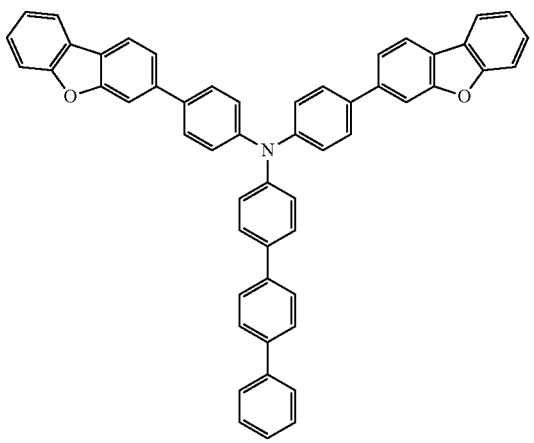
HT42
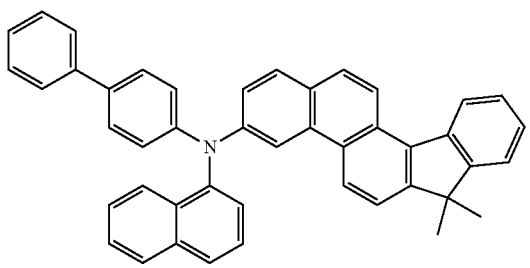
HT43
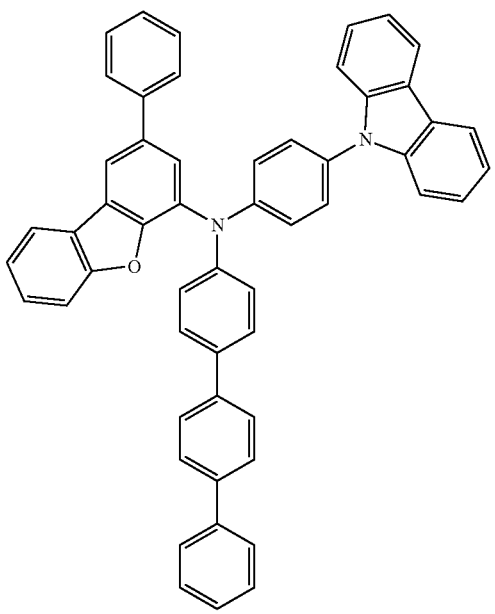

-continued
HT44
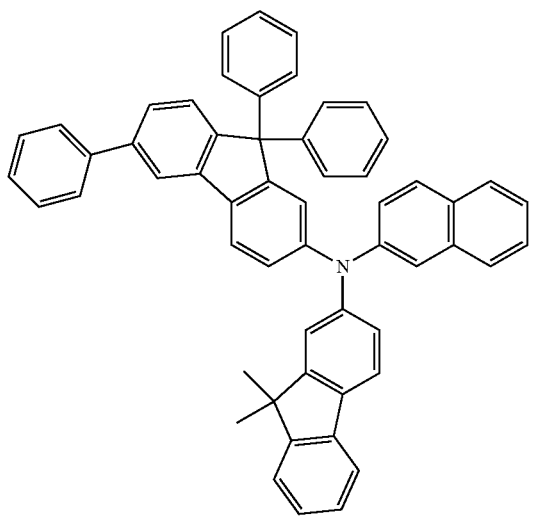
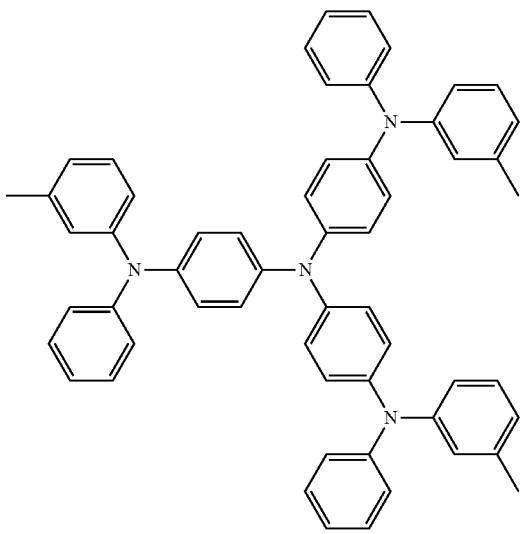
m-MTDATA
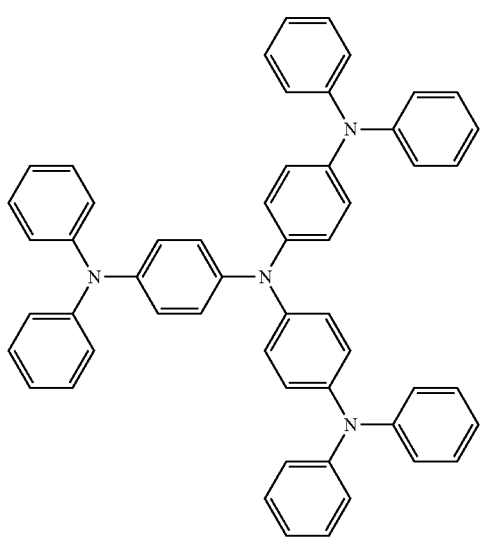
TDATA
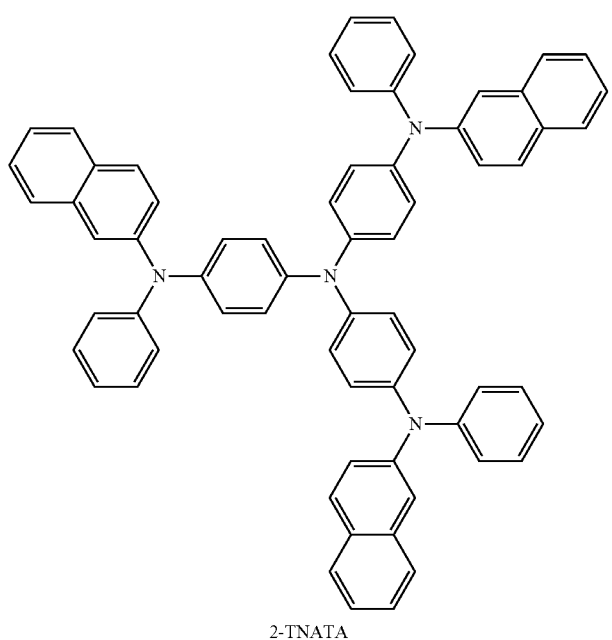
2-TNATA
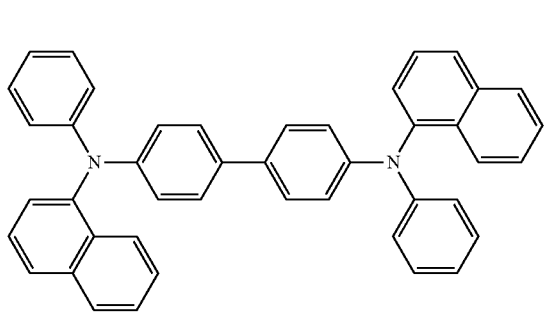
NPB
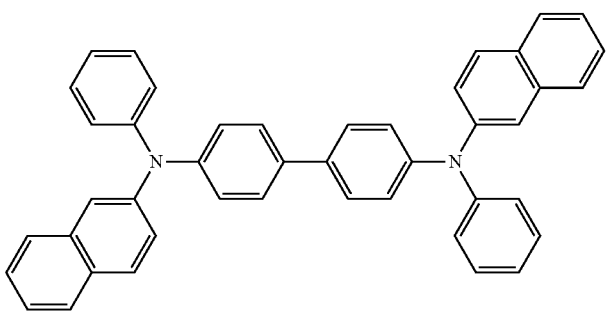
β-NPB -continued

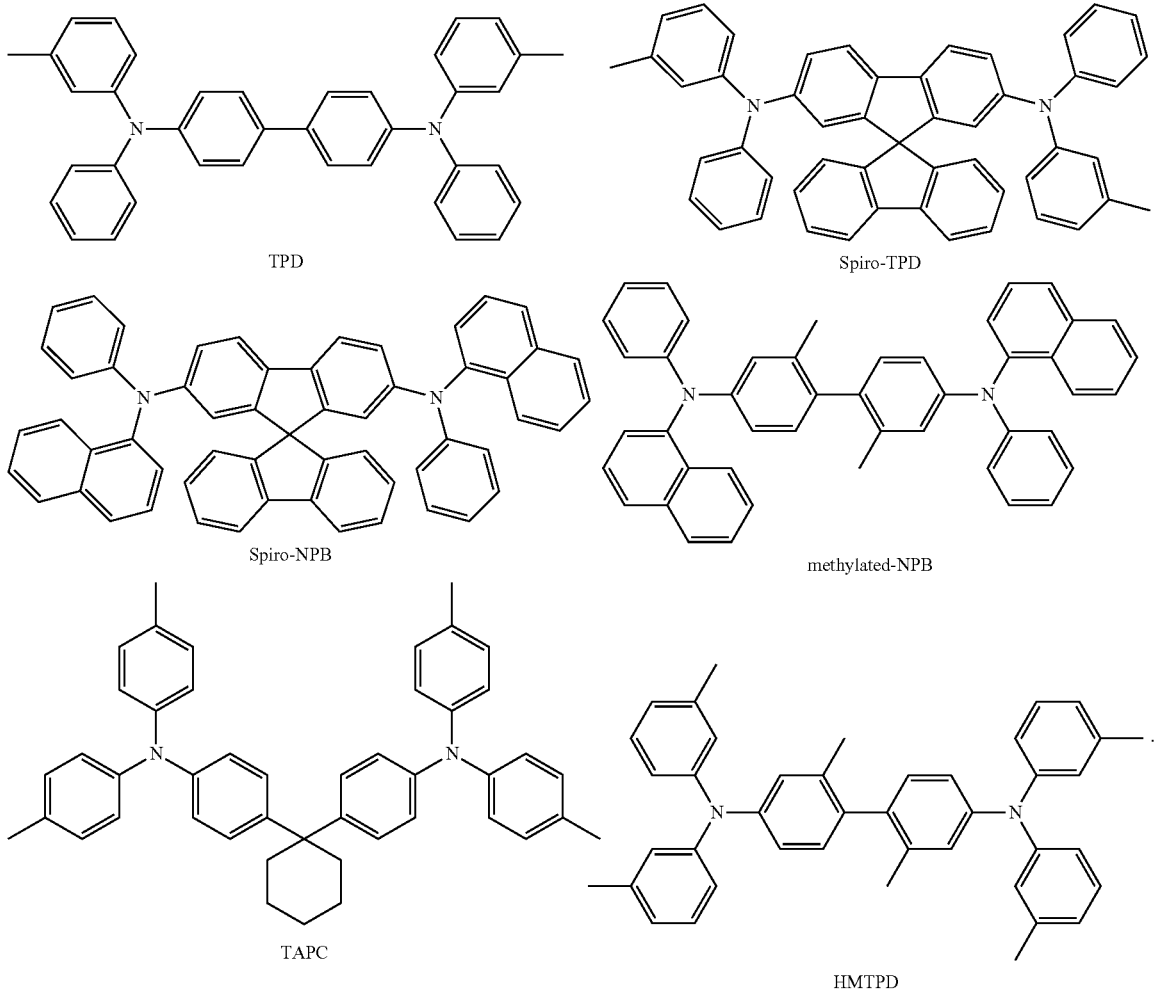

A thickness of the hole transport region may be about 100 Å to about 10,000 Å, for example, about 100 Å to about 1,000 Å. When the hole transport region includes at least one of a hole injection layer and a hole transport layer, a thickness of the hole injection layer may be about 100 Å to about 9,000 Å, for example, about 100 Å to about 1,000 Å, and a thickness of the hole transport layer may be about 50 Å to about 2,000 Å, for example, about 100 Å to about 1,500 Å. When the thicknesses of the hole transport region, the hole injection layer, and the hole transport layer are within these ranges, satisfactory hole transporting characteristics may be obtained without a substantial increase in driving voltage.

The emission auxiliary layer may increase the light-emission efficiency of a device by compensating for an optical resonance distance of a wavelength of light emitted by an emission layer, and the electron blocking layer may block or reduce the flow of electrons from an electron transport region. The emission auxiliary layer and the electron blocking layer may include the materials as described above.

p-Dopant

The hole transport region may include, in addition to these materials, a charge-generation material for improvement of conductive properties. The charge-generation material may be substantially homogeneously or non-homogeneously dispersed in the hole transport region, and in some embodiments may take the form of a layer consisting of the charge-generation material.

The charge-generation material may be, for example, a p-dopant.

In some embodiments, a lowest unoccupied molecular orbital (LUMO) energy level of the p-dopant may be less than or equal to about −3.5 eV.

In an embodiment, the p-dopant may include a quinone derivative, a cyano group-containing compound, an element EL1 and element EL2-containing compound (e.g., a compound containing an element EU and an element EL2), or any combination thereof.

Non-limiting examples of the quinone derivative include TCNQ and F4-TCNQ.

Non-limiting examples of the cyano group-containing compound include HAT-CN and a compound represented by Formula 221:

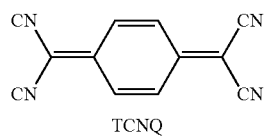

TCNQ

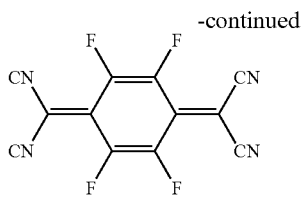

F4-TCNQ

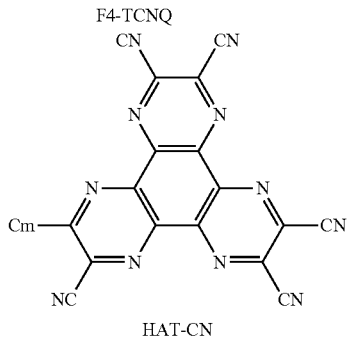

HAT-CN

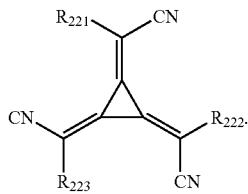

Formula 221

In Formula 221, $R_{221}$ to $R_{223}$ may each independently be a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, and at least one of $R_{221}$ to $R_{223}$ may each independently be a $C_3$-$C_{60}$ carbocyclic group or a $C_1$-$C_{60}$ heterocyclic group, each substituted with: a cyano group; —F; —Cl; —Br; —I; a $C_1$-$C_{20}$ alkyl group substituted with a cyano group, —F, —Cl, —Br, —I, or any combination thereof; or any combination thereof.

In the element EL1 and element EL2-containing compound, the element EU may be a metal, a metalloid, or a combination thereof, and the element EL2 may be a non-metal, a metalloid, or a combination thereof.

Non-limiting examples of the metal include: an alkali metal (for example, lithium (Li), sodium (Na), potassium (K), rubidium (Rb), or cesium (Cs)); an alkaline earth metal (for example, beryllium (Be), magnesium (Mg), calcium (Ca), strontium (Sr), or barium (Ba)); a transition metal (for example, titanium (Ti), zirconium (Zr), hafnium (Hf), vanadium (V), niobium (Nb), tantalum (Ta), chromium (Cr), molybdenum (Mo), tungsten (W), manganese (Mn), technetium (Tc), rhenium (Re), iron (Fe), ruthenium (Ru), osmium (Os), cobalt (Co), rhodium (Rh), iridium (Ir), nickel (Ni), palladium (Pd), platinum (Pt), copper (Cu), silver (Ag), or gold (Au)); a post-transition metal (for example, zinc (Zn), indium (In), or tin (Sn)); and a lanthanide metal (for example, lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), or ruthenium (Lu)).

Non-limiting examples of the metalloid include silicon (Si), antimony (Sb), and tellurium (Te).

Non-limiting examples of the non-metal include oxygen (O) and a halogen (for example, F, Cl, Br, or I).

For example, the element EL1 and element EL2-containing compound may include a metal oxide, a metal halide (for example, a metal fluoride, a metal chloride, a metal bromide, or a metal iodide), a metalloid halide (for example, a metalloid fluoride, a metalloid chloride, a metalloid bromide, or a metalloid iodide), a metal telluride, or any combination thereof.

Non-limiting examples of the metal oxide include a tungsten oxide (for example, WO, $W_2O_3$, $WO_2$, $WO_3$, or $W_2O_5$), a vanadium oxide (for example, VO, $V_2O_3$, $VO_2$, or $V_2O_5$), a molybdenum oxide (MoO, $Mo_2O_3$, $MoO_2$, $MoO_3$, or $Mo_2O_5$), and a rhenium oxide (for example, $ReO_3$).

Non-limiting examples of the metal halide include an alkali metal halide, an alkaline earth metal halide, a transition metal halide, a post-transition metal halide, and a lanthanide metal halide.

Non-limiting examples of the alkali metal halide include LiF, NaF, KF, RbF, CsF, LiCl, NaCl, KCl, RbCl, CsCl, LiBr, a NaBr, KBr, RbBr, CsBr, LiI, NaI, KI, RbI, and CsI.

Non-limiting examples of the alkaline earth metal halide include $BeF_2$, $MgF_2$, $CaF_2$, $SrF_2$, $BaF_2$, $BeCl_2$, $MgCl_2$, $CaCl_2$, $SrCl_2$, $BaCl_2$, $BeBr_2$, $MgBr_2$, $CaBr_2$, $SrBr_2$, $BaBr_2$, $BeI_2$, $MgI_2$, $CaI_2$, $SrI_2$, and $BaI_2$.

Non-limiting examples of the transition metal halide include a titanium halide (for example, $TiF_4$, $TiCl_4$, $TiBr_4$, or $TiI_4$), a zirconium halide (for example, $ZrF_4$, $ZrCl_4$, $ZrBr_4$, or $ZrI_4$), a hafnium halide (for example, $HfF_4$, $HfCl_4$, $HfBr_4$, or $HfI_4$), a vanadium halide (for example, $VF_3$, $VCl_3$, $VBr_3$, or $VI_3$), a niobium halide (for example, $NbF_3$, $NbCl_3$, $NbBr_3$, or $NbI_3$), a tantalum halide (for example, $TaF_3$, $TaCl_3$, $TaBr_3$, or $TaI_3$), a chromium halide (for example, $CrF_3$, $CrCl_3$, $CrBr_3$, or $CrI_3$), a molybdenum halide (for example, $MoF_3$, $MoCl_3$, $MoBr_3$, or $MoI_3$), a tungsten halide (for example, $WF_3$, $WCl_3$, $WBr_3$, or $WI_3$), a manganese halide (for example, $MnF_2$, $MnCl_2$, $MnBr_2$, or $MnI_2$), a technetium halide (for example, $TcF_2$, $TcCl_2$, $TcBr_2$, or $TcI_2$), a rhenium halide (for example, $ReF_2$, $ReCl_2$, $ReBr_2$, or $ReI_2$), an iron halide (for example, $FeF_2$, $FeCl_2$, $FeBr_2$, or $FeI_2$), a ruthenium halide (for example, $RuF_2$, $RuCl_2$, $RuBr_2$, or $RuI_2$), an osmium halide (for example, $OsF_2$, $OsCl_2$, $OsBr_2$, or $OsI_2$), a cobalt halide (for example, $CoF_2$, $CoCl_2$, $CoBr_2$, or $CoI_2$), a rhodium halide (for example, $RhF_2$, $RhCl_2$, $RhBr_2$, or $RhI_2$), an iridium halide (for example, $IrF_2$, $IrCl_2$, $IrBr_2$, or $IrI_2$), a nickel halide (for example, $NiF_2$, $NiCl_2$, $NiBr_2$, or $NiI_2$), a palladium halide (for example, $PdF_2$, $PdCl_2$, $PdBr_2$, or $PdI_2$), a platinum halide (for example, $PtF_2$, $PtCl_2$, $PtBr_2$, or $PtI_2$), a copper halide (for example, CuF, CuCl, CuBr, or CuI), a silver halide (for example, AgF, AgCl, AgBr, or AgI), and a gold halide (for example, AuF, AuCl, AuBr, or AuI).

Non-limiting examples of the post-transition metal halide include a zinc halide (for example, $ZnF_2$, $ZnCl_2$, $ZnBr_2$, or $ZnI_2$), an indium halide (for example, $InI_3$), and a tin halide (for example, $SnI_2$).

Non-limiting examples of the lanthanide metal halide include YbF, $YbF_2$, $YbF_3$, $SmF_3$, YbCl, $YbCl_2$, $YbCl_3$, $SmCl_3$, YbBr, $YbBr_2$, $YbBr_3$, $SmBr_3$, YbI, $YbI_2$, $YbI_3$, and $SmI_3$.

Non-limiting examples of the metalloid halide include an antimony halide (for example, $SbCl_5$).

Non-limiting examples of the metal telluride include an alkali metal telluride (for example, $Li_2Te$, $Na_2Te$, $K_2Te$, $Rb_2Te$, or $Cs_2Te$), an alkaline earth metal telluride (for example, BeTe, MgTe, CaTe, SrTe, or BaTe), a transition metal telluride (for example, $TiTe_2$, $ZrTe_2$, $HfTe_2$, $V_2Te_3$, $Nb_2Te_3$, $Ta_2Te_3$, $Cr_2Te_3$, $Mo_2Te_3$, $W_2Te_3$, MnTe, TcTe, ReTe, FeTe, RuTe, OsTe, CoTe, RhTe, IrTe, NiTe, PdTe, PtTe, $Cu_2Te$, CuTe, $Ag_2Te$, AgTe, or $Au_2Te$), a post-transition metal telluride (for example, ZnTe), and a lanthanide metal telluride (for example, LaTe, CeTe, PrTe, NdTe, PmTe, EuTe, GdTe, TbTe, DyTe, HoTe, ErTe, TmTe, YbTe, or LuTe).

Emission Layer in Interlayer 130

When the light-emitting device 10 is a full-color light-emitting device, the emission layer may be patterned into a red emission layer, a green emission layer, and/or a blue emission layer, according to a sub-pixel. In an embodiment, the emission layer may have a stacked structure of two or more layers among a red emission layer, a green emission layer, and a blue emission layer, in which the two or more layers may contact each other or may be separated from each other. In an embodiment, the emission layer may include two or more materials among a red light-emitting material, a green light-emitting material, and a blue light-emitting material, in which the two or more materials are mixed with each other in a single layer to emit white light.

The emission layer may include a host and a dopant. The dopant may include a phosphorescent dopant, a fluorescent dopant, or any combination thereof.

The emission layer may include the compound represented by Formula 1 according to an embodiment.

An amount of the dopant in the emission layer may be about 0.01 parts by weight to about 15 parts by weight based on 100 parts by weight of the host. However, embodiments of the present disclosure are not limited thereto.

In an embodiment, the emission layer may include a quantum dot.

In some embodiments, the emission layer may include a delayed fluorescence material. The delayed fluorescence material may act as the host or the dopant in the emission layer.

Host

The host may include the compound represented by Formula 1.

The host may further include, in addition to the compound represented by Formula 1, for example, a compound represented by Formula 301:

$$[Ar_{301}]_{xb11}\text{-}[(L_{301})_{xb1}\text{-}R_{301}]_{xb21}.$$ Formula 301

In Formula 301, $Ar_{301}$ and $L_{301}$ may each independently be a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, xb11 may be 1, 2, or 3, xb1 may be an integer from 0 to 5, $R_{301}$ may be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, $-Si(Q_{301})(Q_{302})(Q_{303})$, $-N(Q_{301})(Q_{302})$, $-B(Q_{301})(Q_{302})$, $-C(=O)(Q_{301})$, $-S(=O)_2(Q_{301})$, or $-P(=O)(Q_{301})(Q_{302})$, xb21 may be an integer from 1 to 5, and $Q_{301}$ to $Q_{303}$ may each independently be the same as described in connection with $Q_1$ in the present specification.

In an embodiment, when xb11 in Formula 301 is 2 or more, two or more $Ar_{301}$(s) may be linked to each other via a single bond.

In an embodiment, the host may include a compound represented by Formula 301-1, a compound represented by Formula 301-2, or any combination embodiment:

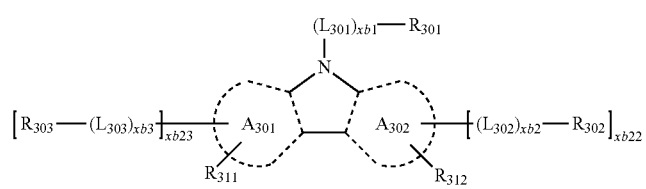

Formula 301-1

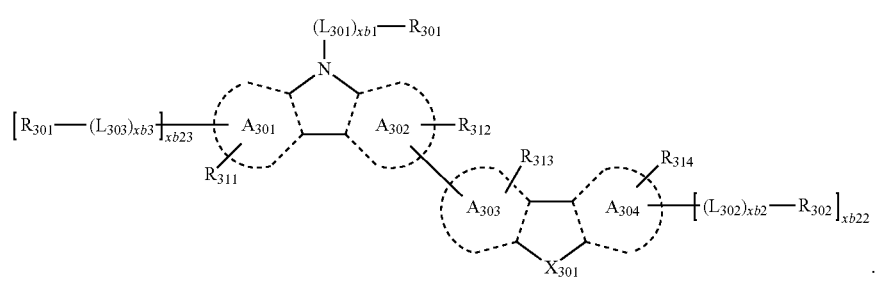

Formula 301-2

A thickness of the emission layer may be about 100 Å to about 1,000 Å, for example, about 200 Å to about 600 Å. When the thickness of the emission layer is within this range, excellent light-emission characteristics may be obtained without a substantial increase in driving voltage.

In Formulae 301-1 and 301-2, ring $A_{301}$ to ring $A_{304}$ may each independently be a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, $X_{301}$ may be O, S, N-[$(L_{304})_{xb4}$-$R_{304}$], C($R_{304}$)($R_{305}$), or Si($R_{304}$)($R_{305}$), xb22 and xb23 may each independently be 0, 1, or 2, $L_{301}$, xb1, and $R_{301}$ may each independently be the same as earlier described, $L_{302}$ to $L_{304}$ may each independently be the same as described in connection with $L_{301}$, xb2 to xb4 may each independently be the same as described in connection with $xb1_7$ and $R_{302}$ to $R_{305}$ and $R_{311}$ to $R_{314}$ may each independently be the same as described in connection with $R_{301}$.

In an embodiment, the host may include an alkaline earth metal complex. For example, the host may be a Be complex (for example, Compound H55), a Mg complex, or any combination thereof. In some embodiments, the host may be a Zn complex.

In an embodiment, the host may include one of Compounds H1 to H124, 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolyl-benzene (mCP), 1,3,5-tri(carbazol-9-yl)benzene (TCP), or any combination thereof.

H1

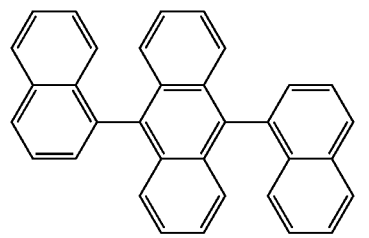

H2

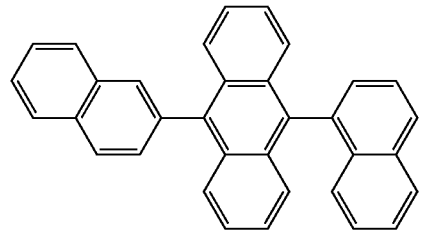

H3

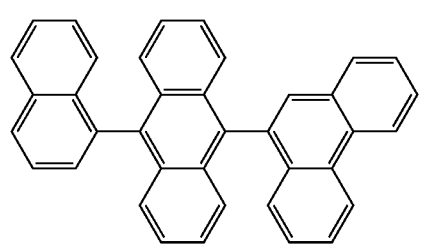

H4

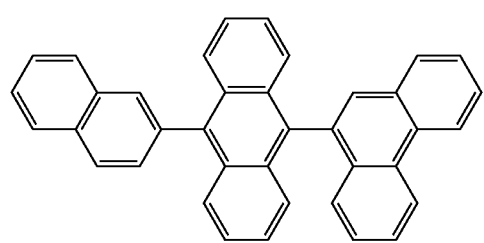

-continued

H5

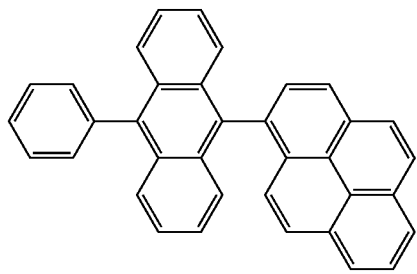

H6

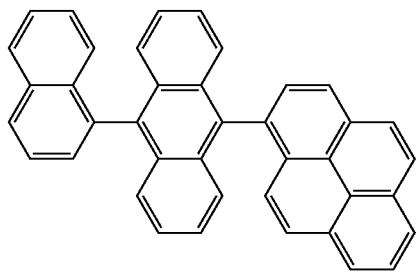

H7

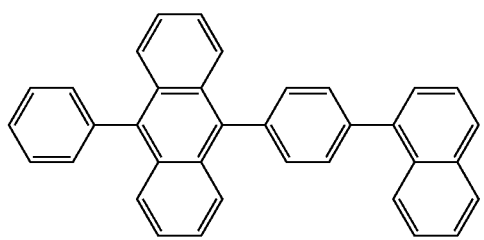

H8

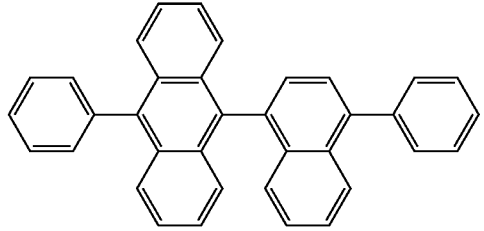

H9

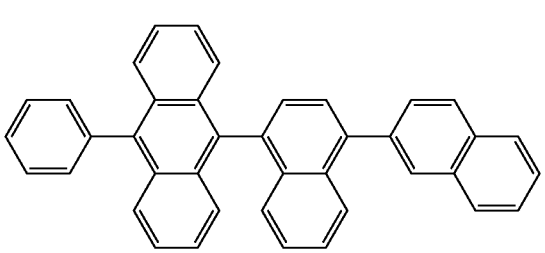

H10

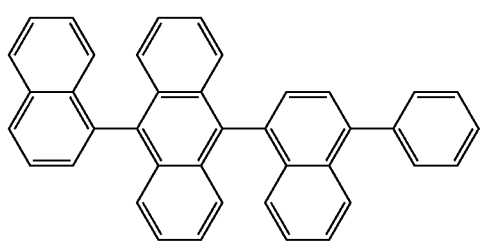

-continued
H11
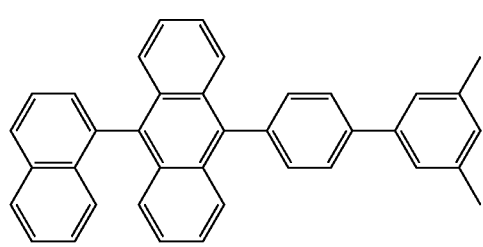
H12
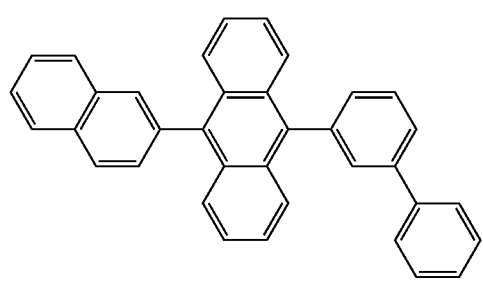
H13
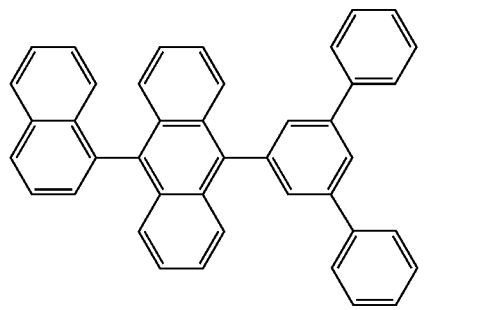
H14
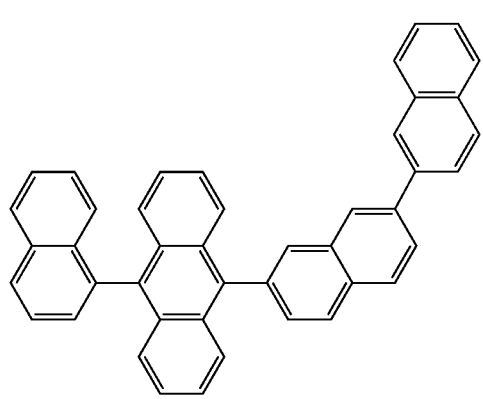
H15
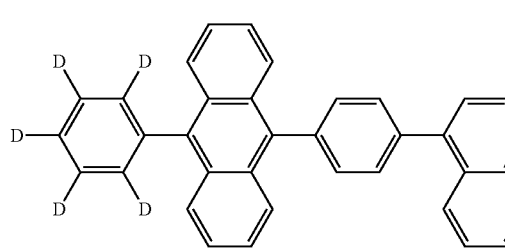
-continued
H16
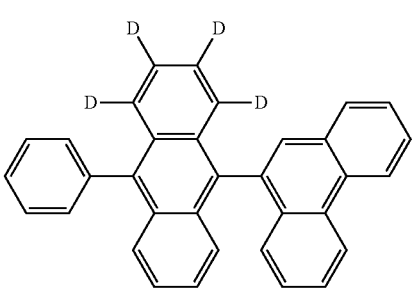
H17
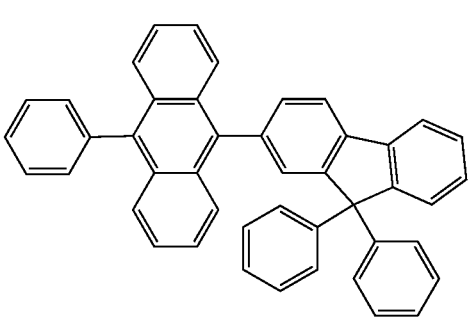
H18
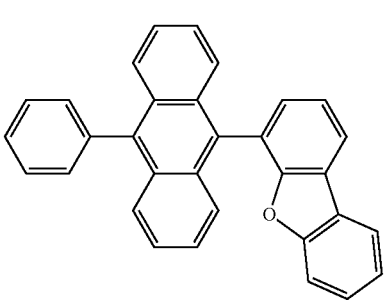
H19
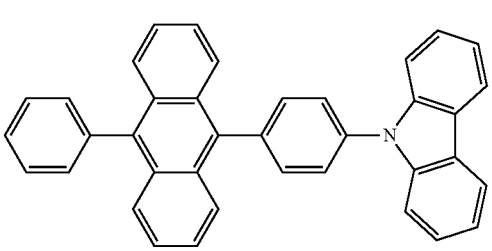
H20
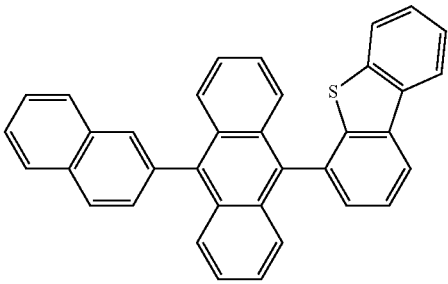

H21
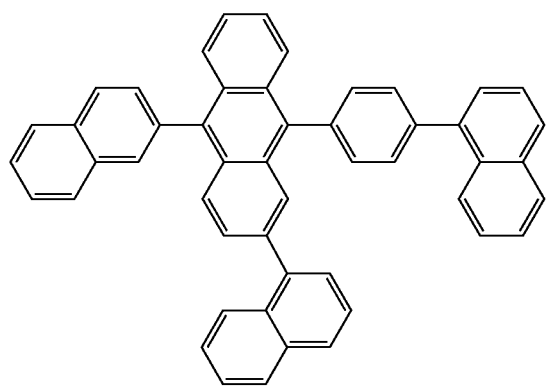
H22
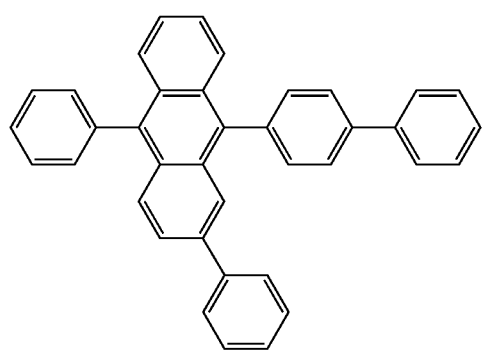
H23
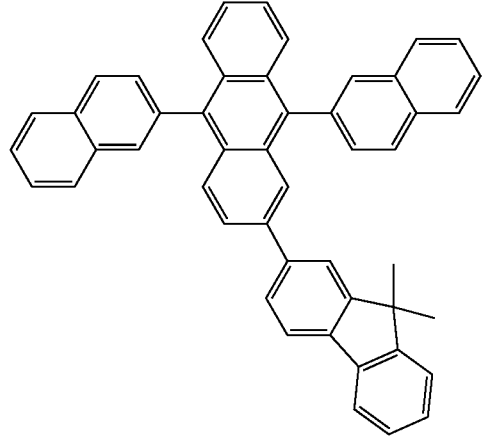
H24
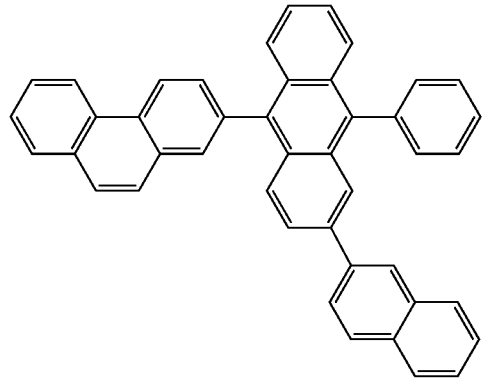
H25
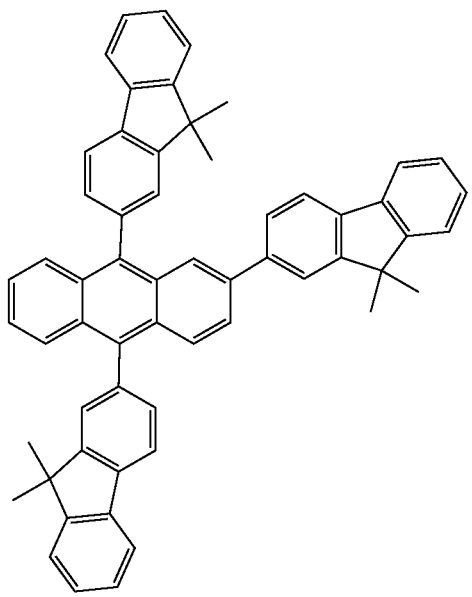
H26
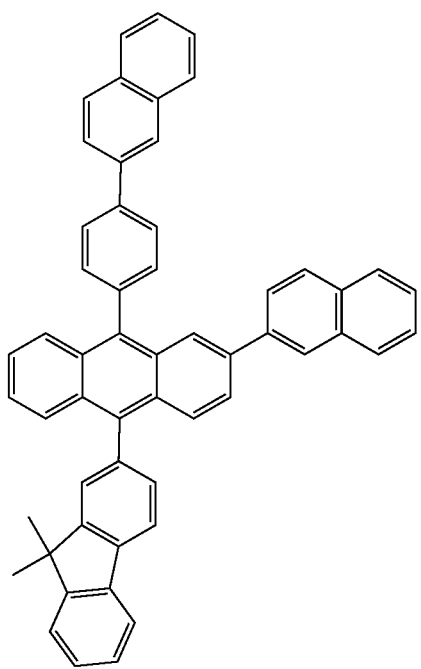

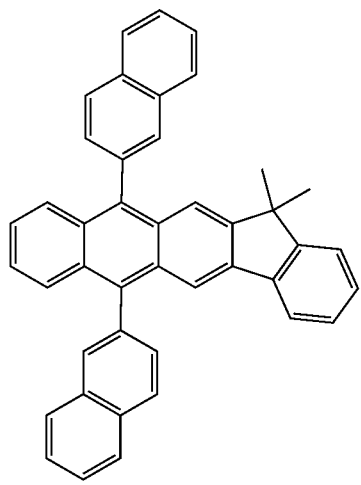
H27
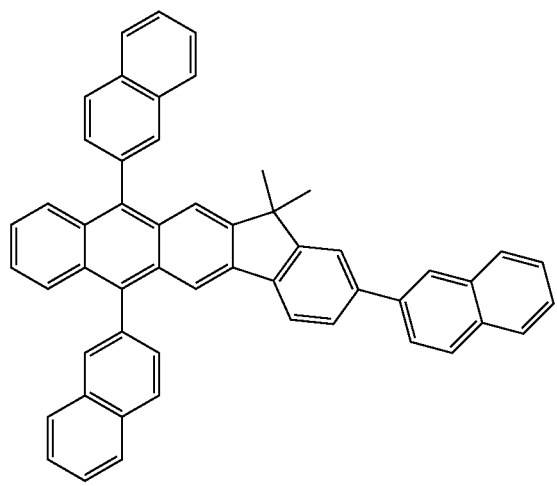
H28
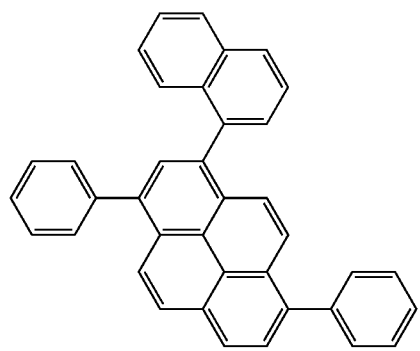
H29
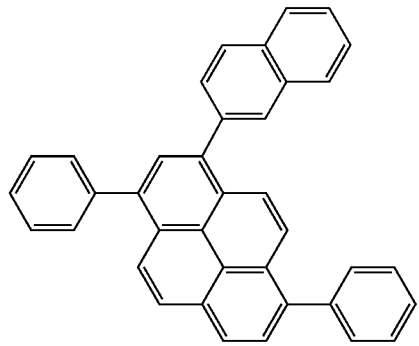
H30
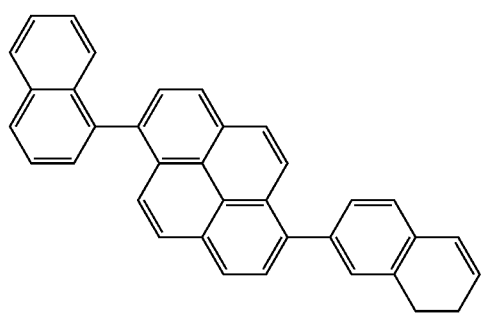
H31
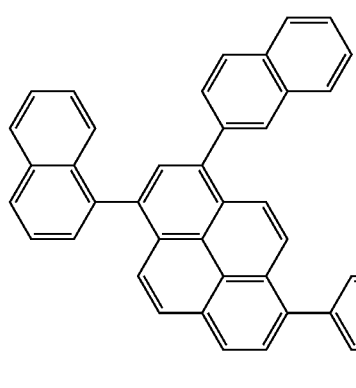
H32
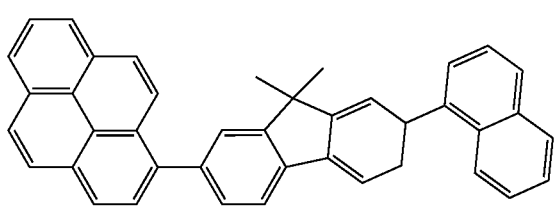
H33
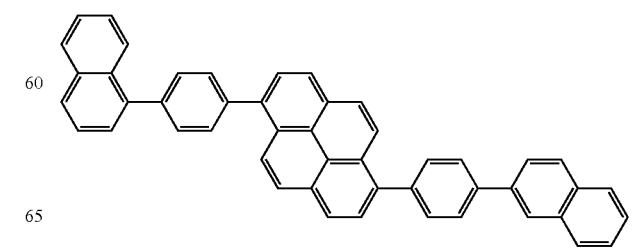
H34

H35
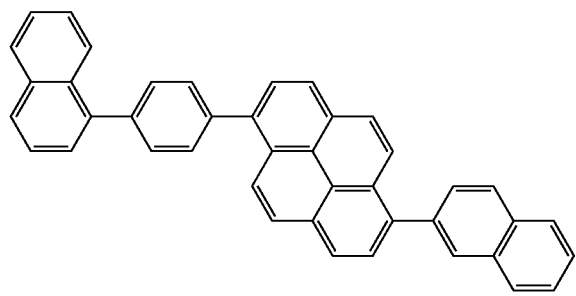
H36
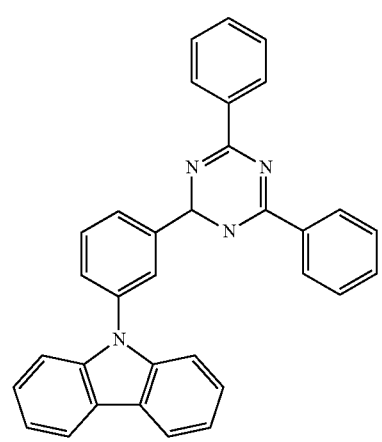
H37
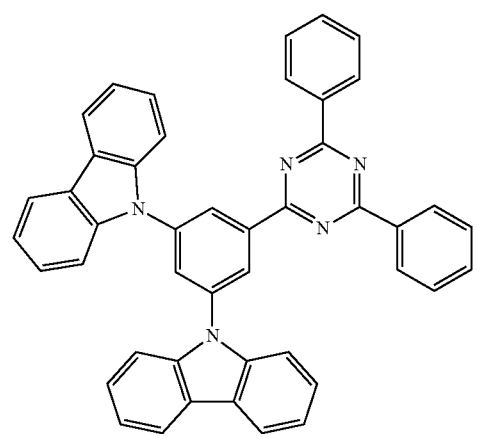
H38
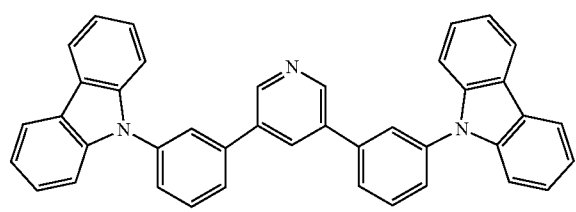
H39
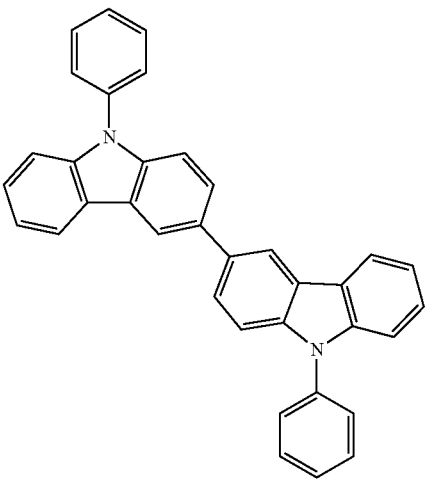
H40
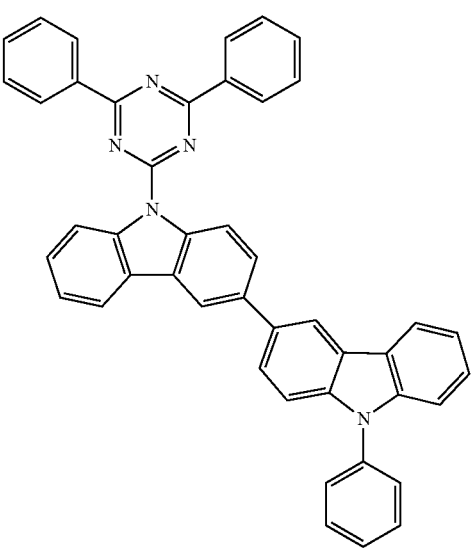
H41
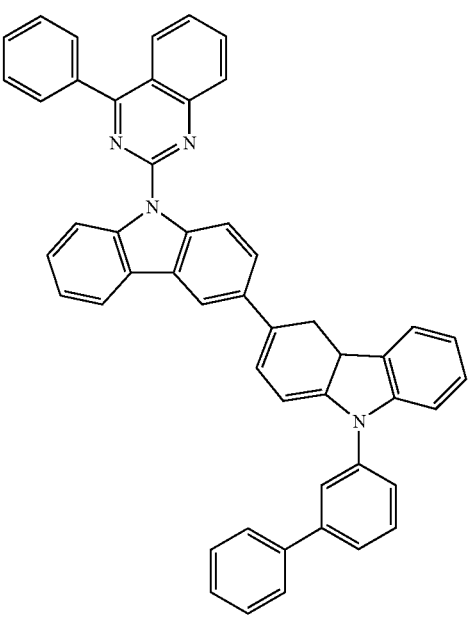

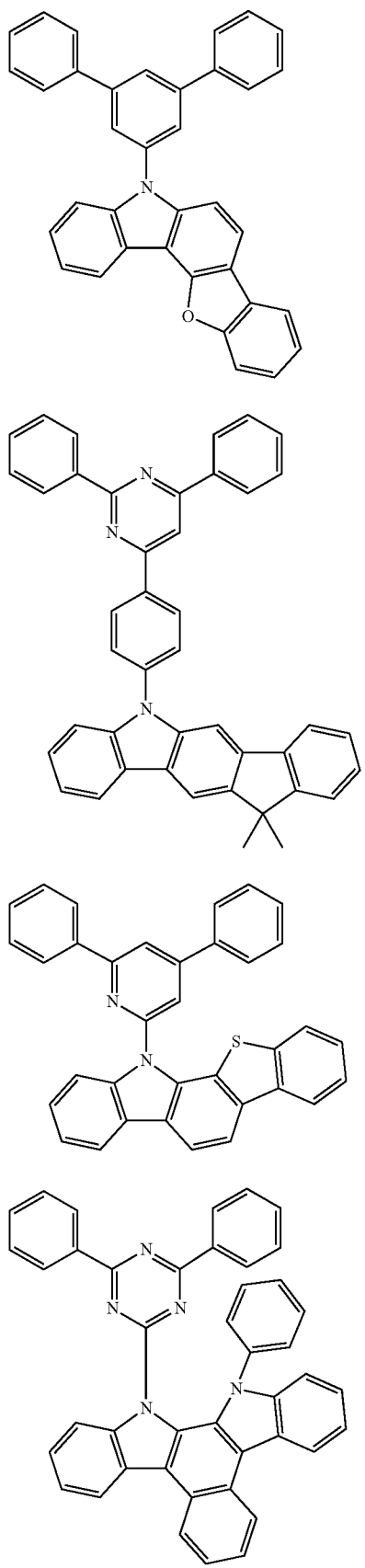
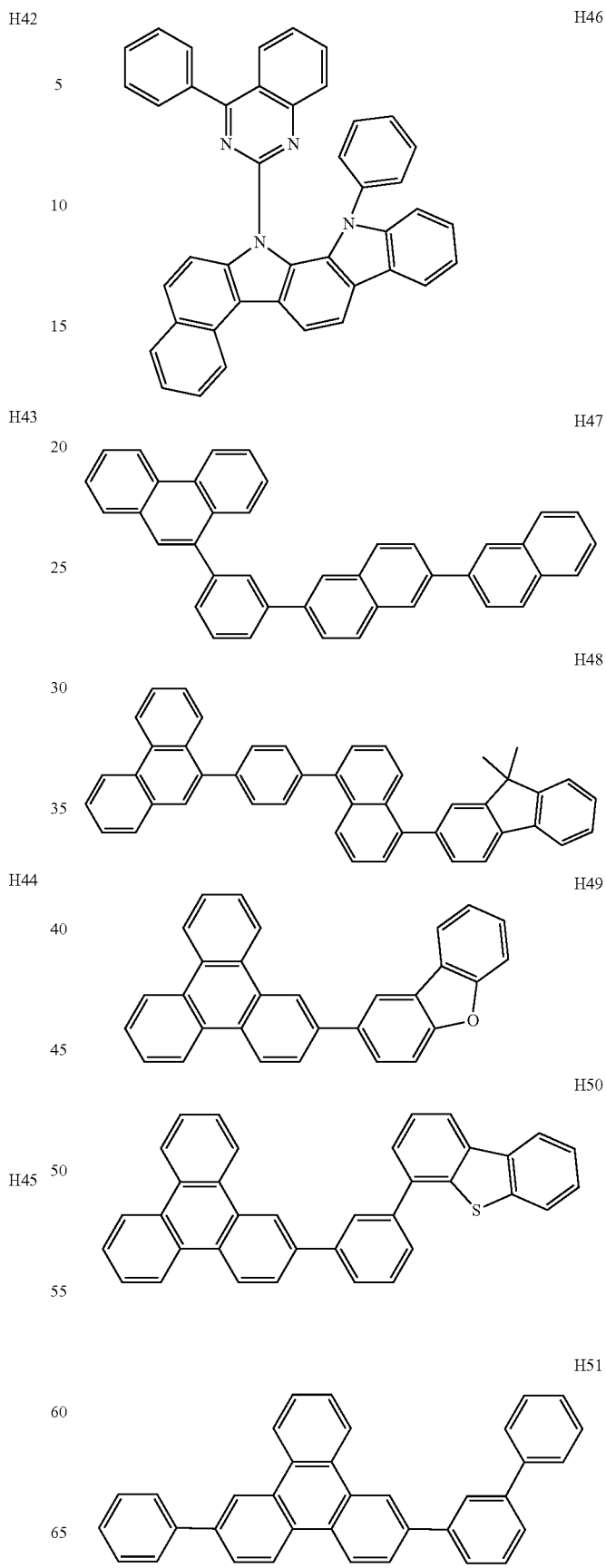

H52
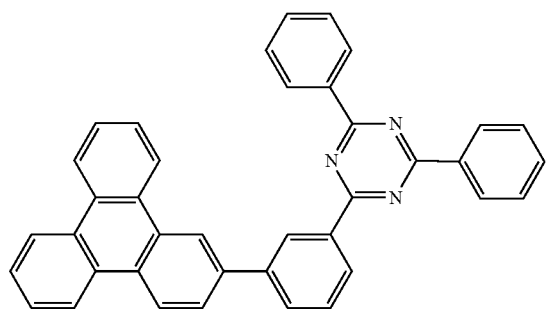
H53
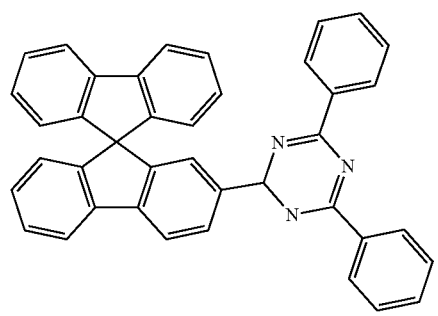
H54
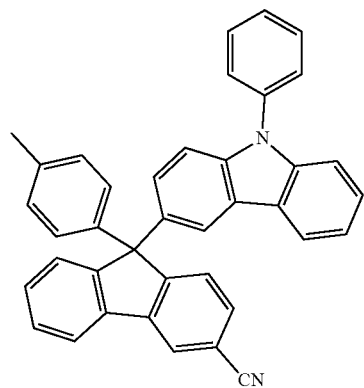
H55
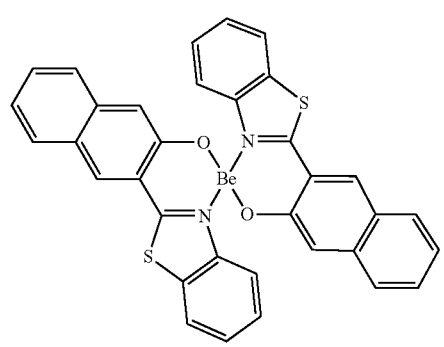
H56
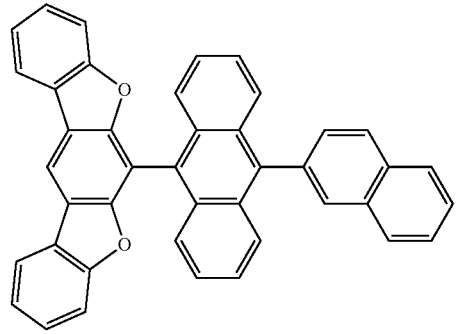
H57
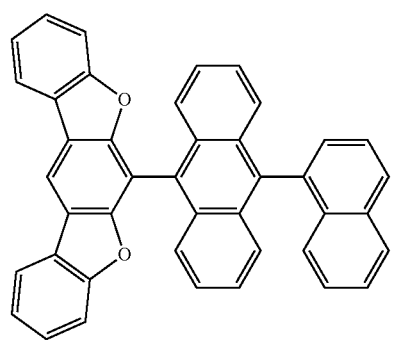
H58
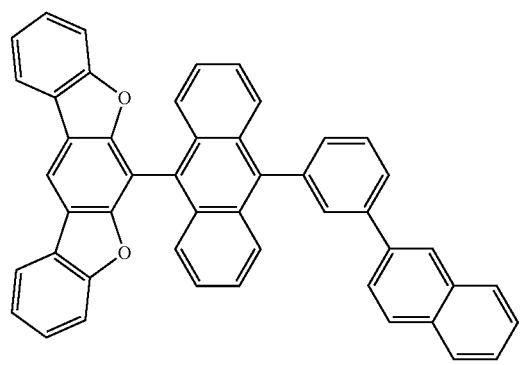
H59
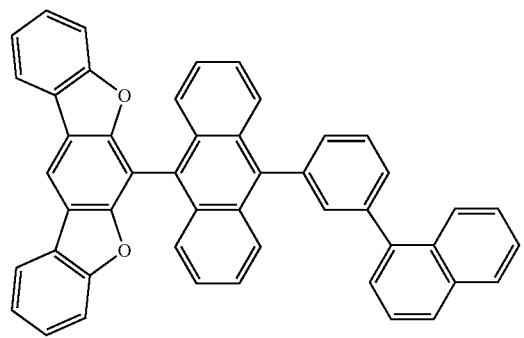

H60
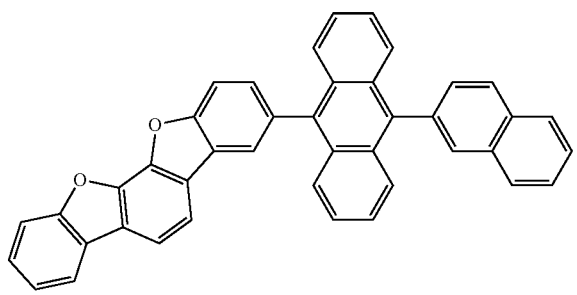
H61
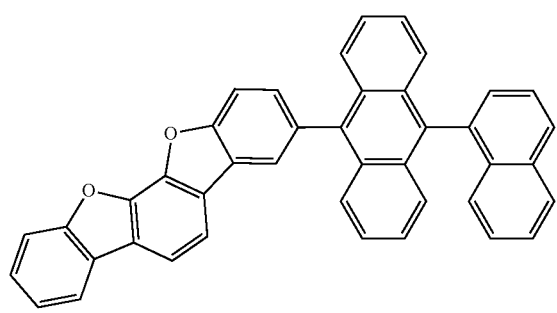
H62
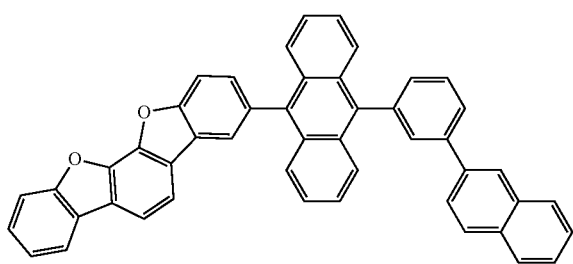
H63
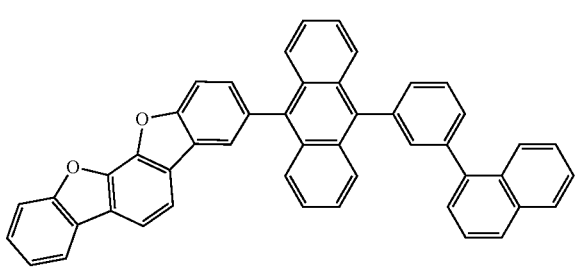
H64
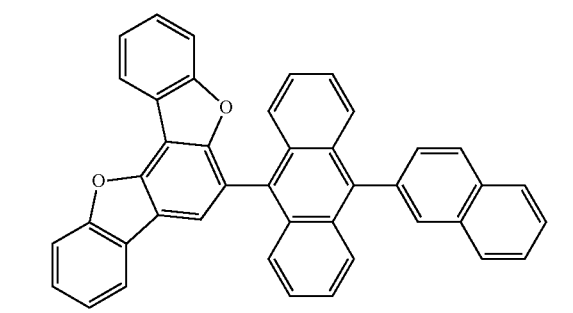
H65
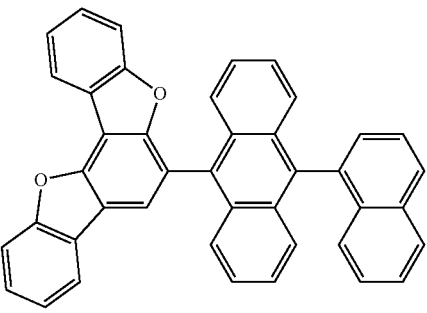
H66
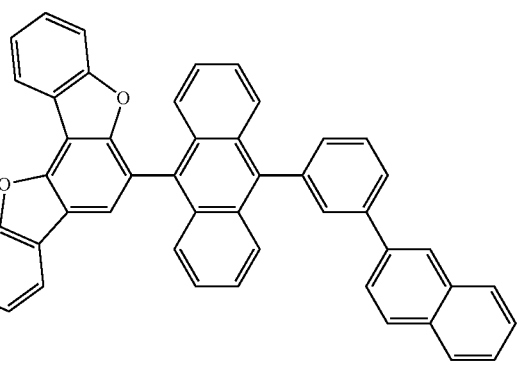
H67
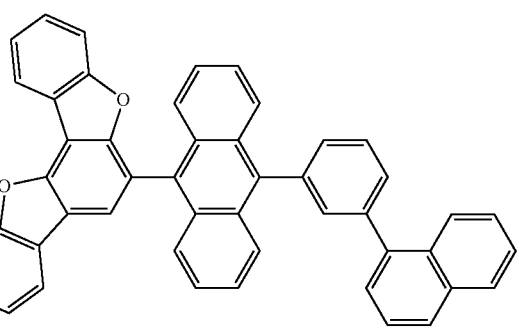
H68
H69
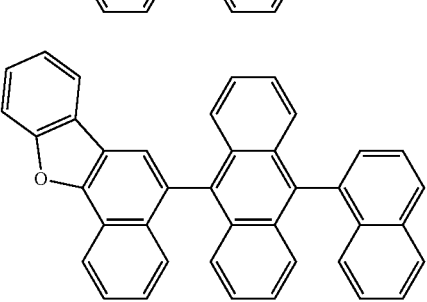

H70
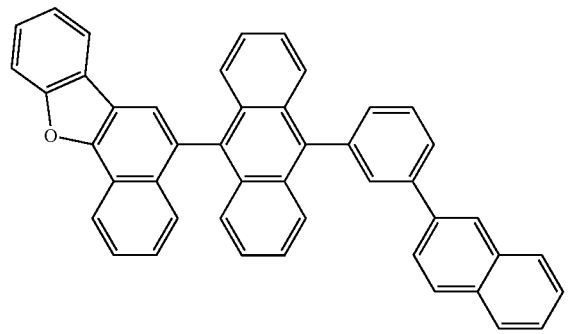
H71
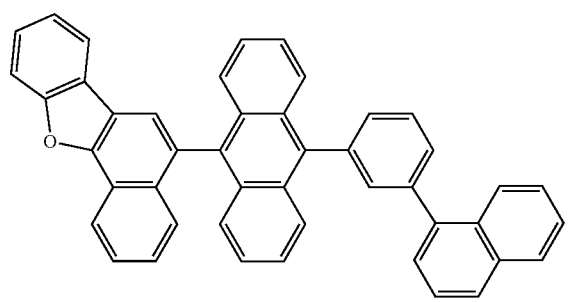
H72
H73
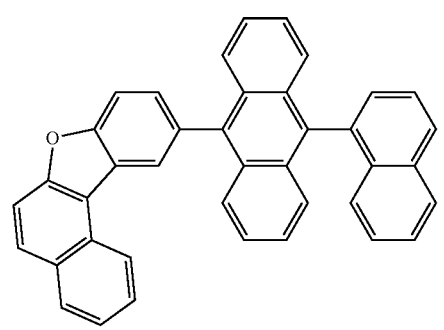
H74
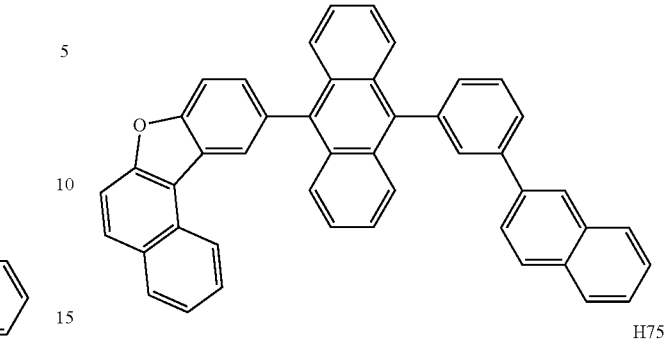
H75
H76
H77
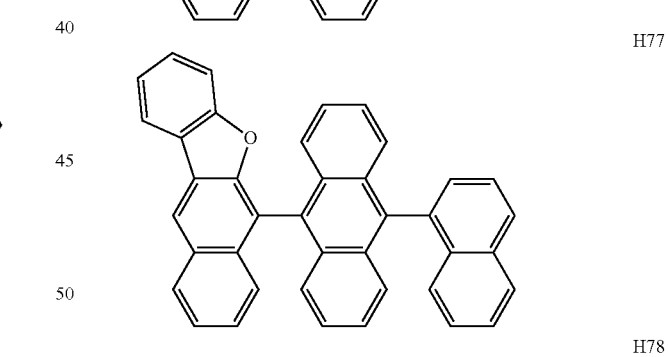
H78
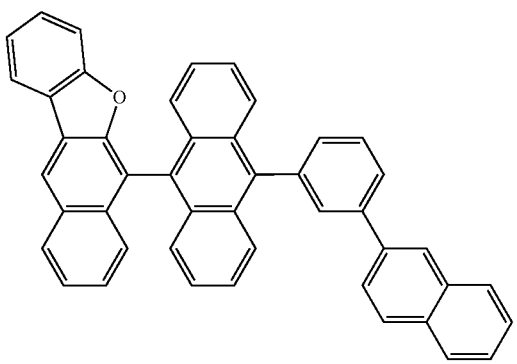

-continued
H79
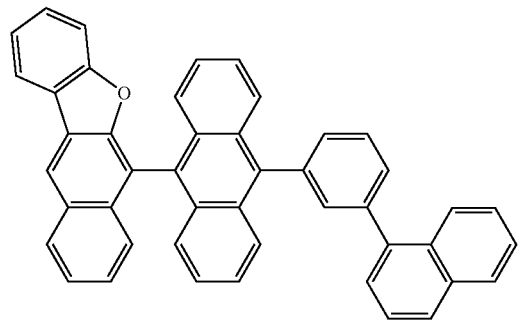
H80
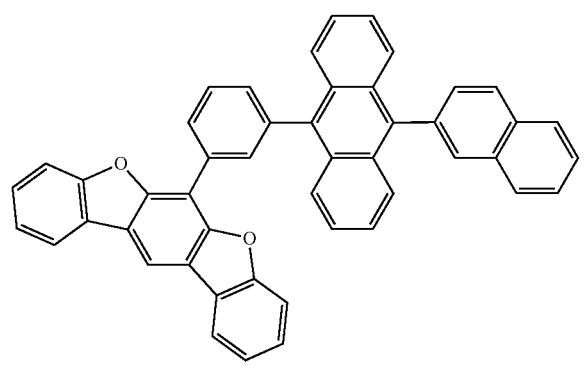
H81
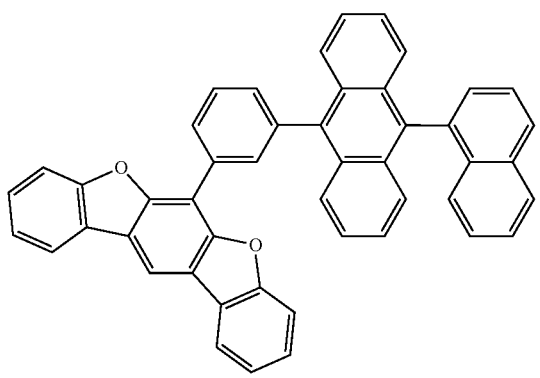
H82
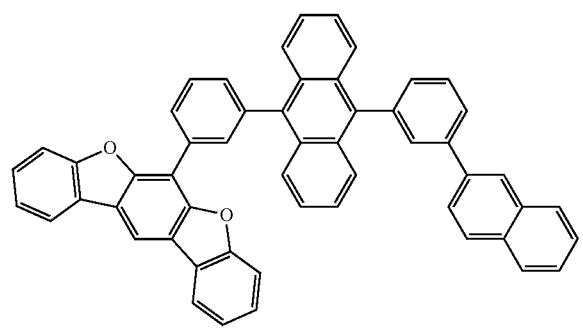
-continued
H83
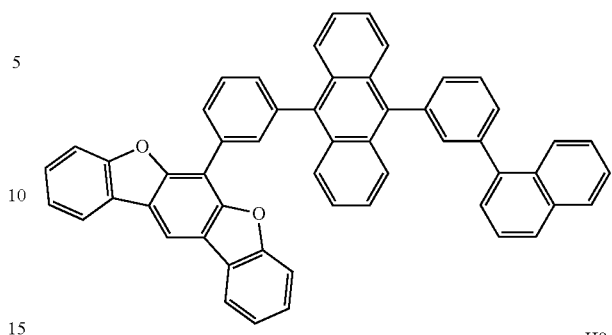
H84
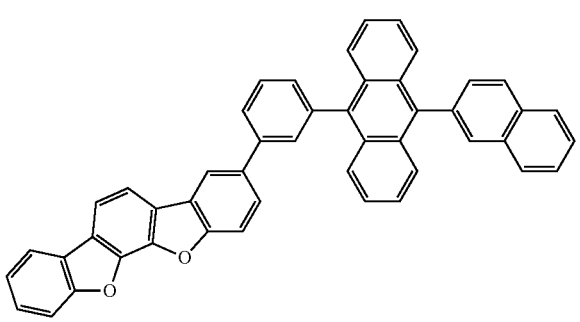
H85
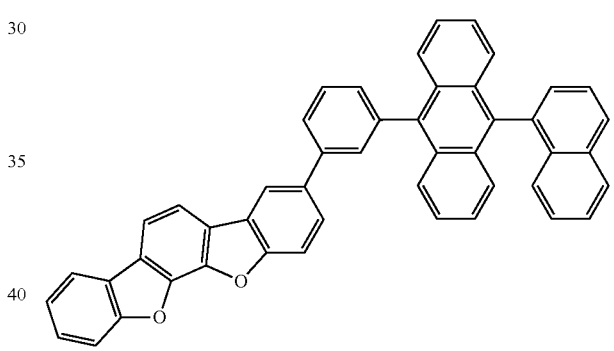
H86
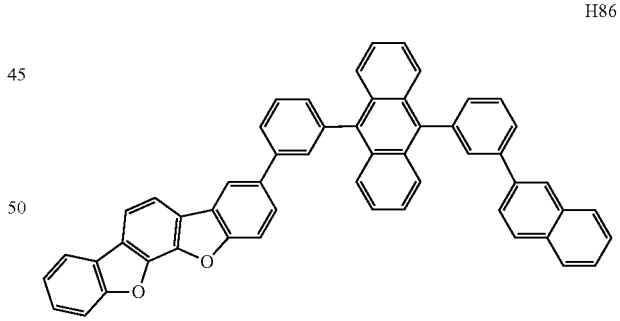
H87
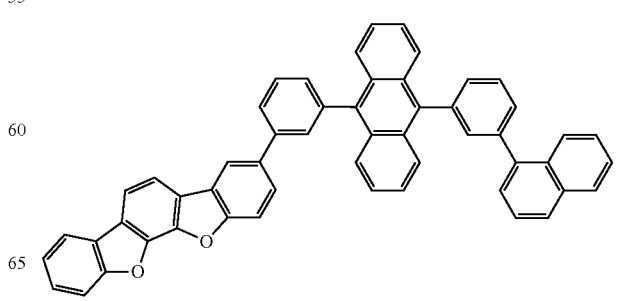

H88
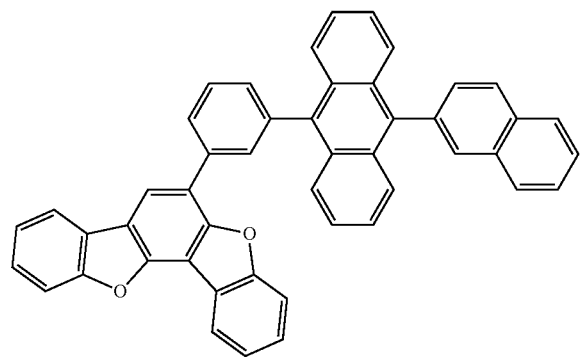
H89
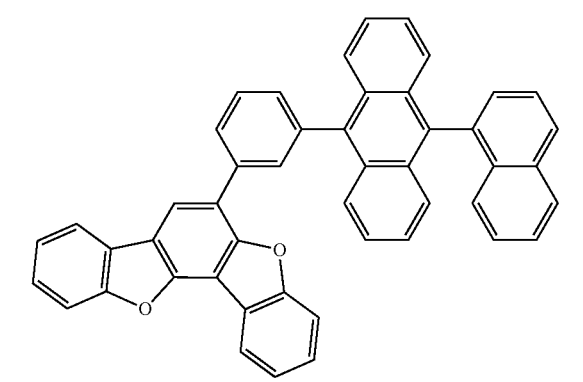
H90
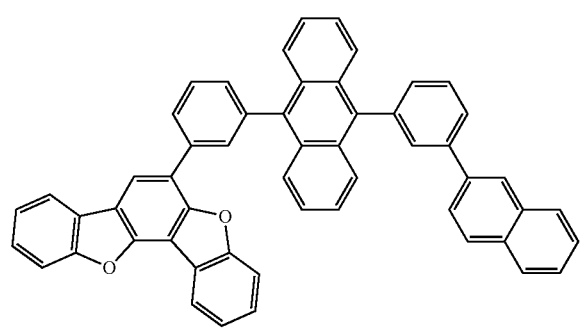
H91
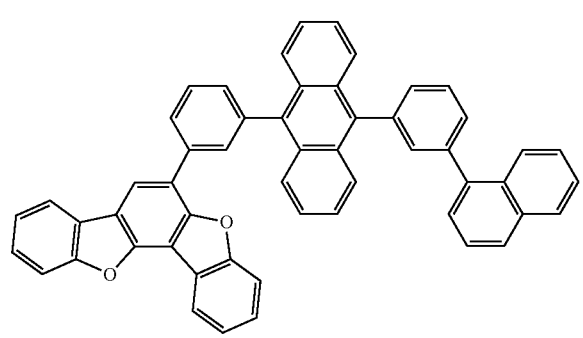
H92
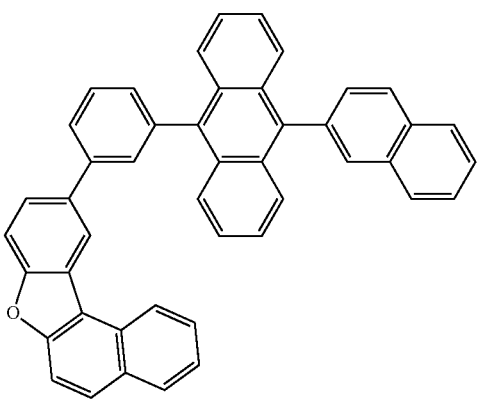
H93
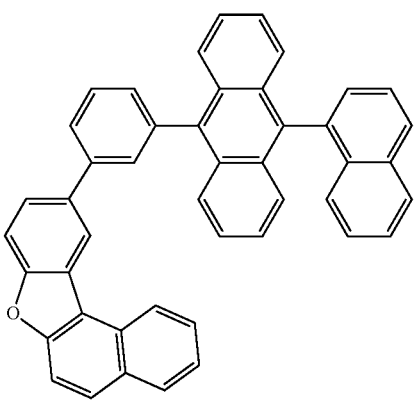
H94
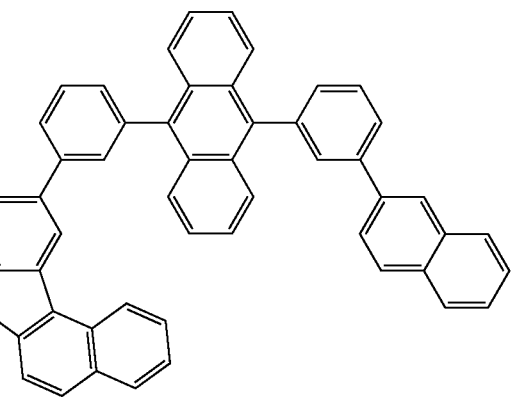
H95
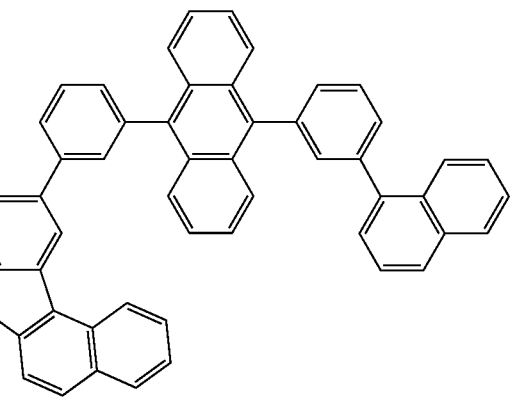

H96
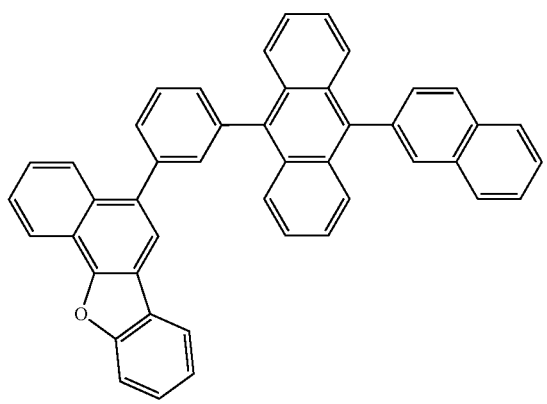
H97
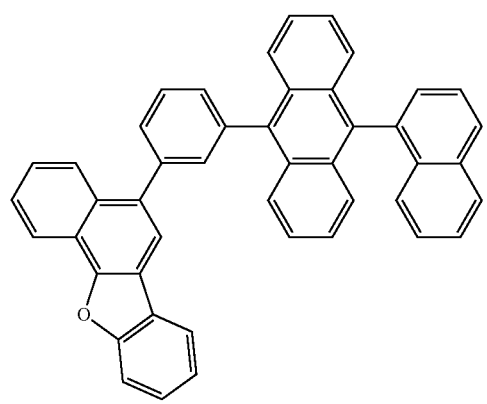
H98
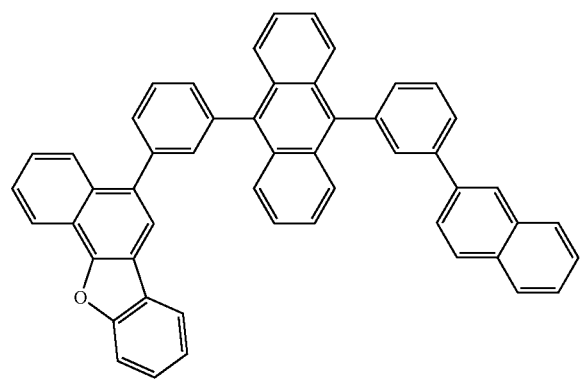
H99
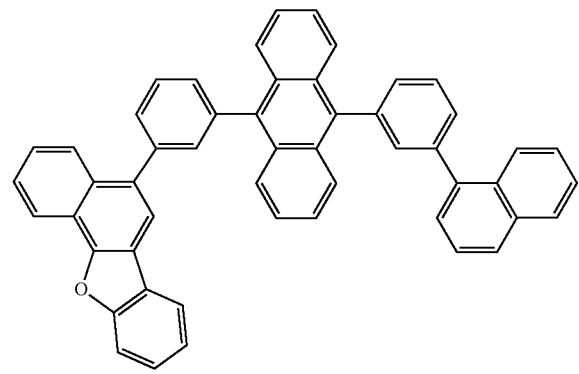
H100
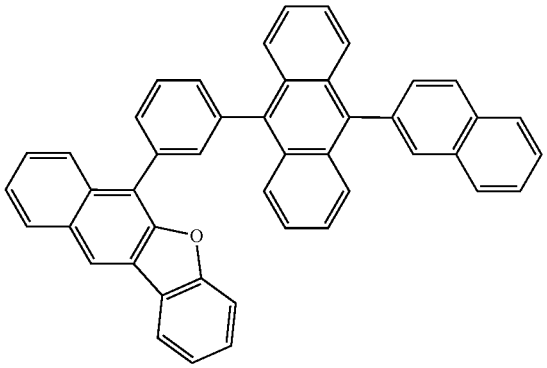
H101
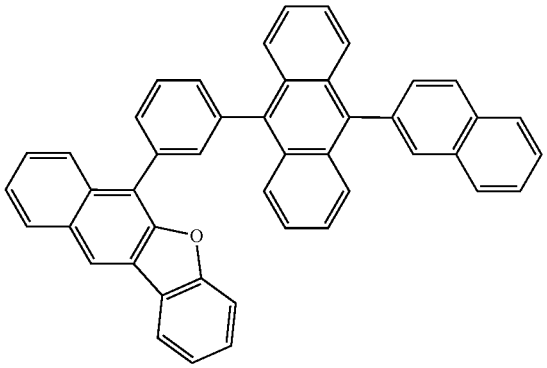
H102
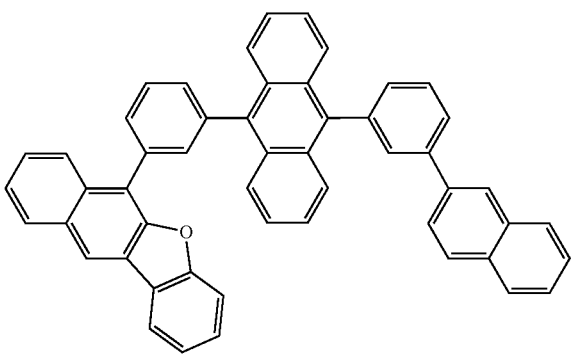
H103
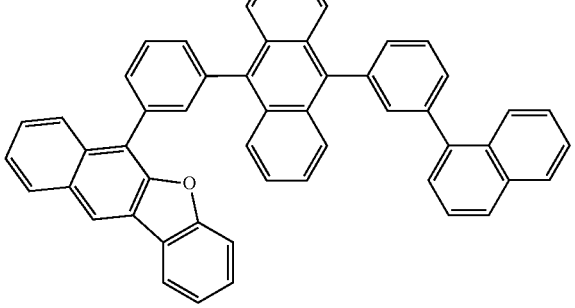

H104
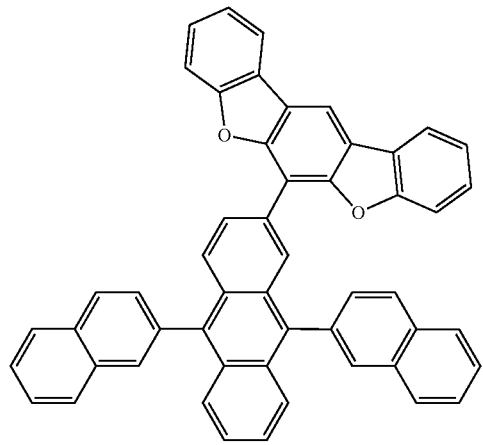
H105
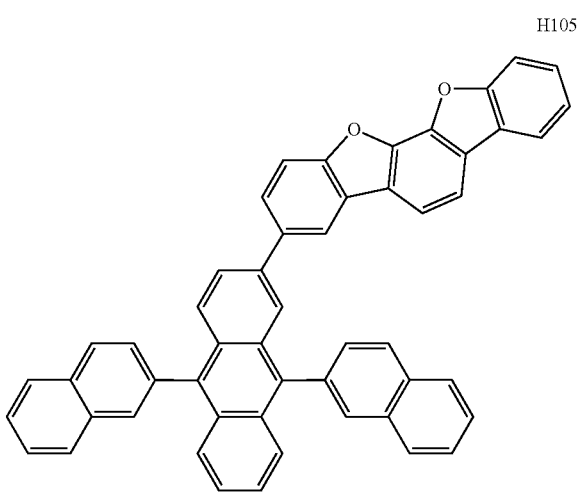
H106
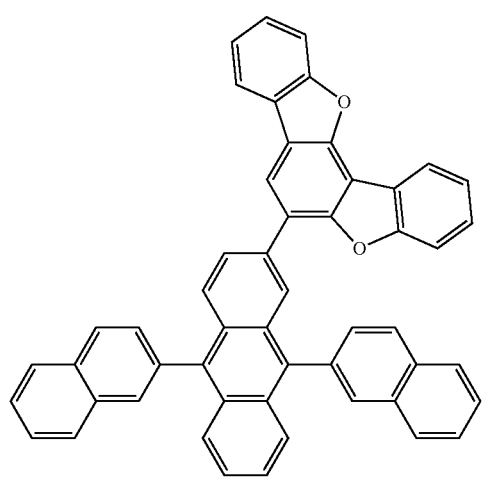
H107
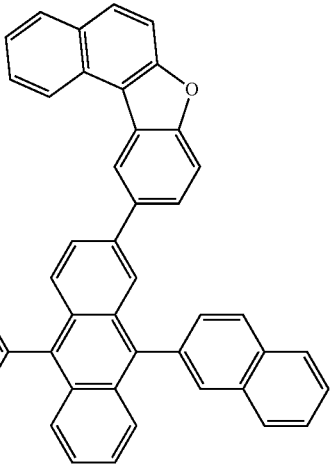
H108
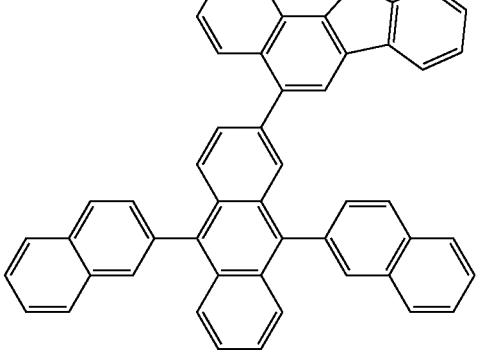
H109
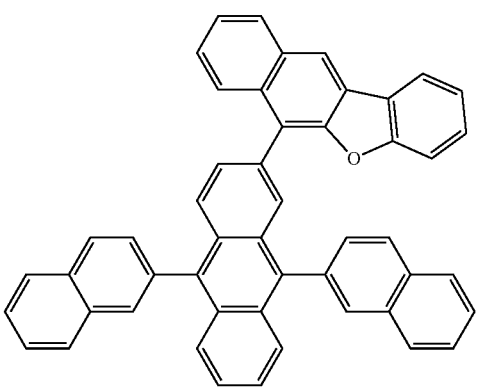
H110
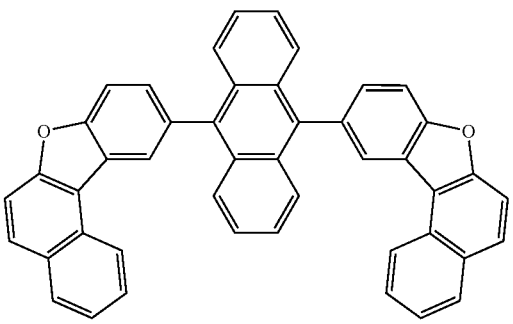

H111
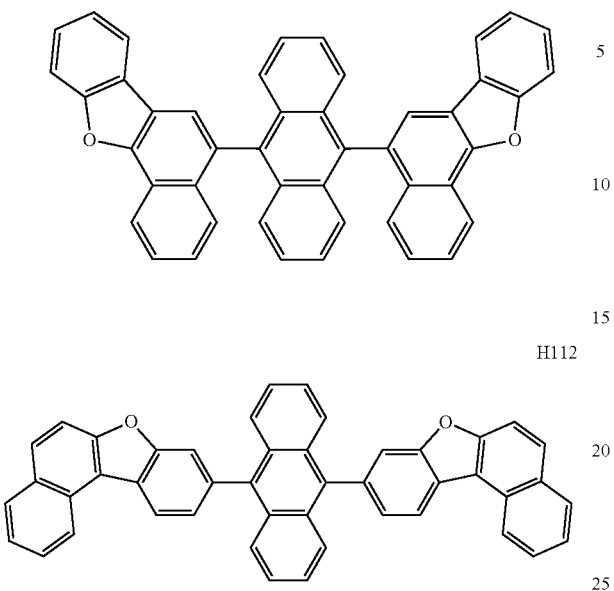
H112
H113
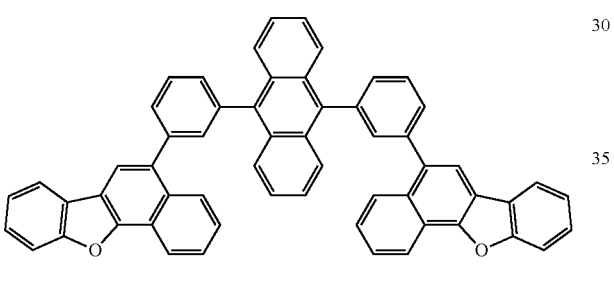
H114
H115
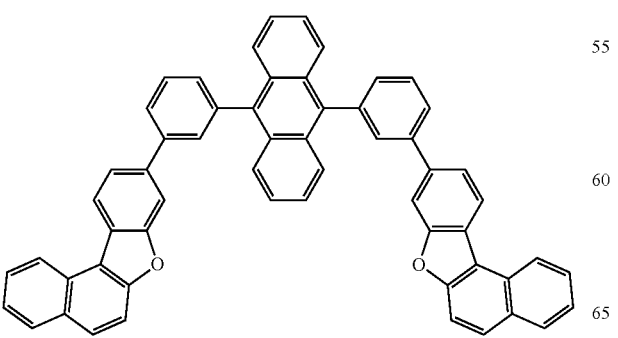
H116
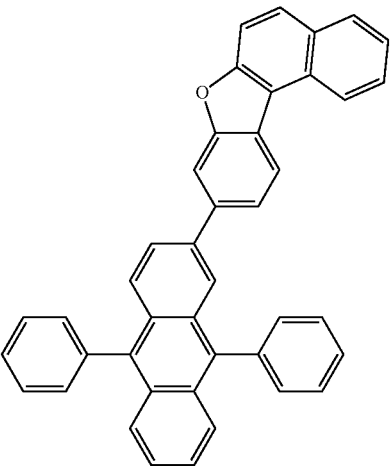
H117
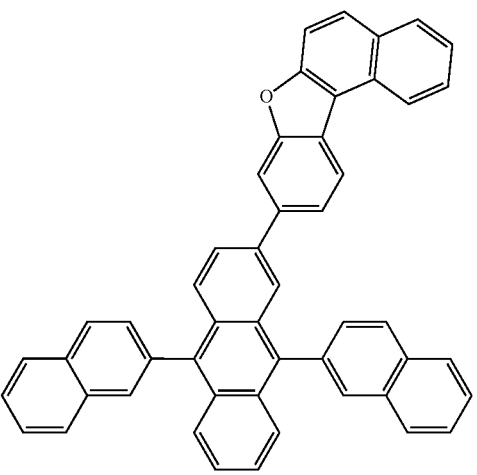
H118
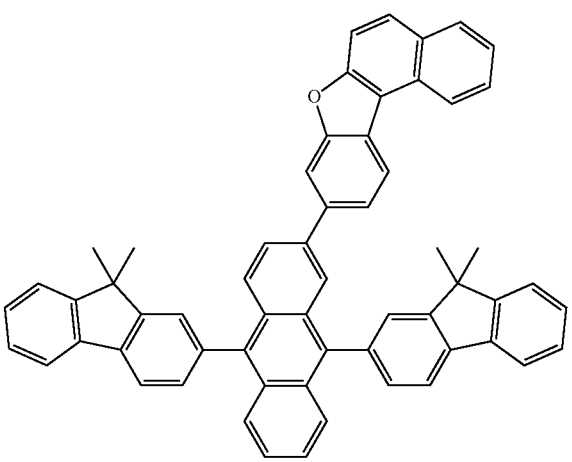

-continued

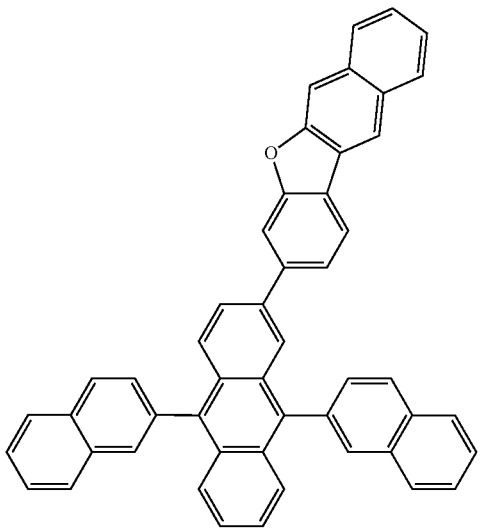

H119

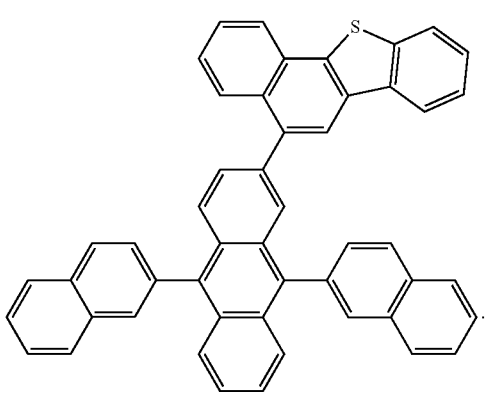

H120

Phosphorescent Dopant

The phosphorescent dopant may include at least one transition metal as a central metal.

The phosphorescent dopant may include one or more of a monodentate ligand, a bidentate ligand, a tridentate ligand, a tetradentate ligand, a pentadentate ligand, a hexadentate ligand, or any combination thereof.

The phosphorescent dopant may be electrically neutral (e.g., may not be charged).

For example, the phosphorescent dopant may include an organometallic compound represented by Formula 401:

$$M\ (L_{401})_{xc1}(L_{402})_{xc2}$$ Formula 401

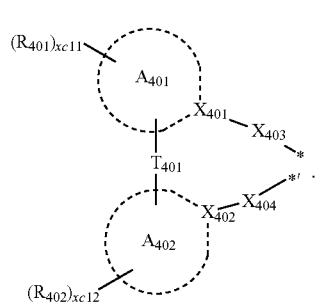

Formula 402

In Formulae 401 and 402,

M may be transition metal (for example, iridium (Ir), platinum (Pt), palladium (Pd), osmium (Os), titanium (Ti), gold (Au), hafnium (Hf), europium (Eu), terbium (Tb), rhodium (Rh), rhenium (Re), or thulium (Tm)), $L_{401}$ may be a ligand represented by Formula 402, and xc1 may be 1, 2, or 3, wherein, when xc1 is 2 or more, the two or more $L_{401}$(s) may be identical to or different from each other, $L_{402}$ may be an organic ligand, xc2 may be 0, 1, 2, 3, or 4, and when xc2 is 2 or more, the two or more $L_{402}$(s) may be identical to or different from each other, $X_{401}$ and $X_{402}$ may each independently be nitrogen or carbon, ring $A_{401}$ and ring $A_{402}$ may each independently be a $C_5$-$C_{60}$ carbocyclic group or a $C_1$-$C_{60}$ heterocyclic group, $T_{401}$ may be a single bond, —O—, —S—, —C(=O)—, —N($Q_{411}$)-, —C($Q_{411}$)($Q_{412}$)-, —C($Q_{411}$)=C($Q_{412}$)-, —C($Q_{411}$)=, or =C($Q_{411}$)=, $X_{403}$ and $X_{404}$ may each independently be a chemical bond (for example, a covalent bond or a coordinate bond), O, S, N($Q_{413}$), B($Q_{413}$), P($Q_{413}$), C($Q_{413}$)($Q_{414}$), or Si($Q_{413}$)($Q_{414}$), $Q_{411}$ to $Q_{414}$ may each independently be the same as described in connection with $Q_1$, $R_{401}$ and $R_{402}$ may each independently be hydrogen, deuterium, —F, —Cl, —Br, —I, a hydroxyl group, a cyano group, a nitro group, a $C_1$-$C_{20}$ alkyl group unsubstituted or substituted with at least one $R_{10a}$, a $C_1$-$C_{20}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), or —P(=O)($Q_{401}$)($Q_{402}$), $Q_{401}$ to $Q_{403}$ may each independently be the same as described in connection with $Q_1$, xc11 and xc12 may each independently be an integer from 0 to 10, and

* and *' in Formula 402 each indicate a binding site to M in Formula 401.

In an embodiment, in Formula 402, i) $X_{401}$ may be nitrogen, and $X_{402}$ may be carbon, or ii) both $X_{401}$ and $X_{402}$ may (e.g., simultaneously) be nitrogen.

In an embodiment, when xc1 in Formula 402 is 2 or more, two ring $A_{401}$(s) in two or more $L_{401}$(s) may optionally be linked to each other via $T_{402}$, which is a linking group, or two ring $A_{402}$(s) in two or more $L_{401}$(s) may optionally be linked to each other via $T_{403}$, which is a linking group (see Compounds PD1 to PD4 and PD7). $T_{402}$ and $T_{403}$ may each independently be the same as described in connection with $T_{401}$.

$L_{402}$ in Formula 401 may be an organic ligand. For example, $L_{402}$ may be a halogen group, a diketone group (for example, an acetylacetonate group), a carboxylic acid group (for example, picolinate group), —C(=O), an isonitrile group, a —CN group, a phosphorus group (for example, a phosphine group or a phosphite group), or any combination thereof.

The phosphorescent dopant may include, for example, one of Compounds PD1 to PD25 or any combination thereof:

PD1
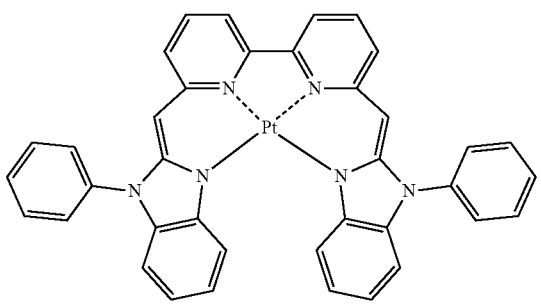
PD2
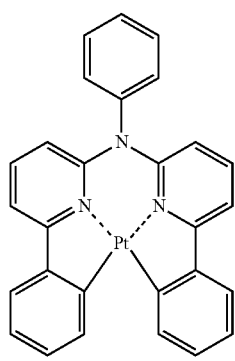
PD3
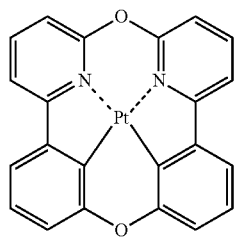
PD4
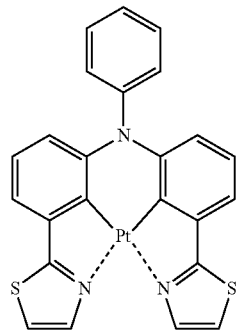
PD5
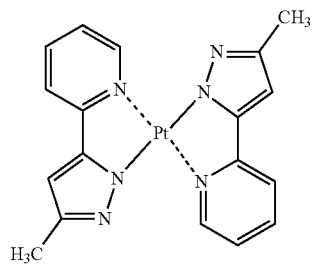
PD6
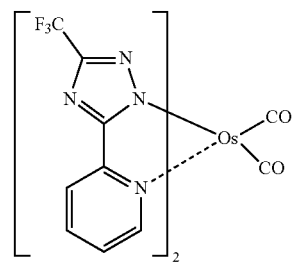
PD7
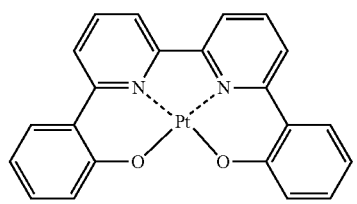
PD8
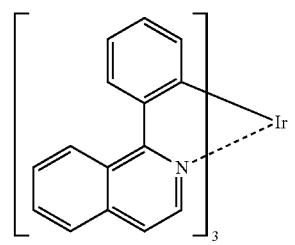
PD9
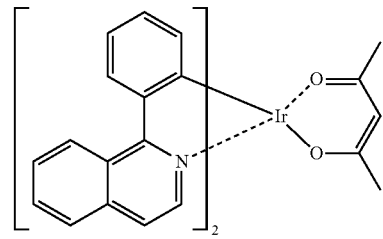
PD10
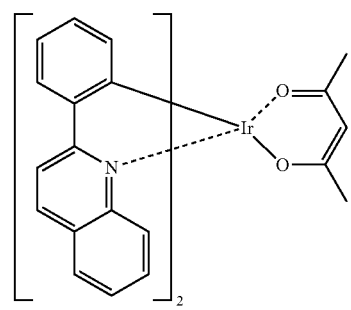
PD11
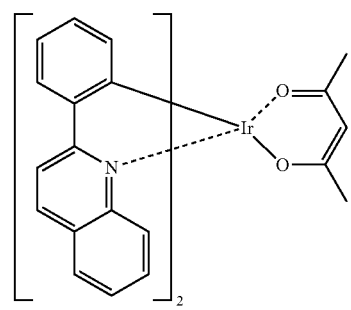

PD12 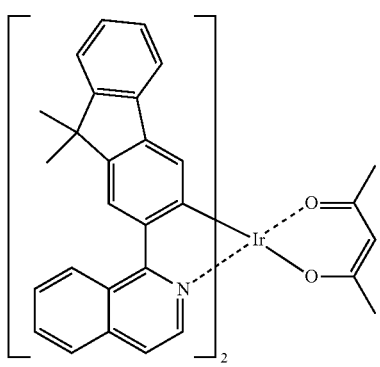
PD13 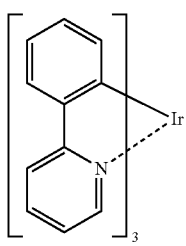
PD14 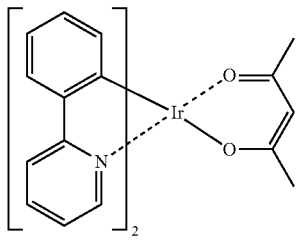
PD15 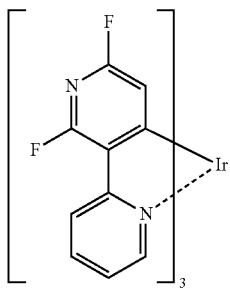
PD16 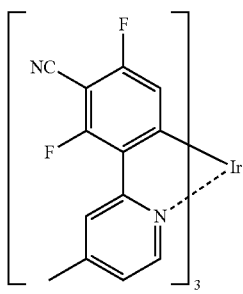
PD17 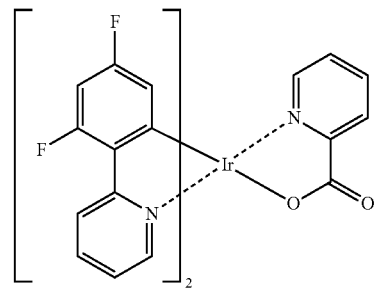
PD18 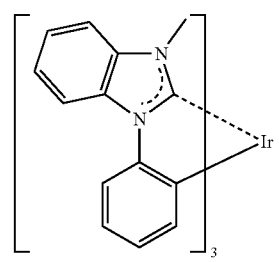
PD19 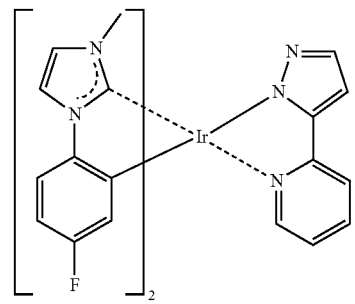
PD20 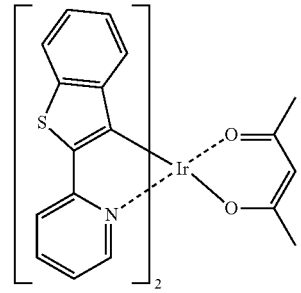
PD21 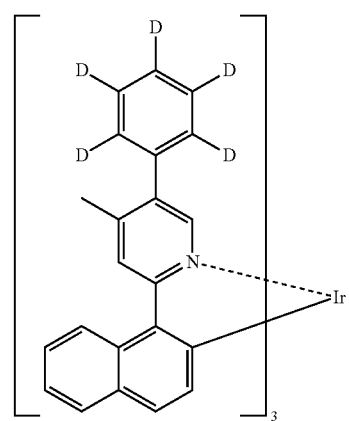

PD22
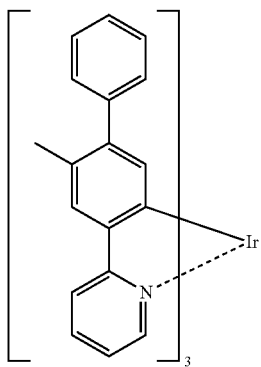

PD23
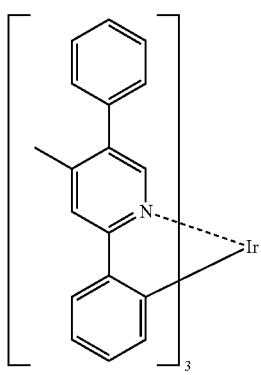

PD24
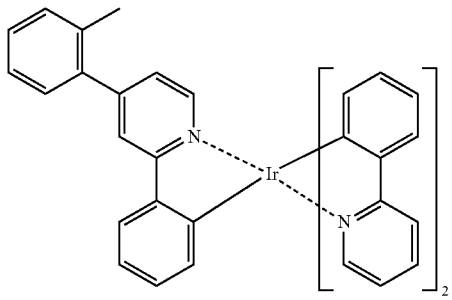

PD25
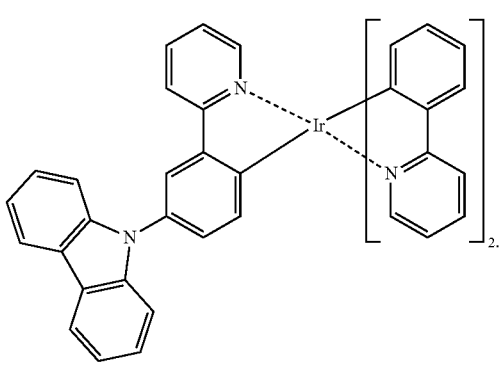

Fluorescent Dopant

The fluorescent dopant may include an amine group-containing compound, a styryl group-containing compound, or any combination thereof.

For example, the fluorescent dopant may include a compound represented by Formula 501:

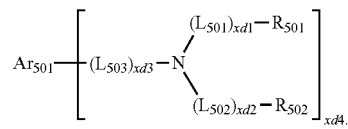

Formula 501

In Formula 501, $Ar_{501}$, $L_{501}$ to $L_{503}$, $R_{501}$, and $R_{502}$ may each independently be a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, xd1 to xd3 may each independently be 0, 1, 2, or 3, and xd4 may be 1, 2, 3, 4, 5, or 6.

In an embodiment, in Formula 501, $Ar_{501}$ may include a condensed cyclic group (for example, an anthracene group, a chrysene group, or a pyrene group) in which three or more monocyclic groups are condensed.

In an embodiment, xd4 in Formula 501 may be 2.

In an embodiment, the fluorescent dopant may include: one of Compounds FD1 to FD36; DPVBi; DPAVBi; or any combination thereof:

FD1
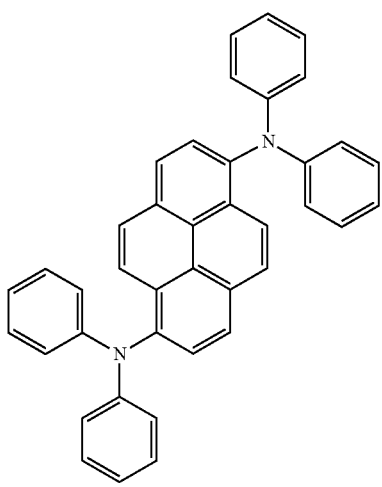

FD2
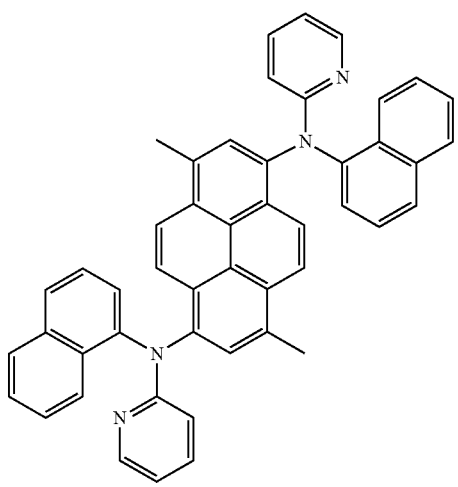

117
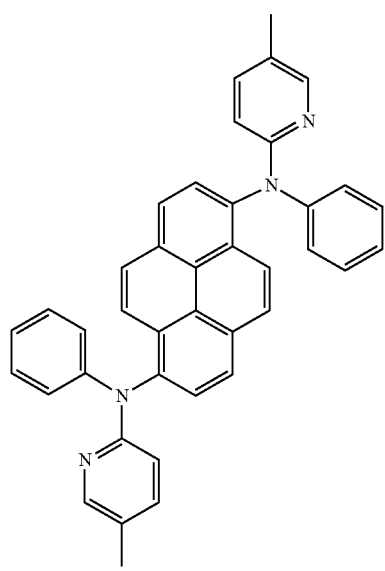
-continued
FD3
118
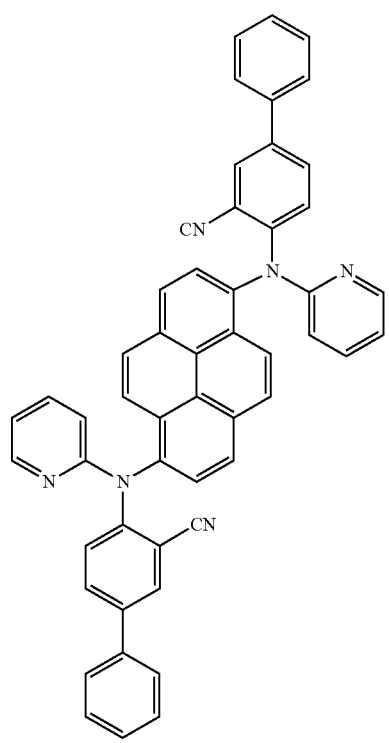
FD4
FD5
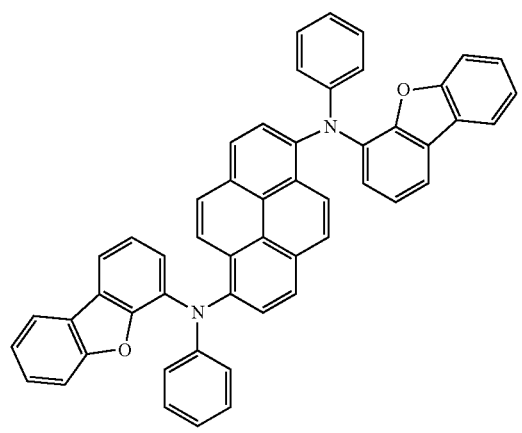
FD6
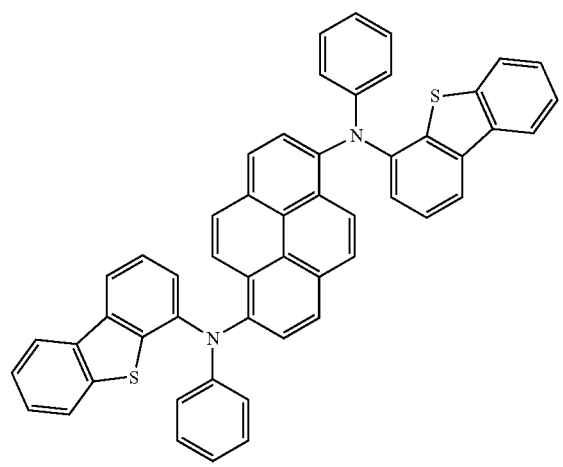

-continued
FD7
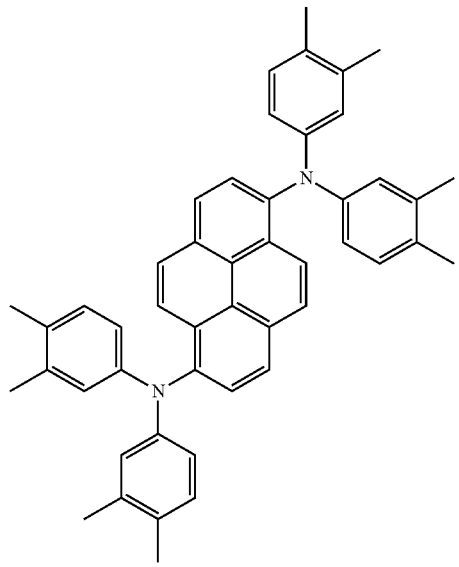
FD8
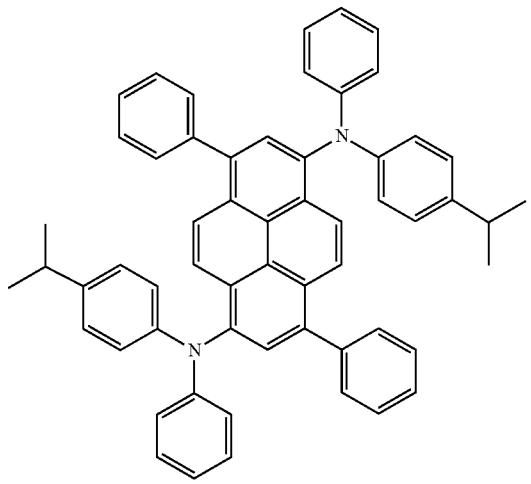
FD9
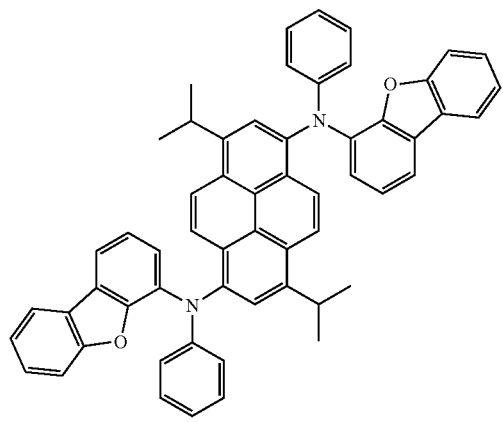
FD10
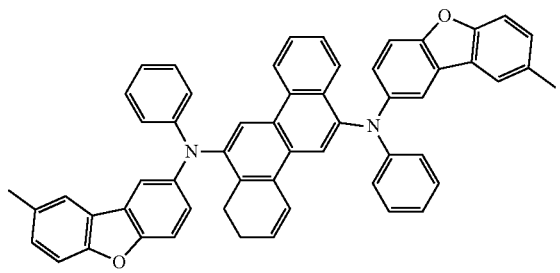
FD11
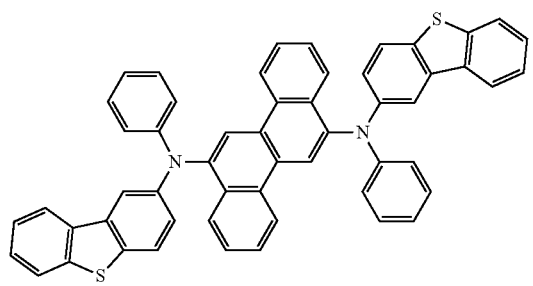
FD12
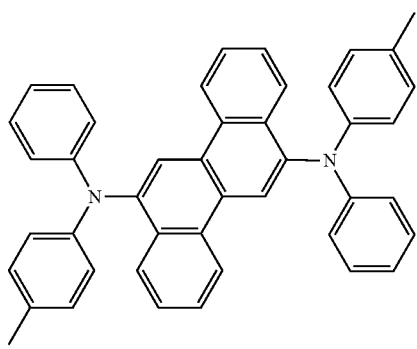

-continued
FD13 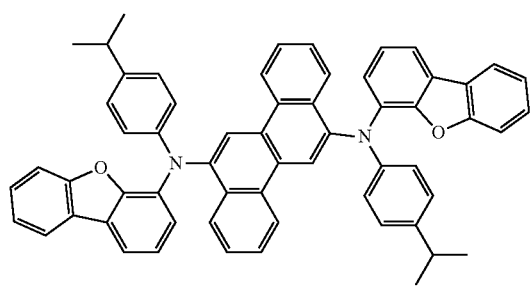 FD14 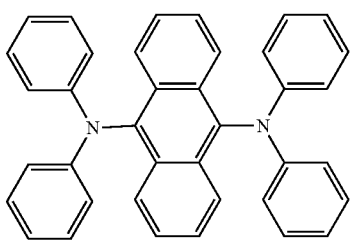
FD15 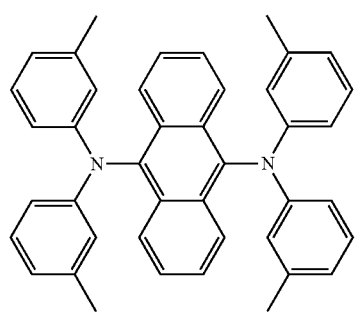 FD16 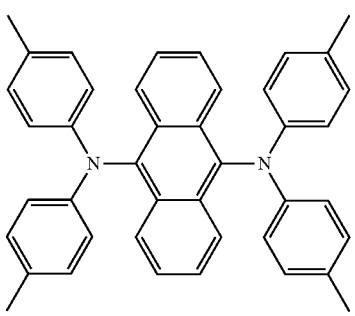
FD17 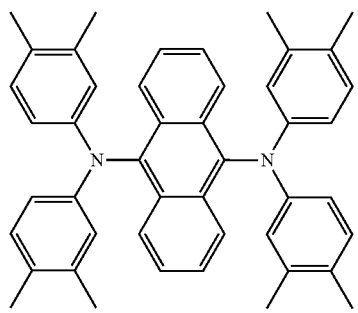 FD18 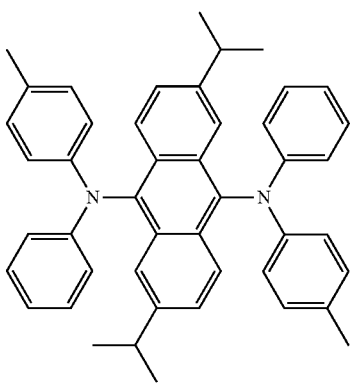
FD19 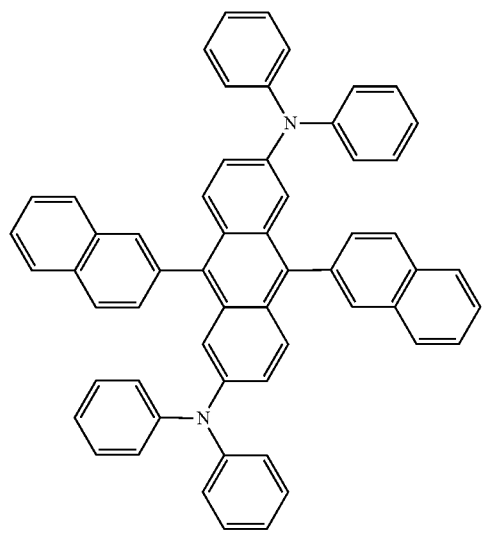 FD20 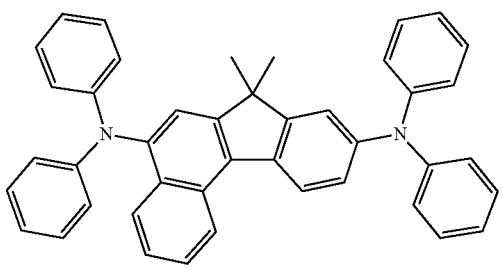

-continued
FD21
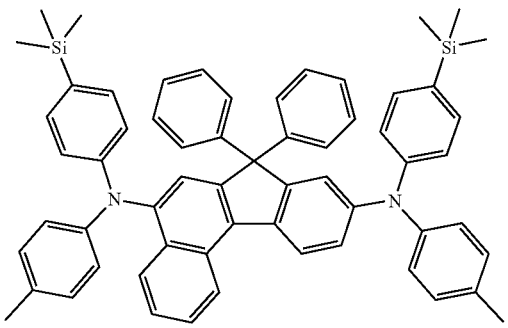
FD22
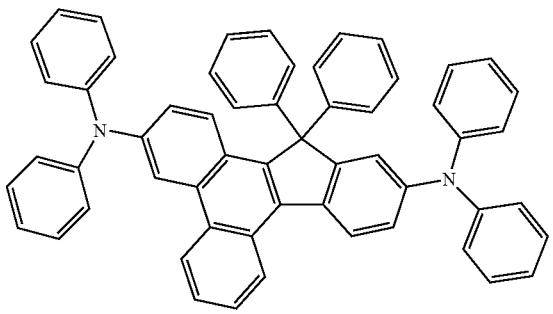
FD23
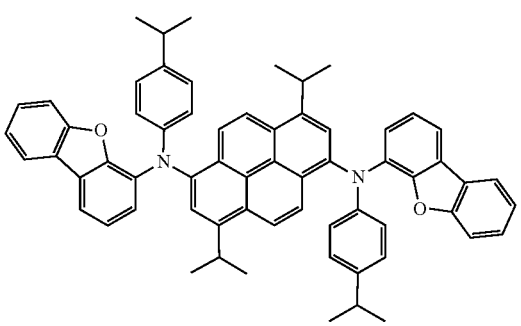
FD24
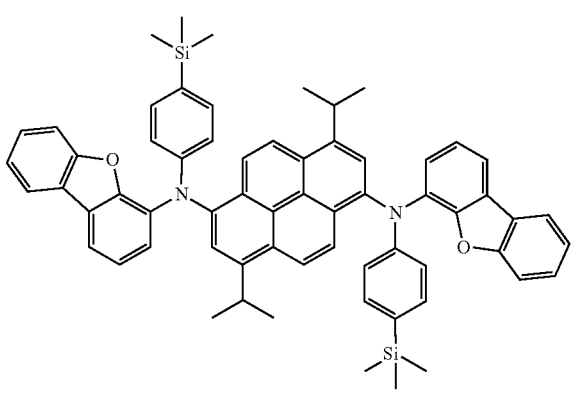
FD25
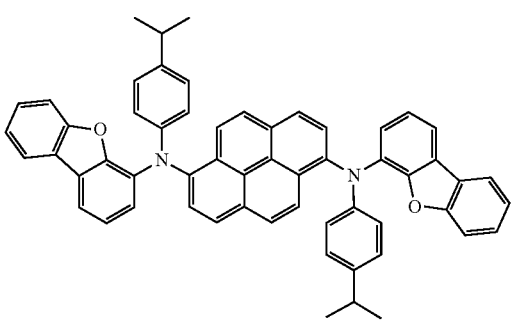
FD26
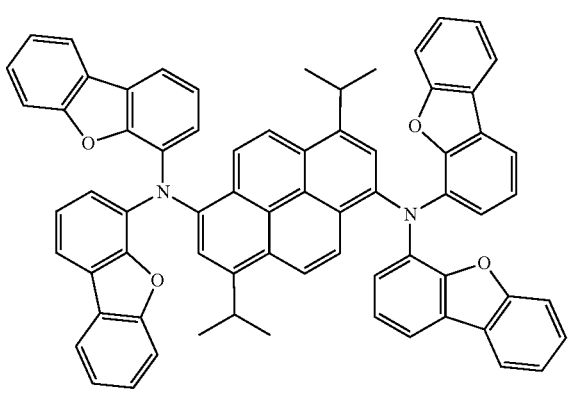
FD27
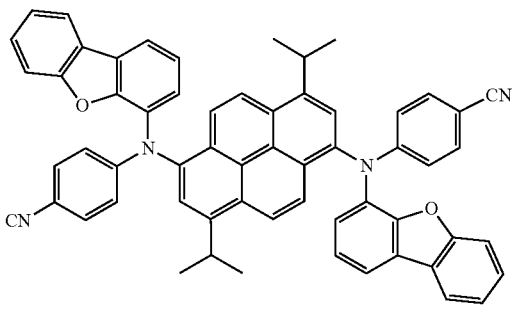
FD28
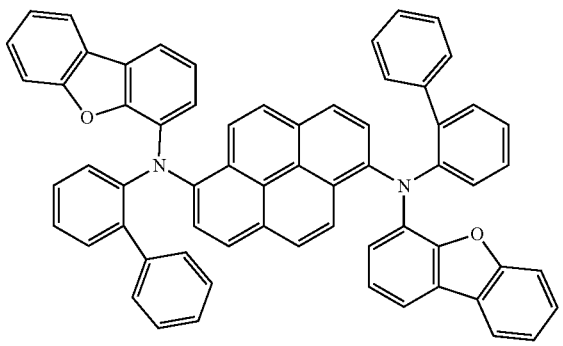

-continued
FD29
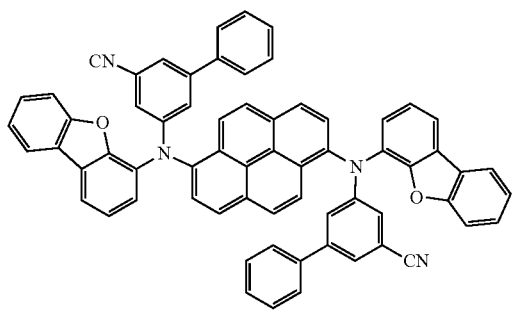
FD30
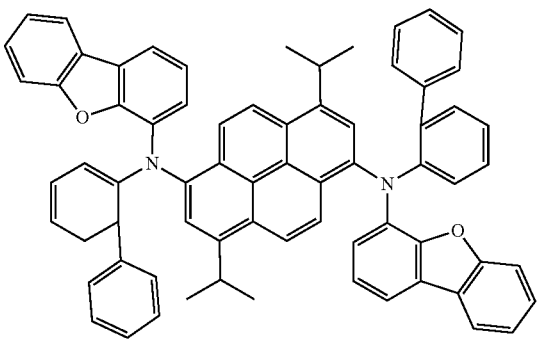
FD31
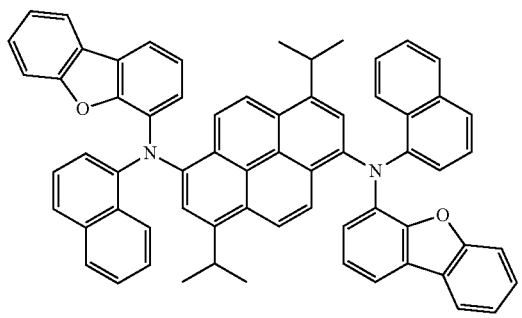
FD32
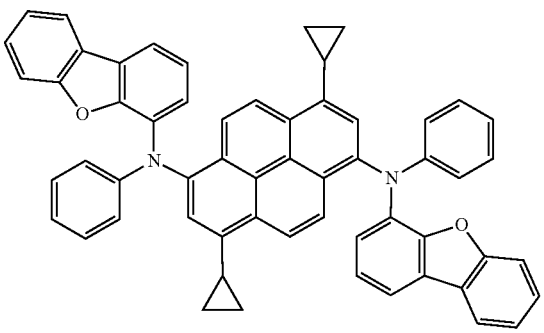
FD33
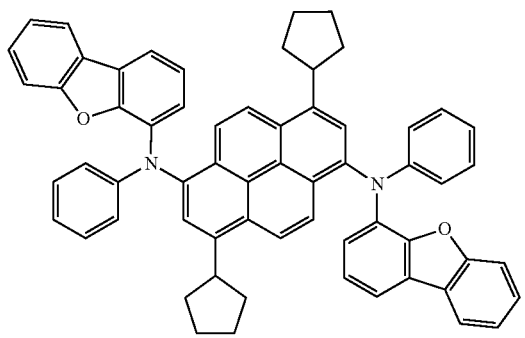
FD34
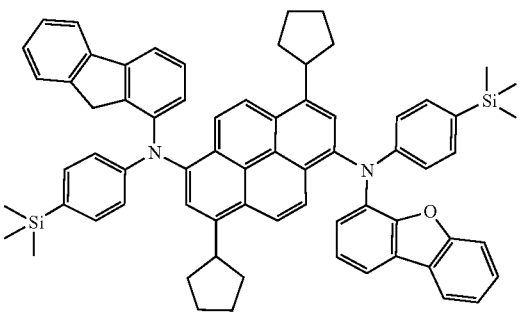
FD35
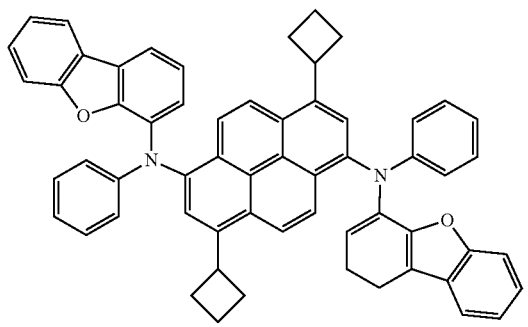
FD36
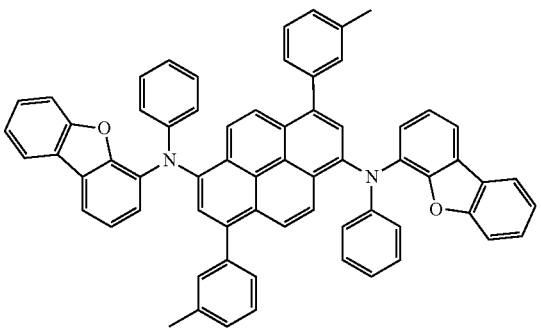

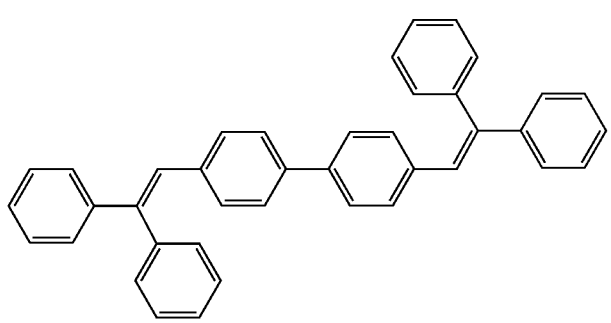

DPVBi

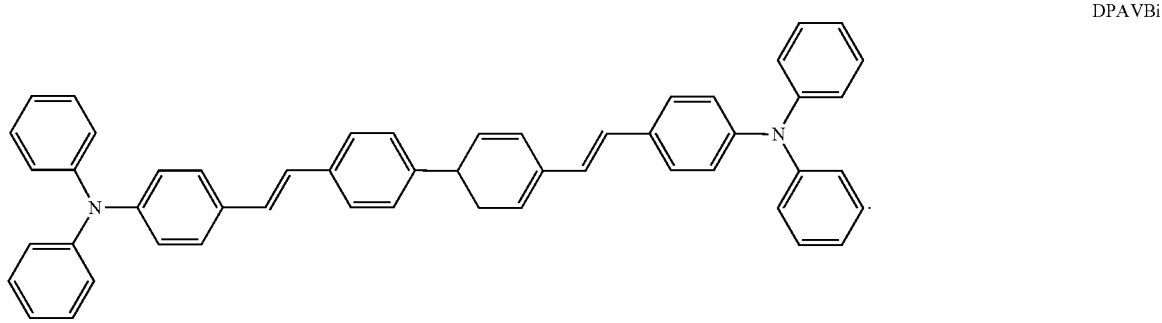

DPAVBi

Delayed Fluorescence Material

The emission layer may include a delayed fluorescence material.

The delayed fluorescence material in the present specification may be selected from a compound configured to emit delayed fluorescence according to a delayed fluorescence emission mechanism.

The delayed fluorescence material included in the emission layer may act as a host or a dopant, depending on the other materials included in the emission layer.

In an embodiment, a difference between a triplet energy level (eV) of the delayed fluorescence material and a singlet energy level (eV) of the delayed fluorescence material may be greater than or equal to about 0 eV and less than or equal to about 0.5 eV. When the difference between a triplet energy level (eV) of the delayed fluorescence material and a singlet energy level (eV) of the delayed fluorescence material satisfies the above-described range, up-conversion from a triplet state to a singlet state in the delayed fluorescence material may be effectively performed, such that the luminescence efficiency of the light-emitting device 10 may be improved.

For example, the delayed fluorescence material may include: i) a material including at least one electron donor (for example, a π-electron-rich $C_3$-$C_{60}$ cyclic group, such as a carbazole group) and at least one electron acceptor (for example, a sulfoxide group, a cyano group, and a π-electron-deficient nitrogen-containing $C_1$-$C_{60}$ cyclic group), or ii) a material including a $C_8$-$C_{60}$ polycyclic group including two or more cyclic groups that are condensed while sharing boron (B) (e.g., with a boron atom therebetween).

Non-limiting examples of the delayed fluorescence material may include at least one of Compounds DF1 to DF9:

DF1(DMAC-DPS)

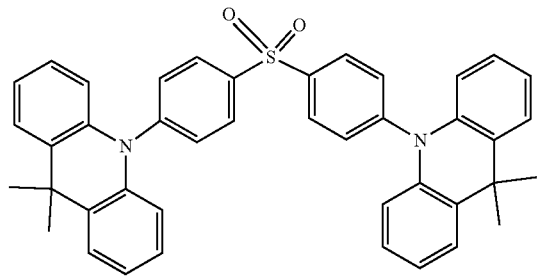

DF2(ACRFLCN)

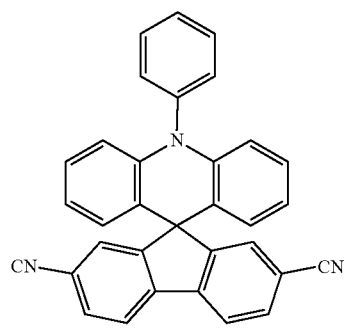

-continued

DF3(ACRSA)

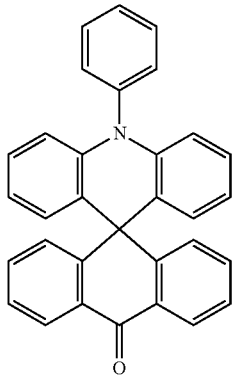

DF4(CC2TA)

DF5(PIC-TRZ)

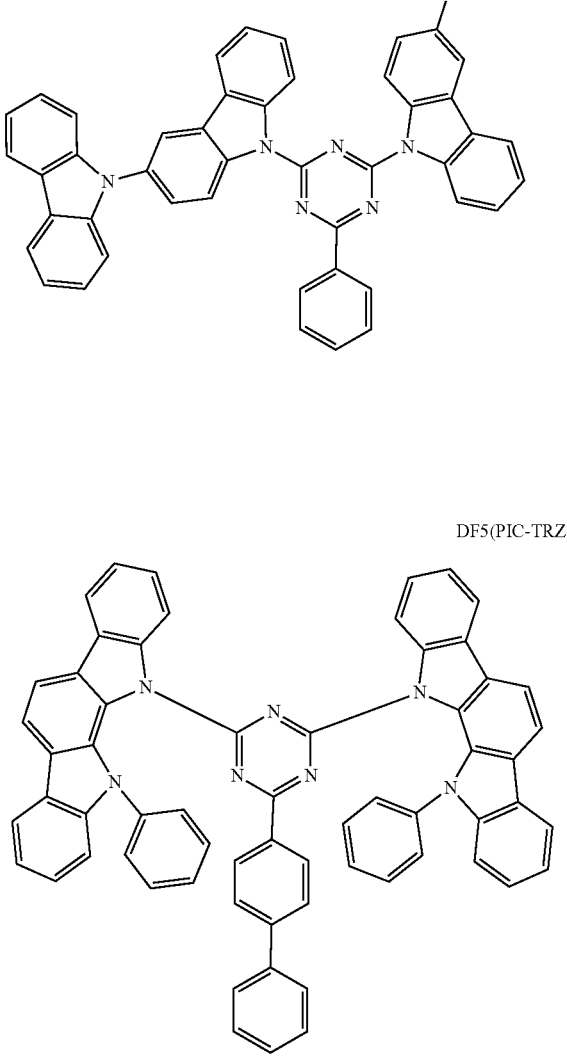

-continued

DF6(PIC-TRZ2)

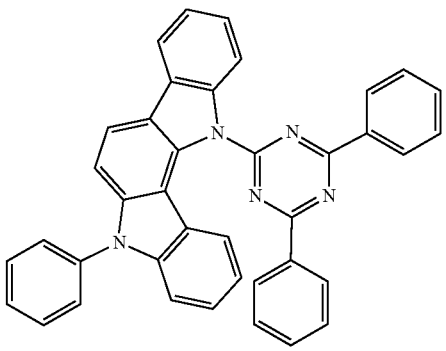

DF7(PXZ-TRZ)

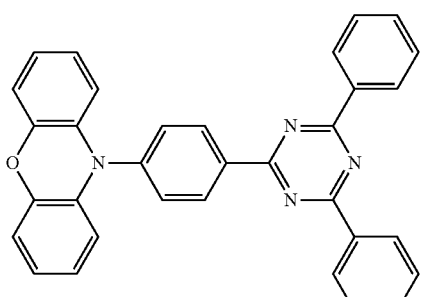

DF8(DABNA-1)

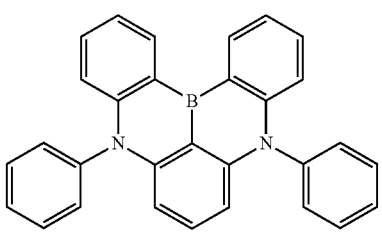

DF9(DABNA-2)

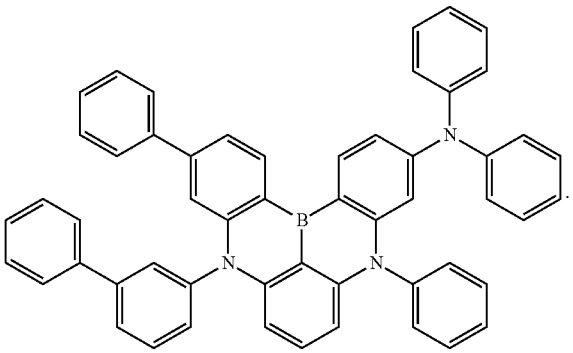

Electron Transport Region in Interlayer 130

The electron transport region may have: i) a single-layered structure consisting of a single material, ii) a single-layered structure consisting of a plurality of different materials, or iii) a multi-layered structure including a plurality of layers including different materials.

The electron transport region may include a hole blocking layer, an electron transport layer, an electron injection layer, or any combination thereof, but embodiments of the present disclosure are not limited thereto.

For example, the electron transport region may have an electron transport layer/electron injection layer structure or a hole blocking layer/electron transport layer/electron injection layer structure, wherein the constituting layers of each structure are sequentially stacked from the emission layer. However, embodiments of the structure of the electron transport region are not limited thereto.

The electron transport region (for example, the hole blocking layer and/or an electron transport layer) may include a metal-free (organic) compound including at least one π-electron-deficient nitrogen-containing $C_1$-$C_{60}$ cyclic group.

For example, the electron transport region may include a compound represented by Formula 601:

[Ar$_{601}$]$_{xe11}$-[(L$_{601}$)$_{xe1}$-R$_{601}$]$_{xe21}$.  Formula 601

In Formula 601,
Ar$_{601}$ and L$_{601}$ may each independently be a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$,
xe11 may be 1, 2, or 3,
xe1 may be 0, 1, 2, 3, 4, or 5,
$R_{601}$ may be a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si(Q$_{601}$)(Q$_{602}$)(Q$_{603}$), —C(=O)(Q$_{601}$), —S(=O)$_2$(Q$_{601}$), or —P(=O)(Q$_{601}$)(Q$_{602}$),
$Q_{601}$ to $Q_{603}$ may each independently be the same as described in connection with $Q_1$,
xe21 may be 1, 2, 3, 4, or 5, and
at least one of Ar$_{601}$, L$_{601}$, and R$_{601}$ may each independently be a π-electron-deficient nitrogen-containing $C_1$-$C_{60}$ cyclic group unsubstituted or substituted with at least one $R_{10a}$.

In an embodiment, when xe11 in Formula 601 is 2 or more, two or more Ar$_{601}$(s) may be linked to each other via a single bond.

In an embodiment, Ar$_{601}$ in Formula 601 may be a substituted or unsubstituted anthracene group.

In an embodiment, the electron transport region may include a compound represented by Formula 601-1:

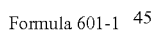

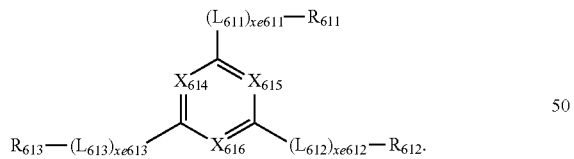

Formula 601-1

In Formula 601-1,
$X_{614}$ may be N or C(R$_{614}$), $X_{615}$ may be N or C(R$_{615}$), $X_{616}$ may be N or C(R$_{616}$), and at least one of $X_{614}$ to $X_{616}$ may be N,
$L_{611}$ to $L_{613}$ may each independently be the same as described in connection with $L_{601}$,
xe611 to xe613 may each independently be the same as described in connection with xe1
$R_{611}$ to $R_{613}$ may each independently be the same as described in connection with $R_{601}$, and
$R_{614}$ to $R_{616}$ may each independently be hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$.

For example, in Formulae 601 and 601-1, xe1 and xe611 to xe613 may each independently be 0, 1, or 2.

The electron transport region may include one of Compounds ET1 to ET45, 2,9-dimethyl-4,7-diphenyl-1,10-phenanthroline (BCP), 4,7-diphenyl-1,10-phenanthroline (Bphen), Alq$_3$, BAlq, TAZ, NTAZ, or any combination thereof:

ET1

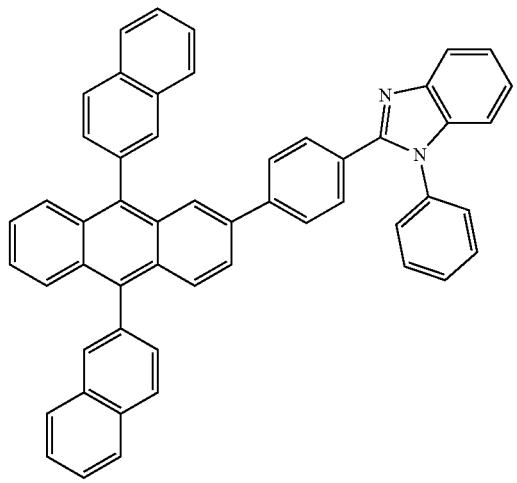

ET2

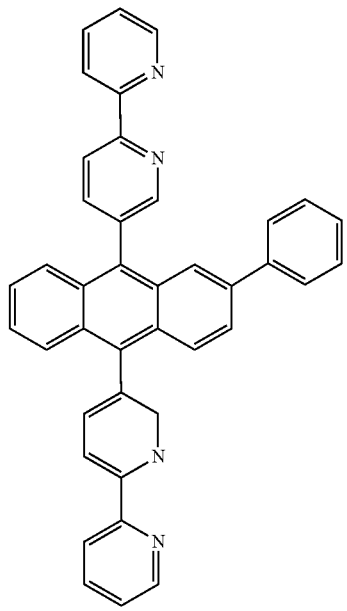

ET3
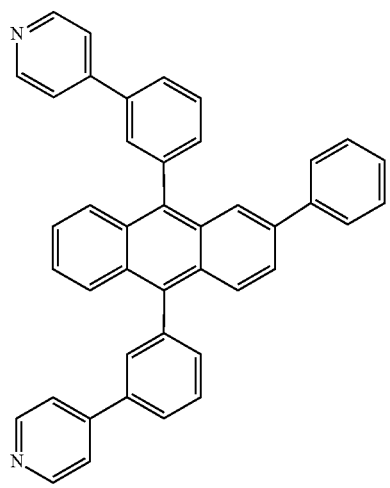
ET4
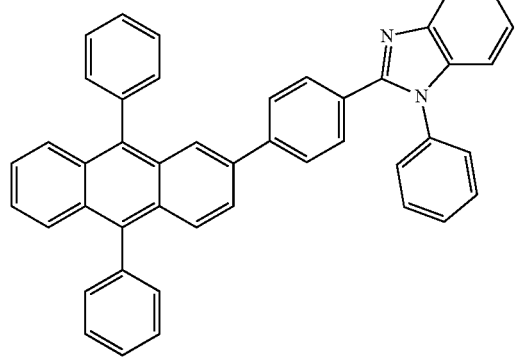
ET5
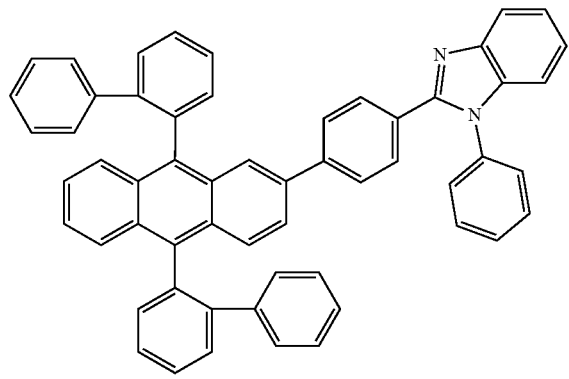
ET6
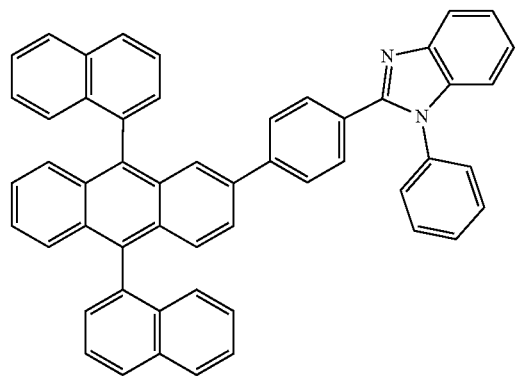
ET7
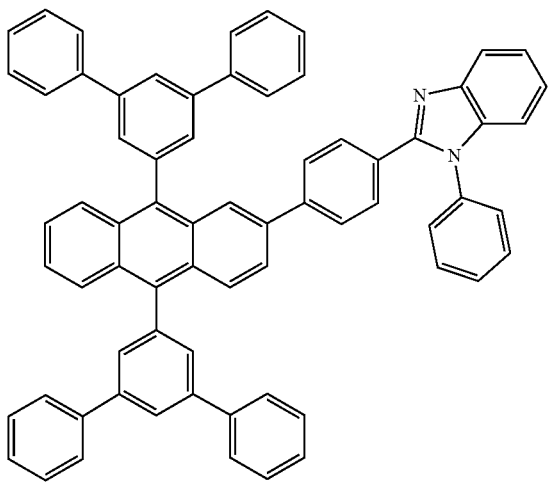
ET8
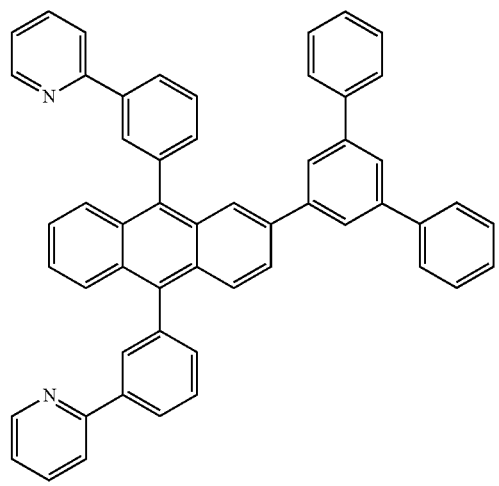

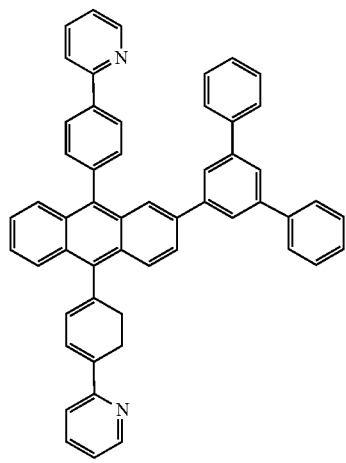
ET9
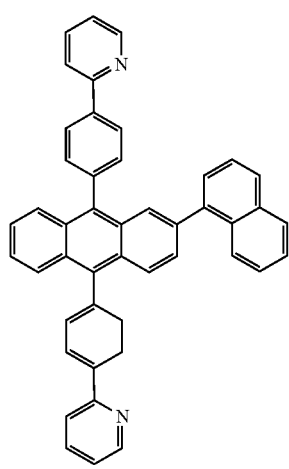
ET10
ET11
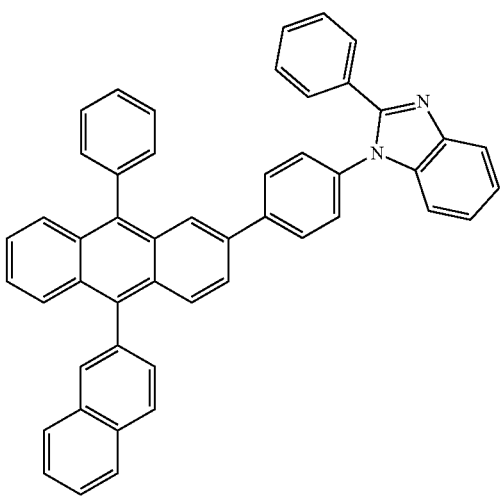
ET12
ET13
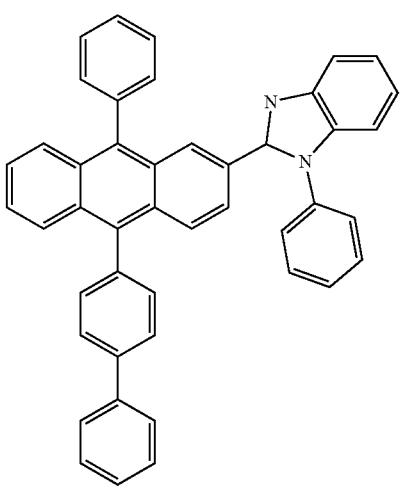
ET14

ET15
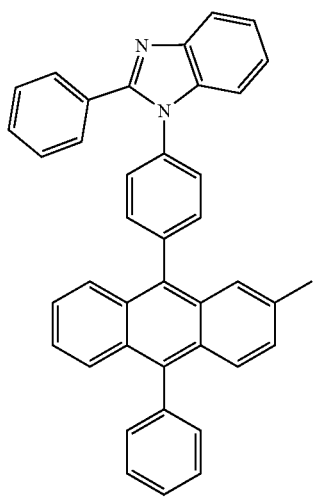
ET16
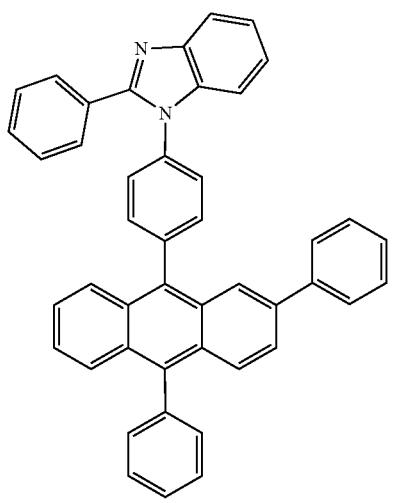
ET17
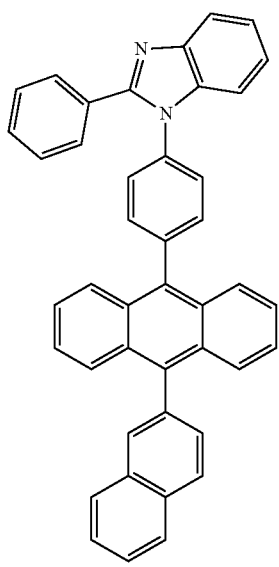
ET18
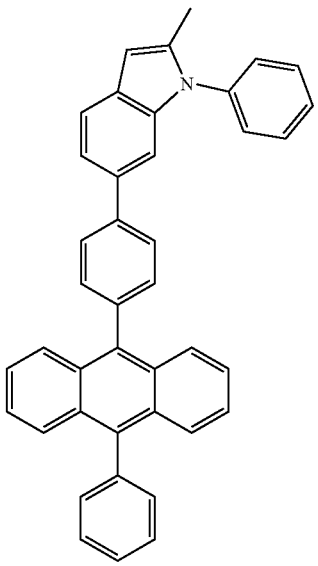
ET19
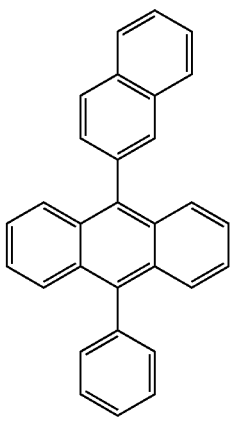
ET20
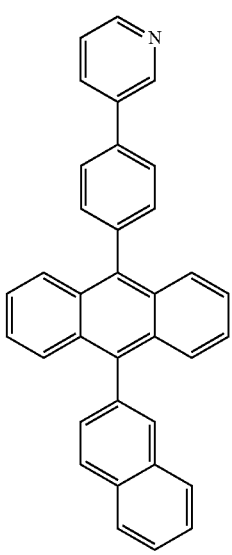

-continued
ET21
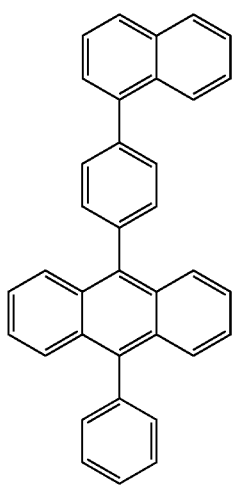
ET22
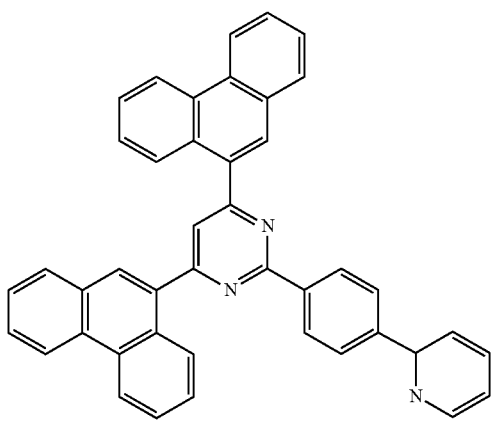
ET23
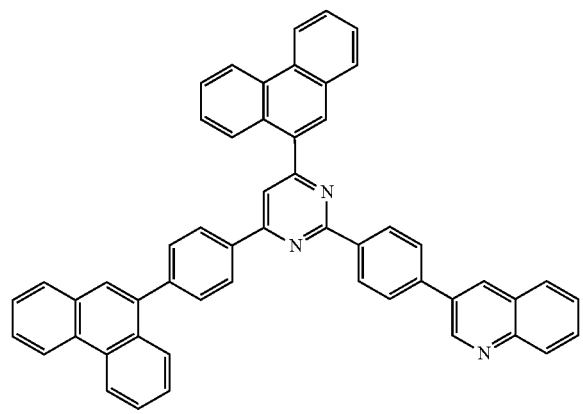
-continued
ET24
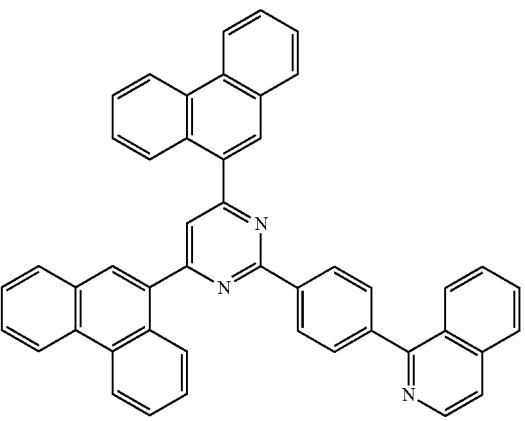
ET25
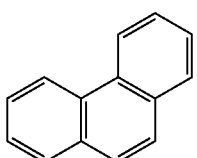
ET26
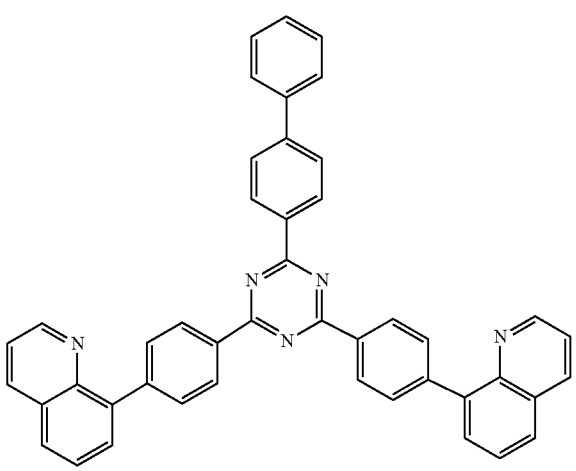

ET27
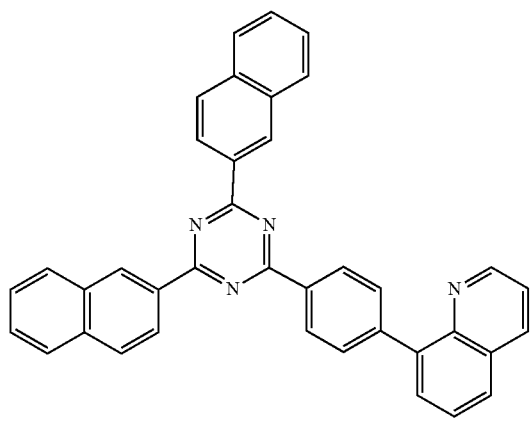
ET30
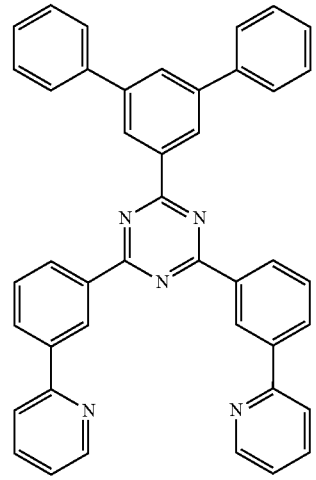
ET28
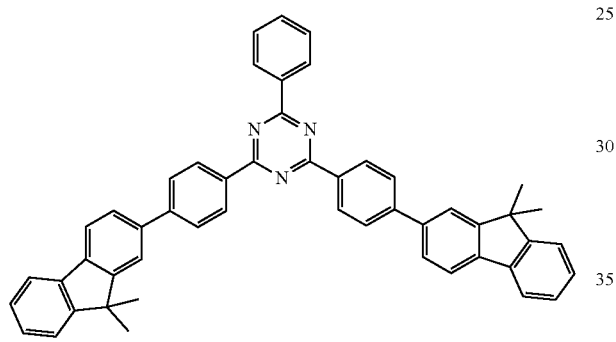
ET31
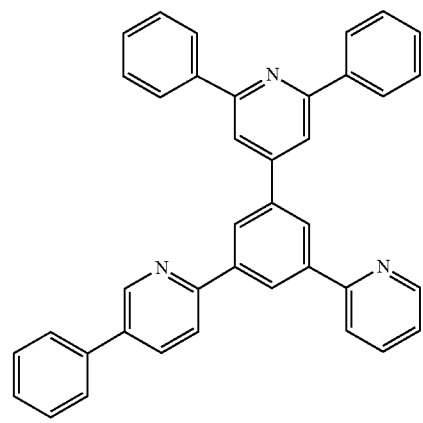
ET29
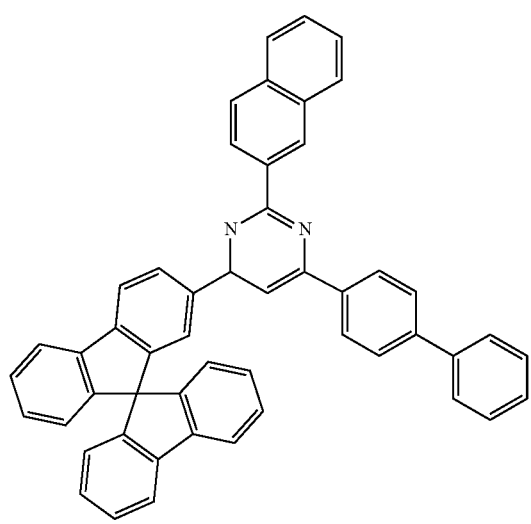
ET32
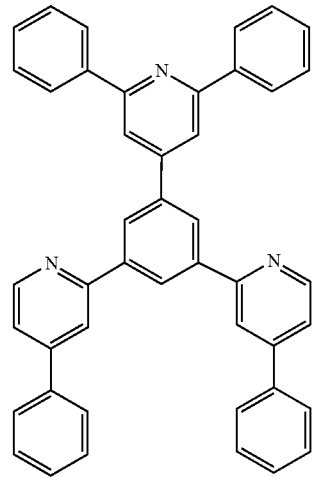

ET33
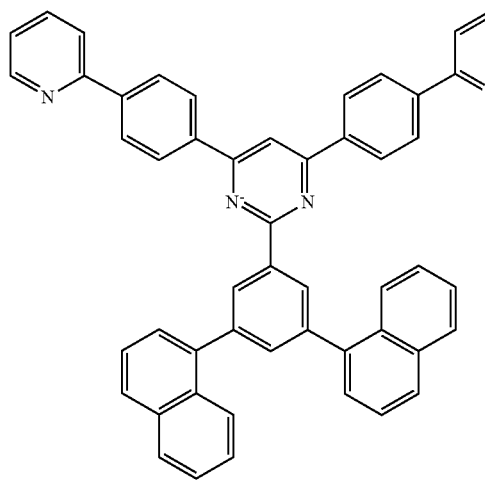
ET34
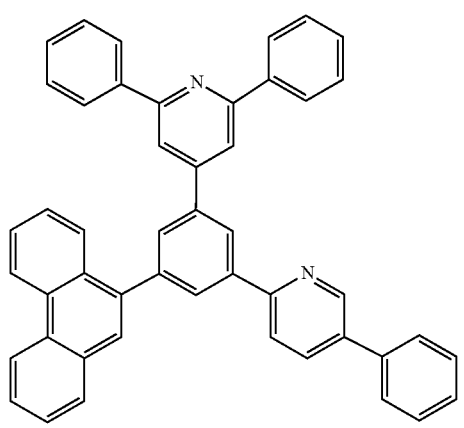
ET35
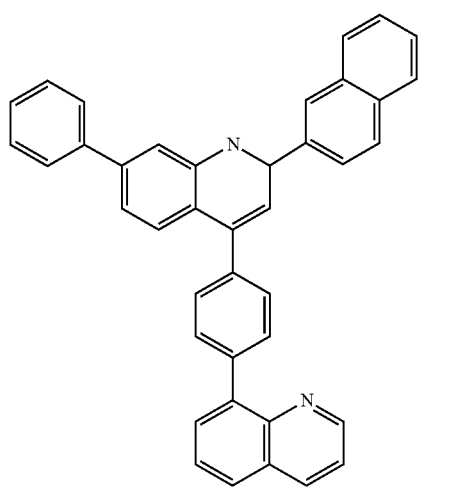
ET36
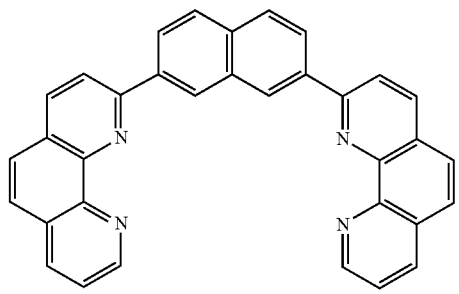
ET37
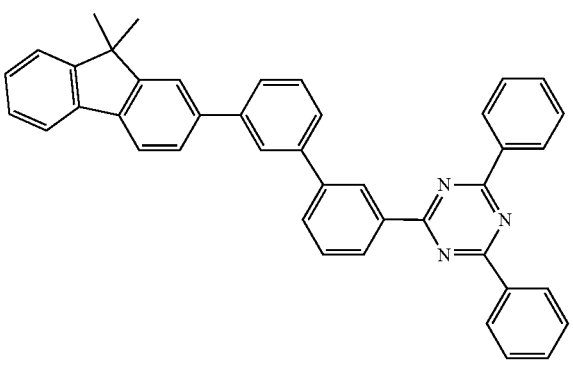
ET38
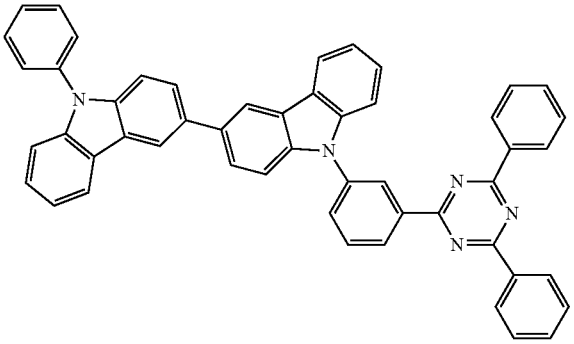
ET39
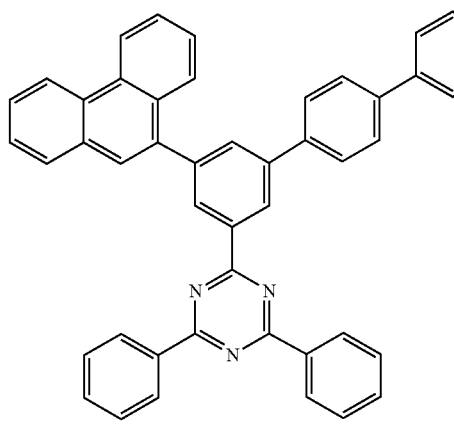

ET40
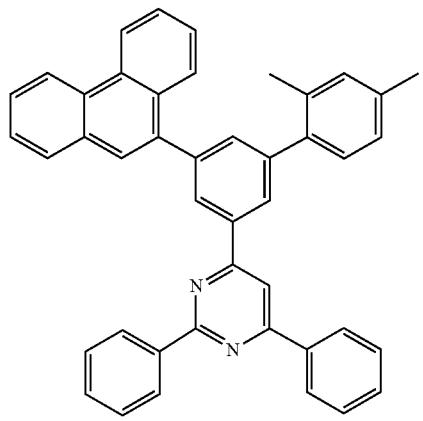
ET41
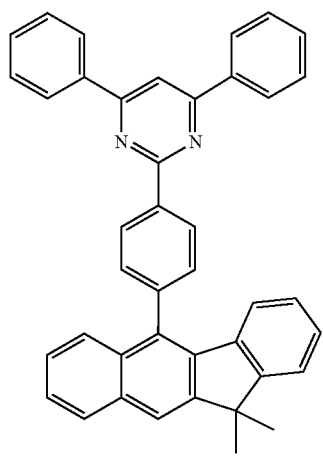
ET42
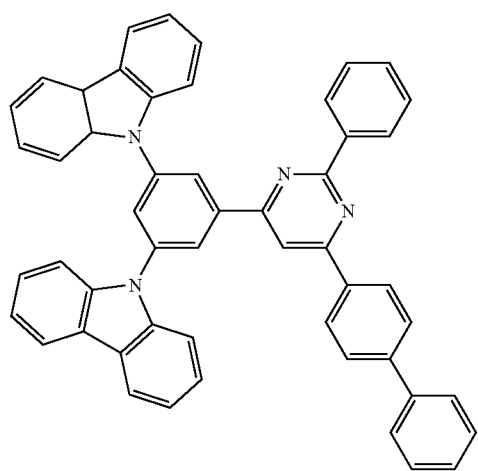
ET43
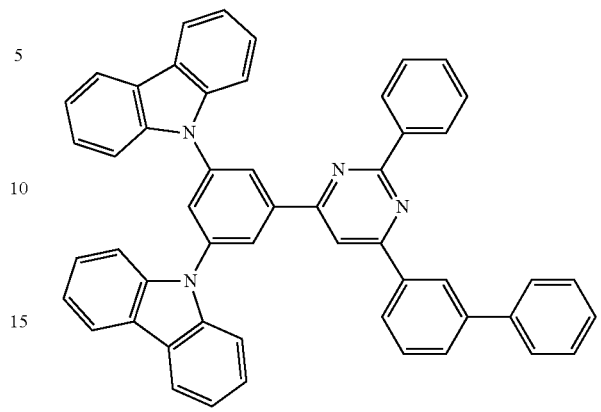
ET44
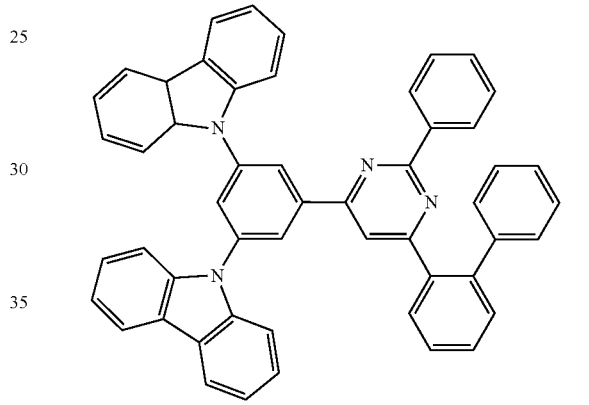
ET45
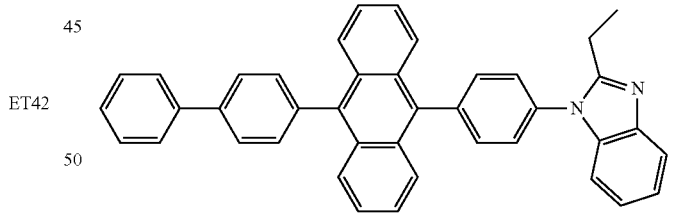
Alq3
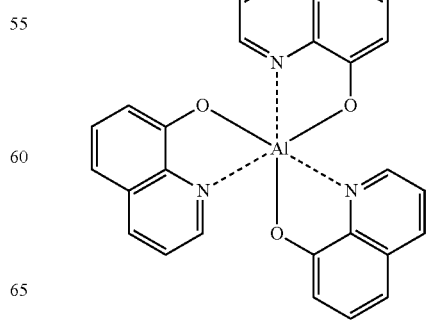

BALq

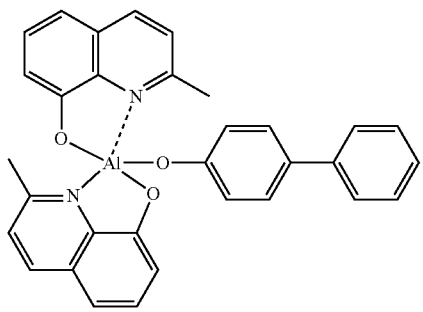

TAZ

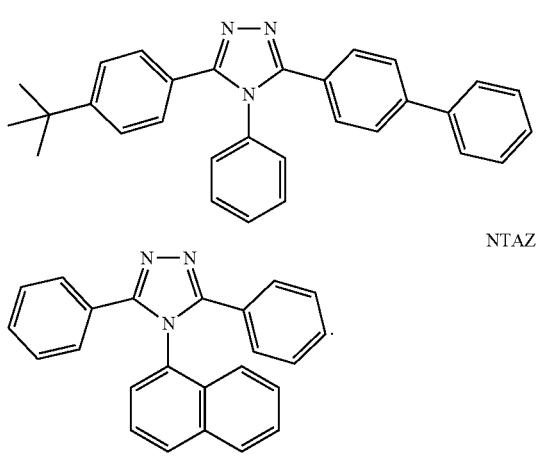

NTAZ

A thickness of the electron transport region may be about 160 Å to about 5,000 Å, for example, about 100 Å to about 4,000 Å. When the electron transport region includes a hole blocking layer, an electron transport layer, or any combination thereof, the thicknesses of the hole blocking layer or the electron transport layer may each independently be about 20 Å to about 1,000 Å, for example, about 30 Å to about 300 Å, and the thickness of the electron transport layer may be about 100 Å to about 1,000 Å, for example, about 150 Å to about 500 Å. When the thickness of the hole blocking layer and/or the electron transport layer is within the range described above, satisfactory electron transport characteristics may be obtained without a substantial increase in driving voltage.

The electron transport region (for example, the electron transport layer in the electron transport region) may further include, in addition to the materials described above, a metal-containing material.

The metal-containing material may include an alkali metal complex, an alkaline earth-metal complex, or any combination thereof. A metal ion of the alkali metal complex may be a Li ion, a Na ion, a K ion, a Rb ion, or a Cs ion, and a metal ion of the alkaline earth-metal complex may be a Be ion, a Mg ion, a Ca ion, a Sr ion, or a Ba ion. Each ligand coordinated with the metal ion of the alkali metal complex or the alkaline earth-metal complex may independently be a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy diphenyloxadiazole, a hydroxy diphenylthiadiazole, a hydroxy phenylpyridine, a hydroxy phenylbenzimidazole, a hydroxy phenylbenzothiazole, a bipyridine, a phenanthroline, a cyclopentadiene, or any combination thereof.

For example, the metal-containing material may include a Li complex. The Li complex may include, for example, Compound ET-D1 (LiQ) or ET-D2:

ET-D1

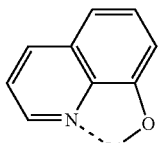

ET-D2

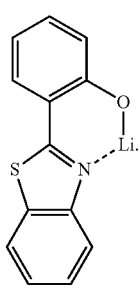

The electron transport region may include an electron injection layer that facilitates electron injection from the second electrode 150. The electron injection layer may directly contact the second electrode 150.

The electron injection layer may have: i) a single-layered structure consisting of a single material, ii) a single-layered structure including a plurality of different materials, or iii) a multi-layered structure including a plurality of layers including different materials.

The electron injection layer may include an alkali metal, an alkaline earth metal, a rare earth metal, an alkali metal-containing compound, an alkaline earth metal-containing compound, a rare earth metal-containing compound, an alkali metal complex, an alkaline earth-metal complex, a rare earth metal complex, or any combination thereof.

The alkali metal may include Li, Na, K, Rb, Cs, or any combination thereof. The alkaline earth metal may include Mg, Ca, Sr, Ba, or any combination thereof. The rare earth metal may include Sc, Y, Ce, Tb, Yb, Gd, or any combination thereof.

The alkali metal-containing compound, the alkaline earth metal-containing compound, and the rare earth metal-containing compound may each independently be oxides and halides (for example, fluorides, chlorides, bromides, or iodides) of the alkali metal, the alkaline earth metal, and the rare earth metal, or any combination thereof.

The alkali metal-containing compound may be an alkali metal oxide (such as $Li_2O$, $Cs_2O$, or $K_2O$), an alkali metal halide (such as LiF, NaF, CsF, KF, LiI, NaI, CsI, or KI), or any combination thereof. The alkaline earth metal-containing compound may include an alkaline earth metal compound (such as BaO, SrO, CaO, $Ba_xSr_{1-x}O$ (where x is a real number satisfying 0<x<1), or $Ba_xCa_{1-x}O$ (where x is a real number satisfying 0<x<1)). The rare earth metal-containing compound may include $YbF_3$, $ScF_3$, $Sc_2O_3$, $Y_2O_3$, $Ce_2O_3$, $GdF_3$, $TbF_3$, $YbI_3$, $ScI_3$, $TbI_3$, or any combination thereof. In an embodiment, the rare earth metal-containing compound may include a lanthanide metal telluride. Non-limiting examples of the lanthanide metal telluride include LaTe, CeTe, PrTe, NdTe, PmTe, SmTe, EuTe, GdTe, TbTe, DyTe, HoTe, ErTe, TmTe, YbTe, LuTe, $La_2Te_3$, $Ce_2Te_3$, $Pr_2Te_3$, $Nd_2Te_3$, $Pm_2Te_3$, $Sm_2Te_3$, $Eu_2Te_3$, $Gd_2Te_3$, $Tb_2Te_3$, $Dy_2Te_3$, $Ho_2Te_3$, $Er_2Te_3$, $Tm_2Te_3$, $Yb_2Te_3$, and $Lu_2Te_3$.

The alkali metal complex, the alkaline earth-metal complex, and the rare earth metal complex may include i) the alkali metal ion, the alkaline earth metal ion, or the rare earth metal ion, and ii) as a ligand linked to the metal ion, for example, a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy diphenyloxadiazole, a hydroxy diphenylthiadiazole, a hydroxy phenylpyridine, a hydroxy phenylbenzimidazole, a hydroxy phenylbenzothiazole, a bipyridine, a phenanthroline, a cyclopentadiene, or any combination thereof.

The electron injection layer may consist of an alkali metal, an alkaline earth metal, a rare earth metal, an alkali metal-containing compound, an alkaline earth metal-containing compound, a rare earth metal-containing compound, an alkali metal complex, an alkaline earth-metal complex, a rare earth metal complex, or any combination thereof, and in some embodiments may further include an organic material (for example, a compound represented by Formula 601).

In an embodiment, the electron injection layer may include (e.g., consist of) i) an alkali metal-containing compound (for example, an alkali metal halide), or ii) a) an alkali metal-containing compound (for example, an alkali metal halide) and b) an alkali metal, an alkaline earth metal, a rare earth metal, or any combination thereof. For example, the electron injection layer may be a KI:Yb co-deposited layer or a RbI:Yb co-deposited layer.

When the electron injection layer further includes an organic material, the alkali metal, the alkaline earth metal, the rare earth metal, the alkali metal-containing compound, the alkaline earth metal-containing compound, the rare earth metal-containing compound, the alkali metal complex, the alkaline earth-metal complex, the rare earth metal complex, or any combination thereof may be homogeneously or non-homogeneously dispersed in a matrix including the organic material.

A thickness of the electron injection layer may be about 1 Å to about 100 Å, for example, about 3 Å to about 90 Å. When the thickness of the electron injection layer is within the range described above, satisfactory electron injection characteristics may be obtained without a substantial increase in driving voltage.

Second Electrode 150

The second electrode 150 may be located on the interlayer 130. The second electrode 150 may be a cathode, which is an electron injection electrode, and as the material for forming the second electrode 150, a metal, an alloy, an electrically conductive compound, or any combination thereof, each having a low work function, may be used.

The second electrode 150 may include lithium (Li), silver (Ag), magnesium (Mg), aluminum (Al), aluminum-lithium (Al—Li), calcium (Ca), magnesium-indium (Mg—In), magnesium-silver (Mg—Ag), ytterbium (Yb), silver-ytterbium (Ag—Yb), ITO, IZO, or any combination thereof. The second electrode 150 may be a transmissive electrode, a semi-transmissive electrode, or a reflective electrode.

The second electrode 150 may have a single-layered structure or a multi-layered structure including two or more layers.

Capping Layer

A first capping layer may be located outside (under) the first electrode 110, and/or a second capping layer may be located outside (over) the second electrode 150. For example, the light-emitting device 10 may have a structure in which the first capping layer, the first electrode 110, the interlayer 130, and the second electrode 150 are sequentially stacked in this stated order, a structure in which the first electrode 110, the interlayer 130, the second electrode 150, and the second capping layer are sequentially stacked in this stated order, or a structure in which the first capping layer, the first electrode 110, the interlayer 130, the second electrode 150, and the second capping layer are sequentially stacked in this stated order.

Light generated in the emission layer of the interlayer 130 of the light-emitting device 10 may be extracted toward the outside through the first electrode 110, which may be a semi-transmissive electrode or a transmissive electrode, and the first capping layer; or light generated in the emission layer of the interlayer 130 of the light-emitting device 10 may be extracted toward the outside through the second electrode 150, which may be a semi-transmissive electrode or a transmissive electrode, and the second capping layer.

The first capping layer and the second capping layer may increase the external luminescence efficiency of the device, according to the principle of constructive interference. As a result, light extraction efficiency of the light-emitting device 10 may increase, and thus, luminescence efficiency of the light-emitting device 10 may be improved.

Each of the first capping layer and the second capping layer may include a material having a refractive index (at 589 nm) of about 1.6 or more.

The first capping layer and the second capping layer may each independently be an organic capping layer including an organic material, an inorganic capping layer including an inorganic material, or a composite capping layer including an organic material and an inorganic material.

At least one of the first capping layer and the second capping layer may each independently include a carbocyclic compound, a heterocyclic compound, an amine group-containing compound, a porphyrin derivative, a phthalocyanine derivative, a naphthalocyanine derivative, an alkali metal complex, an alkaline earth-metal complex, or any combination thereof. The carbocyclic compound, the heterocyclic compound, and the amine group-containing compound may each independently be optionally substituted with a substituent containing O, N, S, Se, Si, F, Cl, Br, I, or any combination thereof. In an embodiment, at least one of the first capping layer and the second capping layer may each independently include an amine group-containing compound.

For example, at least one of the first capping layer and second capping layer may each independently include a compound represented by Formula 201, a compound represented by Formula 202, or any combination thereof.

In an embodiment, at least one of the first capping layer and the second capping layer may each independently include one of Compounds HT28 to HT33, one of Compounds CP1 to CP6, β-NPB, or any combination thereof, but embodiments of the present disclosure are not limited thereto:

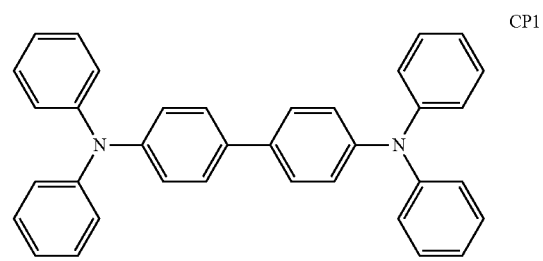

CP1

-continued

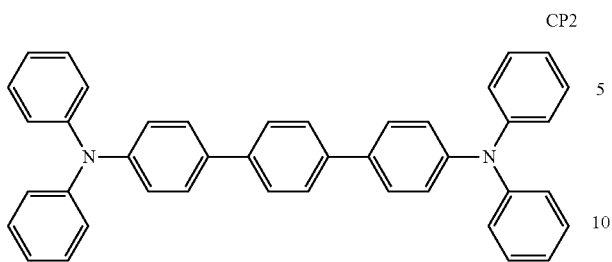
CP2

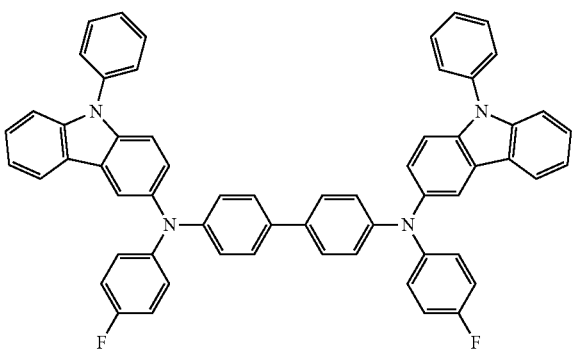
CP3

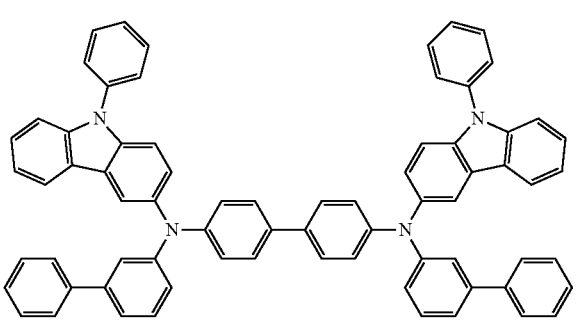
CP4

CP5

-continued

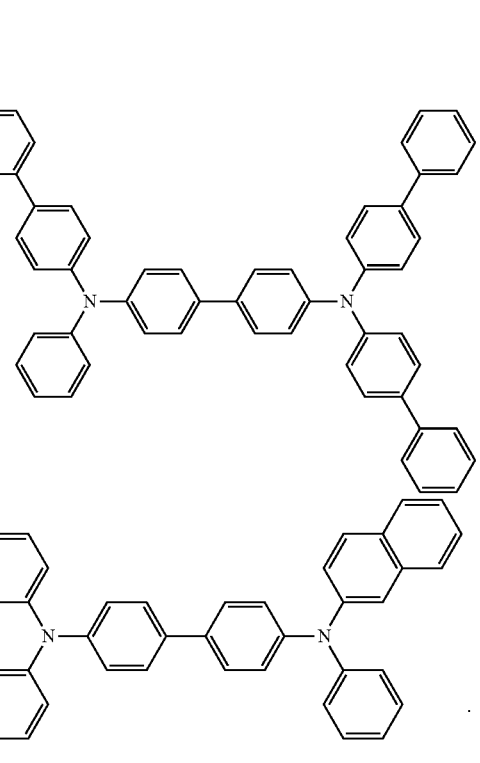
CP6 b-NPB

Electronic Apparatus

The light-emitting device may be included in any suitable electronic apparatus. For example, an electronic apparatus including the light-emitting device may be a light-emitting apparatus or an authentication apparatus.

The electronic apparatus (for example, a light-emitting apparatus) may further include, in addition to the light-emitting device, i) a color filter, ii) a color conversion layer, or iii) the color conversion layer and the color conversion layer. The color filter and/or the color conversion layer may be disposed on or along at least one travel path of light emitted from the light-emitting device. In an embodiment, the light emitted from the light-emitting device may be blue light or white light. The light-emitting device may be the same as described above. In an embodiment, the color conversion layer may include one or more quantum dots. The quantum dots may be, for example, the same as described in the present specification.

The electronic apparatus may include a first substrate. The first substrate may include a plurality of subpixel areas, the color filter may include a plurality of color filter areas respectively corresponding to the plurality of subpixel areas, and the color conversion layer may include a plurality of color conversion areas respectively corresponding to the plurality of subpixel areas.

A pixel-defining layer may be located between the plurality of subpixel areas to thereby define each of the subpixel areas.

The color filter may further include the plurality of color filter areas and light-blocking patterns between the plurality of color filter areas, and the color conversion layer may further include the plurality of color conversion areas and light-blocking patterns between the plurality of color conversion areas.

The plurality of color filter areas (or, the plurality of color conversion areas) may include: a first region emitting first-color light; a second region emitting second-color light; and/or a third region emitting third-color light, wherein the first-color light, the second-color light, and/or the third-color light may have different maximum emission wavelengths from one another. In an embodiment, the first color light may be red light, the second color light may be green light, and the third color light may be blue light. In an embodiment, the plurality of color filter areas (or, the plurality of color conversion areas) may include a quantum dot. For example, the first region may include a red quantum dot, the second region may include a green quantum dot, and the third region may not include a quantum dot. Each quantum dot may be the same as described in the present specification. The first region, the second region, and/or the third region may each further include light scatterers.

In an embodiment, the light-emitting device may be to emit first light, the first region may be to absorb the first light to emit first first-color light, the second region may be to absorb the first light to emit second first-color light, and the third region may be to absorb the first light to emit third first-color light. In this regard, the first first-color light, the second first-color light, and the third first-color light may have different maximum emission wavelengths from one another. For example, the first light may be blue light, the first first-color light may be red light, the second first-color light may be green light, and the third first-color light may be blue light.

The electronic apparatus may further include a thin-film transistor, in addition to the light-emitting device as described above. The thin-film transistor may include a source electrode, a drain electrode, and an activation layer, wherein any one of the source electrode and the drain electrode may be electrically connected to any one of the first electrode and the second electrode of the light-emitting device.

The thin-film transistor may further include a gate electrode, a gate insulation layer, and/or the like.

The activation layer may include crystalline silicon, amorphous silicon, organic semiconductor, oxide semiconductor, and/or the like.

The electronic apparatus may further include a sealing portion for sealing a light-emitting device. The sealing portion may be located between the color filter and/or the color conversion layer and the light-emitting device. The sealing portion may allow light from the light-emitting device to be extracted to the outside, while simultaneously (e.g., concurrently) preventing or reducing external air and/or moisture from penetrating into the light-emitting device. The sealing portion may be a sealing substrate including a transparent glass substrate and/or a plastic substrate. The sealing portion may be a thin-film encapsulation layer including at least one organic layer and/or inorganic layer. When the sealing portion is a thin-film encapsulation layer, the electronic apparatus may be flexible.

In addition to the color filter and/or the color conversion layer, various functional layers may be additionally located on the sealing portion according to a use of the electronic apparatus. Non-limiting examples of a functional layer include a touchscreen layer and a polarization layer. The touchscreen layer may be a pressure-sensitive touchscreen layer, a capacitive touchscreen layer, or an infrared touchscreen layer. The authentication apparatus may be, for example, a biometric authentication apparatus for authenticating an individual by using biometric information of a biometric body (for example, a fingertip or a pupil).

The authentication apparatus may further include, in addition to the light-emitting device, a biometric information collector.

Non-limiting examples of the electronic apparatus include various displays, light sources, lighting, personal computers (for example, mobile personal computers), mobile phones, digital cameras, electronic notebooks, electronic dictionaries, electronic game machines, medical devices (for example, electronic thermometers, blood pressure monitors, blood glucose meters, pulse measuring devices, pulse wave measuring devices, electrocardiogram display devices, ultrasonic diagnostic devices, or endoscope display devices), fish finders, various measuring devices, instruments (for example, vehicles, aircrafts, or ship instruments), and projectors.

Figure 3:
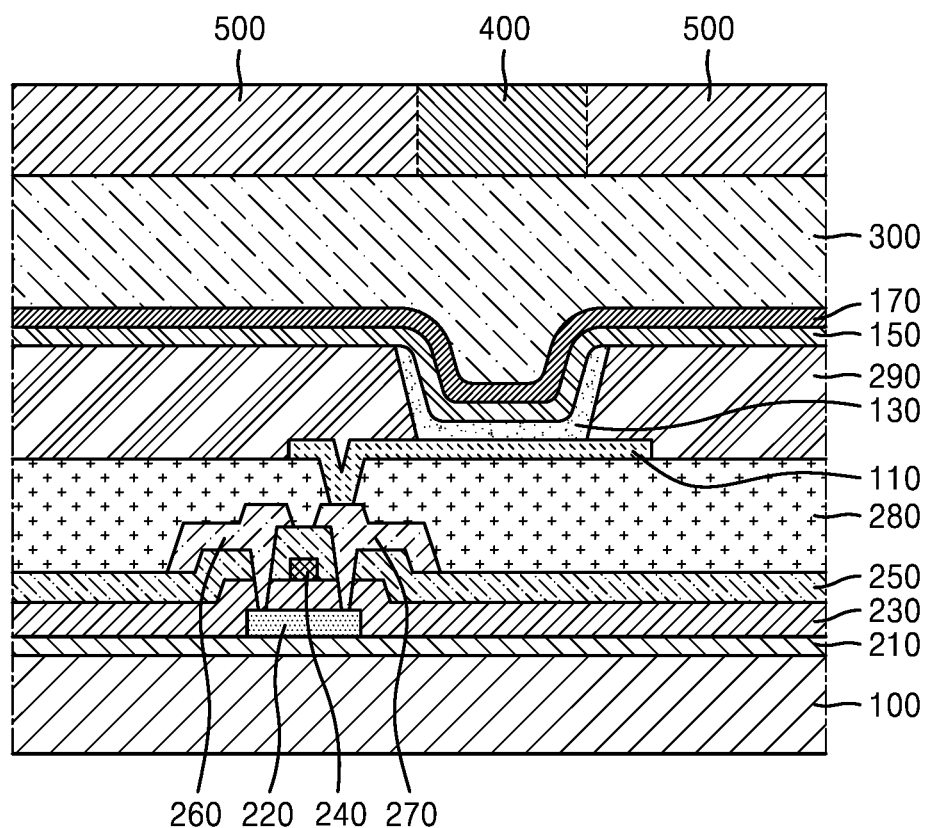
FIG. 3 is a cross-sectional view of a light-emitting apparatus, according to an embodiment of the disclosure.

Description of FIGS. 2 and 3

FIG. 2 is a cross-sectional view of a light-emitting apparatus, according to an embodiment of the disclosure.

The light-emitting apparatus of FIG. 2 includes a substrate 100, a thin-film transistor, a light-emitting device, and an encapsulating portion 300 for sealing the light-emitting device.

The substrate 100 may be a flexible substrate, a glass substrate, and/or a metal substrate. A buffer layer 210 may be located on the substrate 100. The buffer layer 210 may serve to prevent or reduce penetration of impurities through the substrate 100 and provide a flat surface on the substrate 100.

The thin-film transistor may be located on the buffer layer 210. The thin-film transistor may include an activation layer 220, a gate electrode 240, a source electrode 260, and a drain electrode 270.

The activation layer 220 may include an inorganic semiconductor (such as silicon or polysilicon), an organic semiconductor, or an oxide semiconductor, and includes a source region, a drain region, and a channel region.

A gate insulation layer 230 for insulating the activation layer 220 and the gate electrode 240 may be located on the activation layer 220, and the gate electrode 240 may be located on the gate insulation layer 230.

An interlayer insulation layer 250 may be located on the gate electrode 240. The interlayer insulation layer 250 is located between the gate electrode 240 and the source electrode 260 and between the gate electrode 240 and the drain electrode 270 to insulate them.

The source electrode 260 and the drain electrode 270 may be located on the interlayer insulation layer 250. The interlayer insulation layer 250 and the gate insulation layer 230 may be formed to expose the source region and the drain region of the activation layer 220, and the source electrode 260 and the drain electrode 270 may be located to contact the exposed source region and the exposed drain region of the activation layer 220.

The thin-film transistor is electrically connected to the light-emitting device to drive the light-emitting device, and is protected by being covered with a passivation layer 280. The passivation layer 280 may include an inorganic insulation layer, an organic insulation layer, or a combination thereof. The light-emitting device is provided on the passivation layer 280. The light-emitting device includes the first electrode 110, the interlayer 130, and the second electrode 150.

The first electrode 110 may be located on the passivation layer 280. The passivation layer 280 may be located to expose a certain or predetermined region without covering the entire drain electrode 270, and the first electrode 110 may be connected to the exposed drain electrode 270.

A pixel-defining layer 290 including insulating material may be located on the first electrode 110. The pixel-defining layer 290 exposes a certain or predetermined region of the first electrode 110, and the interlayer 130 may be formed on the exposed region. The pixel-defining layer 290 may be a polyimide or polyacryl-based organic layer. In some embodiments, some layers in the interlayer 130 may extend to an upper portion of the pixel-defining layer 290 and may be located in the form of a common layer.

The second electrode 150 is located on the interlayer 130, and a capping layer 170 may be additionally formed on the second electrode 150. The capping layer 170 may be formed to cover the second electrode 150.

The encapsulating portion 300 may be located on the capping layer 170. The encapsulating portion 300 is located on the light-emitting device to protect the light-emitting device from moisture or oxygen. The encapsulating portion 300 may include an inorganic layer including silicon nitride ($SiN_x$), silicon oxide ($SiO_x$), indium tin oxide (ITO), indium zinc oxide (IZO), or any combination thereof, an organic layer including polyethylene terephthalate, polyethylene naphthalate, polycarbonate, polyimide, polyethylene sulfonate, polyoxymethylene, polyarylate, hexamethyldisiloxane, acryl-based resin (for example, polymethyl methacrylate, or polyacrylic acid), epoxy-based resin (for example, aliphatic glycidyl ether (AGE)), or any combination thereof, or a combination of the inorganic layer and the organic layer.

FIG. 3 is a cross-sectional view of a light-emitting apparatus according to an embodiment of the disclosure.

The light-emitting apparatus of FIG. 3 is the same as the light-emitting apparatus of FIG. 2, except that light-blocking patterns 500 and a functional region 400 are additionally located on the encapsulating portion 300. The functional region 400 may be i) a color filter area, ii) a color conversion area, or iii) a combination of the color filter area and the color conversion area. In an embodiment, the light-emitting device included in the light-emitting apparatus of FIG. 3 may be a tandem light-emitting device.

Preparation Method

The layers constituting the hole transport region, the emission layer, and the layers constituting the electron transport region may each be formed in a certain or predetermined region using one or more suitable methods selected from vacuum deposition, spin coating, casting, Langmuir-Blodgett (LB) deposition, ink-jet printing, laser-printing, and laser-induced thermal imaging (LITI).

When the layers constituting the hole transport region, the emission layer, and the layers constituting the electron transport region are formed by vacuum deposition, the deposition may be performed at a deposition temperature of about 100° C. to about 500° C., a vacuum degree of about $10^{-8}$ torr to about $10^{-3}$ torr, and a deposition speed of about 0.01 Å/sec to about 100 Å/sec, depending on the material to be included and the structure of the layer to be formed.

Definitions of Terms

The term "$C_3$-$C_{60}$ carbocyclic group" as used herein refers to a cyclic group that includes only carbon and consists of 3 to 60 carbon atoms, and the term "$C_1$-$C_{60}$ heterocyclic group" as used herein refers to a cyclic group that further includes a heteroatom, in addition to carbon, and has 1 to 60 carbon atoms. The $C_3$-$C_{60}$ carbocyclic group and the $C_1$-$C_{60}$ heterocyclic group may each be a monocyclic group consisting of one ring or a polycyclic group having two or more rings condensed with each other. For example, the number of ring-forming atoms of the $C_1$-$C_{60}$ heterocyclic group may be 3 to 61.

The term "cyclic group" as used herein encompasses both of the $C_3$-$C_{60}$ carbocyclic group and the $C_1$-$C_{60}$ heterocyclic group.

The term "π-electron-rich $C_3$-$C_{60}$ cyclic group" refers to a cyclic group that does not include *—N=*' as a ring-forming moiety, and has 3 to 60 carbon atoms, and the term "π-electron-deficient nitrogen-containing $C_1$-$C_{60}$ cyclic group" refers to a heterocyclic group that includes *—N=*' as a ring-forming moiety, and has 1 to 60 carbon atoms.

For example, the $C_3$-$C_{60}$ carbocyclic group may be i) a group T1 (defined below) or ii) a condensed cyclic group having two or more groups T1 condensed with each other (for example, a cyclopentadiene group, an adamantane group, a norbornane group, a benzene group, a pentalene group, a naphthalene group, an azulene group, an indacene group, an acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spiro-bifluorene group, a benzofluorene group, an indeno phenanthrene group, or an indenoanthracene group), the $C_1$-$C_{60}$ heterocyclic group may be i) a group T2 (defined below), ii) a condensed cyclic group having two or more groups T2 condensed with each other, or iii) a condensed cyclic group having at least one group T2 and at least one group T1 condensed with each other (for example, a pyrrole group, a thiophene group, a furan group, an indole group, a benzoindole group, a naphtho indole group, an isoindole group, a benzo isoindole group, a naphtho isoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofuro carbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofuro dibenzofuran group, a benzofuro dibenzothiophene group, a benzothieno dibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, or an azadibenzofuran group), the π-electron-rich $C_3$-$C_{60}$ cyclic group may be i) a group T1, ii) a condensed cyclic group having two or more groups T1 condensed with each other, iii) a group T3 (defined below), iv) a condensed cyclic group having two or more groups T3 condensed with each other, or v) a condensed cyclic group having at least one group T3 and at least one group T1 condensed with each other (for example, the $C_3$-$C_{60}$ carbocyclic group, a pyrrole group, a thiophene group, a furan group, an indole group, a benzoindole group, a naphtho indole group, an isoindole group, a benzo isoindole group, a naphtho isoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofuro carbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofuro dibenzofuran group, a benzofuro dibenzothiophene group, or a benzothieno dibenzothiophene group), the π-electron-deficient nitrogen-containing $C_1$-$C_{60}$ cyclic group may be i) a group T4 (defined below), ii) a condensed cyclic group having two or more groups T4 condensed with each other, iii) a condensed cyclic group having at least one group T4 and at least one group T1 condensed with each other, iv) a condensed cyclic group having at least one group T4 and at least one group T3 condensed with each other, or v) a condensed cyclic group having at least one group T4, at least one group T1, and at least one group T3 condensed with each other (for example, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, or an azadibenzofuran group), the group T1 may be a cyclopropane group, a cyclobutane group, a cyclopentane group, a cyclohexane group, a cycloheptane group, a cyclooctane group, a cyclobutene group, a cyclopentene group, a cyclopentadiene group, a cyclohexene group, a cyclohexadiene group, a cycloheptene group, an adamantane group, a norbornane (or bicyclo[2.2.1]heptane) group, a norbornene group, a bicyclo[1.1.1]pentane group, a bicyclo[2.1.1]hexane group, a bicyclo[2.2.2]octane group, or a benzene group, the group T2 may be a furan group, a thiophene group, a 1H-pyrrole group, a silole group, a borole group, a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group, the group T3 may be a furan group, a thiophene group, a 1H-pyrrole group, a silole group, or a borole group, and the group T4 may be a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group.

Herein, the terms "cyclic group", "$C_3$-$C_{60}$ carbocyclic group", "$C_1$-$C_{60}$ heterocyclic group", "π-electron-rich $C_3$-$C_{60}$ cyclic group", and/or "π-electron-deficient nitrogen-containing $C_1$-$C_{60}$ cyclic group" may each refer to a condensed cyclic group (e.g., moiety), a monovalent group, or a multivalent group (for example, a divalent group, a trivalent group, or a tetravalent group), according to a structure of a formula in which the term is used. For example, the term "benzene group" may be a benzo group, a phenyl group, or a phenylene group, which will be understood by those of ordinary skill in the art according to a structure of a formula including the benzene group (e.g., according to the context).

Non-limiting examples of a monovalent $C_3$-$C_{60}$ carbocyclic group and a monovalent $C_1$-$C_{60}$ heterocyclic group may include a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, and non-limiting examples of a divalent $C_3$-$C_{60}$ carbocyclic group and a divalent $C_1$-$C_{60}$ heterocyclic group may include a $C_3$-$C_{10}$ cycloalkylene group, a $C_1$-$C_{10}$ heterocycloalkylene group, a $C_3$-$C_{10}$ cycloalkenylene group, a $C_1$-$C_{10}$ heterocycloalkenylene group, a $C_6$-$C_{60}$ arylene group, a $C_1$-$C_{60}$ heteroarylene group, a divalent non-aromatic condensed polycyclic group, and a substituted or unsubstituted divalent non-aromatic condensed heteropolycyclic group.

The term "$C_1$-$C_{60}$ alkyl group" as used herein refers to a linear or branched aliphatic hydrocarbon monovalent group having 1 to 60 carbon atoms, and non-limiting examples thereof include a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group. The term "$C_1$-$C_{60}$ alkylene group" as used herein refers to a divalent group having substantially the same structure as the $C_1$-$C_{60}$ alkyl group.

The term "$C_2$-$C_{60}$ alkenyl group" as used herein refers to a monovalent hydrocarbon group having at least one carbon-carbon double bond in the middle or at the terminus of a $C_2$-$C_{60}$ alkyl group, and non-limiting examples thereof include an ethenyl group, a propenyl group, and a butenyl group. The term "$C_2$-$C_{60}$ alkenylene group" as used herein refers to a divalent group having substantially the same structure as the $C_2$-$C_{60}$ alkenyl group.

The term "$C_2$-$C_{60}$ alkynyl group" as used herein refers to a monovalent hydrocarbon group having at least one carbon-carbon triple bond in the middle or at the terminus of a $C_2$-$C_{60}$ alkyl group, and non-limiting examples thereof include an ethynyl group and a propynyl group. The term "$C_2$-$C_{60}$ alkynylene group" as used herein refers to a divalent group having substantially the same structure as the $C_2$-$C_{60}$ alkynyl group.

The term "$C_1$-$C_{60}$ alkoxy group" as used herein refers to a monovalent group represented by —$OA_{101}$ (wherein $A_{101}$ is a $C_1$-$C_{60}$ alkyl group), and non-limiting examples thereof include a methoxy group, an ethoxy group, and an isopropyloxy group.

The term "$C_3$-$C_{10}$ cycloalkyl group" as used herein refers to a monovalent saturated hydrocarbon cyclic group having 3 to 10 carbon atoms, and non-limiting examples thereof include a cyclopropyl group, a cyclobutyl group, a cyclopentyl group, a cyclohexyl group, a cycloheptyl group, a cyclooctyl group, an adamantanyl group, a norbornanyl group (or a bicyclo[2.2.1]heptyl group), a bicyclo[1.1.1]pentyl group, a bicyclo[2.1.1]hexyl group, and a bicyclo[2.2.2]octyl group. The term "$C_3$-$C_{10}$ cycloalkylene group" as used herein refers to a divalent group having substantially the same structure as the $C_3$-$C_{10}$ cycloalkyl group.

The term "$C_1$-$C_{10}$ heterocycloalkyl group" as used herein refers to a monovalent cyclic group that further includes at least one heteroatom as a ring-forming atom, in addition to 1 to 10 carbon atoms, and non-limiting examples thereof include a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having substantially the same structure as the $C_1$-$C_{10}$ heterocycloalkyl group.

The term "$C_3$-$C_{10}$ cycloalkenyl group" as used herein refers to a monovalent cyclic group that has 3 to 10 carbon atoms, at least one carbon-carbon double bond in the ring thereof, and no aromaticity, and non-limiting examples thereof include a cyclopentenyl group, a cyclohexenyl group, and a cycloheptenyl group. The term "$C_3$-$C_{10}$ cycloalkenylene group" as used herein refers to a divalent group having substantially the same structure as the $C_3$-$C_{10}$ cycloalkenyl group.

The term "$C_1$-$C_{10}$ heterocycloalkenyl group" as used herein refers to a monovalent cyclic group that further includes at least one heteroatom as a ring-forming atom, in addition to 1 to 10 carbon atoms, and at least one double bond in its ring. Non-limiting examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group" as used herein refers to a divalent group having substantially the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Non-limiting examples of the $C_6$-$C_{60}$ aryl group include a phenyl group, a pentalenyl group, a naphthyl group, an azulenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a heptalenyl group, a naphthacenyl group, a picenyl group, a hexacenyl group, a pentacenyl group, a rubicenyl group, a coronenyl group, and an ovalenyl group. When the $C_6$-$C_{60}$ aryl group and the $C_6$-$C_{60}$ arylene group each include two or more rings, the two or more rings may be condensed with each other.

The term "$C_1$-$C_{60}$ heteroaryl group" as used herein refers to a monovalent group having an aromatic system that further includes at least one heteroatom as a ring-forming atom, in addition to 1 to 60 carbon atoms, and the term "$C_1$-$C_{60}$ heteroarylene group" as used herein refers to a divalent group having an aromatic system that further includes at least one heteroatom as a ring-forming atom, in addition to a carbon atom, and has 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, a benzoquinolinyl group, an isoquinolinyl group, a benzoisoquinolinyl group, a quinoxalinyl group, a benzoquinoxalinyl group, a quinazolinyl group, a benzoquinazolinyl group, a cinnolinyl group, a phenanthrolinyl group, a phthalazinyl group, and a naphthyridinyl group. When the $C_1$-$C_{60}$ heteroaryl group and the $C_1$-$C_{60}$ heteroarylene group each include two or more rings, the two or more rings may be condensed with each other.

The term "monovalent non-aromatic condensed polycyclic group" as used herein refers to a monovalent group having two or more rings condensed with each other, only carbon atoms as ring-forming atoms (for example, 8 to 60 carbon atoms), and non-aromaticity in its entire molecular structure. Non-limiting examples of the monovalent non-aromatic condensed polycyclic group include an indenyl group, a fluorenyl group, a spiro-bifluorenyl group, a benzofluorenyl group, an indenophenanthrenyl group, and an indenoanthracenyl group. The term "divalent non-aromatic condensed polycyclic group" as used herein refers to a divalent group having substantially the same structure as the monovalent non-aromatic condensed polycyclic group.

The term "monovalent non-aromatic condensed heteropolycyclic group" as used herein refers to a monovalent group that has two or more rings condensed with each other and non-aromaticity in its entire molecular structure, and further includes, as a ring-forming atom, at least one heteroatom other than carbon atoms (for example, 1 to 60 carbon atoms). Non-limiting examples of the monovalent non-aromatic condensed heteropolycyclic group include a pyrrolyl group, a thiophenyl group, a furanyl group, an indolyl group, a benzoindolyl group, a naphthoindolyl group, an isoindolyl group, a benzoisoindolyl group, a naphthoisoindolyl group, a benzosilolyl group, a benzothiophenyl group, a benzofuranyl group, a carbazolyl group, a dibenzosilolyl group, a dibenzothiophenyl group, a dibenzofuranyl group, an azacarbazolyl group, an azafluorenyl group, an azadibenzosilolyl group, an azadibenzothiophenyl group, an azadibenzofuranyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, a thiadiazolyl group, a benzopyrazolyl group, a benzimidazolyl group, a benzoxazolyl group, a benzothiazolyl group, a benzoxadiazolyl group, a benzothiadiazolyl group, an imidazopyridinyl group, an imidazopyrimidinyl group, an imidazotriazinyl group, an imidazopyrazinyl group, an imidazopyridazinyl group, an indenocarbazolyl group, an indolocarbazolyl group, a benzofurocarbazolyl group, a benzothienocarbazolyl group, a benzosilolocarbazolyl group, a benzoindolocarbazolyl group, a benzocarbazolyl group, a benzonaphthofuranyl group, a benzonaphthothiophenyl group, a benzonaphthosilolyl group, a benzofurodibenzofuranyl group, a benzofurodibenzothiophenyl group, and a benzothienodibenzothiophenyl group. The term "divalent non-aromatic condensed heteropolycyclic group" as used herein refers to a divalent group having substantially the same structure as the monovalent non-aromatic condensed heteropolycyclic group.

The term "$C_6$-$C_{60}$ aryloxy group" as used herein refers to —$OA_{102}$ (wherein $A_{102}$ is a $C_6$-$C_{60}$ aryl group), and the term "$C_6$-$C_{60}$ arylthio group" used herein refers to —$SA_{103}$ (wherein $A_{103}$ is a $C_6$-$C_{60}$ aryl group).

"$R_{10a}$" as used herein may be:
deuterium (-D), —F, —Cl, —Br, —I, a hydroxyl group, a cyano group, or a nitro group;
a $C_1$-$C_{60}$ alkyl group, a $C_2$-$C_{60}$ alkenyl group, a $C_2$-$C_{60}$ alkynyl group, or a $C_1$-$C_{60}$ alkoxy group, each being unsubstituted or substituted with deuterium, —F, —Cl, —Br, —I, a hydroxyl group, a cyano group, a nitro group, a $C_3$-$C_{60}$ carbocyclic group, a $C_1$-Coo heterocyclic group, a $C_6$-$C_{60}$ aryloxy group, a $C_6$-$C_{60}$ arylthio group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), —P(=O)($Q_{11}$)($Q_{12}$), or any combination thereof;
a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each being unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof; or
—Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$).

Herein, $Q_1$ to $Q_3$, $Q_{11}$ to $Q_{13}$, $Q_{21}$ to $Q_{23}$, and $Q_{31}$ to $Q_{33}$ may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each being unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

The term "heteroatom" as used herein refers to an atom except a carbon atom (e.g., any non-carbon and non-hydrogen atom). Non-limiting examples of the heteroatom include O, S, N, P, Si, B, Ge, Se, or any combination thereof.

The term "Ph" as used herein refers to a phenyl group, the term "Me" as used herein refers to a methyl group, the term "Et" as used herein refers to an ethyl group, the term "ter-Bu" or "But" as used herein refers to a tert-butyl group, and the term "OMe" as used herein refers to a methoxy group.

The term "biphenyl group" as used herein refers to "a phenyl group substituted with a phenyl group". The "biphenyl group" is a substituted phenyl group having a $C_6$-$C_{60}$ aryl group as a substituent.

The term "terphenyl group" as used herein refers to "a phenyl group substituted with a biphenyl group". The "terphenyl group" is a substituted phenyl group having, as a substituent, a $C_6$-$C_{60}$ aryl group substituted with a $C_6$-$C_{60}$ aryl group.

* and *' as used herein, unless defined otherwise, each refer to a binding site to a neighboring atom in a corresponding formula.

In the definitions of terms, the maximum number of carbon atoms is provided as an example. For example, the maximum number of 60 carbon atoms in the $C_1$-$C_{60}$ alkyl group is an example, and in some embodiments may be applied to the $C_1$-$C_{20}$ alkyl group. Other cases are the same or similar.

Hereinafter, a compound according to embodiments and a light-emitting device according to embodiments will be described in more detail with reference to Synthesis Examples and Examples. The wording "B was used instead of A" used in describing Synthesis Examples indicates that an identical molar equivalent of B was used in place of A.

EXAMPLES

Synthesis Example: Synthesis of Compounds

Synthesis of Compound 1

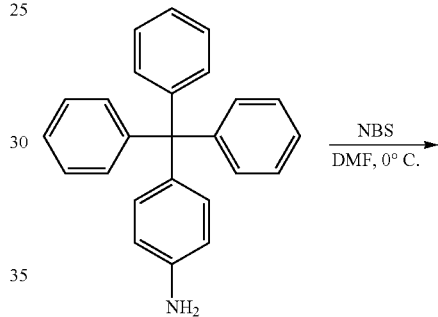

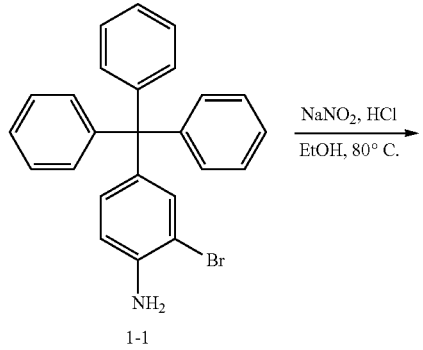

1-1

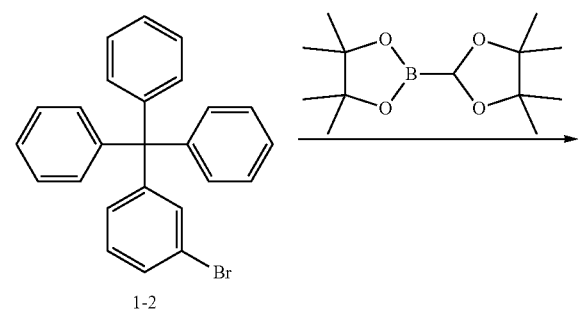

1-2

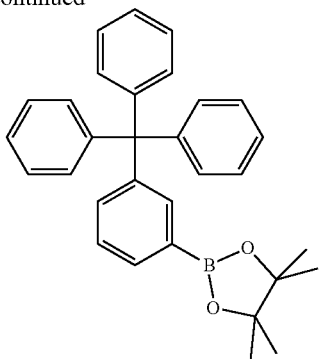

1-3

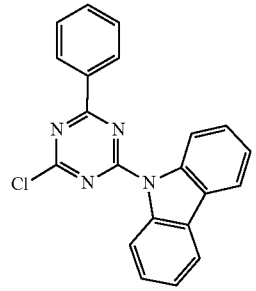

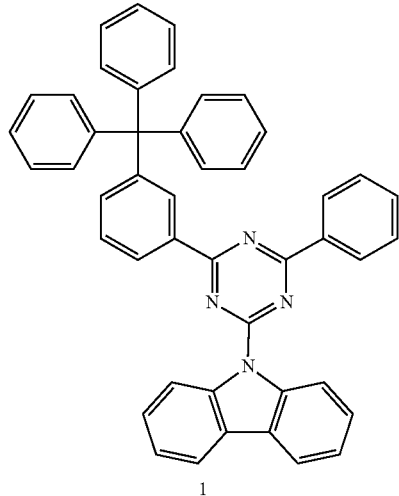

1

Synthesis of Intermediate 1-1

10 g of 4-tritylaniline was dissolved in 150 mL of a DMF solvent, 5.3 g of NBS was slowly added thereto at 0° C., and the mixture was reacted at room temperature and then purified to thereby obtain 11.7 g (yield: 95%) of Intermediate 1-1. Intermediate 1-1 was confirmed by LC-MS.

($C_{25}H_{20}BrN$: M+1 414.08)

Synthesis of Intermediate 1-2

11.7 g of Intermediate 1-1 was dissolved in 200 mL of an ethanol solvent, and excess HCl (3 eq or more) was slowly added dropwise thereto at room temperature. After stirring, 3.9 g of $NaNO_2$ was added thereto, and the mixture was reacted at 80° C. and then purified to thereby obtain 7.89 g (yield: 70%) of Intermediate 1-2. Intermediate 1-2 was confirmed by LC-MS.

($C_{25}H_{10}Br$: M+1 399.07)

Synthesis of Intermediate 1-3

7.89 g of Intermediate 1-2 was reacted with 10 g of bis(pinacolato)diboron, 3.8 g of K(OAc), and 0.69 g of $Pd(PPh_3)Cl_2$ in 100 mL of a toluene solvent at 110° C. while refluxing, and then purified to thereby obtain 5.28 g (yield: 60%) of Intermediate 1-3. Intermediate 1-3 was confirmed by LC-MS.

($C_{31}H_{31}BO_2$: M+1 447.24)

Synthesis of Compound 1

2.5 g of Intermediate 1-3, 2 g of CAS #1268244-56-9 (lower left structure), 0.32 g of $Pd(PPh_3)_4$, 7 mL of a 2M $K_2CO_3$ aqueous solution, 7 mL of ethanol, and 28 mL of toluene were reacted while refluxing for 12 hours at 110° C. After the reaction is completed, the reaction solution was extracted to collect an organic layer, which was then dried. The residue was separated and purified by silica gel column chromatography and then subject to sublimation purification, to thereby obtain 2.87 g (yield: 80%) of Compound 1. Compound 1 was confirmed by LC-MS and $^1H$ NMR.

2. Synthesis of Compound 2

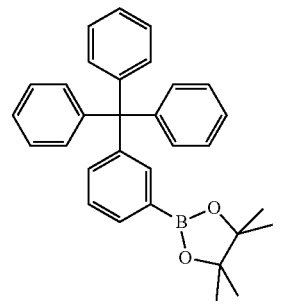

1-3

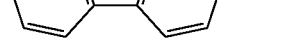

2

Synthesis of Compound 2

2 g of CAS #877615-05-9 (left structure), 2 g of Intermediate 1-3, 0.32 g of Pd(PPh$_3$)$_4$, 7 mL of a 2M K$_2$CO$_3$ aqueous solution, 7 mL of ethanol, and 28 mL of toluene were reacted while refluxing for 12 hours at 110° C. After the reaction was completed, the reaction solution was extracted to collect an organic layer, which was then dried. The residue was separated and purified by silica gel column chromatography and then subject to sublimation purification, to thereby obtain 2.78 g (yield: 85%) of Compound 2. Compound 2 was confirmed by LC-MS and $^1$H NMR.

3. Synthesis of Compound 7

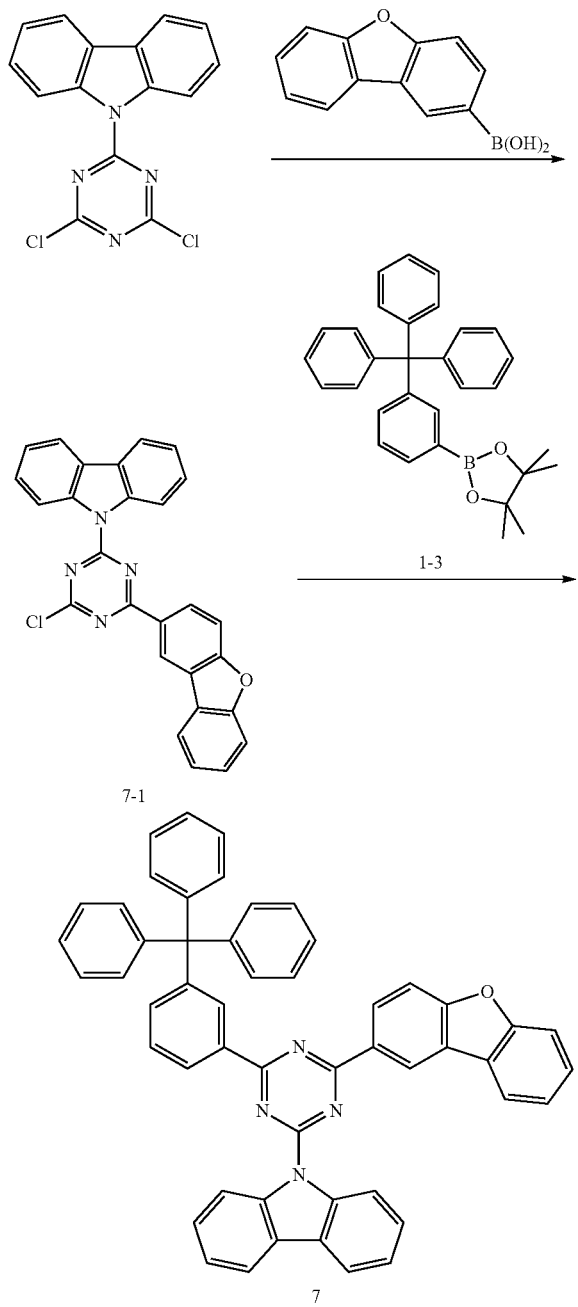

7-1

7

Synthesis of Intermediate 7-1

2 g of CAS #24209-95-8 (left structure) and 1.34 g of dibenzo[b,d]furan-2-ylboronic acid were reacted with 8 mL of a 2M K$_2$CO$_3$ aqueous solution, 0.37 g of Pd(PPh$_3$)$_4$, and 30 mL of THF while stirring and refluxing at 80° C., followed by purification to thereby obtain 2.55 g (yield: 90%) of Intermediate 7-1. Intermediate 7-1 was confirmed by LC-MS.

(C$_{27}$H$_{15}$ClN$_4$O: M+1 447.09)

Synthesis of Compound 7

2 g of Intermediate 7-1, 2 g of Intermediate 1-3, 0.32 g of Pd(PPh$_3$)$_4$, 7 mL of a 2M K$_2$CO$_3$ aqueous solution, 7 mL of ethanol, and 30 mL of toluene were reacted while refluxing for 12 hours at 110° C. After the reaction is completed, the reaction solution was extracted to collect an organic layer, which was then dried. The residue was separated and purified by silica gel column chromatography and then subject to sublimation purification, to thereby obtain 2.63 g (yield: 80%) of Compound 7. Compound 7 was confirmed by LC-MS and $^1$H NMR.

4. Synthesis of Compound 26

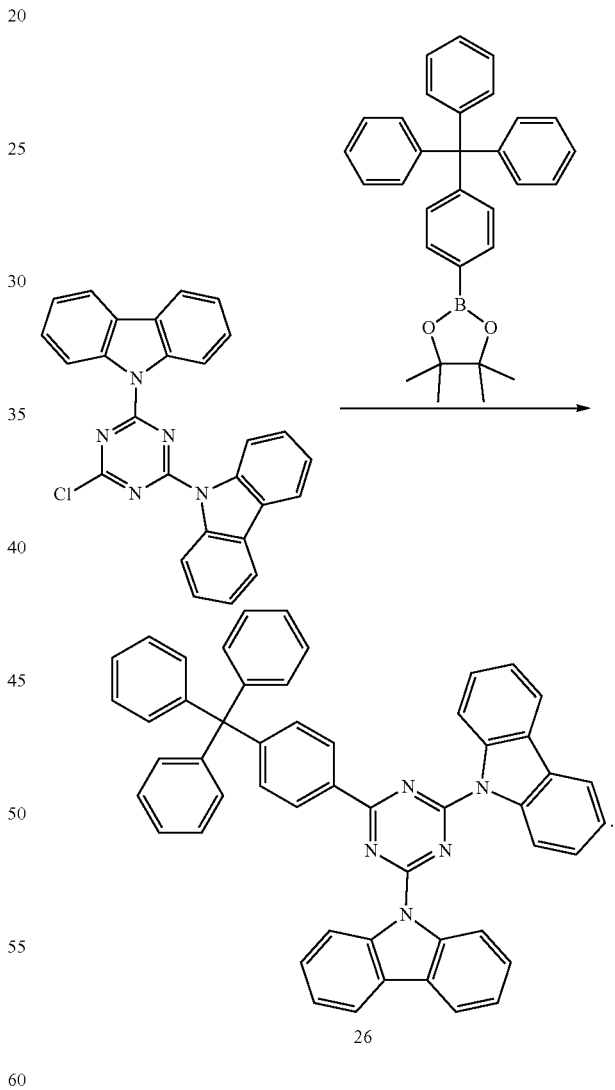

26

Synthesis of Compound 26

2 g of CAS #877615-05-9 (left structure), 2 g of CAS #1290057-48-5 (above arrow), 0.26 g of Pd(PPh$_3$)$_4$, 7 mL of a 2M K$_2$CO$_3$ aqueous solution, 7 mL of ethanol, and 30 mL of toluene were reacted while refluxing for 12 hours. After the reaction is completed, the reaction solution was extracted to collect an organic layer, which was then dried.

The residue was separated and purified by silica gel column chromatography and then subject to sublimation purification, to thereby obtain 2.85 g (yield: 87%) of Compound 26. Compound 26 was confirmed by LC-MS and $^1$H NMR.

5. Synthesis of Compound 49

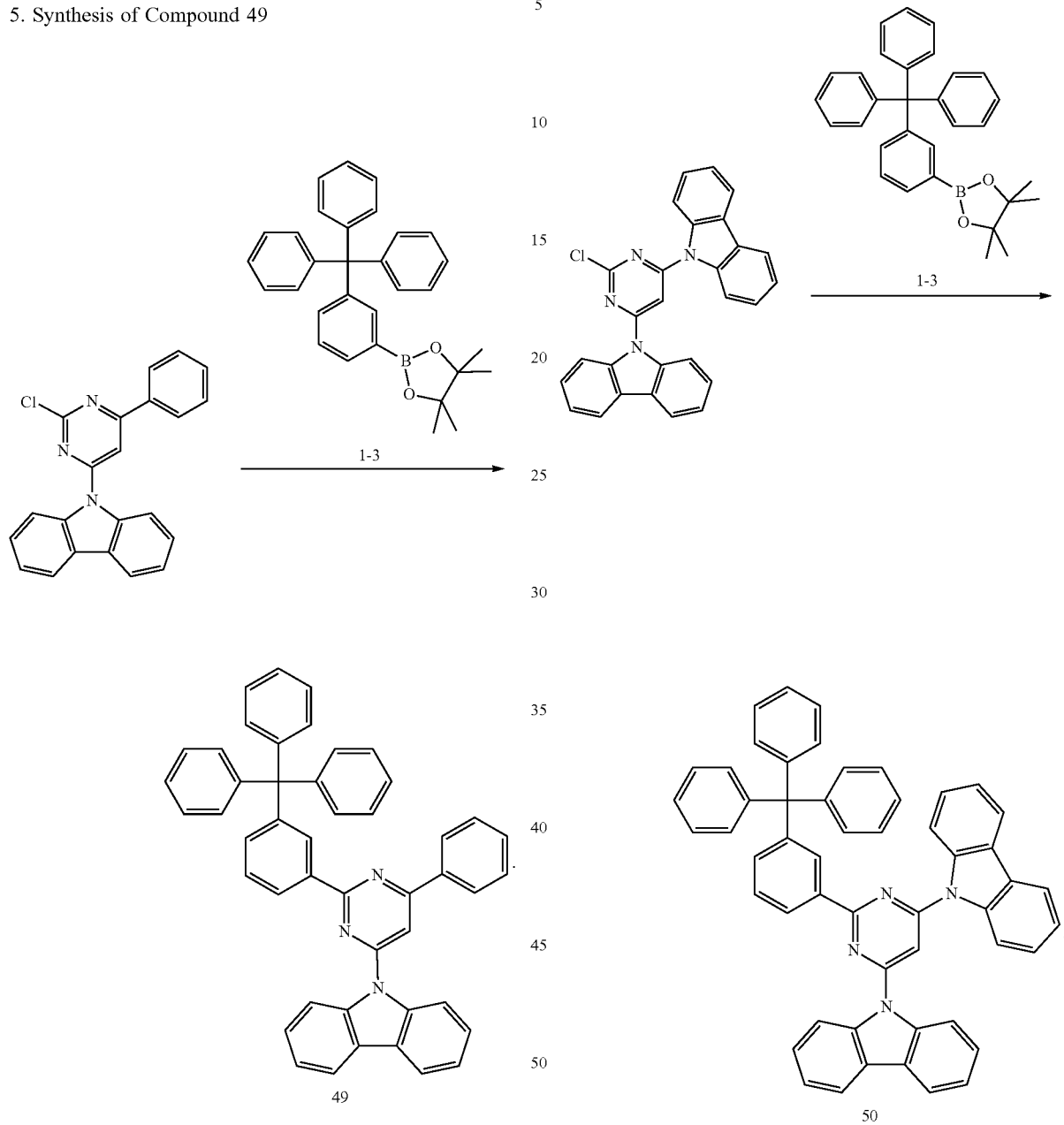

6. Synthesis of Compound 50

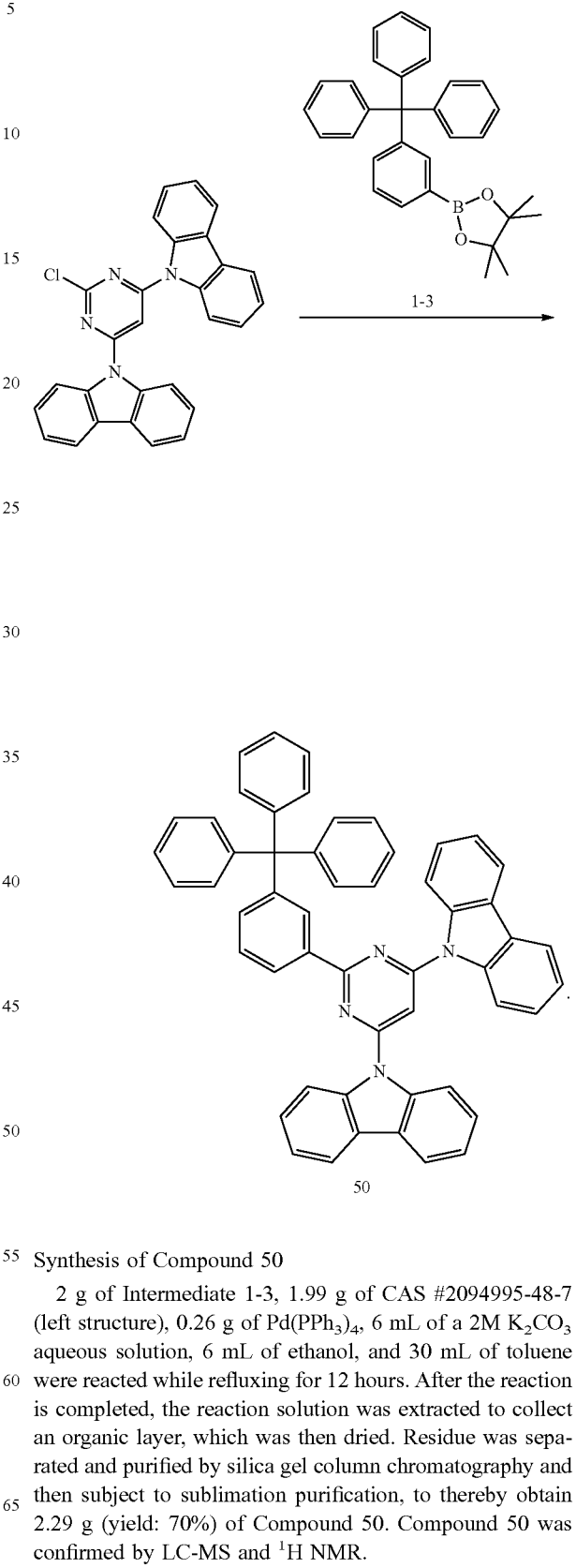

Synthesis of Compound 49

2 g of Intermediate 1-3, 1.59 g of CAS #1426818-83-8 (left structure), 0.26 g of Pd(PPh$_3$)$_4$, 6 mL of a 2M K$_2$CO$_3$ aqueous solution, 6 mL of ethanol, and 30 mL of toluene were reacted while refluxing for 12 hours. After the reaction is completed, the reaction solution was extracted to collect an organic layer, which was then dried. Residue was separated and purified by silica gel column chromatography and then subject to sublimation purification, to thereby obtain 1.73 g (yield: 60%) of Compound 49. Compound 49 was confirmed by LC-MS and $^1$H NMR.

Synthesis of Compound 50

2 g of Intermediate 1-3, 1.99 g of CAS #2094995-48-7 (left structure), 0.26 g of Pd(PPh$_3$)$_4$, 6 mL of a 2M K$_2$CO$_3$ aqueous solution, 6 mL of ethanol, and 30 mL of toluene were reacted while refluxing for 12 hours. After the reaction is completed, the reaction solution was extracted to collect an organic layer, which was then dried. Residue was separated and purified by silica gel column chromatography and then subject to sublimation purification, to thereby obtain 2.29 g (yield: 70%) of Compound 50. Compound 50 was confirmed by LC-MS and $^1$H NMR.

7. Synthesis of Compound 55

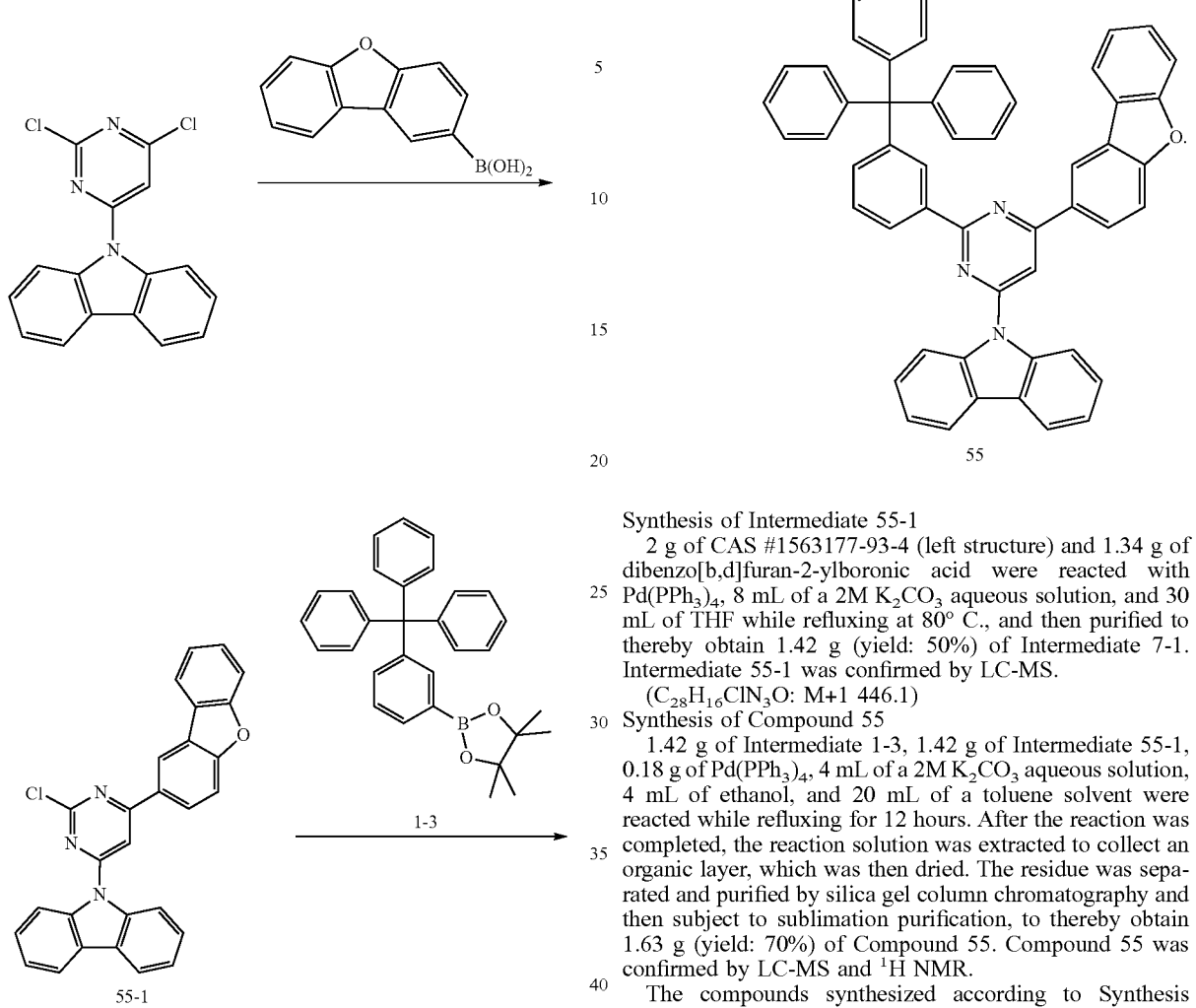

Synthesis of Intermediate 55-1

2 g of CAS #1563177-93-4 (left structure) and 1.34 g of dibenzo[b,d]furan-2-ylboronic acid were reacted with Pd(PPh$_3$)$_4$, 8 mL of a 2M K$_2$CO$_3$ aqueous solution, and 30 mL of THF while refluxing at 80° C., and then purified to thereby obtain 1.42 g (yield: 50%) of Intermediate 7-1. Intermediate 55-1 was confirmed by LC-MS.

(C$_{28}$H$_{16}$ClN$_3$O: M+1 446.1)

Synthesis of Compound 55

1.42 g of Intermediate 1-3, 1.42 g of Intermediate 55-1, 0.18 g of Pd(PPh$_3$)$_4$, 4 mL of a 2M K$_2$CO$_3$ aqueous solution, 4 mL of ethanol, and 20 mL of a toluene solvent were reacted while refluxing for 12 hours. After the reaction was completed, the reaction solution was extracted to collect an organic layer, which was then dried. The residue was separated and purified by silica gel column chromatography and then subject to sublimation purification, to thereby obtain 1.63 g (yield: 70%) of Compound 55. Compound 55 was confirmed by LC-MS and $^1$H NMR.

The compounds synthesized according to Synthesis Examples above were identified by $^1$H NMR and MS/FAB, and the results are shown in Table 1:

TABLE 1

| Compound | $^1$H NMR (CDCl$_3$, 500 MHz) | MS/FAB found | MS/FAB calc. |
|---|---|---|---|
| 1 | 8.55(d, 1H), 8.36(d, 2H), 8.18-8.20(d, 2H), 7.80-7.94(m, 2H), 7.50-7.62(m, 4H), 7.00-7.35(m, 21H) | 641.26 | 640.79 |
| 2 | 8.55(d, 2H), 8.18(d, 3H), 7.94(d, 2H), 7.80(d, 1H), 7.50-7.58(m, 5H), 7.35(t, 2H), 7.10-7.26(m, 20H) | 730.29 | 729.89 |
| 7 | 8.55(d, 1H), 8.19(d, 2H), 7.94(d, 1H), 7.98(d, 1H), 7.79-7.88(m, 4H), 7.50-7.58(m, 4H), 7.10-7.39 (21H) | 731.27 | 730.87 |
| 26 | 8.55-8.56(m, 4H), 8.19(d, 2H), 7.94(d, 2H), 7.58(d, 2H), 7.35-7.52(m, 5H), 7.10-7.36(m, 20H) | 730.29 | 729.89 |
| 49 | 8.55(d, 1H), 8.19(d, 2H), 7.94(d, 3H), 7.80(d, 1H), 7.49-7.58(m, 6H), 7.35(t, 1H), 7.10-7.26(m, 19H) | 640.80 | 639.27 |
| 50 | 8.55(d, 2H), 8.18-8.19(d, 3H), 7.94(d, 2H), 7.80(d, 1H), 7.50-7.58(m,5H), 7.00-7.35(m, 23H) | 729.29 | 728.90 |
| 55 | 8.55(d, 1H), 8.18(d, 2H), 7.94-7.98(m, 2H), 7.83-7.88(m, 2H), 7.50-7.79(m, 7H), 7.10-7.39(m, 21H) | 730.28 | 729.88 |

Manufacture of Light-Emitting Device

Example 1

As an anode, a glass substrate with 15 Ωcm² (1,200 Å) ITO thereon (manufactured by Corning Inc.) was cut to a size of 50 mm×50 mm×0.7 mm, sonicated using isopropyl alcohol and pure water for 5 minutes each, and then cleaned by irradiation of ultraviolet rays and exposure of ozone thereto for 30 minutes. Then, the resultant glass substrate was loaded onto a vacuum deposition apparatus.

Compound NPD was vacuum-deposited on the substrate to form a hole injection layer having a thickness of 300 Å, and TCTA was vacuum-deposited on the hole injection layer to form a hole transport layer having a thickness of 200 Å. CzSi as a compound for the hole transport layer was vacuum-deposited on the hole transport layer to a thickness of 100 Å. Compound 1 of the present disclosure and Ir(pmp)₃ as a dopant were co-deposited on the hole transport layer at a weight ratio of 92:8 to form an emission layer having a thickness of 250 Å.

Subsequently, TSPO1 was deposited on the emission layer to a thickness of 200 Å, and TPBI was deposited thereon to a thickness of 300 Å, to thereby form an electron transport layer.

LiF (a halogenated alkaline metal) was deposited on the electron transport layer having a thickness of 10 Å, and then, Al was vacuum-deposited thereon to form an LiF/Al electrode (cathode) having a thickness of 3,000 Å, thereby completing the manufacture of a light-emitting device.

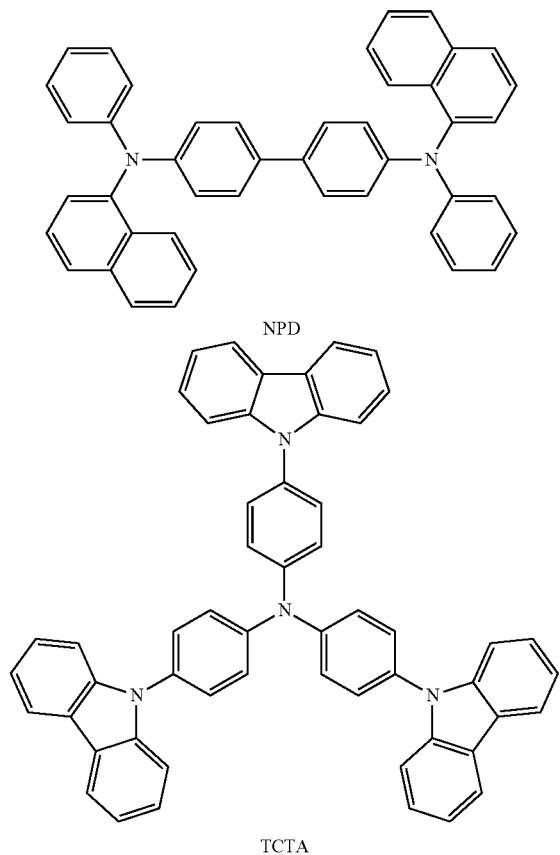

NPD

TCTA

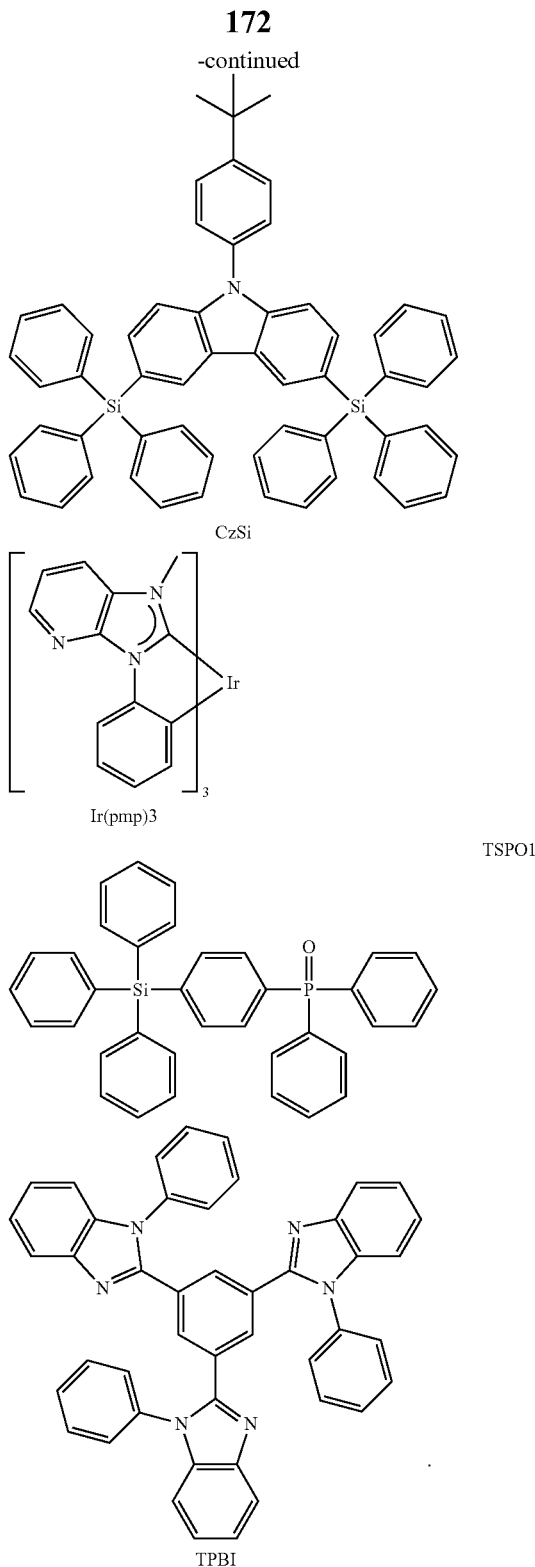

CzSi

Ir(pmp)3

TSPO1

TPBI

Examples 2 to 7

Additional light-emitting devices were manufactured in substantially the same manner as in Example 1, except that the compounds of Table 2 were used to form emission layers.

Comparative Example 1

A light-emitting device was manufactured in substantially the same manner as in Example 1, except that the mCP was used as a host to form an emission layer.

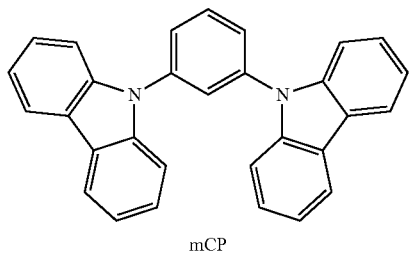

mCP

Comparative Example 2

A light-emitting device was manufactured in substantially the same manner as in Example 1, except that Compound 200 was used as a host to form an emission layer.

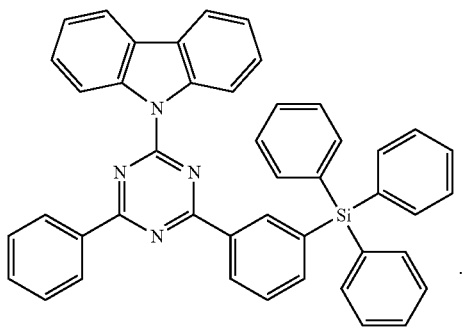

200

Comparative Example 3

A light-emitting device was manufactured in substantially the same manner as in Example 1, except that Compound 201 was used as a host to form an emission layer.

201

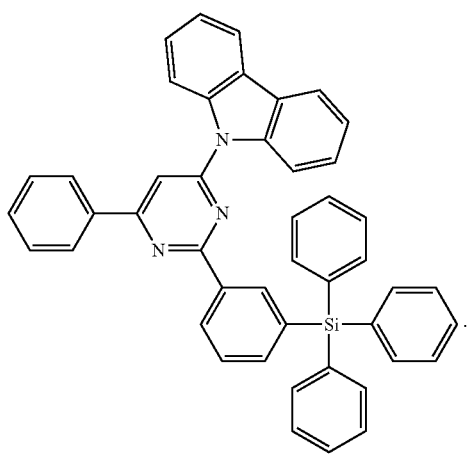

With respect to each of the light-emitting devices manufactured according to Examples 1 to 7 and Comparative Examples 1 to 3, the driving voltage and efficiency of each device at a current density of 2.3 mA/cm$^2$, and T1 energy value of each host compound is shown in Table 2:

TABLE 2

| | Emission layer host | Driving voltage (V) | Current density (mA/cm$^2$) | Efficiency (cd/A) | Emission color | T1 (eV) |
|---|---|---|---|---|---|---|
| Example 1 | 1 | 4.5 | 2.3 | 20.7 | Blue | 3.07 |
| Example 2 | 2 | 4.2 | 2.3 | 22.5 | Blue | 3.03 |
| Example 3 | 7 | 4.3 | 2.3 | 19.5 | Blue | 3.02 |
| Example 4 | 26 | 4.2 | 2.3 | 22.2 | Blue | 3.03 |
| Example 5 | 49 | 4.6 | 2.3 | 18.3 | Blue | 3.00 |
| Example 6 | 50 | 4.5 | 2.3 | 20.2 | Blue | 2.95 |
| Example 7 | 55 | 4.7 | 2.3 | 19.8 | Blue | 2.99 |
| Comparative Example 1 | mCP | 5.3 | 2.3 | 10.2 | Blue | 2.90 |
| Comparative Example 2 | Compound 200 | 5.5 | 2.3 | 17.1 | Blue | 3.07 |
| Comparative Example 3 | Compound 201 | 5.8 | 2.3 | 13.9 | Blue | 2.95 |

As shown in Table 2, the T1 values of the various example compounds represented by Formula 1 of the present disclosure are generally higher than the T1 values of the compounds in the Comparative Examples. In addition, the light-emitting devices of Examples 1 to 7 show excellent results (e.g., in terms of driving voltage and efficiency), compared to the light-emitting devices of Comparative Examples 1 to 3.

A light-emitting device including the compound represented Formula 1 according to an embodiment shows excellent efficiency and improved lifespan.

As used herein, the terms "substantially," "about," and similar terms are used as terms of approximation and not as terms of degree, and are intended to account for the inherent deviations in measured or calculated values that would be recognized by those of ordinary skill in the art.

Any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the drawings, it will be understood by those of ordinary skill in the art that various changes in form and details may be made therein without departing from the spirit and scope as defined by the following claims and equivalents thereof.

What is claimed is:
1. A compound represented by Formula 1:

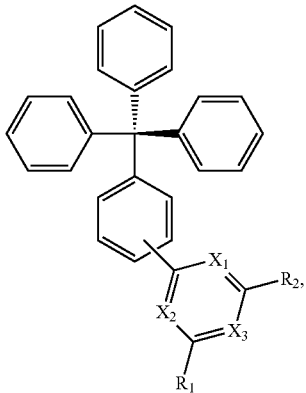

Formula 1 wherein, in Formula 1,
$X_1$ is N or $CR_3$, $X_2$ is N or $CR_4$, and $X_3$ is N or $CR_5$, and at least one of $X_1$, $X_2$ or $X_3$ is N, $R_1$ and $R_2$ are each independently selected from hydrogen, a hydroxyl group, a $C_2$-$C_{60}$ alkynyl group unsubstituted or substituted with at least one $R_{10a}$, a $C_1$-$C_{60}$ alkoxy group unsubstituted or substituted with at least one $R_{10a}$, or a $C_6$-$C_{60}$ aryloxy group unsubstituted or substituted with at least one $R_{10a}$, $-B(Q_1)(Q_2)$, $-C(=O)(Q_1)$, or $-P(=O)(Q_1)(Q_2)$, $R_3$ to $R_5$ are each independently selected from hydrogen, deuterium, $-F$, $-Cl$, $-Br$, $-I$, a hydroxyl group, a cyano group, a nitro group, a $C_1$-$C_{60}$ alkyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, or a $C_6$-$C_{60}$ arylthio group unsubstituted or substituted with at least one $R_{10a}$, $-B(Q_1)(Q_2)$, $-C(=O)(Q_1)$, $Si(Q_1)(Q_2)(Q_3)$, or $-P(=O)(Q_1)(Q_2)$, $R_{10a}$ is:
deuterium (-D), $-F$, $-Cl$, $-Br$, $-I$, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each being unsubstituted or substituted with deuterium, $-F$, $-Cl$, $-Br$, $-I$, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, $-Si(Q_{11})(Q_{12})(Q_{13})$, $-N(Q_{11})(Q_{12})$, $-B(Q_{11})(Q_{12})$, $-C(=O)(Q_{11})$, $-S(=O)_2(Q_{11})$, $-P(=O)(Q_{11})(Q_{12})$, or any combination thereof;

a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each being unsubstituted or substituted with deuterium, $-F$, $-Cl$, $-Br$, $-I$, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, $-Si(Q_{21})(Q_{22})(Q_{23})$, $-N(Q_{21})(Q_{22})$, $-B(Q_{21})(Q_{22})$, $-C(=O)(Q_{21})$, $-S(=O)_2(Q_{21})$, $-P(=O)(Q_{21})(Q_{22})$, or any combination thereof; or $-Si(Q_{31})(Q_{32})(Q_{33})$, $-N(Q_{31})(Q_{32})$, $-B(Q_{31})(Q_{32})$, $-C(=O)(Q_{31})$, $-S(=O)_2(Q_{31})$, or $-P(=O)(Q_{31})(Q_{32})$, and wherein $Q_1$ to $Q_3$, $Q_{11}$ to $Q_{13}$, $Q_{21}$ to $Q_{23}$, and $Q_{31}$ to $Q_{33}$ are each independently: hydrogen; deuterium; $-F$; $-Cl$; $-Br$; $-I$; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or $C_1$-$C_{60}$ heterocyclic group, each being unsubstituted or substituted with deuterium, $-F$, a cyano group, a $C_1$-$C_{60}$ alkyl group, a $C_1$-$C_{60}$ alkoxy group, a phenyl group, a biphenyl group, or any combination thereof.

2. The compound of claim 1, wherein the compound represented by Formula 1 is represented by Formula 2:

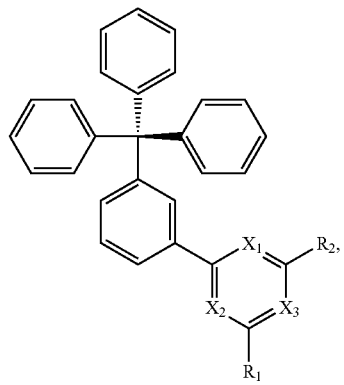

Formula 2 wherein, in Formula 2, $X_1$, $X_2$, $X_3$, $R_1$, and $R_2$ are each independently the same as described in connection with Formula 1.

3. The compound of claim 1, wherein the compound represented by Formula 1 is represented by Formula 3:

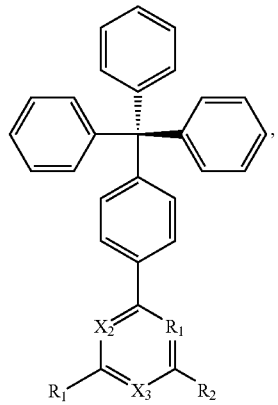

Formula 3 wherein, in Formula 3, $X_1$, $X_2$, $X_3$, $R_1$, and $R_2$ are each independently the same as described in connection with Formula 1.

4. The compound of claim 1, wherein the compound represented by Formula 1 is represented by Formula 4:

Formula 4

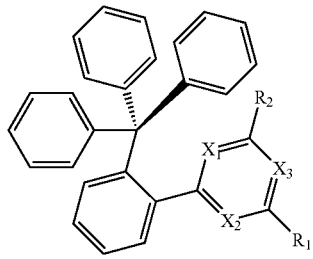

wherein, in Formula 4, $X_1$, $X_2$, $X_3$, $R_1$, and $R_2$ are each independently the same as described in connection with Formula 1.

5. The compound of claim 1, wherein a

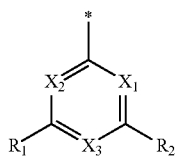

moiety in Formula 1 is selected from Formulae 2a to 2d:

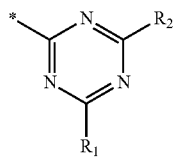
2a

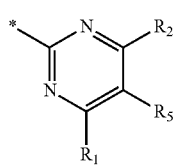
2b

2c

2d and wherein, in Formulae 2a to 2d, * is a binding site to a neighboring atom, and $R_1$ to $R_5$ are each independently the same as described in connection with Formula 1.

6. The compound of claim 2, wherein a

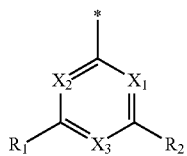

moiety in Formula 2 is selected from Formulae 2b to 2d:

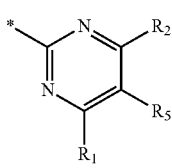
2b

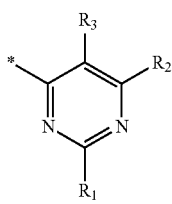
2c

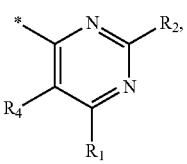
2d and wherein, in Formulae 2ba to 2d, * is binding site to a neighboring atom, and $R_1$ to $R_5$ are each independently as described in connection with Formula 2.

7. A compound, wherein the compound is selected from the following compounds:

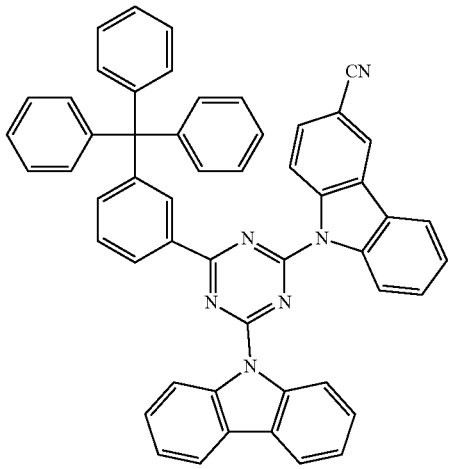
3

179
-continued
2
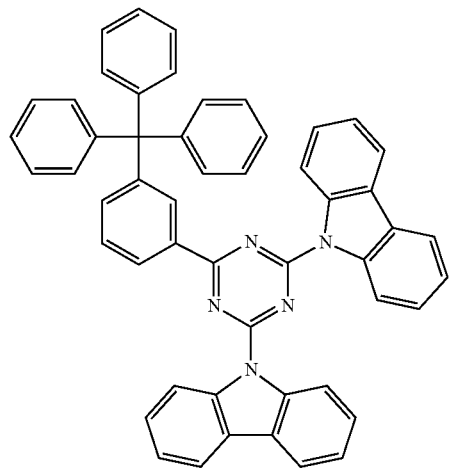
4
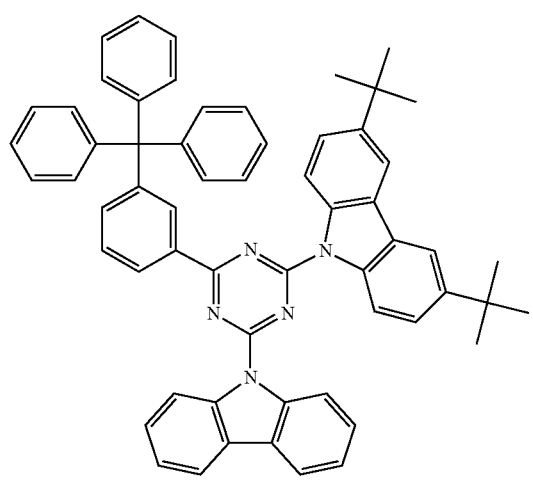
5
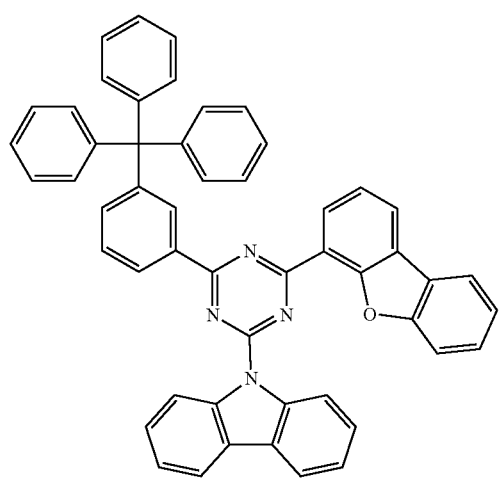
180
-continued
6
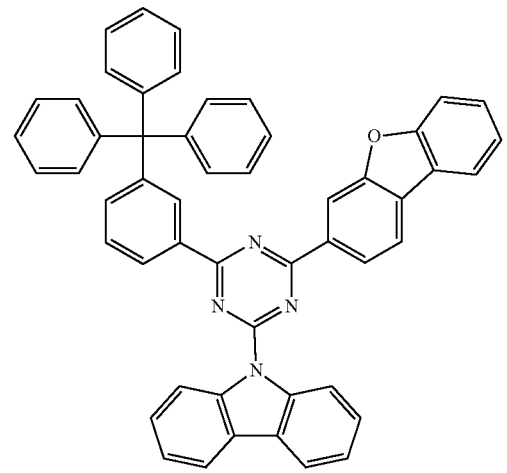
7
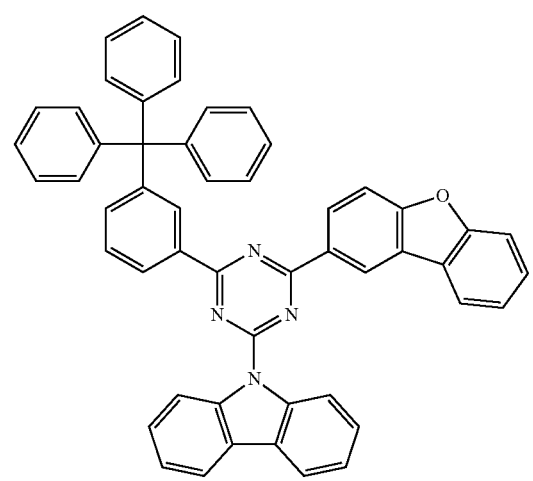
8
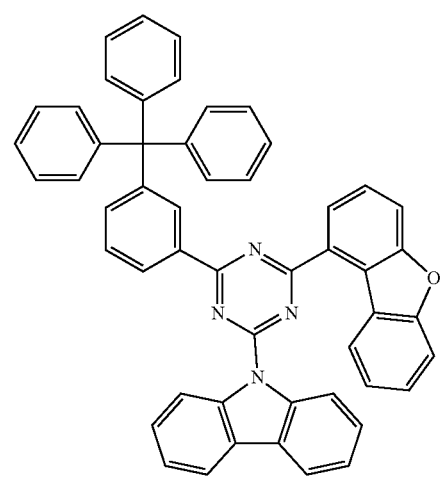

9
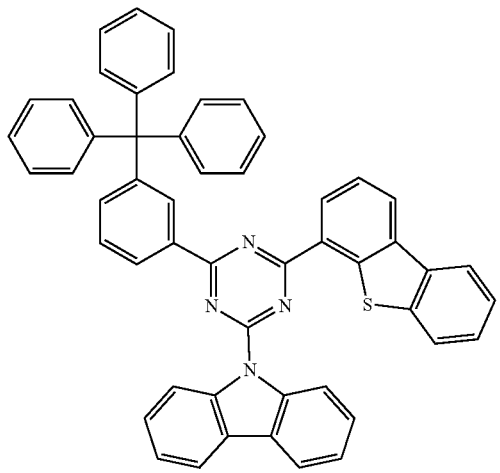
10
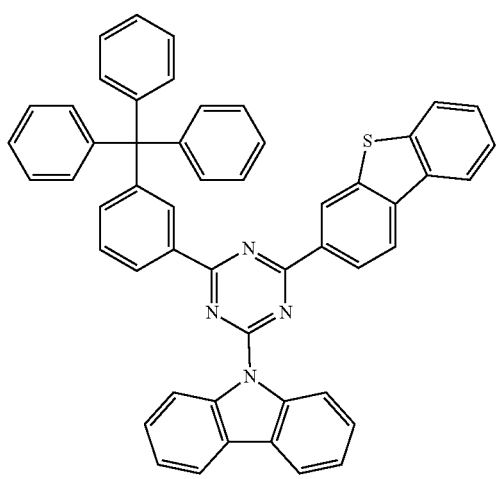
11
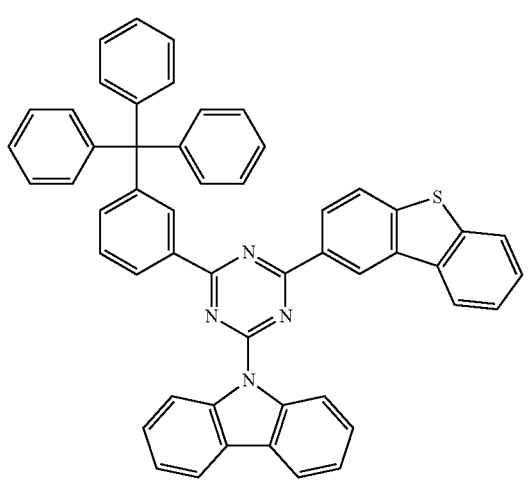
12
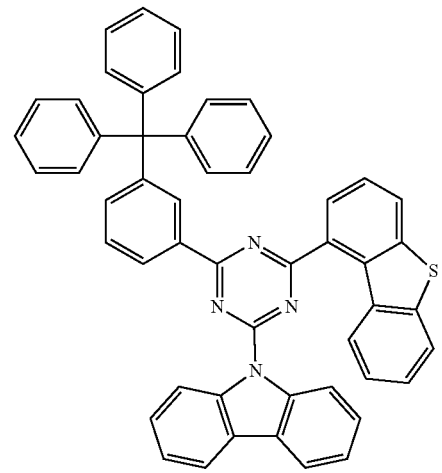
13
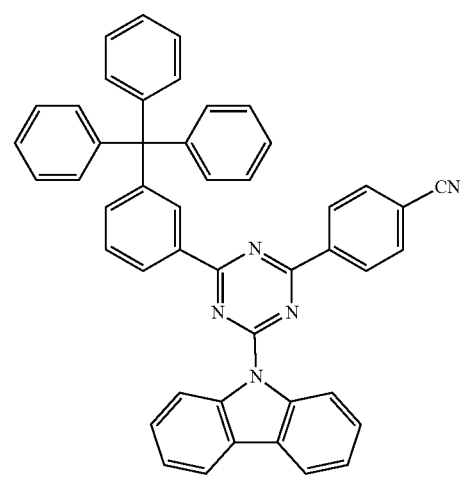
14
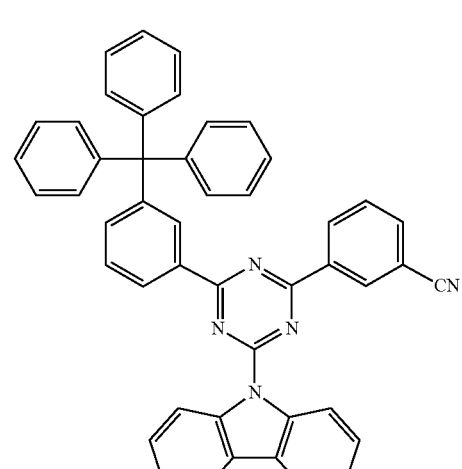

15
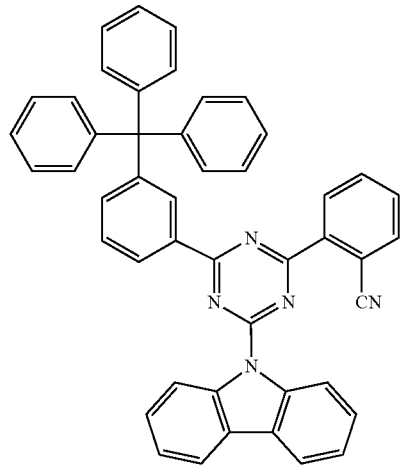
18
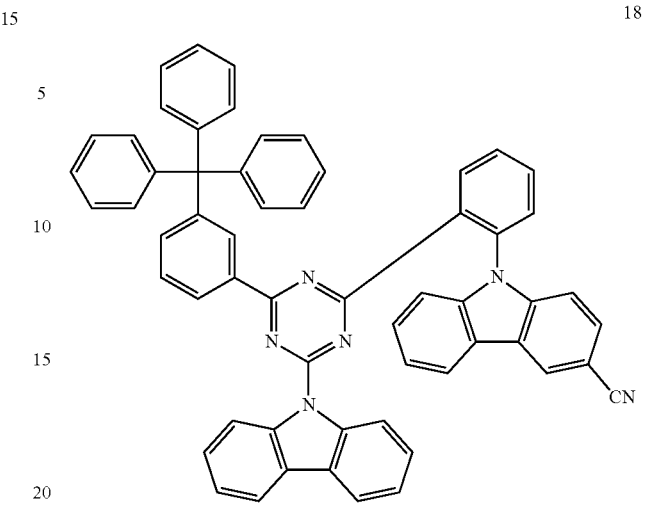
16
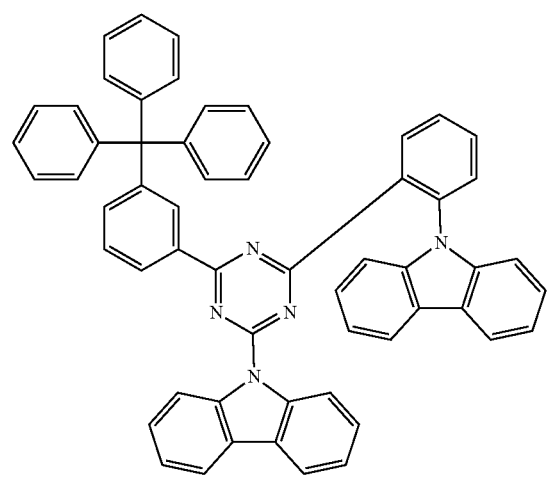
19
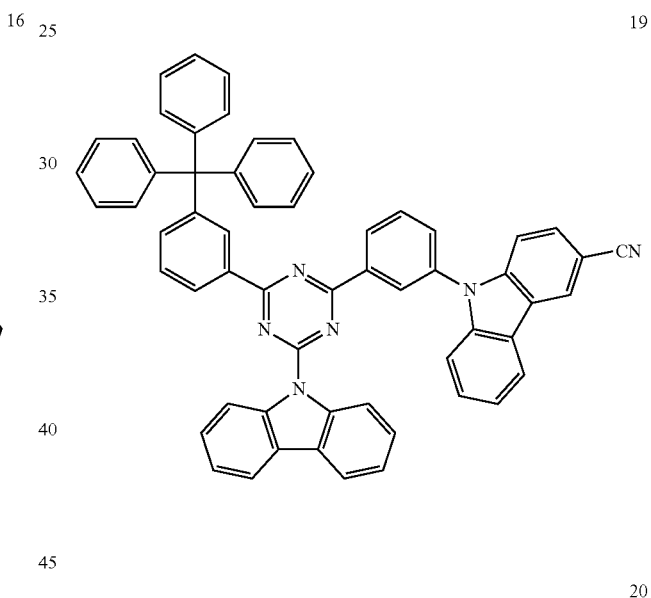
17
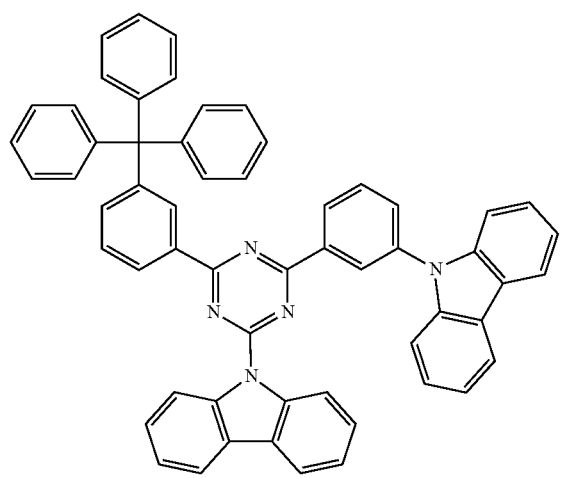
20
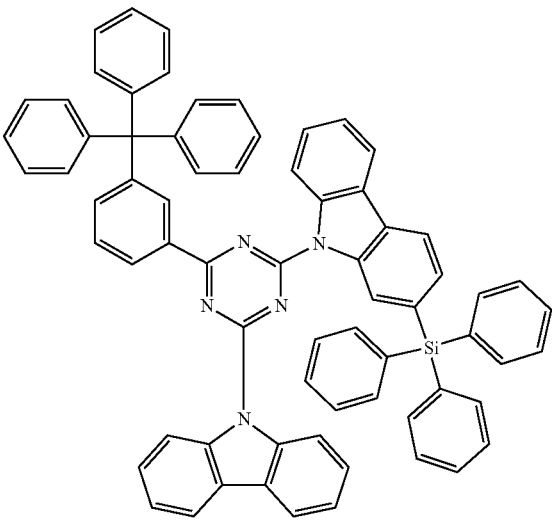

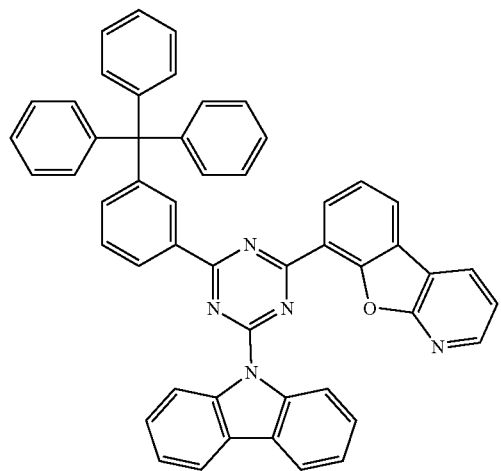
21
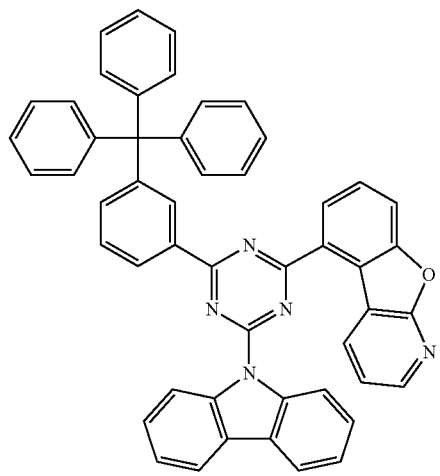
24
22
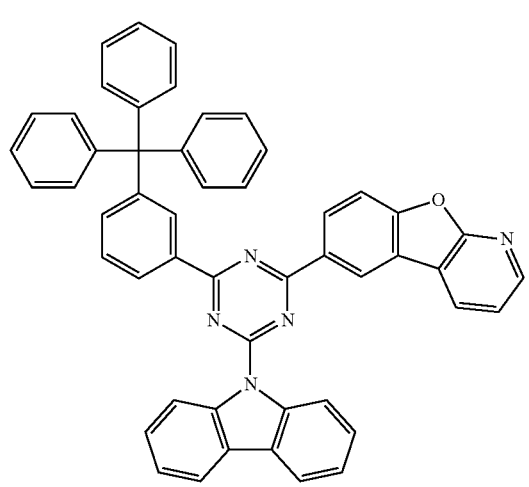
25
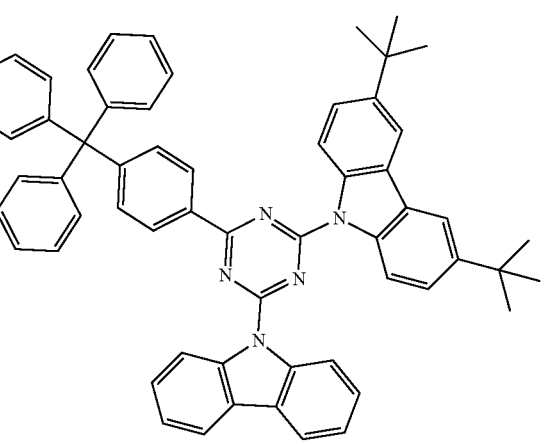
27
23
28

27
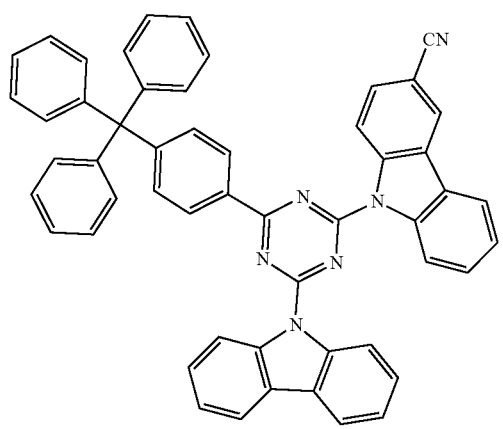
31
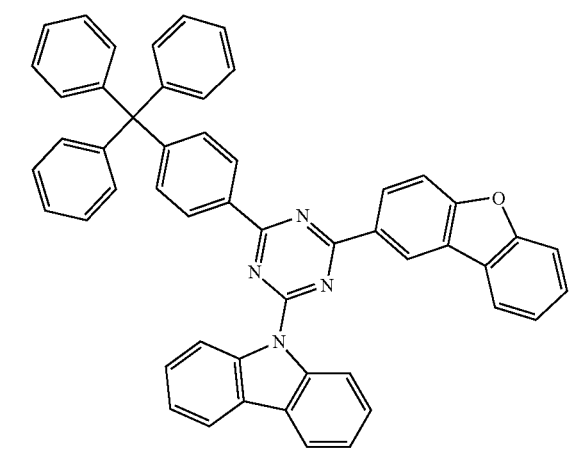
29
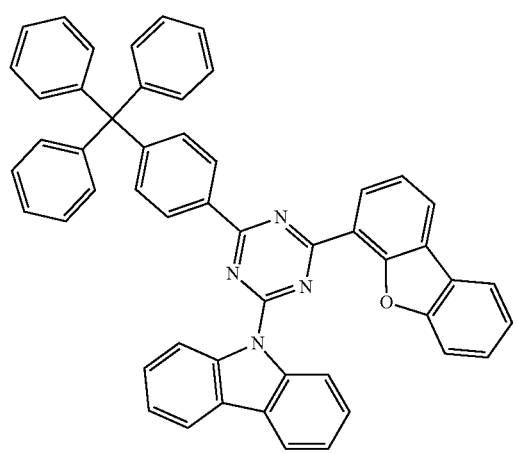
32
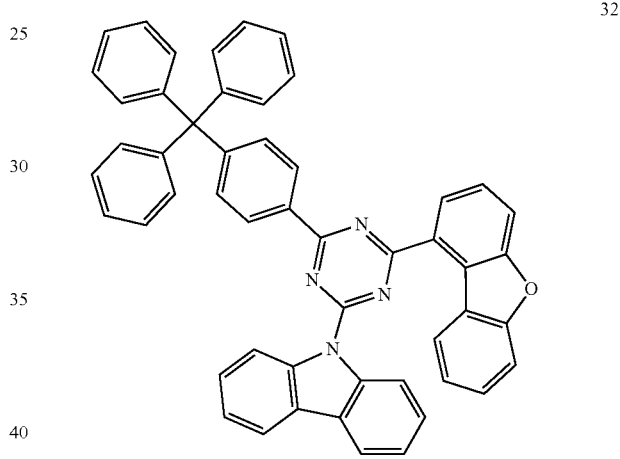
30
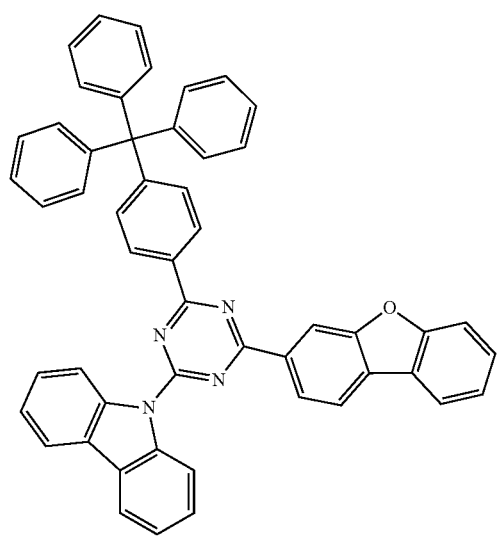
33
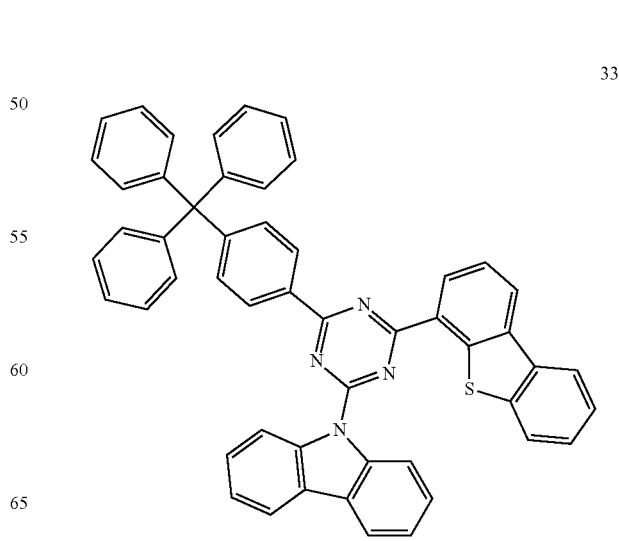

34
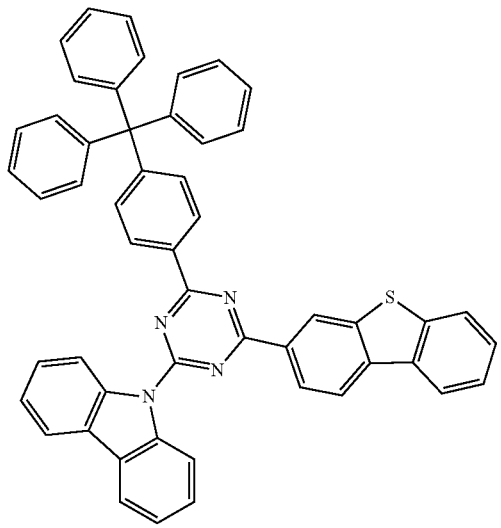
35
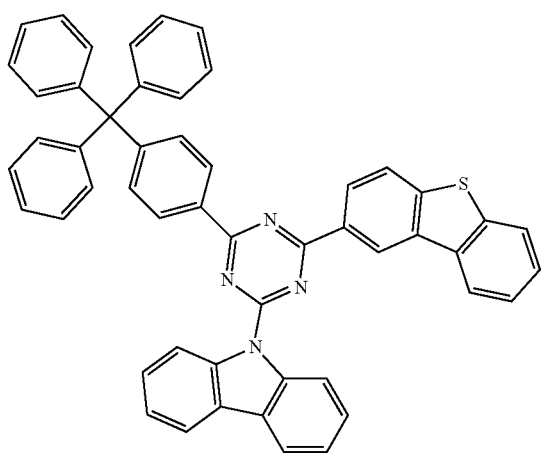
36
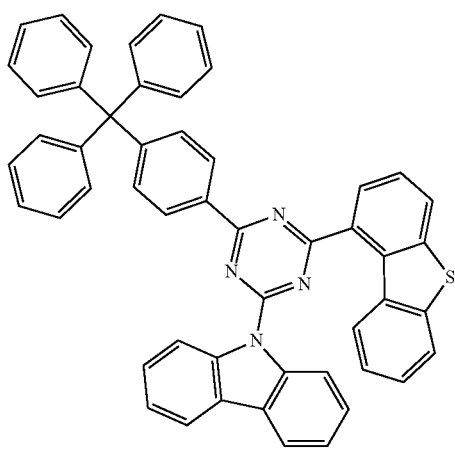
37
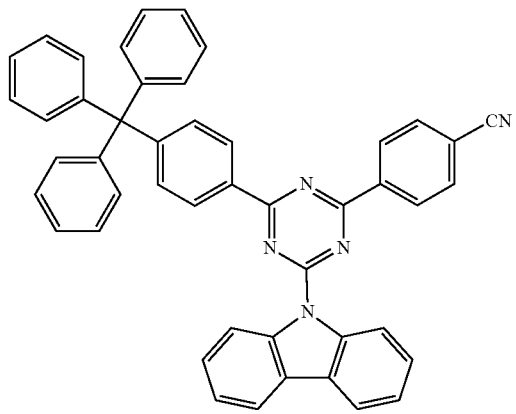
38
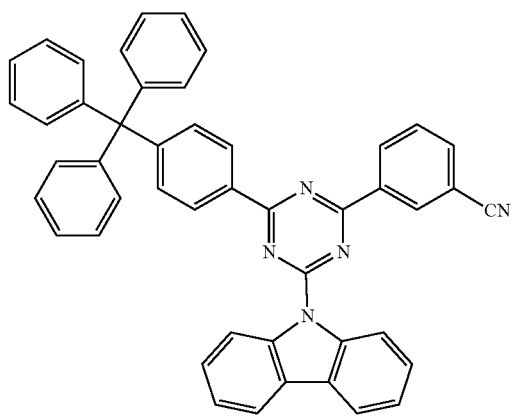
39

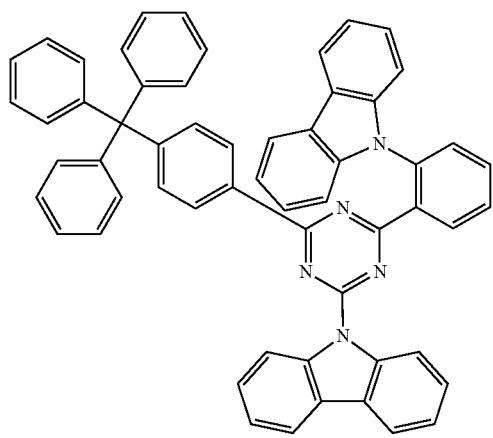
40
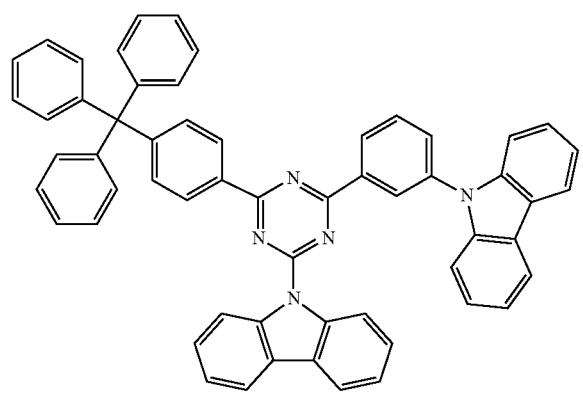
41
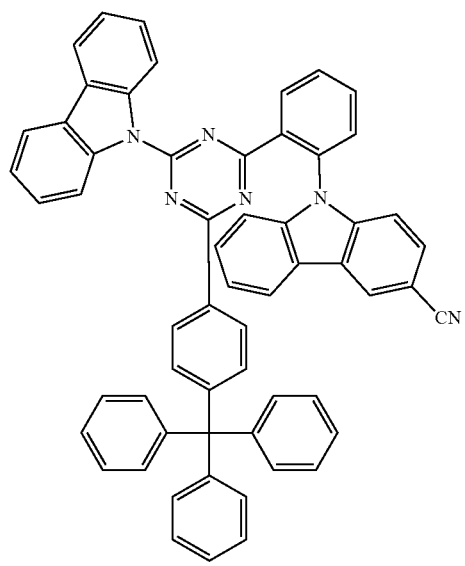
42
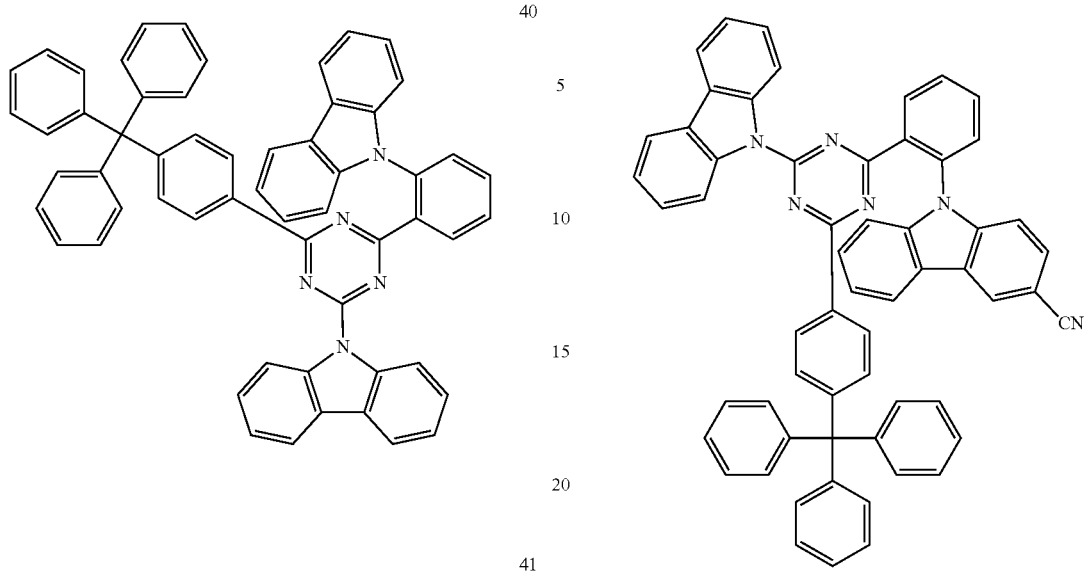
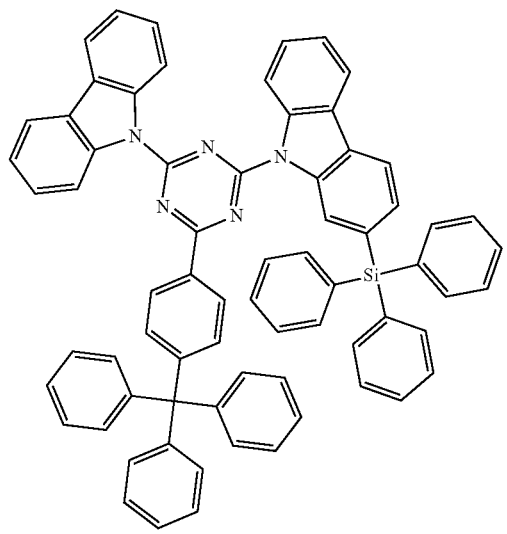
44

45
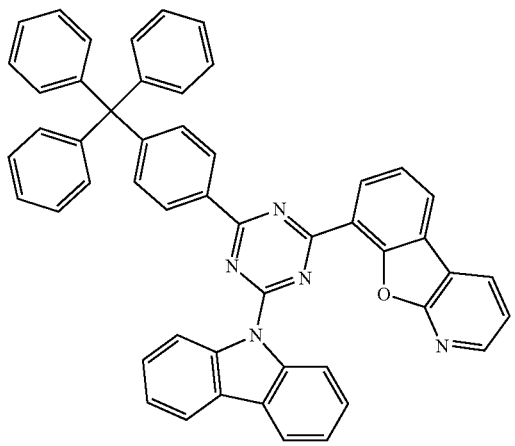
46
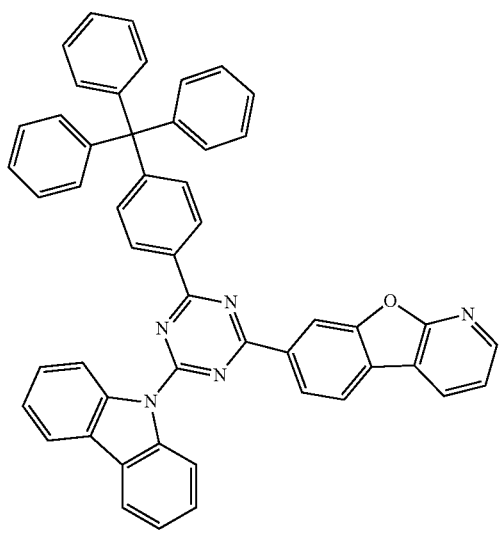
47
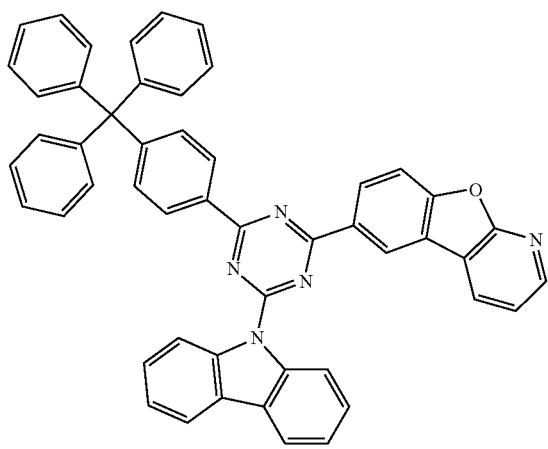
48
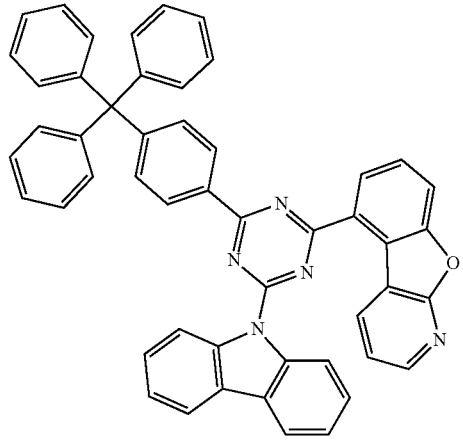
49
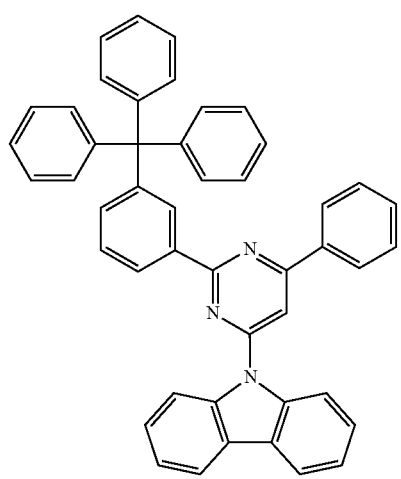
51
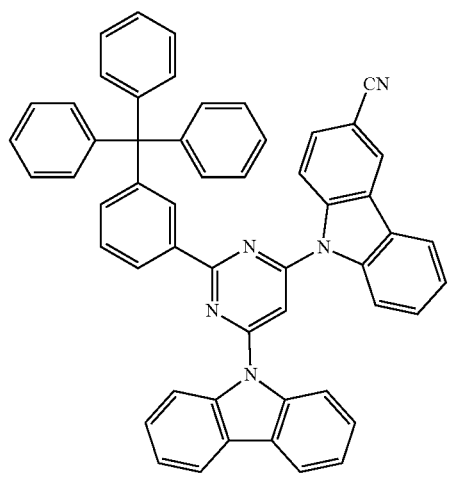

52
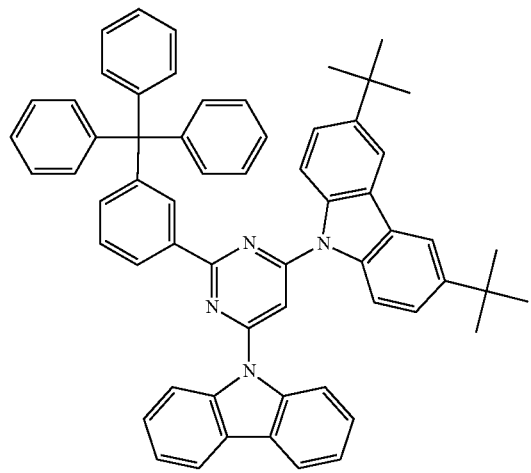
53
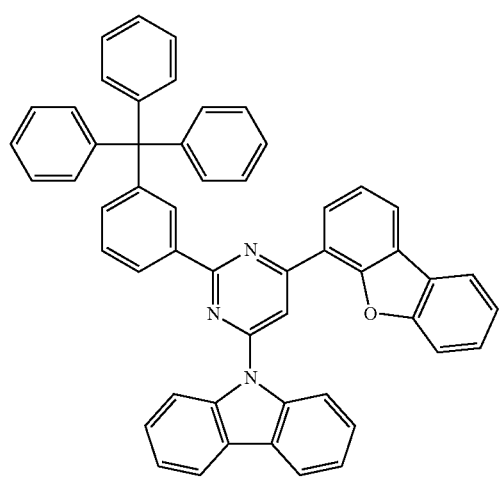
54
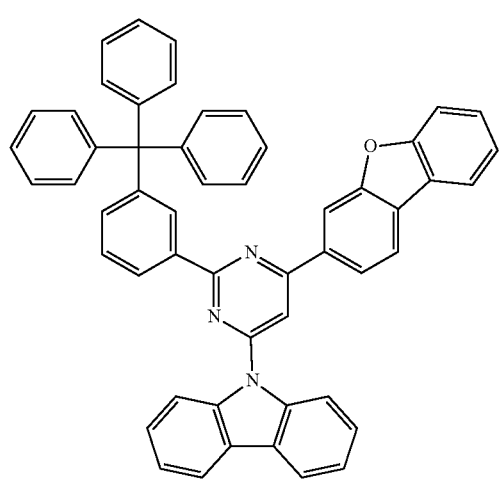
55
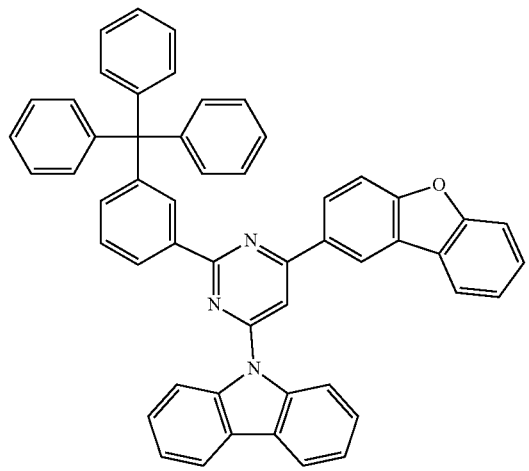
56
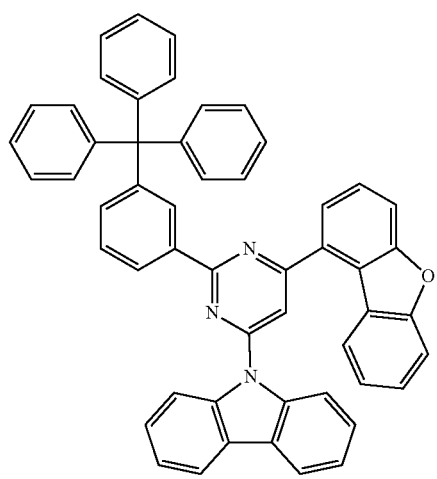
57
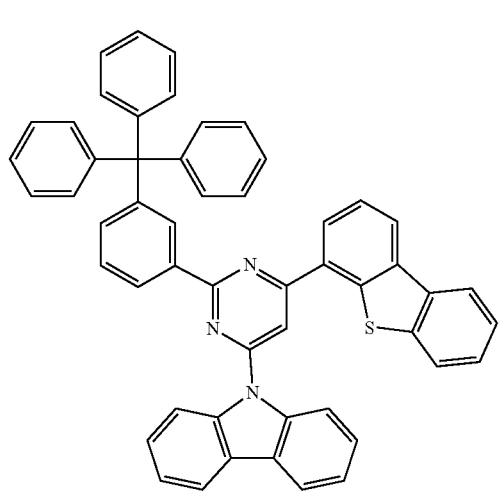

-continued
58
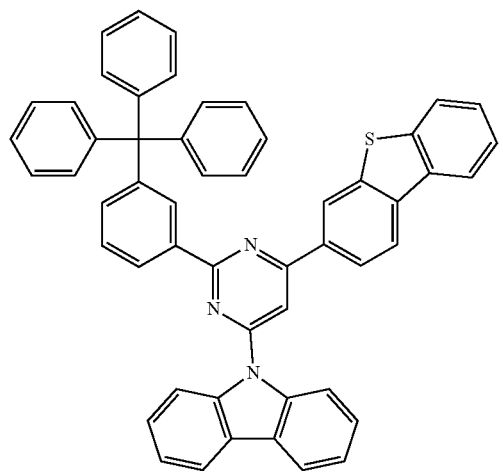
59
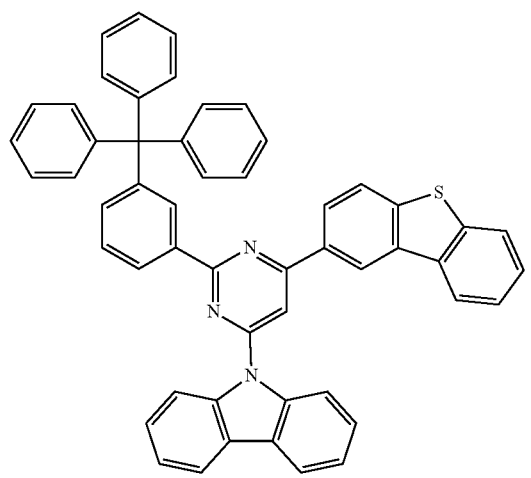
60
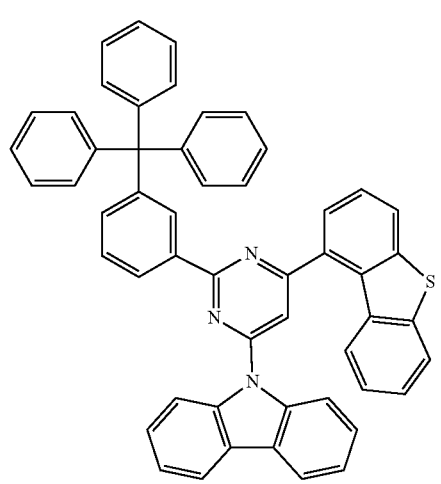
-continued
61
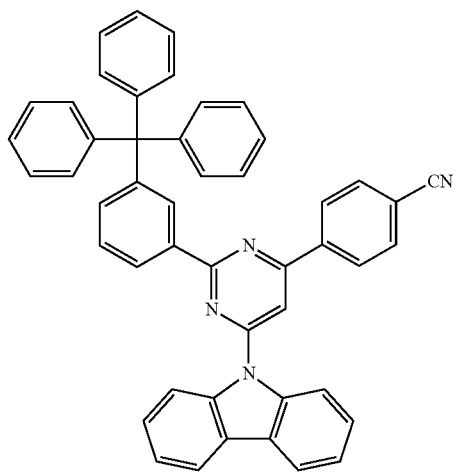
62
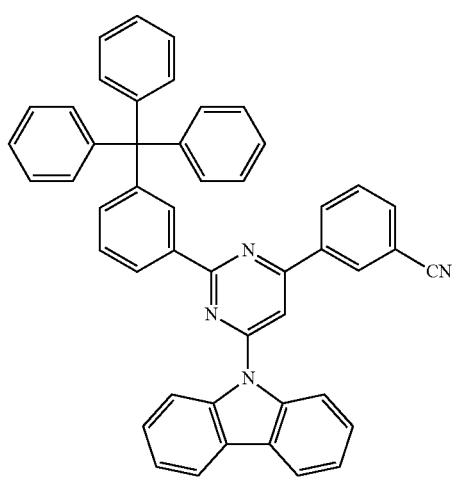
63
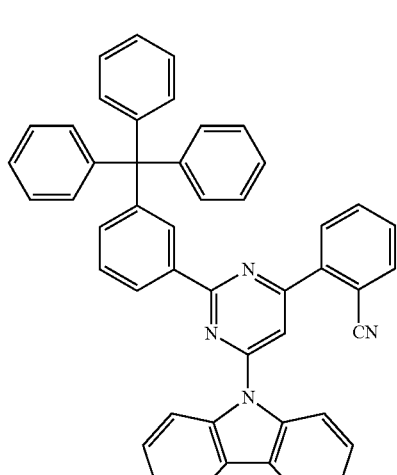

64
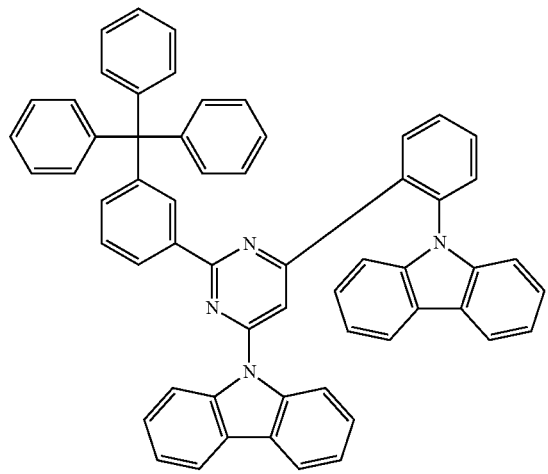
65
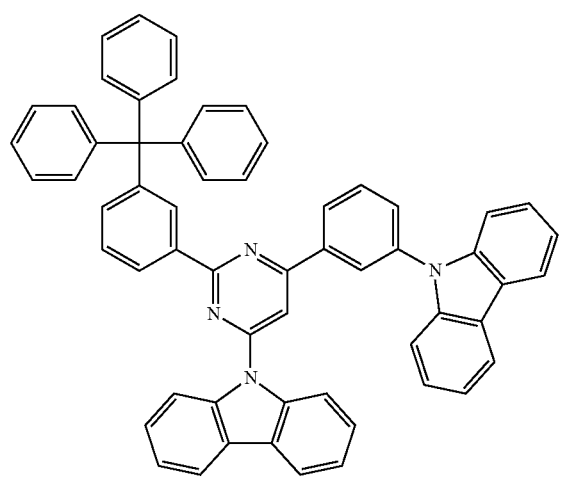
66
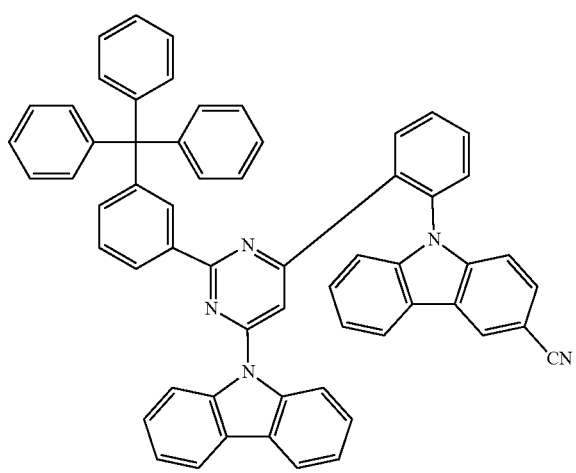
67
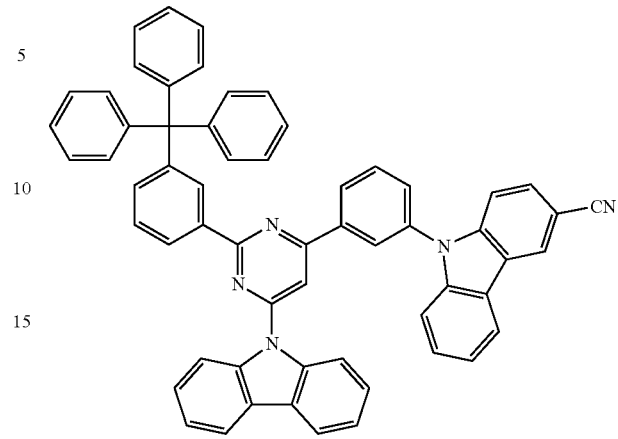
68
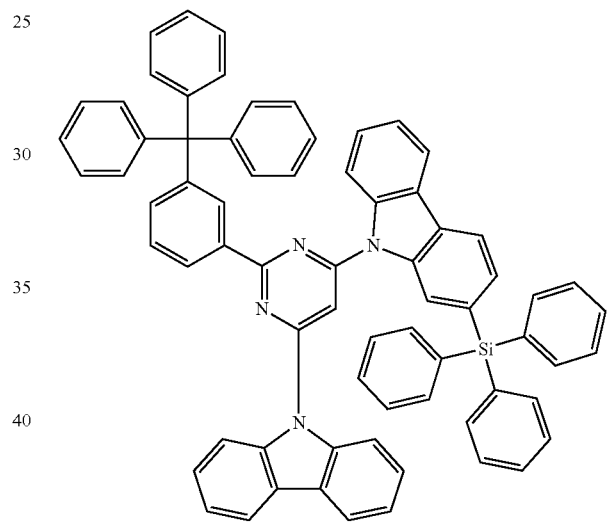
69
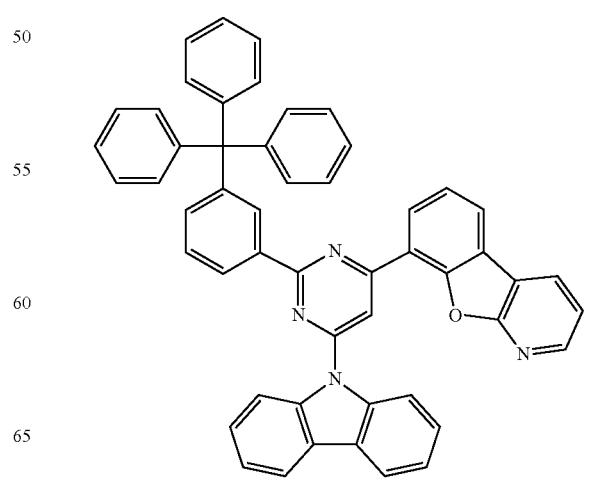

201
-continued
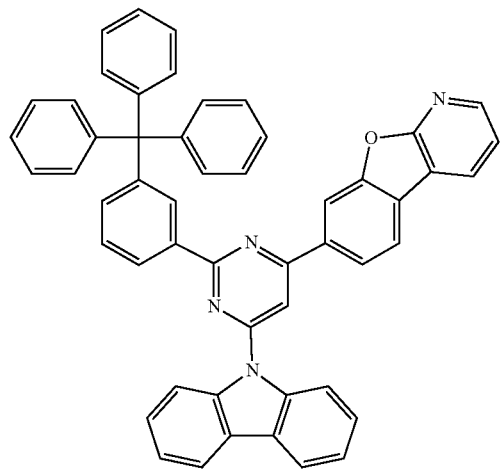
70
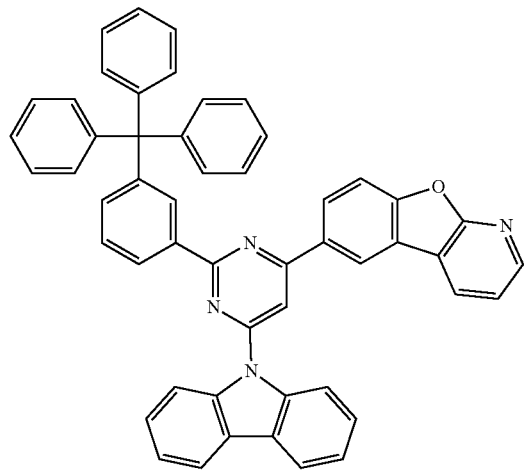
71
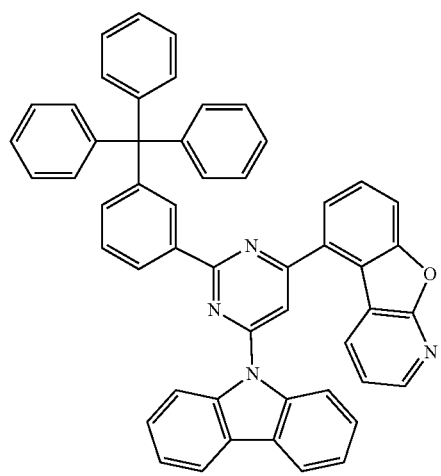
72
202
-continued
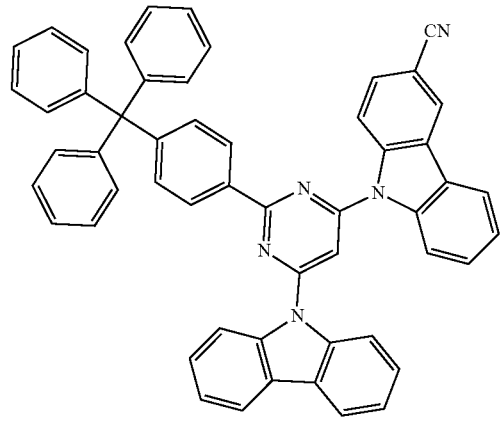
75
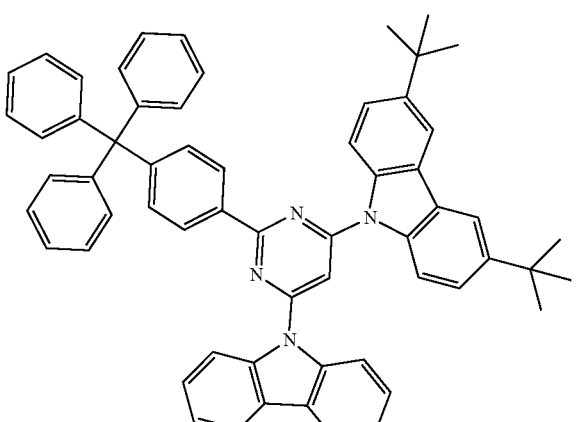
76
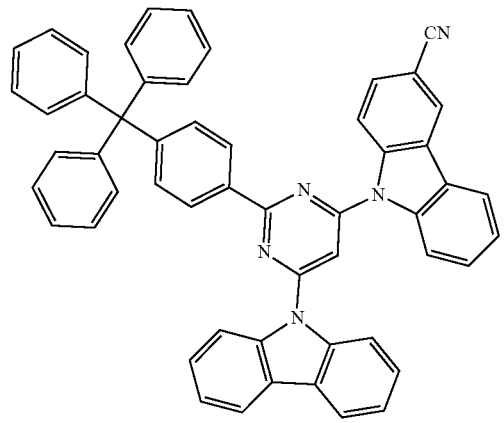
75

77
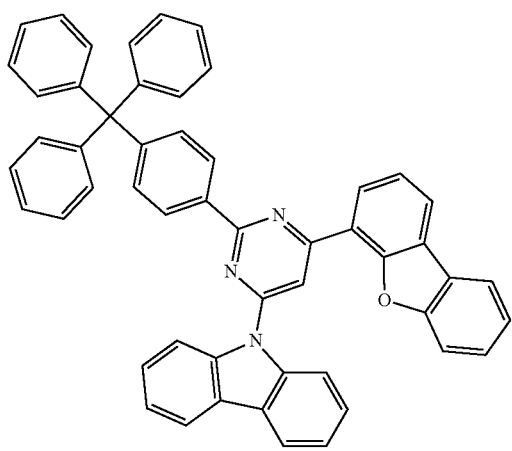
78
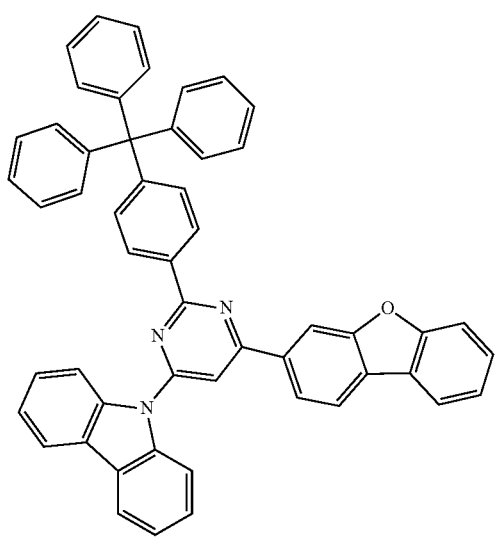
79
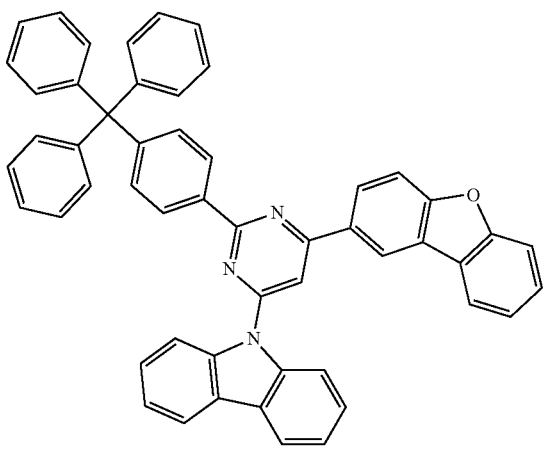
80
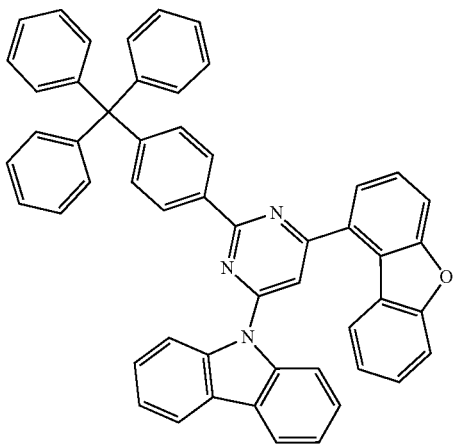
81
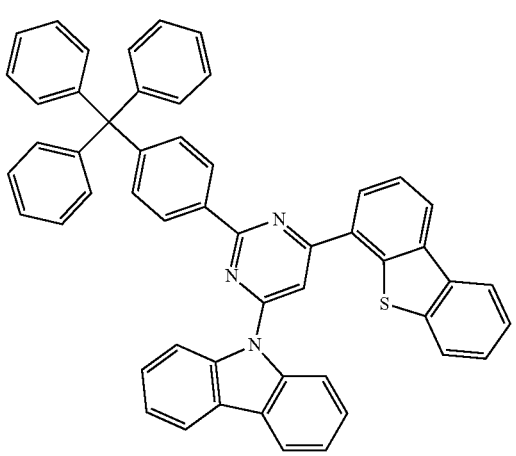
82
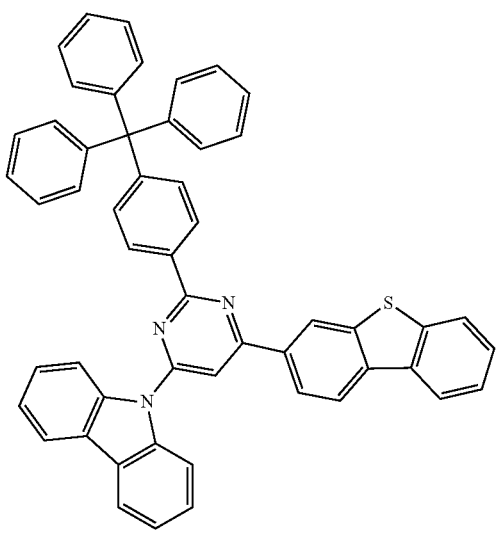

205
-continued
83
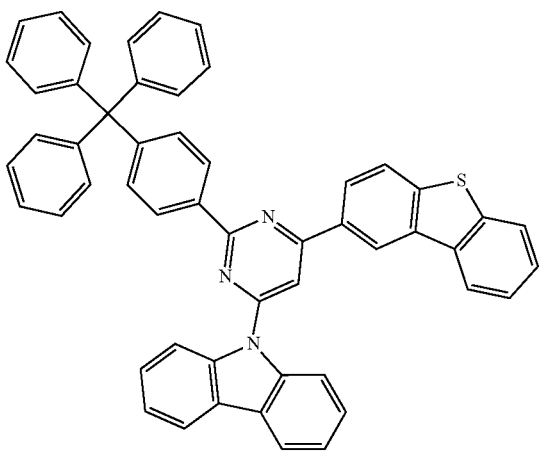
84
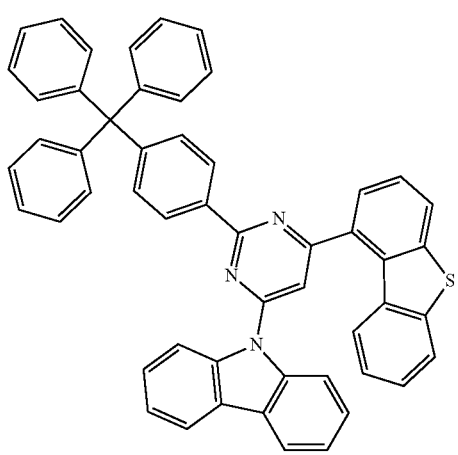
85
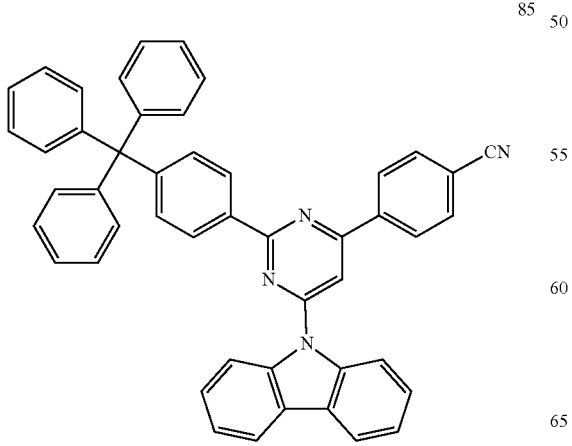
206
-continued
86
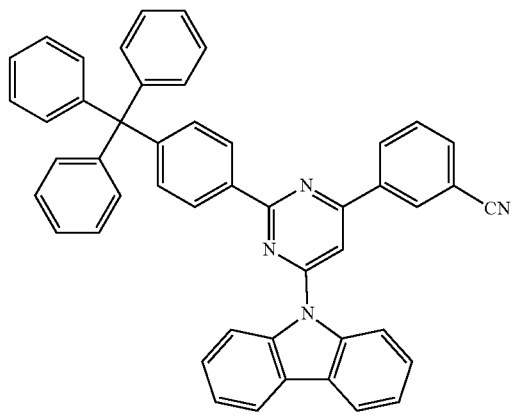
87
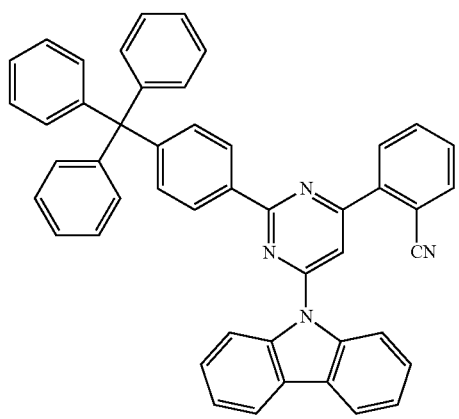
88
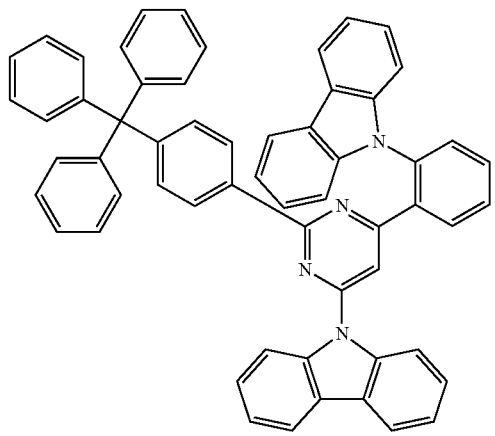

89
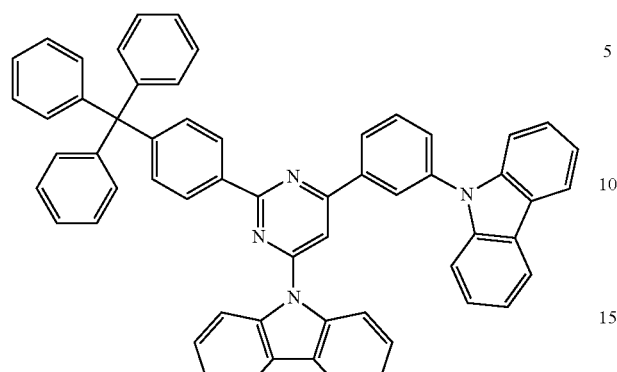
90
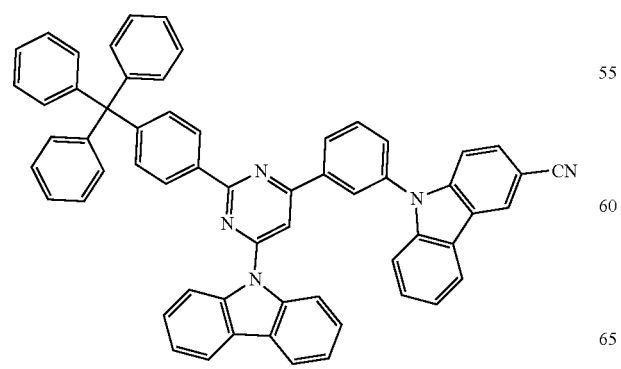
91
92
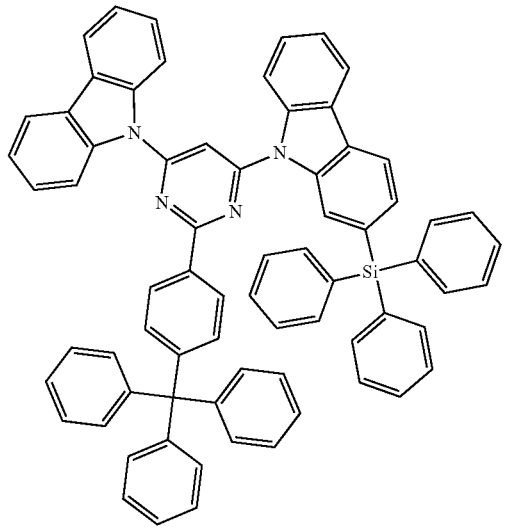
93
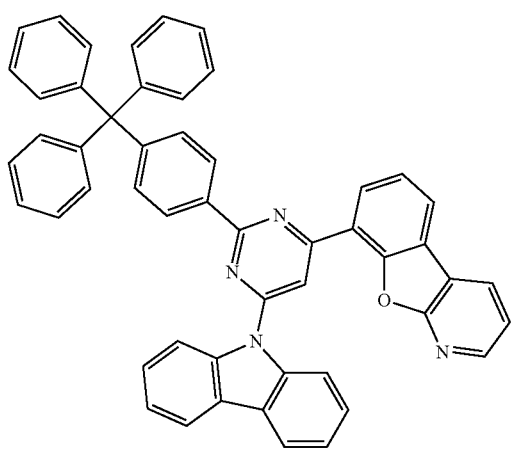
94
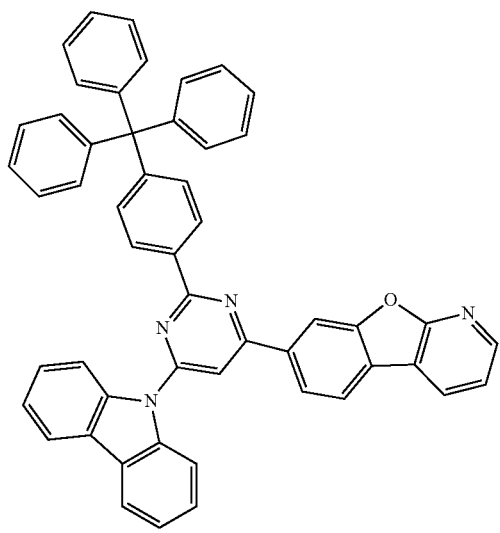

209
-continued
95
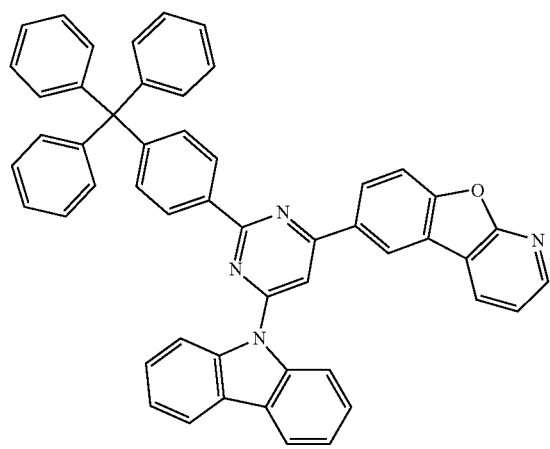
96
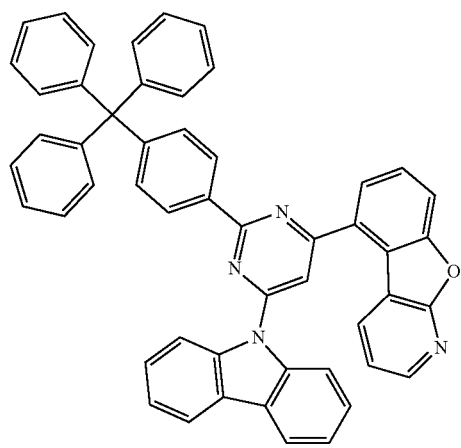
97
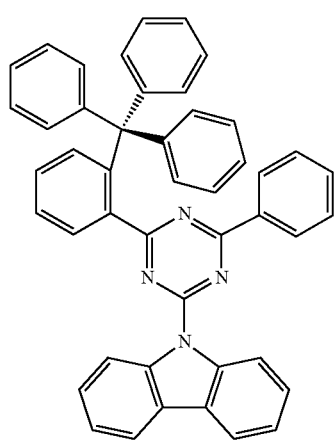
210
-continued
99
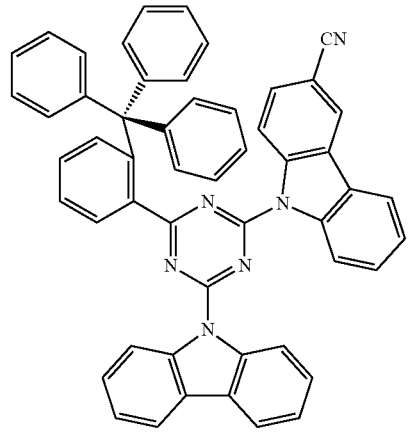
100
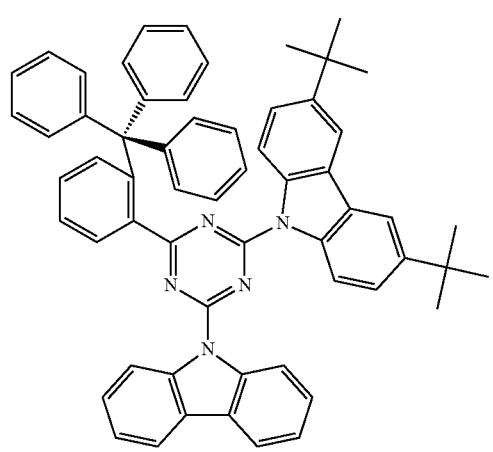
101
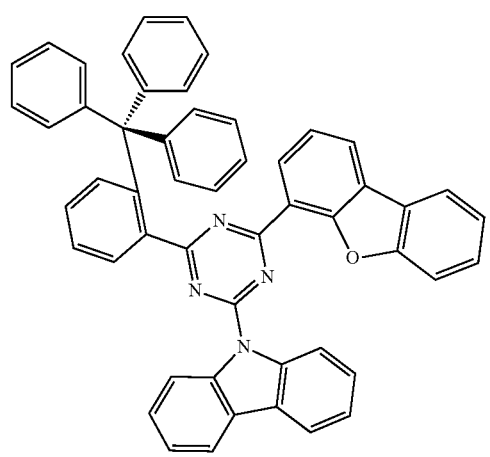

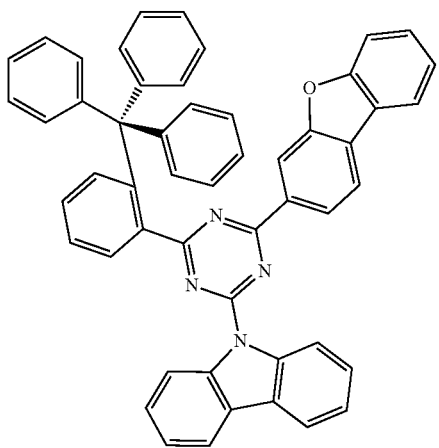
102
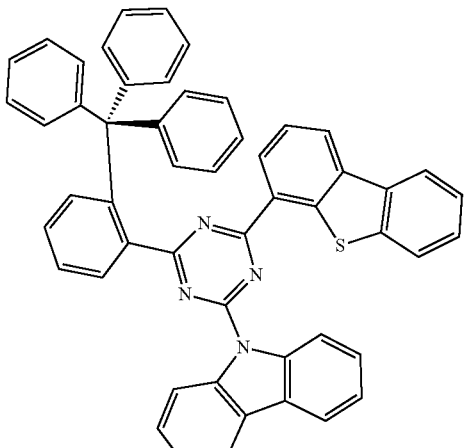
105
103
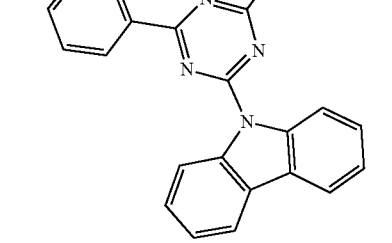
106
104
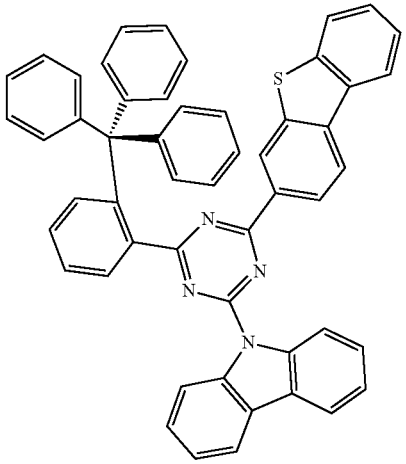
106

213
-continued
107
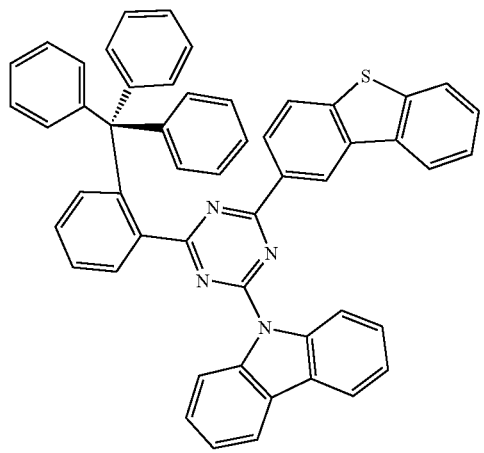
108
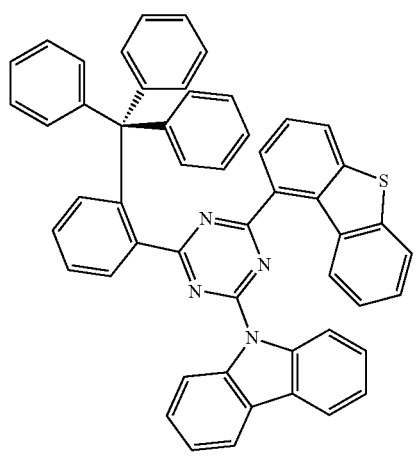
109
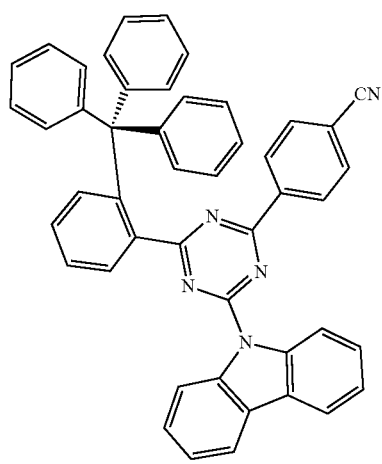
214
-continued
110
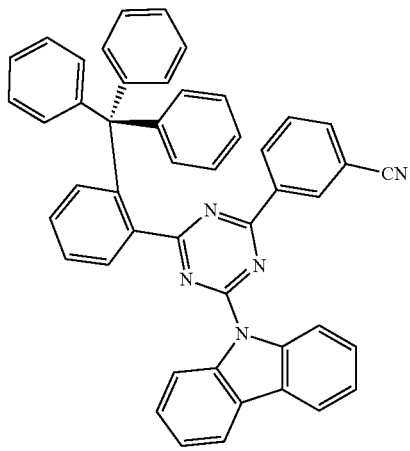
111
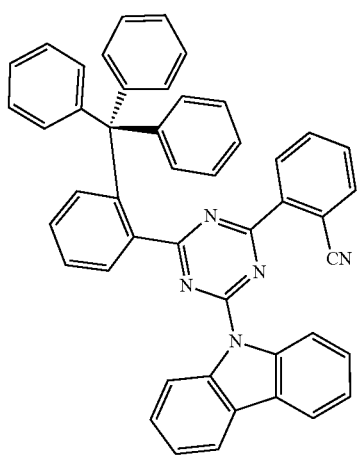
112
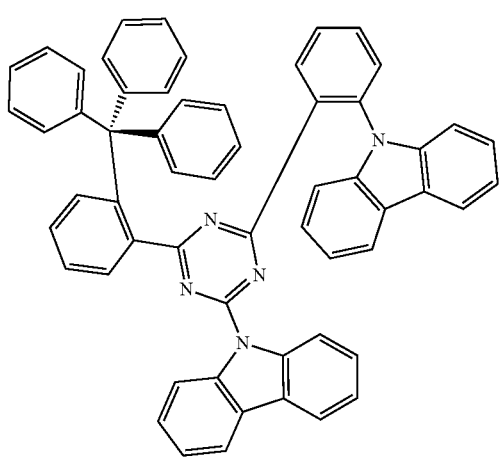

-continued
112
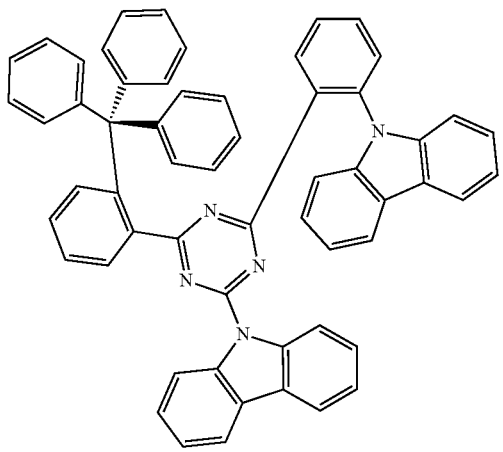
113
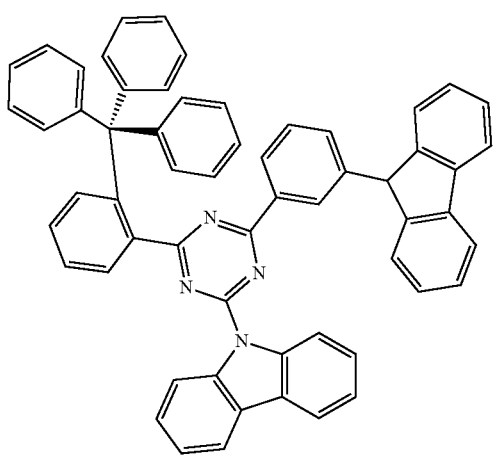
114
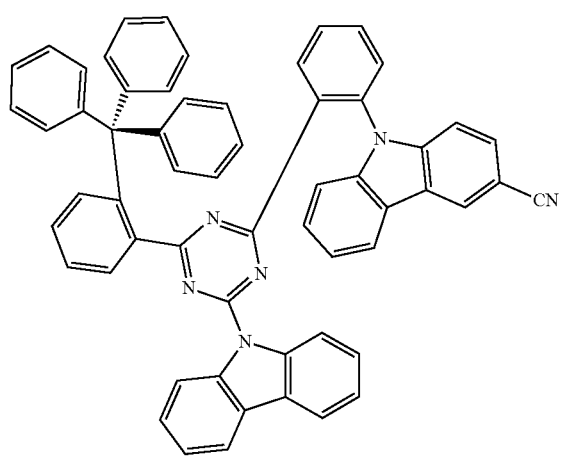
-continued
115
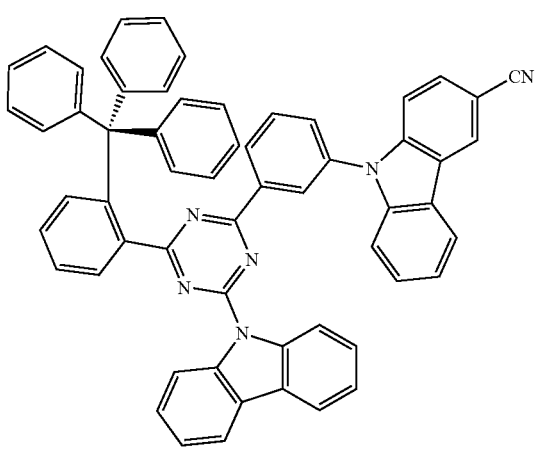
116
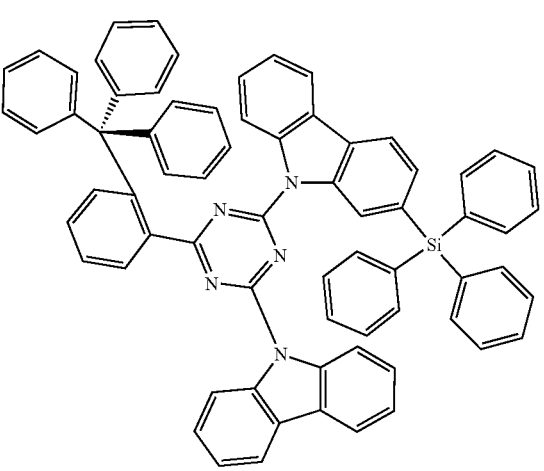
117
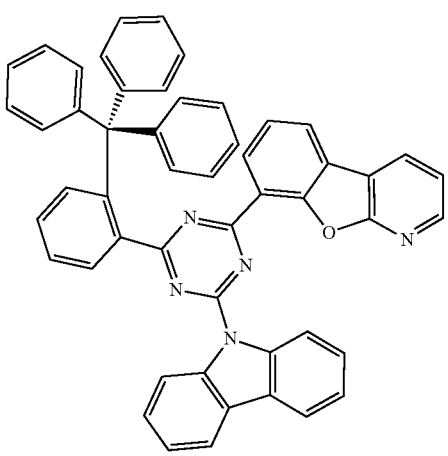

-continued

118

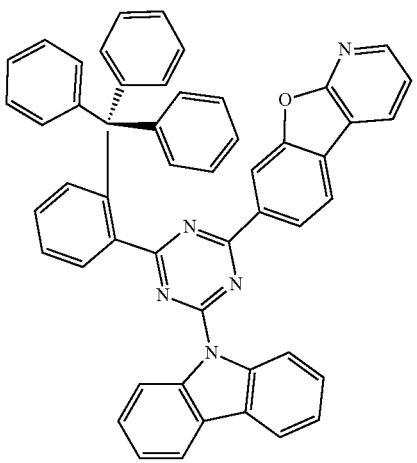

119

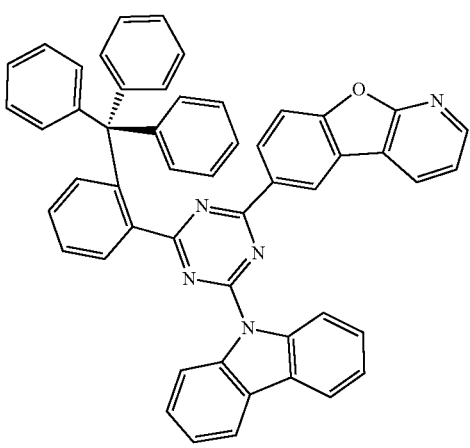

120

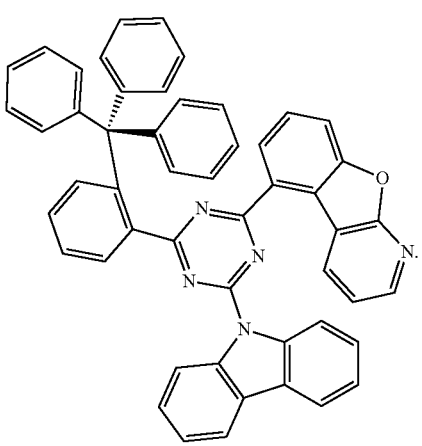

8. A light-emitting device comprising:
a first electrode;
a second electrode facing the first electrode; and
an interlayer between the first electrode and the second electrode and comprising an emission layer,
wherein the interlayer comprises the compound of claim 1.

9. The light-emitting device of claim 8, wherein the emission layer is a phosphorescent emission layer comprising the compound.

10. The light-emitting device of claim 8, wherein the emission layer is a fluorescent emission layer.

11. The light-emitting device of claim 10, wherein the emission layer comprises the compound of claim 1 as a thermally activated delayed fluorescence (TADF) material.

12. The light-emitting device of claim 8, wherein the first electrode is an anode,
the second electrode is a cathode,
the interlayer further comprises a hole transport region between the first electrode and the emission layer and an electron transport region between the emission layer and the second electrode,
the hole transport region comprises a hole injection layer, a hole transport layer, an emission auxiliary layer, an electron blocking layer, or any combination thereof, and
the electron transport region comprises a hole blocking layer, an electron transport layer, an electron injection layer, or any combination thereof.

13. An electronic apparatus comprising the light-emitting device of claim 8.

14. A light-emitting device comprising:
a first electrode;
a second electrode facing the first electrode; and
an interlayer between the first electrode and the second electrode and comprising an emission layer,
wherein the interlayer comprises a compound selected from the following compounds:

3

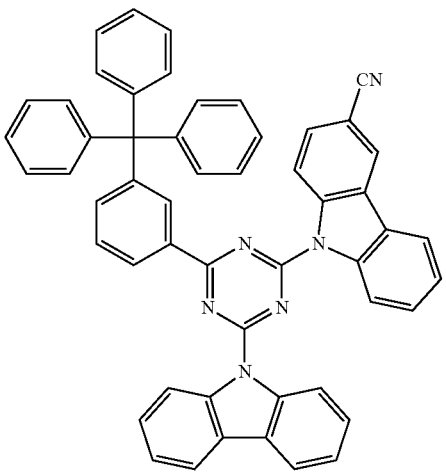

4

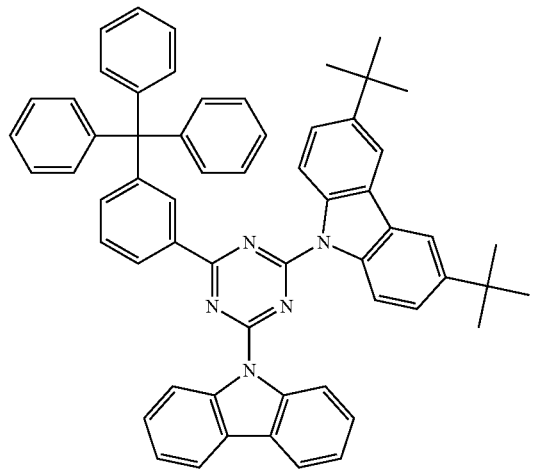

219
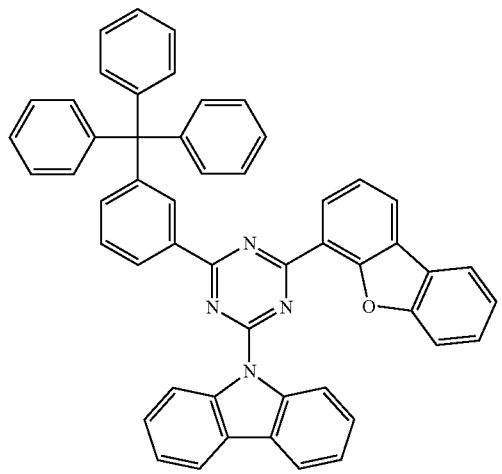
5
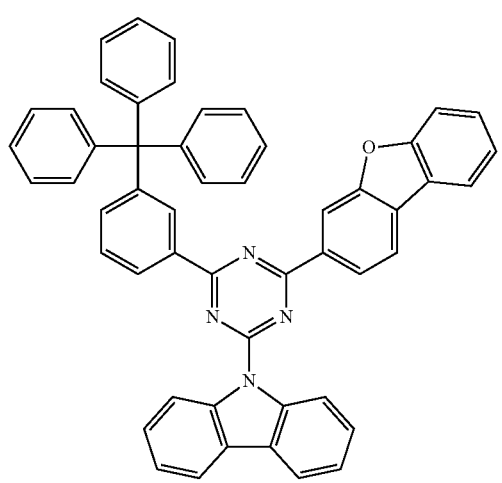
6
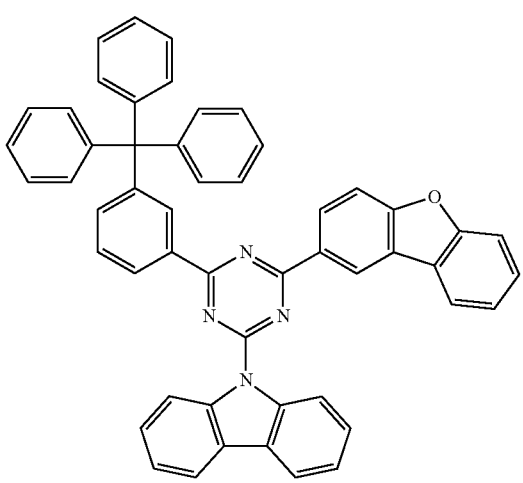
7
220
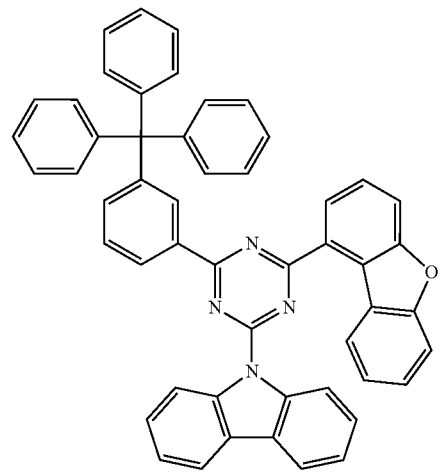
8
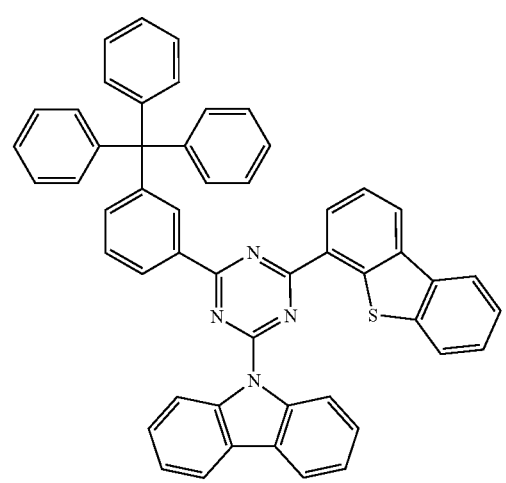
9
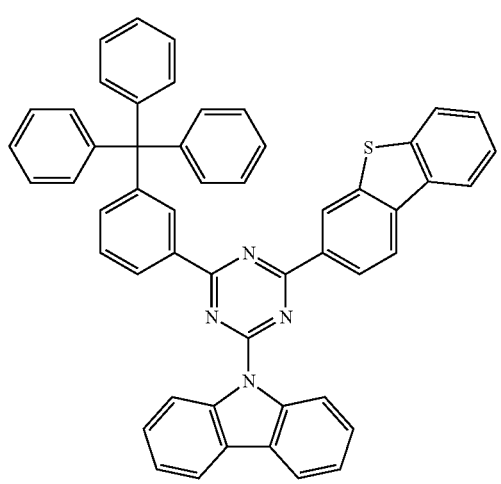
10

-continued
11
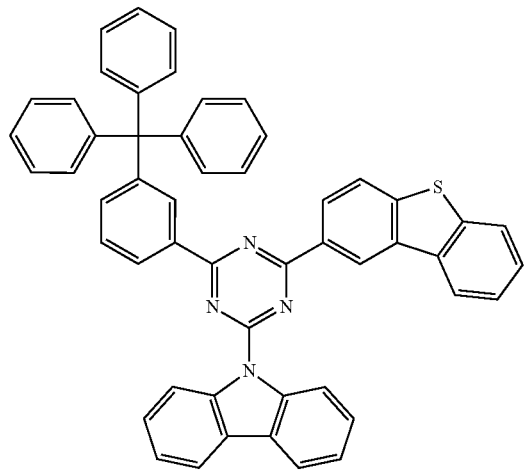
12
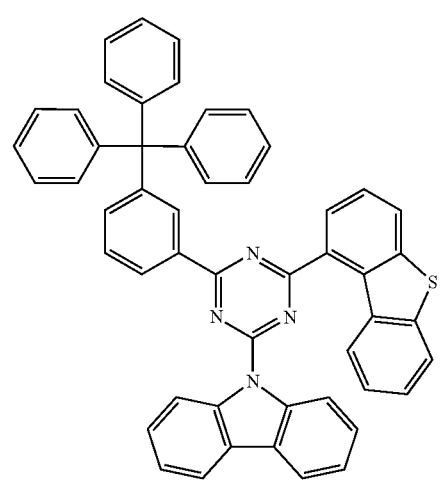
13
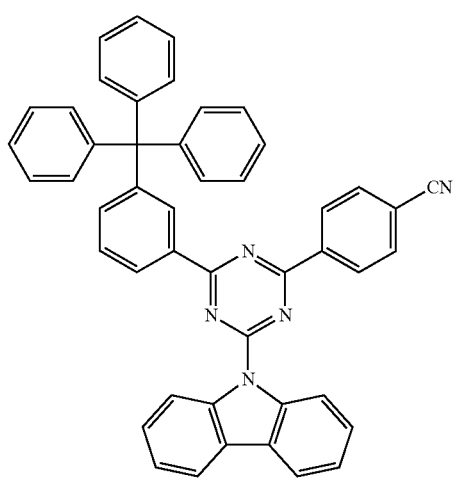
-continued
14
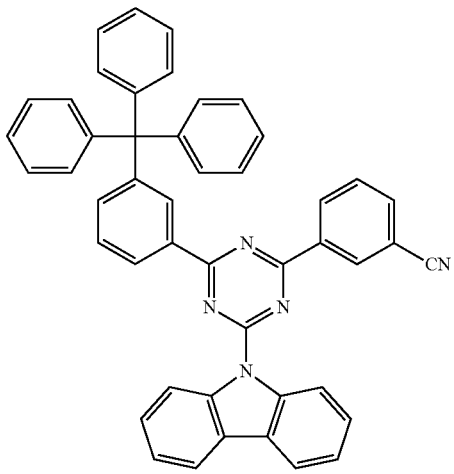
15
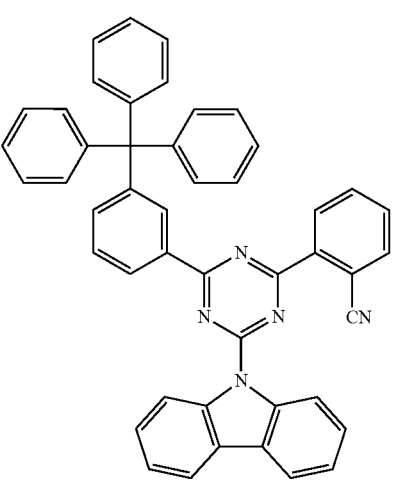
16
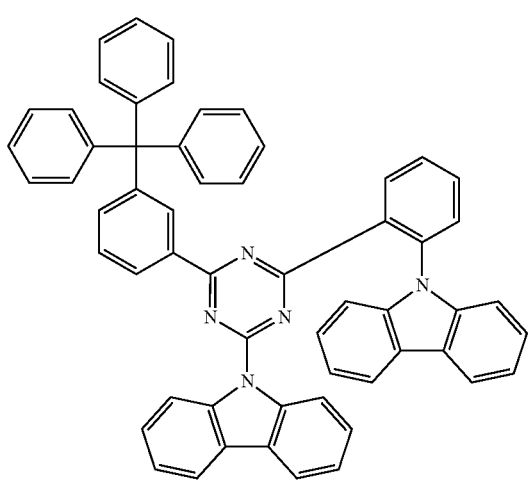

17
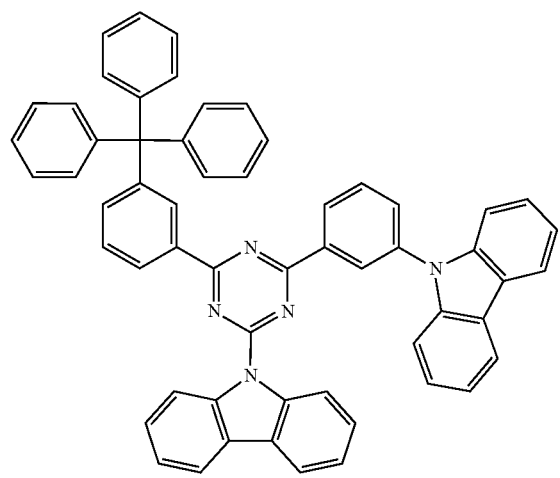
18
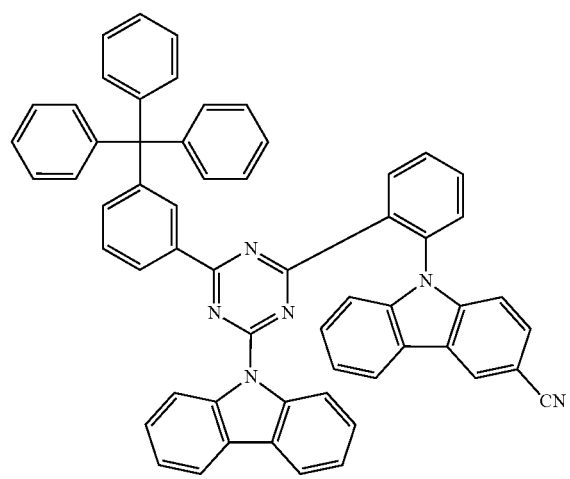
19
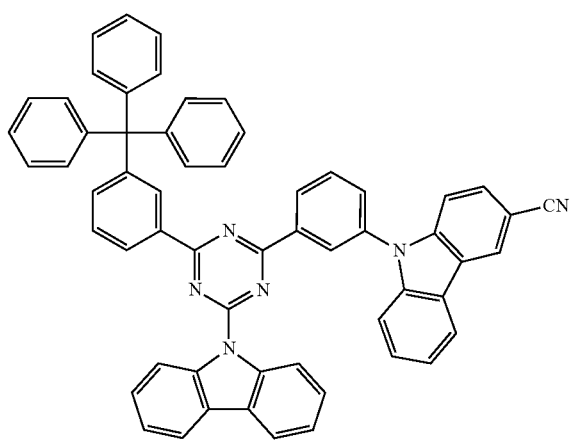
20
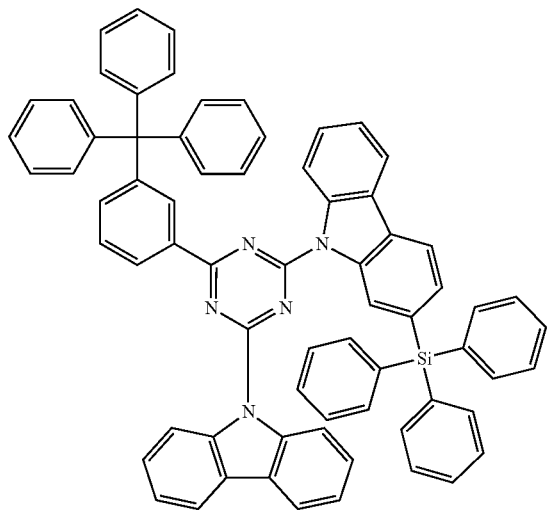
21
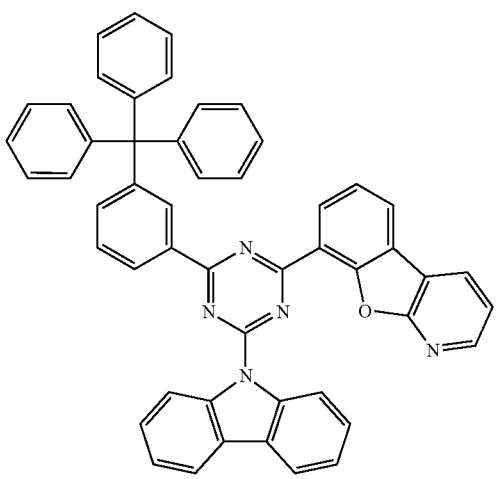
22
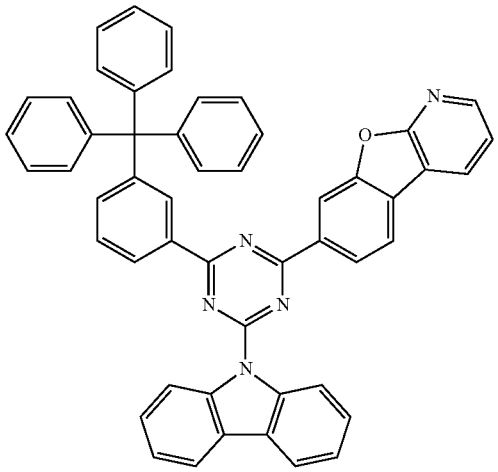

23
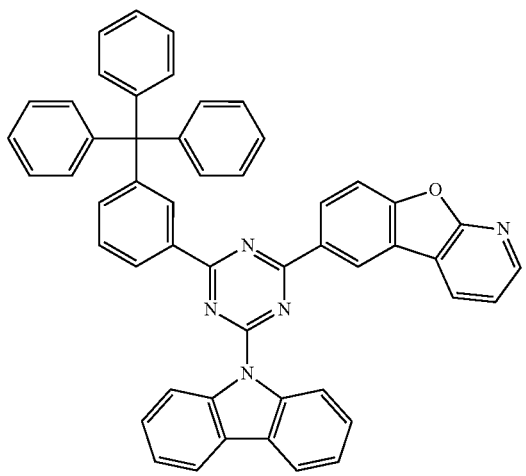
24
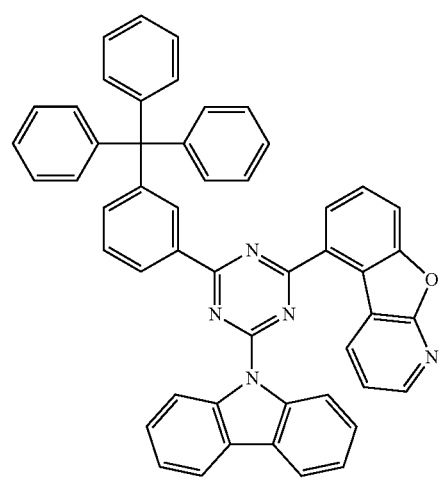
27
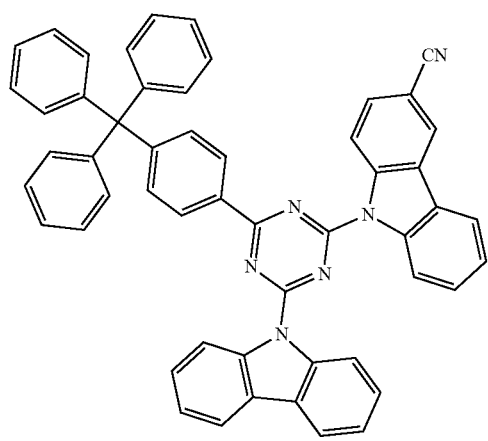
28
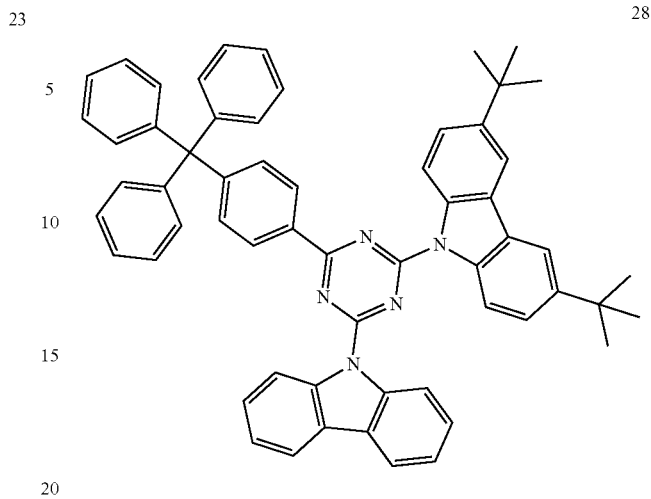
29
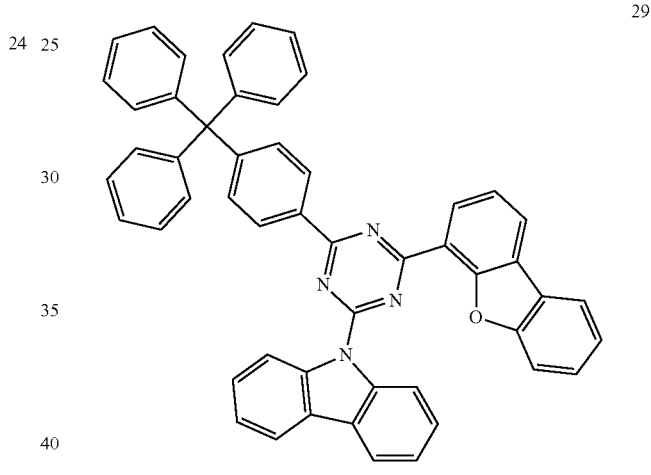
30
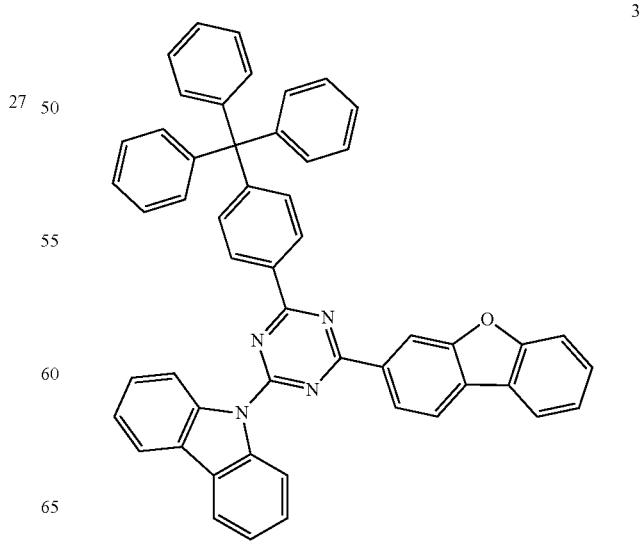

31
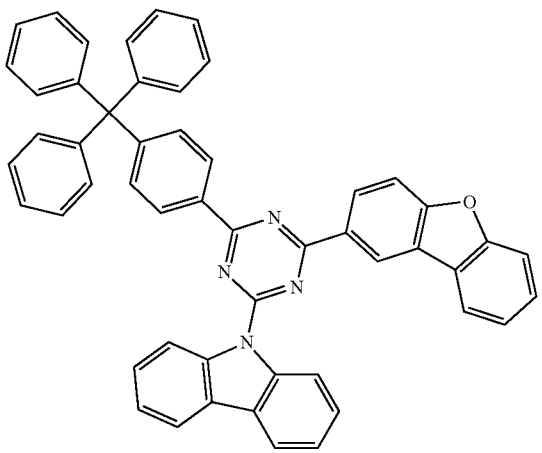
32
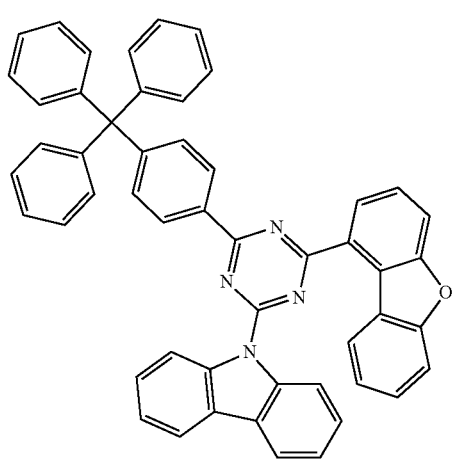
33
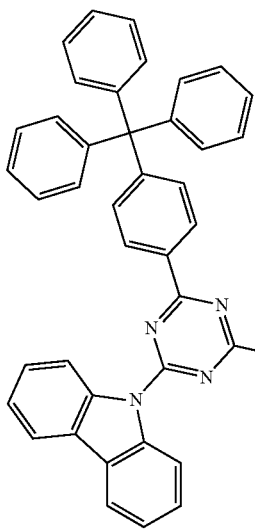
34
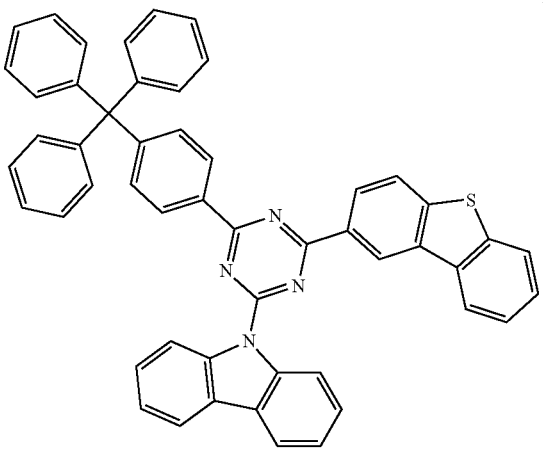
35
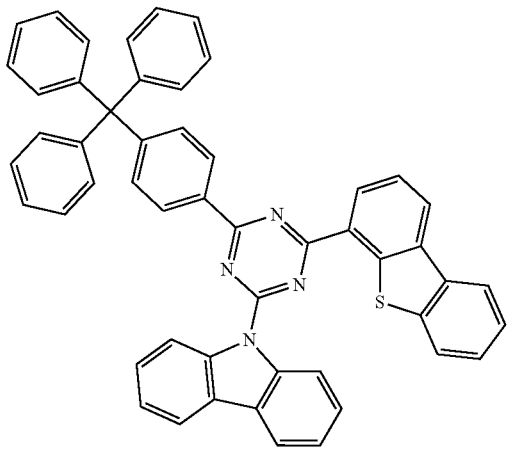
36
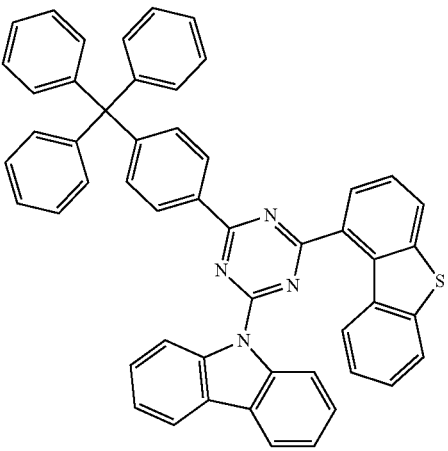

37
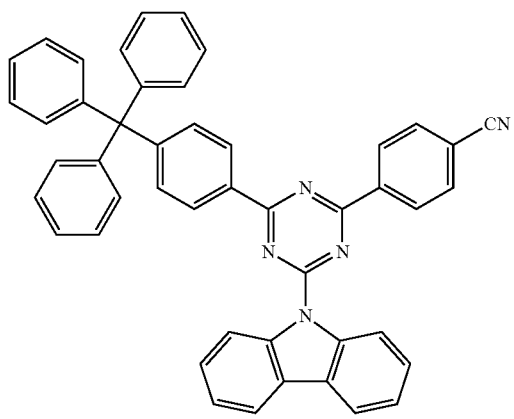
38
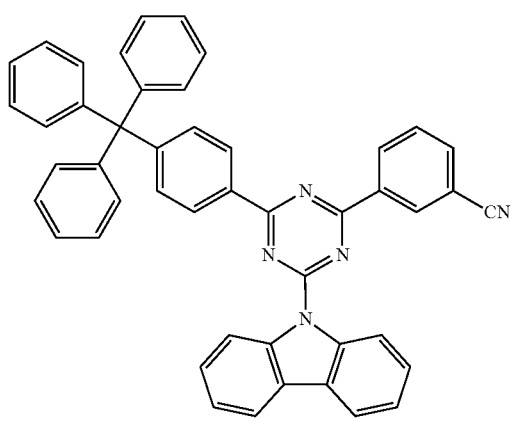
39
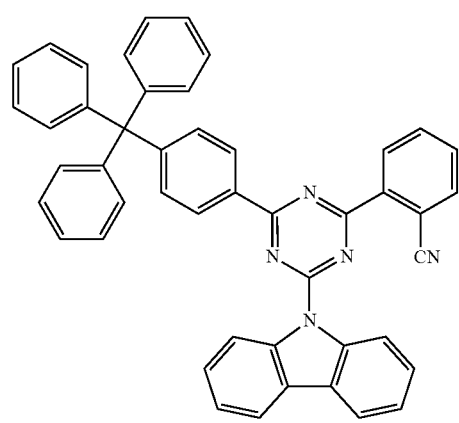
40
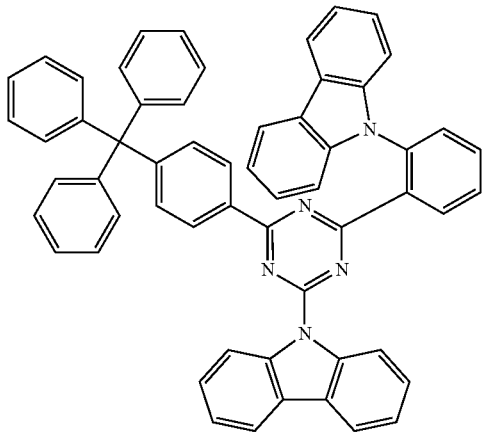
41
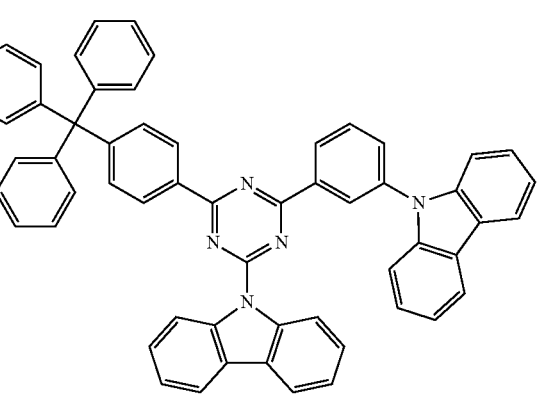
42
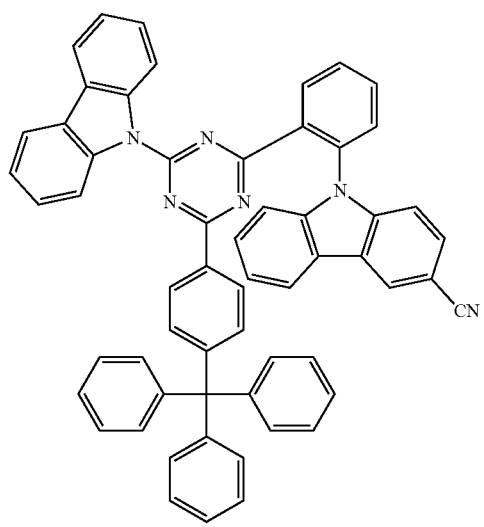

43
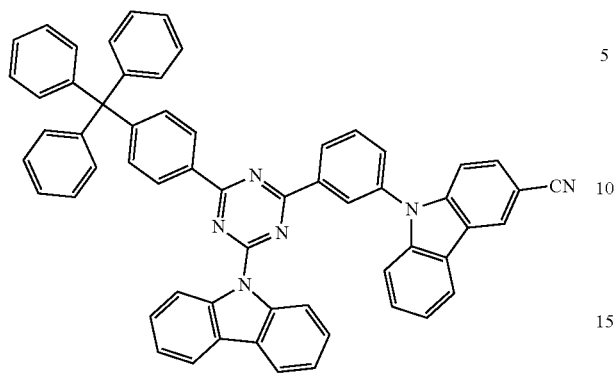
44
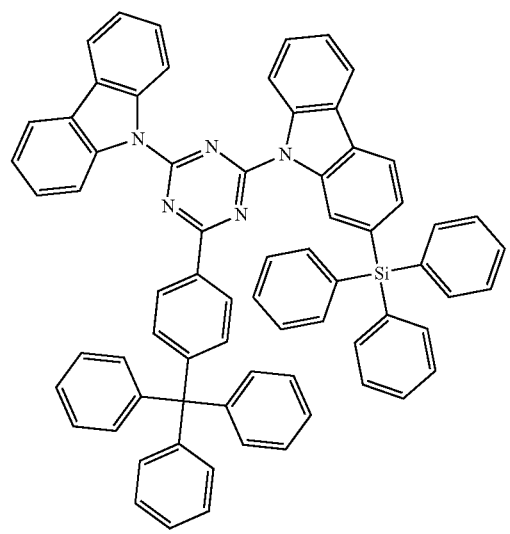
45
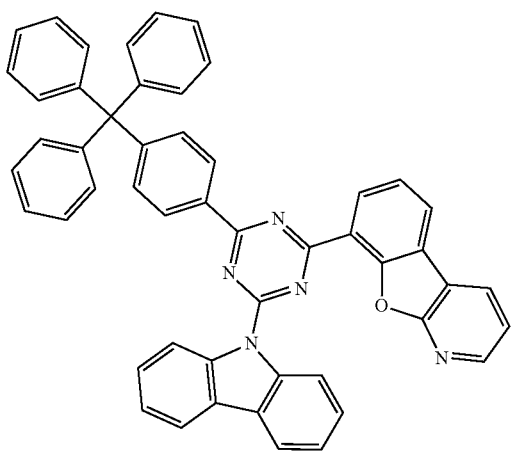
46
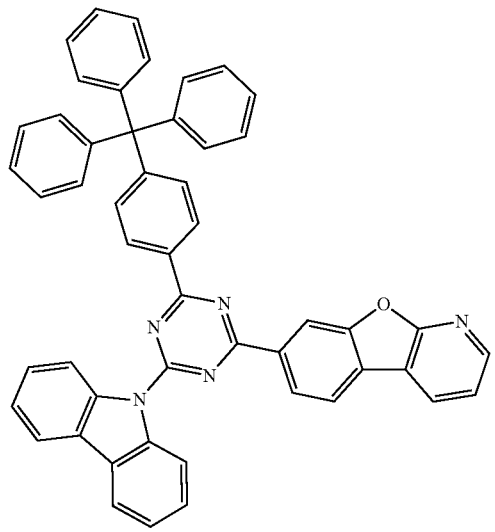
47
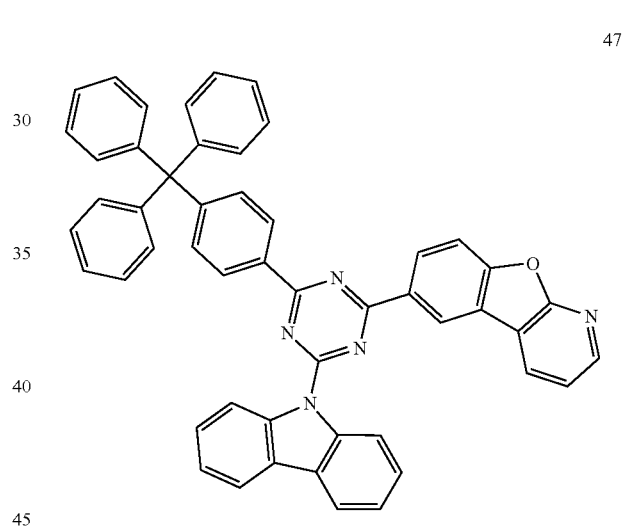
48
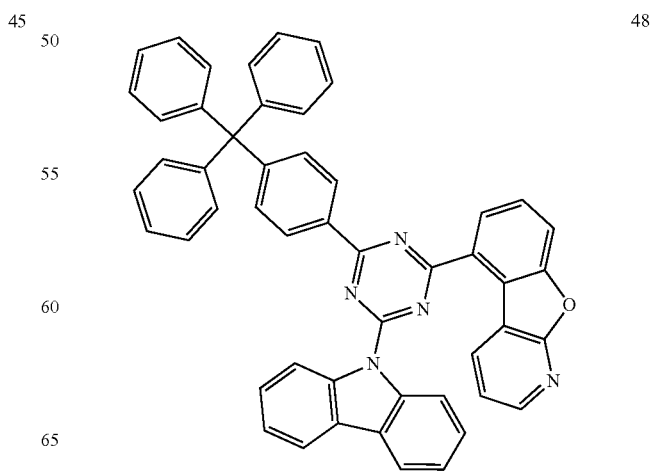

51
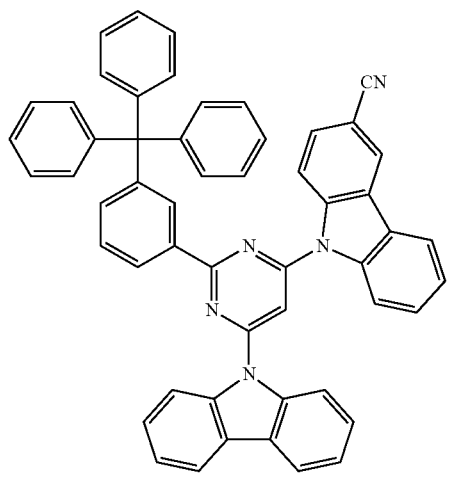
54
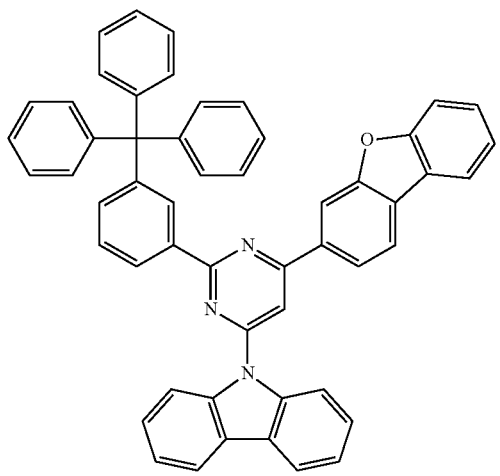
52
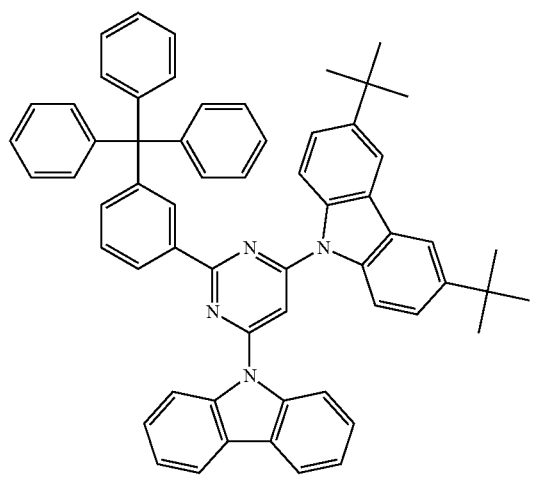
55
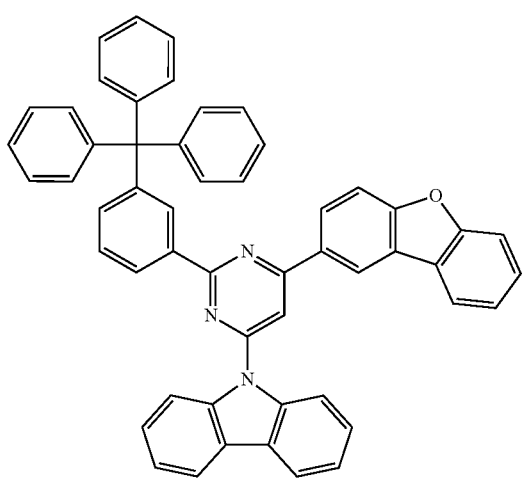
53
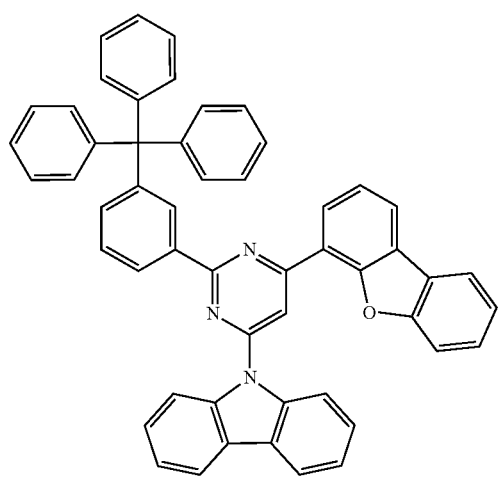
56
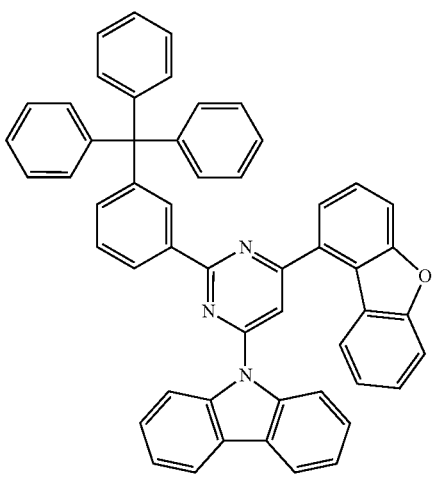

57
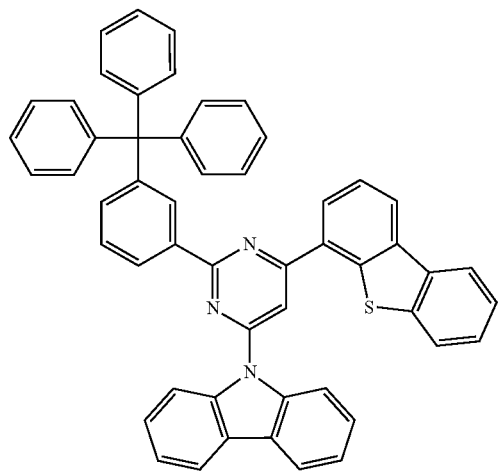
58
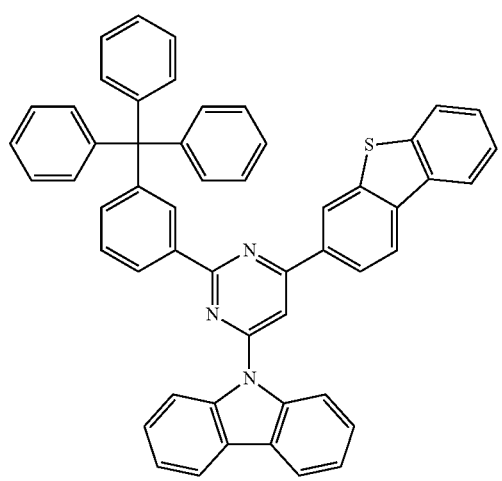
59
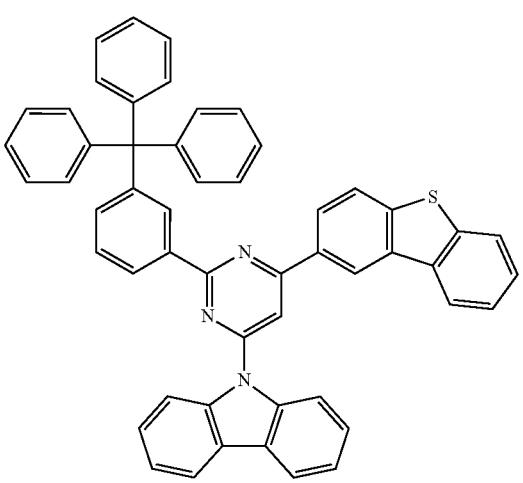
60
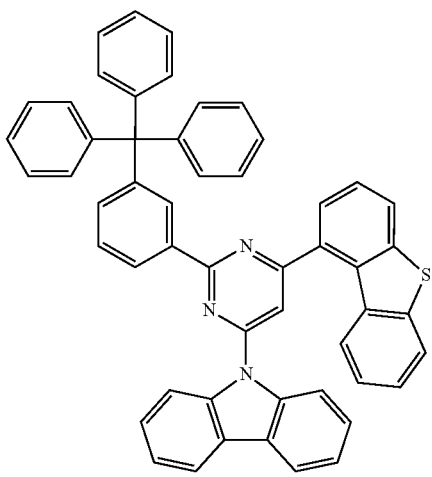
61
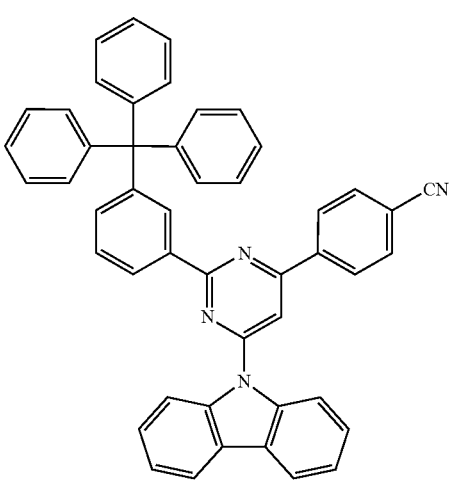
62
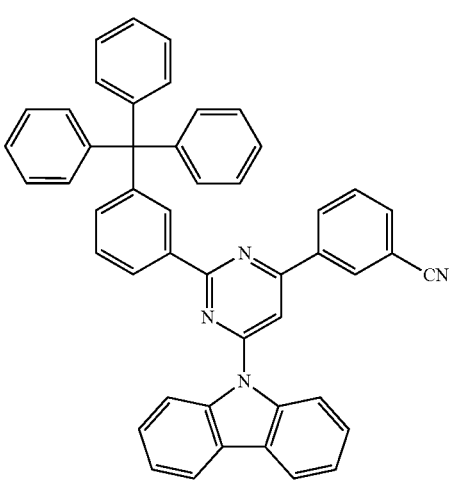

63
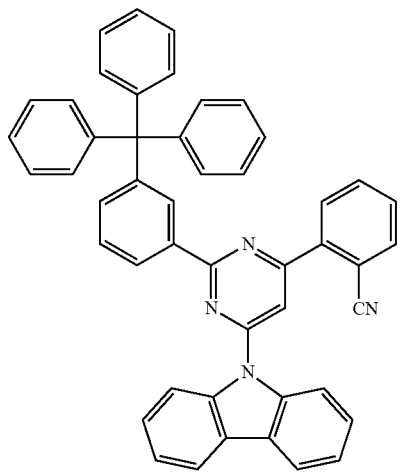
64
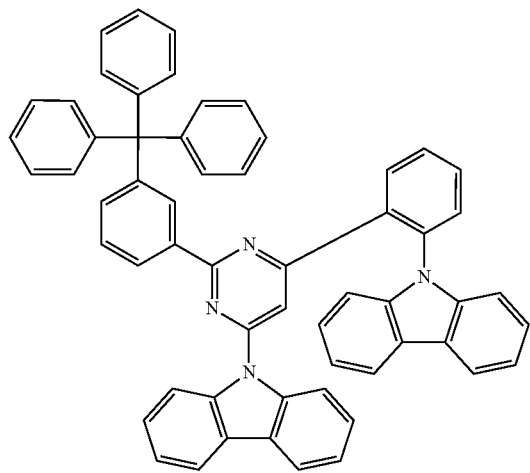
65
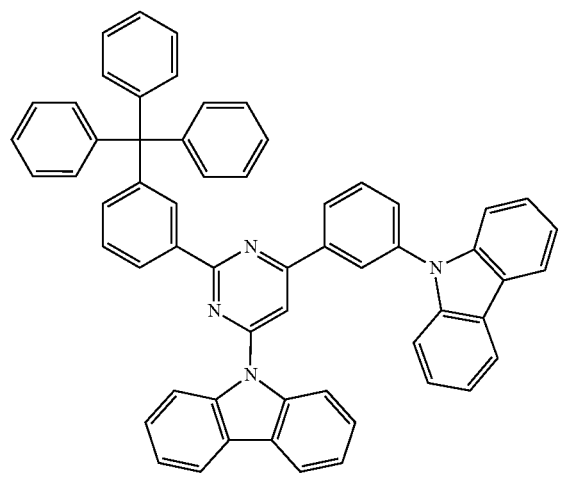
66
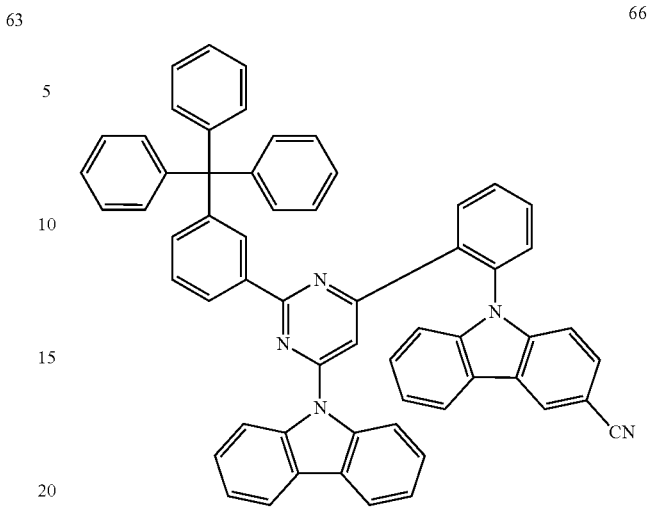
67
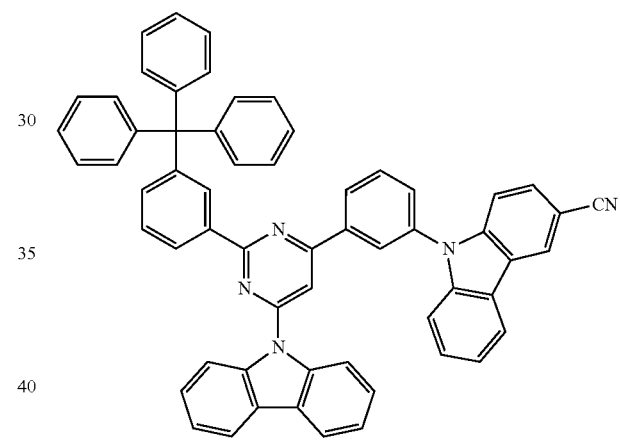
68
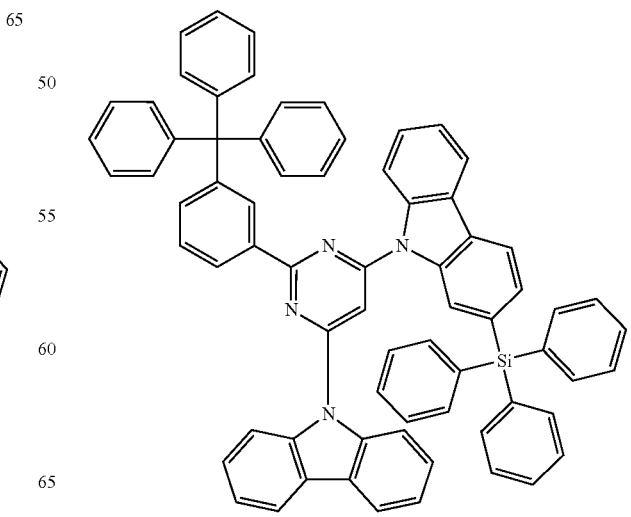

69
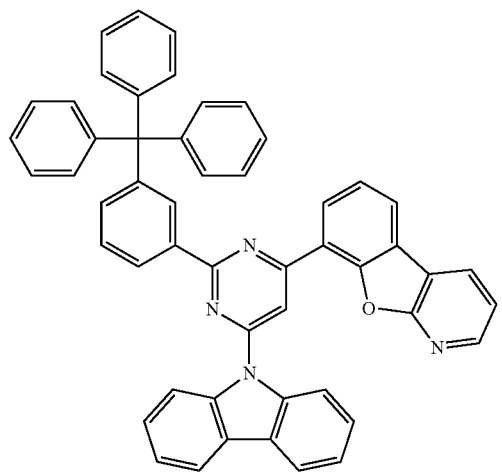
70
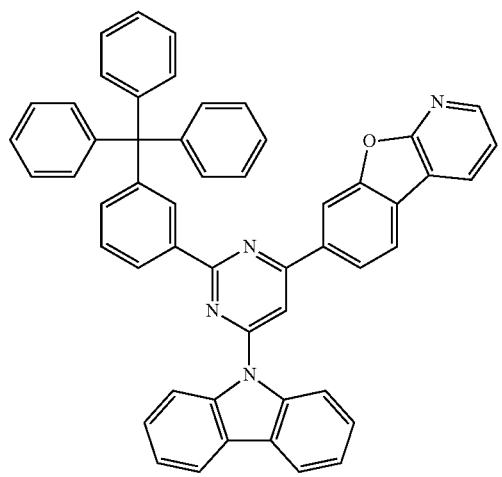
71
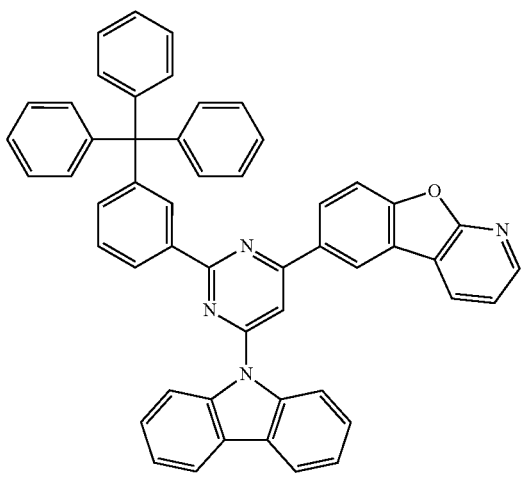
72
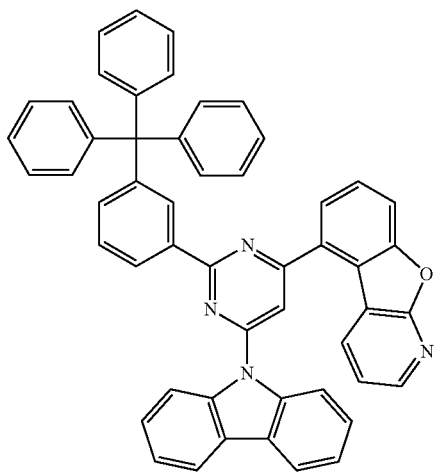
75
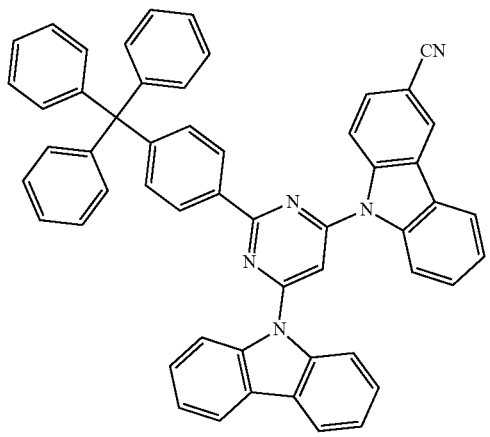
76
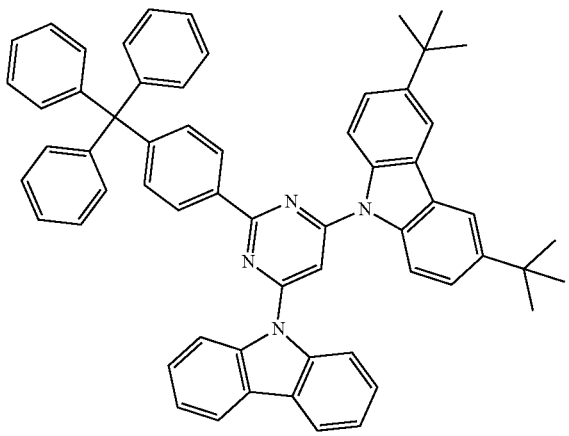

77
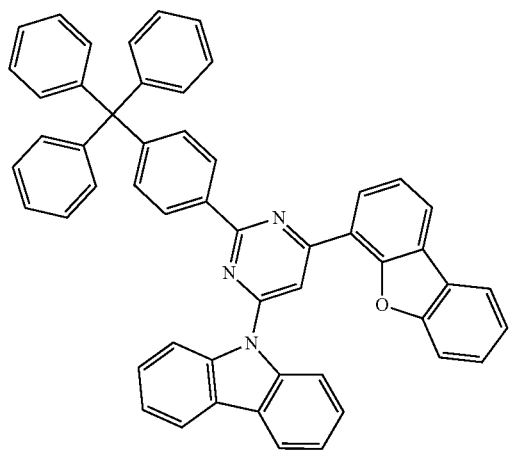
78
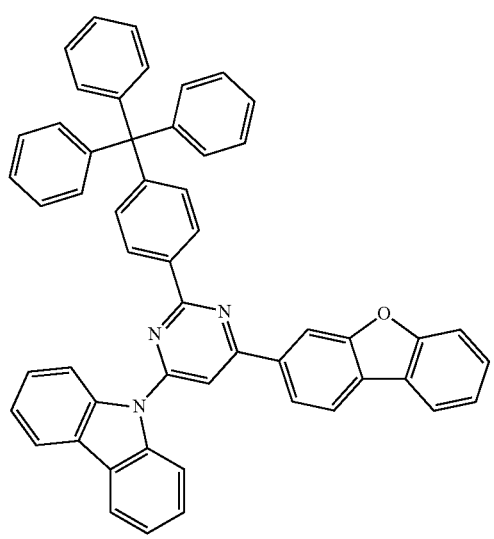
79
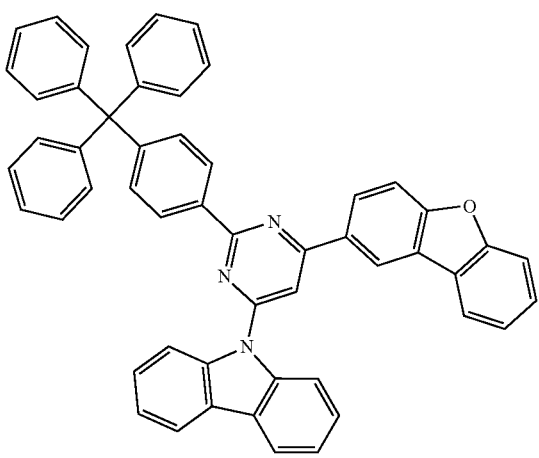
80
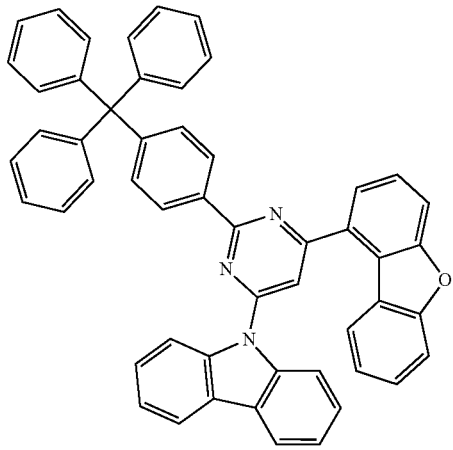
81
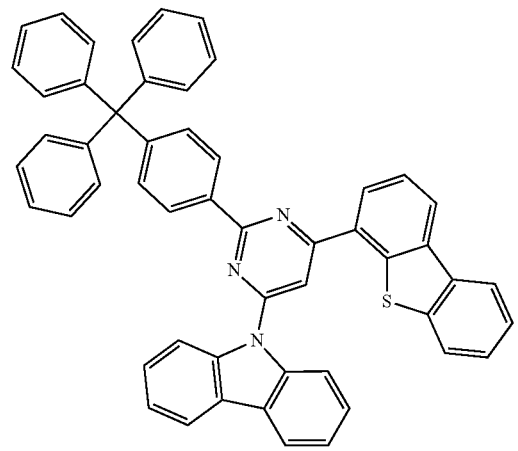
82
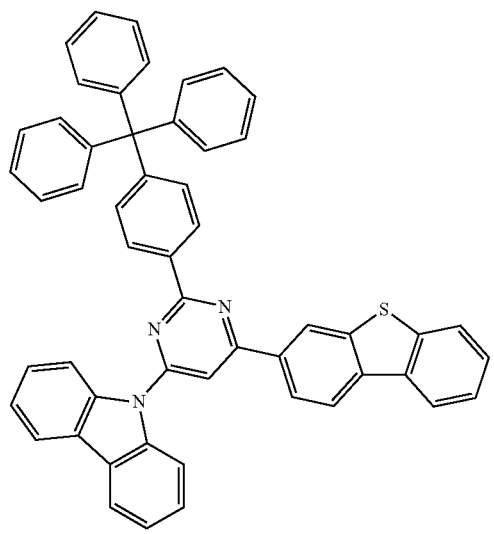

83
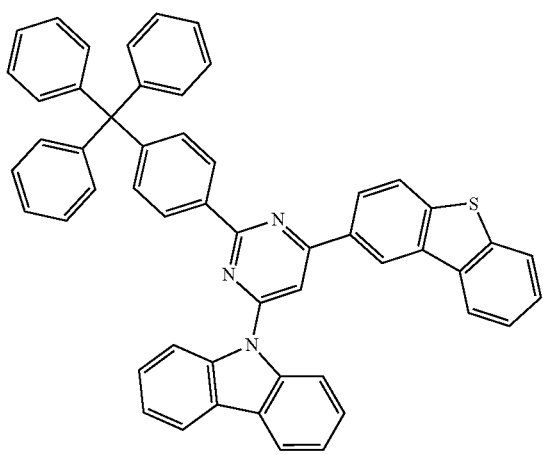
84
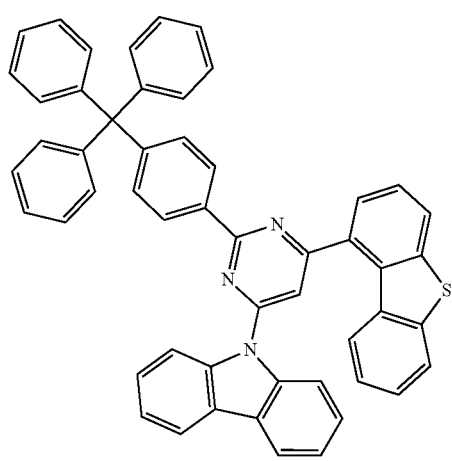
85
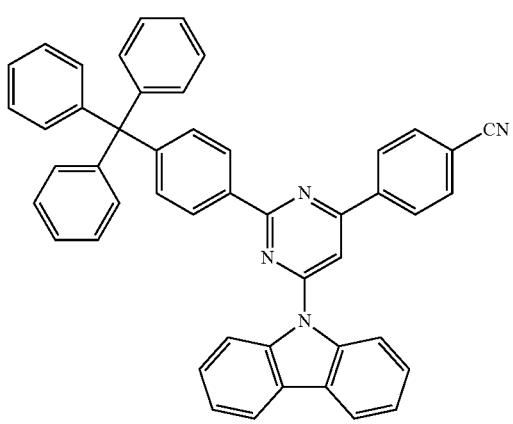
86
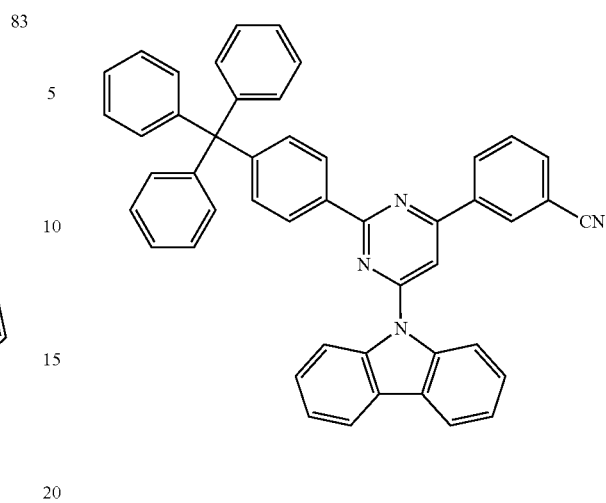
87
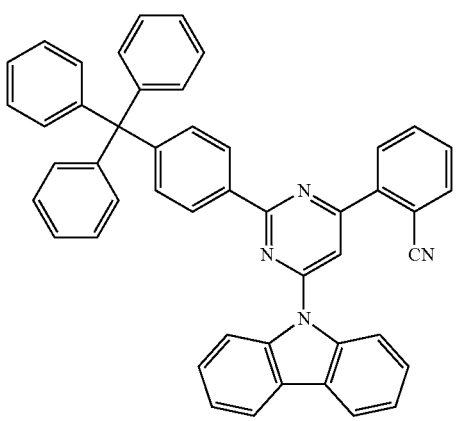
88
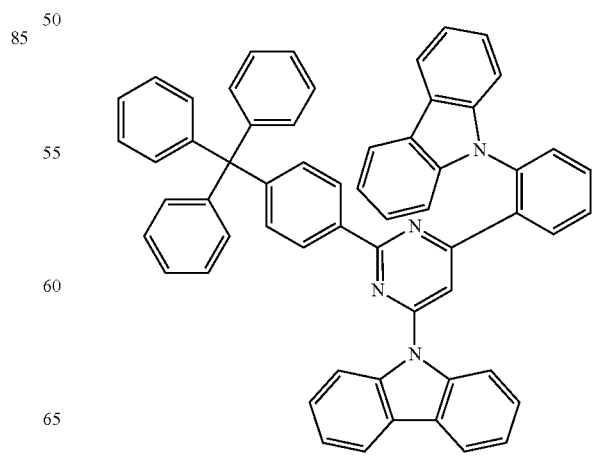

245
-continued

89

90

91

246
-continued

92

93

94

247
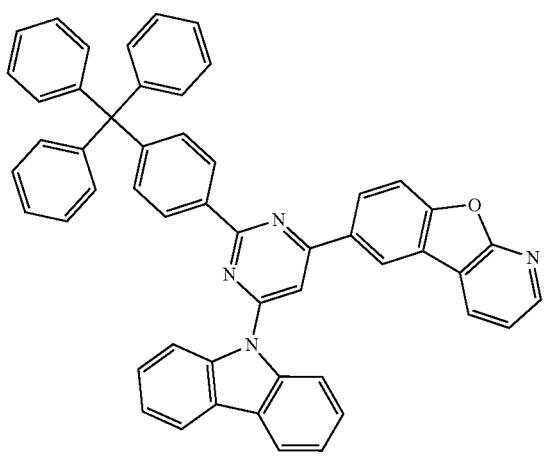
95
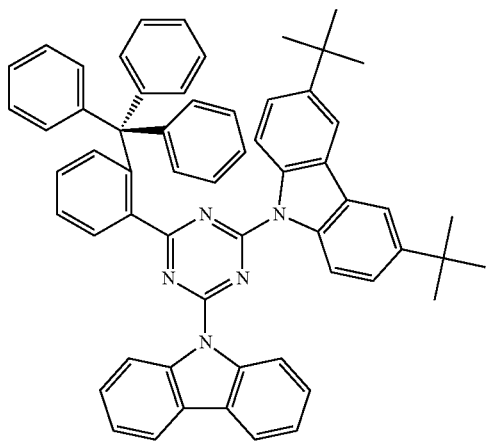
100
96
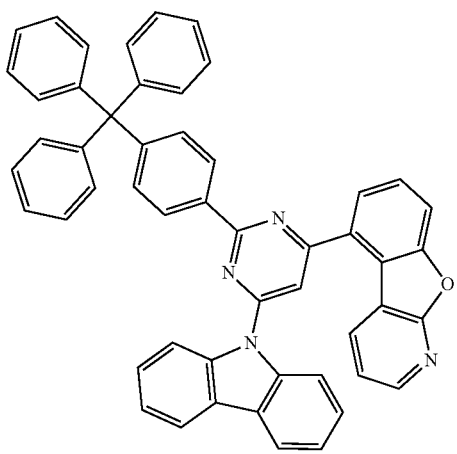
101
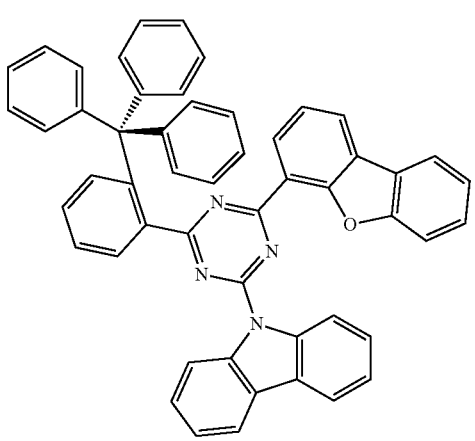
99
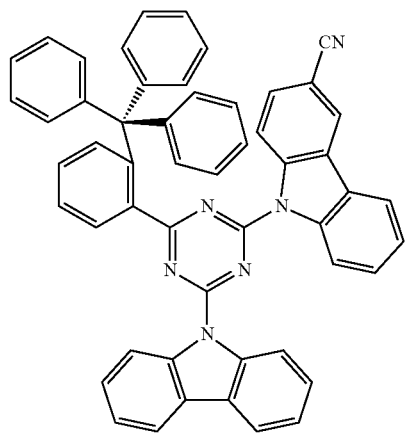
102
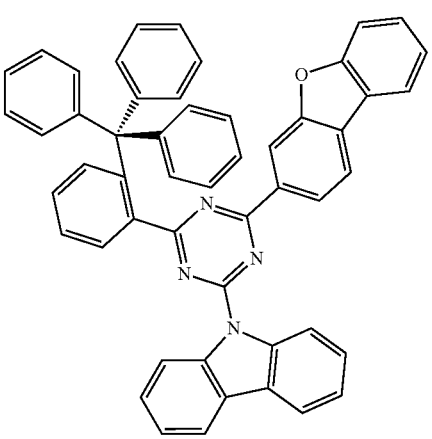

103
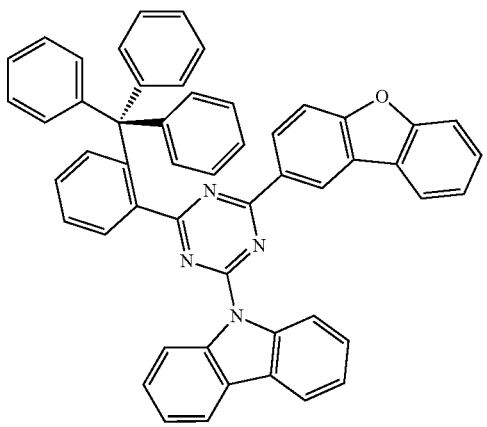
104
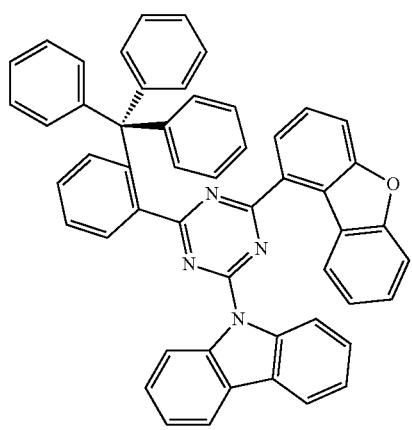
105
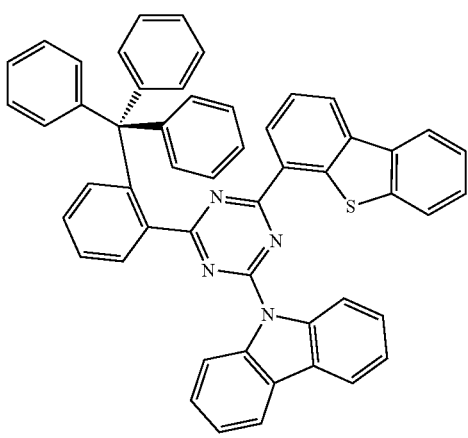
106
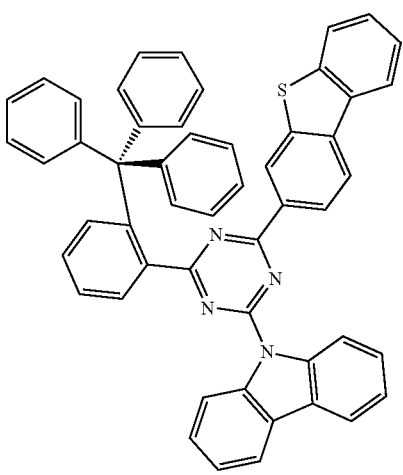
107
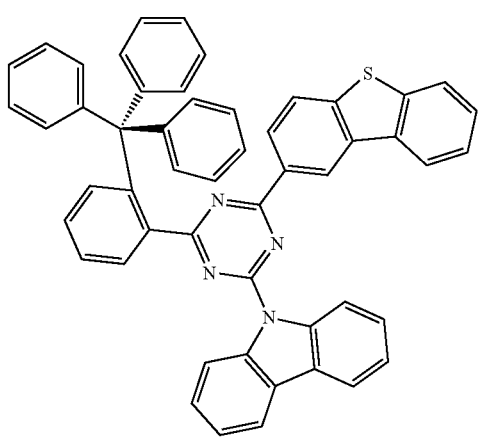
108
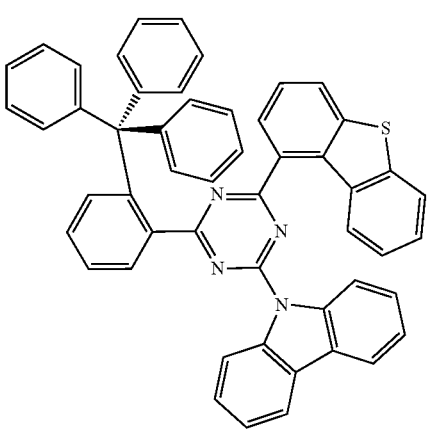

109
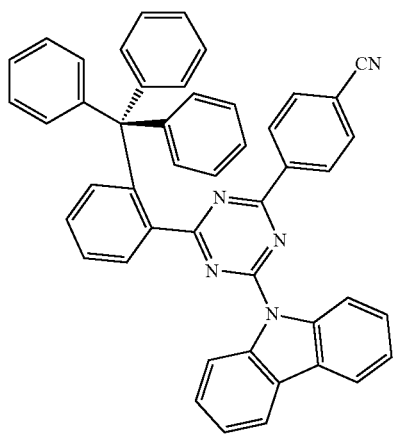
112
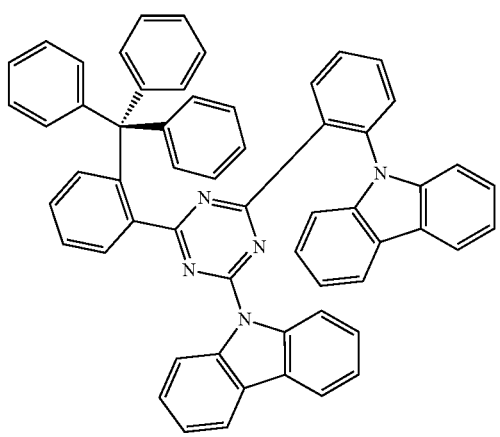
110
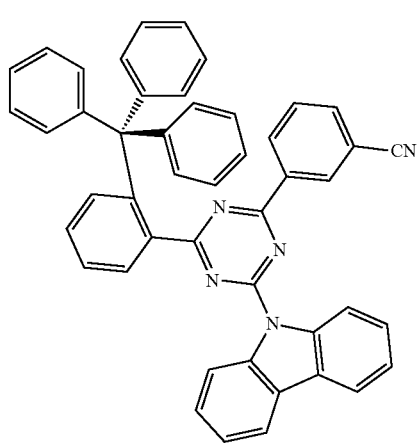
113
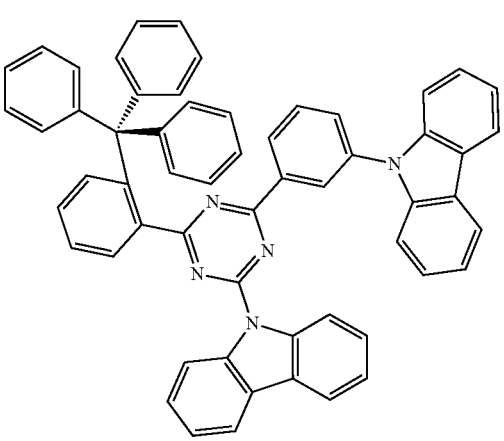
111
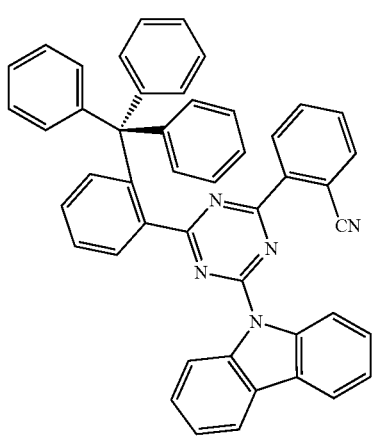
114
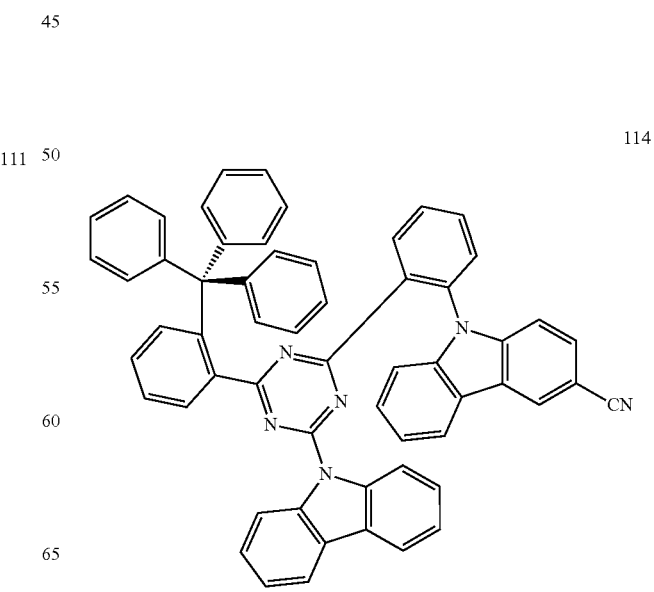

115

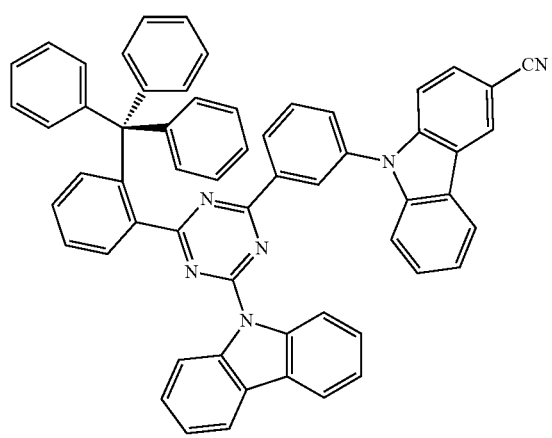

116

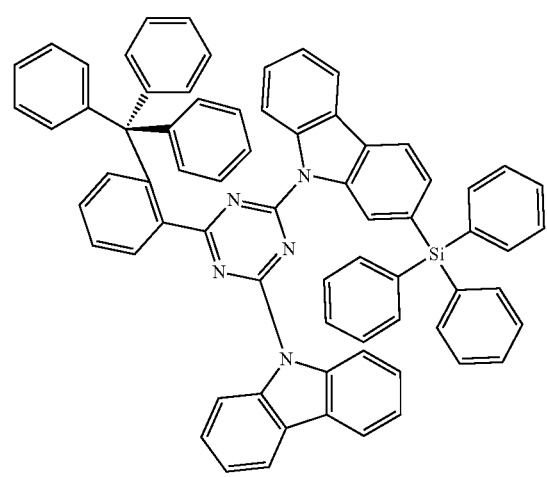

117

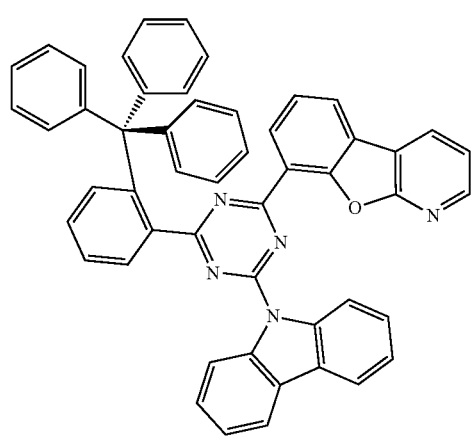

118

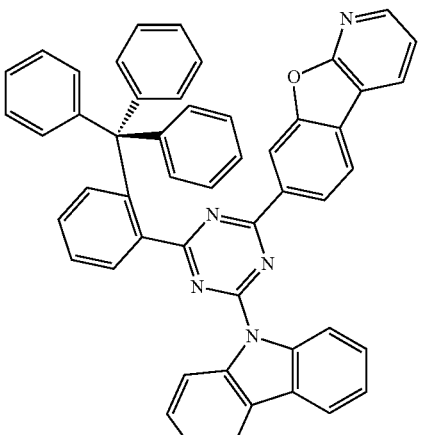

119

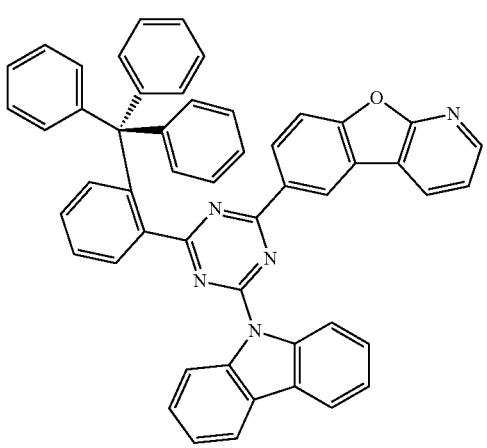

120

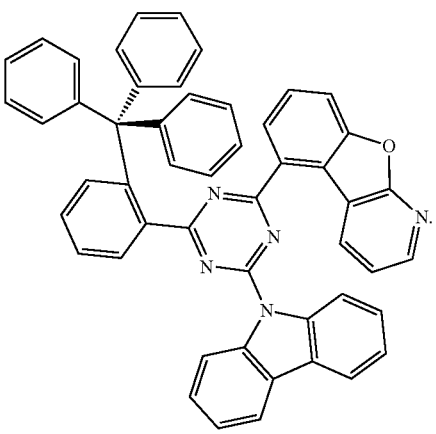

15. The light-emitting device of claim 14, wherein the emission layer is a phosphorescent emission layer.

16. The light-emitting device of claim 15, wherein the phosphorescent emission layer comprises the compound.

17. The light-emitting device of claim 14, wherein the emission layer is a fluorescent emission layer.

18. The light-emitting device of claim 17, wherein the emission layer comprises the compound of claim 14 as a thermally activated delayed fluorescence (TADF) material.

19. The light-emitting device of claim 14, wherein the first electrode is an anode, the second electrode is a cathode, the interlayer further comprises a hole transport region between the first electrode and the emission layer and an electron transport region between the emission layer and the second electrode, the hole transport region comprises a hole injection layer, a hole transport layer, an emission auxiliary layer, an electron blocking layer, or any combination thereof, and the electron transport region comprises a hole blocking layer, an electron transport layer, an electron injection layer, or any combination thereof.

20. An electronic apparatus comprising the light-emitting device of claim 14.

* * * * *